United States Patent
Oi et al.

(10) Patent No.: US 7,547,710 B2
(45) Date of Patent: Jun. 16, 2009

(54) FUSED HETEROCYCLIC COMPOUNDS AS PEPTIDASE INHIBITORS

(75) Inventors: Satoru Oi, Nara (JP); Hironobu Maezaki, Toyonaka (JP); Koji Ikedou, Himeji (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 541 days.

(21) Appl. No.: 10/523,531

(22) PCT Filed: Aug. 7, 2003

(86) PCT No.: PCT/JP03/10054

§ 371 (c)(1),
(2), (4) Date: Feb. 7, 2005

(87) PCT Pub. No.: WO2004/014860

PCT Pub. Date: Feb. 19, 2004

(65) Prior Publication Data

US 2006/0135530 A1    Jun. 22, 2006

(30) Foreign Application Priority Data

Aug. 8, 2002    (JP) .............................. 2002-231950
Feb. 27, 2003   (JP) .............................. 2003-51575

(51) Int. Cl.
    *A61K 31/47*    (2006.01)
    *C07D 215/12*   (2006.01)
(52) U.S. Cl. ...................................... 514/311; 546/173
(58) Field of Classification Search ................. 514/311; 546/173
See application file for complete search history.

(56) References Cited

FOREIGN PATENT DOCUMENTS

| WO | 98/19998 | 5/1998 |
| WO | 01/82925 | 11/2001 |
| WO | 02/062764 | 8/2002 |
| WO | 03/068748 | 8/2003 |

OTHER PUBLICATIONS

Sakurai et al., Bull. Chem. Soc. Japan, (1969), vol. 42(1), pp. 220-223.*
G. M. Coppola et al.,"1-Aminomethylisoquinoline-4-carboxylates as Novel Dipeptidylpeptidase IV Inhibitors", Bioorganic & Medicinal Chemistry Letters, vol. 10, 2000, pp. 1555-1558.
K. Augustyns et al., "The Unique Properties of Dipeptidyl-peptidase IV (DPP IV/CD26) and the Therapeutic Potential of DPP IV Inhibitors", Current Medicinal Chemistry, vol. 6, 1999, pp. 311-327.

* cited by examiner

*Primary Examiner*—Taofiq A Solola
(74) *Attorney, Agent, or Firm*—Wenderoth, Lind & Ponack, L.L.P.

(57) ABSTRACT

A compound represented by the formula wherein ring A is an optionally substituted 5- to 10-membered aromatic ring; $R_1$ and $R_2$ are the same or different and each is an optionally substituted hydrocarbon group or an optionally substituted heterocyclic group; X and Y are the same or different and each is a bound, —O—, —S—, —SO—, —SO?2#191- or —$NR_3$— ($R_3$ is a hydrogen atom or an optionally substituted hydrocarbon group); and L is a divalent hydrocarbon group, or a salt thereof shows a superior peptidase-inhibitory activity and is useful as a prophylactic or therapeutic agent of diabetes and the like.

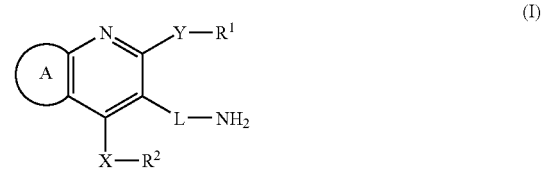

(I)

11 Claims, No Drawings

FUSED HETEROCYCLIC COMPOUNDS AS PEPTIDASE INHIBITORS

This application is a U.S. national stage of International Application No. PCT/JP03/10054 filed Aug. 7, 2003.

TECHNICAL FIELD

The present invention relates to a fused heterocyclic compound having a peptidase inhibitory activity, which is useful as a prophylactic or therapeutic agent of diabetes and the like.

BACKGROUND ART

Peptidase is known to relate to various diseases. Dipeptidyl dipeptidase IV (hereinafter sometimes to be abbreviated as DPP-IV), which is one kind of peptidases, is serine protease that specifically binds with a peptide containing proline (or alanine) at the 2nd from the N terminal and cleaves the C-terminal side of the proline (or alanine) to produce dipeptide. DPP-IV has been shown to be the same molecule as CD26, and reported to be also involved in the immune system. While the role of DPP-IV in mammals has not been entirely clarified, it is considered to play an important role in the metabolism of neuropeptides, activation of T cells, adhesion of cancerous cells to endothelial cells, invasion of HIV into cells and the like. Particularly, from the aspect of glycometabolism, DPP-IV is involved in the inactivation of GLP-1 (glucagon-like peptide-1) and GIP (Gastric inhibitory peptide/Glucose-dependent insulinotropic peptide), which are incretins. With regard to GLP-1, moreover, its half-life in plasma is as short as 1-2 minutes, and GLP-1 is known to be degraded by DPP-IV and markedly lose its physiological activity because GLP-1(9-36)amide, which is a degradation product by DPP-IV, acts on GLP-1 receptor as an antagonist. It is also known that suppression of degradation of GLP-1 by inhibiting activity of DPP-IV leads to potentiation of physiological activity that GLP-1 shows, such as glucose concentration-dependent insulinotropic effect and the like. From these facts, a compound having a DPP-IV inhibitory activity is expected to show effect on impaired glucose tolerance, postprandial hyperglycemia and fasting hyperglycemia observed in type I and type II diabetes and the like, obesity or diabetic complications associated therewith and the like.

As therapeutic agents of diabetes now in use, a sulfonylurea, a biguanide, an α-glucosidase inhibitor and the like are known. While a sulfonylurea produce a potent hypoglycemic action, it sometimes causes serious hypoglycemia and requires attention during use. A biguanide easily causes lactic acidosis which is a relatively serious side effect. An α-glucosidase inhibitor delays digestion and absorption of glucose in the gastrointestinal tract and suppresses increase in the blood glucose level after meal, but side effects of sense of distension, diarrhea and the like are problematic (see JOSLIN'S DIABETES MELLITUS, 13th Edition, pp. 521-522).

As a fused heterocyclic compound having an amino group, the following compounds have been reported.

(1) A compound having a melanin-concentrating hormone antagonistic action, which is represented by the formula

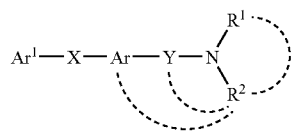

wherein $Ar^1$ is a cyclic group optionally having substituents;

X and Y are the same or different and each is a spacer having 1 to 6 atoms in the main chain;

Ar is a fused polycyclic aromatic ring optionally having substituents;

$R^1$ and $R^2$ are the same or different and each is hydrogen atom or hydrocarbon group optionally having substituents, or $R^1$ and $R^2$ may form, together with the adjacent nitrogen atom, a nitrogen-containing heterocycle optionally having substituents, $R^2$ may form, together with the adjacent nitrogen atom and Y, a nitrogen-containing heterocycle optionally having substituents, and $R^2$ may form, together with the adjacent nitrogen atom, Y and Ar, a fused ring or a salt thereof (see WO01/82925).

(2) a compound having a DPP-IV inhibitory action, which is represented by the formula

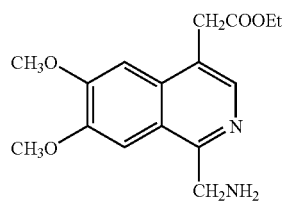

(see Bioorganic & Medicinal Chemistry Letters, vol. 10, pp. 1555-1558 (2000)).

However, there is no report about the compound of the present invention.

There is a demand on the development of a fused heterocyclic compound having a peptidase inhibitory activity, useful as a prophylactic or therapeutic agent of diabetes and the like and having superior properties in terms of efficacy, duration of action, specificity, low toxicity and the like.

DISCLOSURE OF THE INVENTION

The present inventors have first found that a compound of the formula

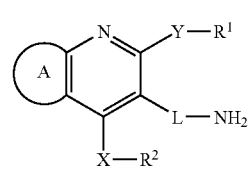

wherein
ring A is an optionally substituted 5- to 10-membered aromatic ring;

$R^1$ and $R^2$ are the same or different and each is an optionally substituted hydrocarbon group or an optionally substituted heterocyclic group;

X and Y are the same or different and each is a bond, —O—, —S—, —SO—, —SO$_2$— or —NR$^3$— ($R^3$ is a hydrogen atom or an optionally substituted hydrocarbon group); and L is a divalent hydrocarbon group, and a salt thereof (hereinafter sometimes to be abbreviated as compound (I)), which are characterized by the chemical structure where an amino group is bonded to a fused heterocycle via a divalent hydrocarbon group, have a superior peptidase inhibitory activity and are useful as a prophylactic or therapeutic agent of diabetes and the like. Based on this finding, the present inventors have conducted intensive studies and completed the present invention.

Accordingly, the present invention relates to:

1) compound (I);

2) the compound of the aforementioned 1), wherein the 5- to 10-membered aromatic ring for ring A is a benzene ring;

3) the compound of the aforementioned 1), wherein the ring A is a 5- to 10-membered aromatic ring optionally having 1 to 3 substituents selected from (1) a halogen atom;

(2) a nitro group;

(3) a cyano group;

(4) an alkylenedioxy group having 1 to 3 carbon atoms;

(5) an alkyl group having 1 to 10 carbon atoms or an alkenyl group having 2 to 10 carbon atoms, each optionally having 1 to 3 substituents selected from a halogen atom, a hydroxy group, a carboxyl group, an alkoxycarbonyl group having 2 to 8 carbon atoms, a carbamoyl group, a cyano group, an amino group, an alkylcarbonylamino group having 2 to 8 carbon atoms, an alkoxycarbonylamino group having 2 to 8 carbon atoms and an alkylsulfonylamino group having 1 to 8 carbon atoms;

(6) an optionally substituted hydroxy group;

(7) an acyl group;

(8) an optionally substituted amino group;

(9) an optionally substituted cycloalkyl group having 3 to 10 carbon atoms;

(10) an aryl group having 6 to 14 carbon atoms;

(11) an optionally substituted thiol group;

(12) an optionally substituted heterocyclic group; and

(13) an amidino group;

4) the compound of the aforementioned 1), wherein $R^1$ is an alkyl group having 1 to 10 carbon atoms which is optionally substituted by a cycloalkyl group having 3 to 10 carbon atoms;

5) the compound of the aforementioned 1), wherein X is a bond;

6) the compound of the aforementioned 1), wherein Y is a bond;

7) the compound of the aforementioned 1), wherein the divalent hydrocarbon group denoted by L is an alkylene group having 1 to 10 carbon atoms;

8) the compound of the aforementioned 1), wherein $R^2$ is an alkyl group having 1 to 10 carbon atoms, an aryl group having 6 to 14 carbon atoms or an aralkyl group having 7 to 13 carbon atoms, each optionally having 1 to 3 substituents selected from halogen atom, hydroxy group, nitro group, amino group, optionally halogenated alkyl group having 1 to 6 carbon atoms, alkoxy group having 1 to 6 carbon atoms, aromatic heterocyclic group and cycloalkyl group having 3 to 10 carbon atoms;

9) the compound of the aforementioned 1), which is (2E)-3-[3-(aminomethyl)-2-isobutyl-4-(4-methylphenyl)quinolin-6-yl]acrylamide;

5-{[3-(aminomethyl)-2-isobutyl-4-(4-methylphenyl)quinolin-6-yl]oxy}pentanoic acid;

4-[3-(aminomethyl)-2-isobutyl-4-(4-methylphenyl)quinolin-6-yl]piperazin-2-one;

1-[3-(aminomethyl)-2-isobutyl-4-(4-methylphenyl)quinolin-6-yl]piperazine-2,5-dione; or a salt thereof;

10) a pharmaceutical agent containing compound (I) or a prodrug thereof;

11) the pharmaceutical agent of the aforementioned 10), which is a prophylactic or therapeutic agent of diabetes;

12) the pharmaceutical agent of the aforementioned 10), which is a prophylactic or therapeutic agent of diabetic complications;

13) the pharmaceutical agent of the aforementioned 10), which is a prophylactic or therapeutic agent of impaired glucose tolerance;

14) the pharmaceutical agent of the aforementioned 10), which is a prophylactic or therapeutic agent of obesity;

15) a peptidase inhibitor containing compound (I) or a prodrug thereof;

16) the inhibitor of the aforementioned 15), wherein the peptidase is dipeptidyl dipeptidase IV;

17) a method for the prophylaxis or treatment of diabetes in a mammal, which comprises administering compound (I) or a prodrug thereof to the mammal;

18) a method for the prophylaxis or treatment of diabetic complications in a mammal, which comprises administering compound (I) or a prodrug thereof to the mammal;

19) a method for the prophylaxis or treatment of impaired glucose tolerance in a mammal, which comprises administering compound (I) or a prodrug thereof to the mammal;

20) a method for the prophylaxis or treatment of obesity in a mammal, which comprises administering compound (I) or a prodrug thereof to the mammal;

21) a method for inhibiting peptidase in a mammal, which comprises administering compound (I) or a prodrug thereof to the mammal;

22) use of compound (I) or a prodrug thereof for the production of a prophylactic or therapeutic agent of diabetes;

23) use of compound (I) or a prodrug thereof for the production of a prophylactic or therapeutic agent of diabetic complications;

24) use of compound (I) or a prodrug thereof for the production of a prophylactic or therapeutic agent of impaired glucose tolerance;

25) use of compound (I) or a prodrug thereof for the production of a prophylactic or therapeutic agent of obesity;

26) use of compound (I) or a prodrug thereof for the production of a peptidase inhibitor;

27) a method of producing a compound represented by the formula

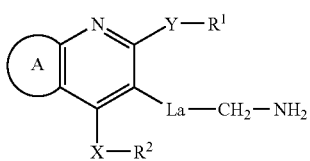

(I-a)

wherein
ring A is an optionally substituted 5- to 10-membered aromatic ring;
$R^1$ and $R^2$ are the same or different and each is an optionally substituted hydrocarbon group or an optionally substituted heterocyclic group;
X and Y are the same or different and each is a bond, —O—, —S—, —SO—, —SO$_2$— or —NR$^3$— ($R^3$ is a hydrogen atom or an optionally substituted hydrocarbon group);
La is a bond or a divalent hydrocarbon group,
or a salt thereof, which comprises reacting a compound represented by the formula

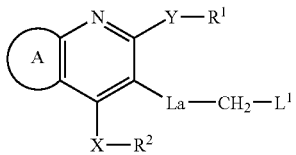

(IV)

wherein $L^1$ is a leaving group, and other symbols are as defined above, or a salt thereof with an aminating agent;

28) a method of producing a compound represented by the formula

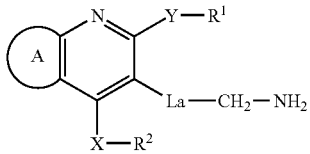

(I-a)

wherein
ring A is an optionally substituted 5- to 10-membered aromatic ring;
$R^1$ and $R^2$ are the same or different and each is an optionally substituted hydrocarbon group or an optionally substituted heterocyclic group;
X and Y are the same or different and each is a bond, —O—, —S—, —SO—, —SO$_2$— or —NR$^3$— ($R^3$ is a hydrogen atom or an optionally substituted hydrocarbon group);
La is a bond or a divalent hydrocarbon group, or a salt thereof, which comprises subjecting a compound represented by the formula

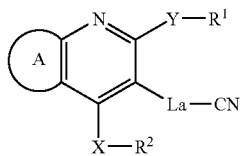

(VIII)

wherein the symbols in the formula are as defined above, or a salt thereof to reduction reaction, and the like.

BEST MODE FOR EMBODYING THE INVENTION

Each symbol of the formula (I) is described in detail in the following.

The "5- to 10-membered aromatic ring" of the "optionally substituted 5- to 10-membered aromatic ring" denoted by ring A is, for example, a 5- to 10-membered aromatic hydrocarbon ring or a 5- to 10-membered aromatic heterocycle.

Preferable examples of the 5- to 10-membered aromatic hydrocarbon ring include benzene, naphthalene and the like.

Preferable examples of the 5- to 10-membered aromatic heterocycle include a 5- to 10-membered aromatic heterocycle containing 1 to 4 heteroatom(s) selected from an oxygen atom, a sulfur atom and a nitrogen atom as a ring-constituting atom, besides carbon atoms, such as furan, thiophene, pyrrole, oxazole, isoxazole, thiazole, isothiazole, imidazole, pyrazole, 1,2,3-oxadiazole, furazan, 1,2,3-thiadiazole, 1,2,3-triazole, pyridine, pyridazine, pyrimidine, triazine, benzofuran, isobenzofuran, benzo[b]thiophene, indole, isoindole, 1H-indazole, benzimidazole, benzoxazole, 1,2-benzoisoxazole, benzothiazole, 1,2-benzoisothiazole, 1H-benzotriazole, quinoline, isoquinoline and the like.

The "5- to 10-membered aromatic ring" is preferably a benzene ring.

The "5- to 10-membered aromatic ring" denoted by ring A optionally has 1 to 3 substituents at substitutable position(s). Examples of the substituent include "halogen atom", "nitro group", "cyano group", "alkylenedioxy group having 1 to 3 carbon atoms", "optionally substituted alkyl group having 1 to 10 carbon atoms", "optionally substituted alkenyl group having 2 to 10 carbon atoms", "optionally substituted alkynyl group having 2 to 10 carbon atoms", "optionally substituted cycloalkyl group having 3 to 10 carbon atoms", "optionally substituted cycloalkenyl group having 3 to 10 carbon atoms", "optionally substituted cycloalkadienyl group having 4 to 10 carbon atoms", "optionally substituted aryl group having 6 to 14 carbon atoms", "optionally substituted heterocyclic group", "acyl group", "optionally substituted amino group", "optionally substituted hydroxy group", "optionally substituted thiol group", "amidino group" and the like.

As the "halogen atom" here, for example, fluorine, chlorine, bromine, iodine and the like can be mentioned, with preference given to fluorine, chlorine and bromine.

Examples of the "alkylenedioxy group having 1 to 3 carbon atoms" include methylenedioxy, ethylenedioxy and the like.

As the "alkyl group" of the "optionally substituted alkyl group having 1 to 10 carbon atoms", for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like can be mentioned.

As the "alkenyl group having 2 to 10 carbon atoms" of the "optionally substituted alkenyl group having 2 to 10 carbon atoms", for example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like can be mentioned.

As the "alkynyl group having 2 to 10 carbon atoms" of the "optionally substituted alkynyl group having 2 to 10 carbon atoms", for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like can be mentioned.

The aforementioned "alkyl group having 1 to 10 carbon atoms", "alkenyl group having 2 to 10 carbon atoms" and "alkynyl group having 2 to 10 carbon atoms" optionally have 1 to 3 substituents at substitutable position(s).

As these substituents, for example, cycloalkyl group having 3 to 10 carbon atoms; aryl group having 6 to 14 carbon atoms (e.g., phenyl, naphthyl and the like); aromatic heterocyclic group (e.g., thienyl, furyl, pyridyl, oxazolyl, thiazolyl, quinolyl and the like); non-aromatic heterocyclic group (e.g., tetrahydrofuryl, morpholino, thiomorpholino, piperidino, pyrrolidinyl, piperazinyl and the like); aralkyl group having 7 to 13 carbon atoms; amino group optionally mono or di-substituted by alkyl group having 1 to 4 carbon atoms or acyl group having 2 to 8 carbon atoms (e.g., alkylcarbonyl group, alkoxycarbonyl group, alkylcarbamoyl group and the like); alkylsulfonylamino group having 1 to 8 carbon atoms; amidino group; acyl group having 2 to 8 carbon atoms (e.g., alkylcarbonyl group, alkoxycarbonyl group and the like); alkylsulfonyl group having 1 to 8 carbon atoms; carbamoyl group optionally mono or di-substituted by alkyl group having 1 to 4 carbon atoms; sulfamoyl group optionally mono or di-substituted by alkyl group having 1 to 4 carbon atoms; carboxyl group; hydroxy group; alkoxy group having 1 to 6 carbon atoms optionally substituted by 1 to 3 halogen atoms (e.g., fluorine, chlorine, bromine, iodine and the like); alkenyloxy group having 2 to 5 carbon atoms optionally substituted by 1 to 3 halogen atoms (e.g., fluorine, chlorine, bromine, iodine and the like); cycloalkyloxy group having 3 to 7 carbon atoms; aralkyloxy group having 7 to 13 carbon atoms; aryloxy group having 6 to 14 carbon atoms (e.g., phenyloxy, naphthyloxy and the like); thiol group; alkylthio group having 1 to 6 carbon atoms optionally having 1 to 3 substituents selected from halogen atoms (e.g., fluorine, chlorine, bromine, iodine and the like), carboxyl group, alkoxycarbonyl group having 2 to 8 carbon atoms and carbamoyl group; aralkylthio group having 7 to 13 carbon atoms; arylthio group having 6 to 14 carbon atoms (e.g., phenylthio, naphthylthio and the like); sulfo group; cyano group; azide group; nitro group; nitroso group; halogen atom (e.g., fluorine, chlorine, bromine, iodine) and the like can be mentioned.

The "cycloalkyl group having 3 to 10 carbon atoms" of the "optionally substituted cycloalkyl group having 3 to 10 carbon atoms" is, for example, cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and the like.

The "cycloalkenyl group having 3 to 10 carbon atoms" of the "optionally substituted cycloalkenyl group having 3 to 10 carbon atoms" is, for example, 2-cyclopenten-1-yl, 3-cyclopenten-1-yl, 2-cyclohexen-1-yl, 3-cyclohexen-1-yl and the like.

The "cycloalkadienyl group having 4 to 10 carbon atoms" of the "optionally substituted cycloalkadienyl group having 4 to 10 carbon atoms" is, for example, 2,4-cyclopentadien-1-yl, 2,4-cyclohexadien-1-yl, 2,5-cyclohexadien-1-yl and the like.

The "aryl group having 6 to 14 carbon atoms" of the "optionally substituted aryl group having 6 to 14 carbon atoms" is, for example, phenyl, naphthyl, anthryl, phenanthryl, acenaphthylenyl, biphenylyl and the like. Of these, phenyl, 1-naphthyl, 2-naphthyl and the like are preferable.

The "heterocyclic group" of the "optionally substituted heterocyclic group" is exemplified by a non-aromatic heterocyclic group and an aromatic heterocyclic group.

The non-aromatic heterocyclic group is, for example, 5- to 7-membered monocyclic non-aromatic heterocyclic group containing 1 to 4 heteroatom(s) selected from an oxygen atom, a sulfur atom and a nitrogen atom as a ring-constituting atom, besides carbon atoms, or a fused non-aromatic heterocyclic group. The fused non-aromatic heterocyclic group is, for example, a group wherein these 5- to 7-membered monocyclic non-aromatic heterocyclic groups and a 6-membered ring containing 1 or 2 nitrogen atom(s), a benzene ring or a 5-membered ring containing one sulfur atom are fused and the like.

Preferable examples of the non-aromatic heterocyclic group include 1-pyrrolidinyl, piperidino, morpholino, thiomorpholino, 1-piperazinyl, hexamethylenimin-1-yl, oxazolidin-3-yl, thiazolidin-3-yl, imidazolidin-3-yl, 2-oxoimidazolidin-1-yl, 2,4-dioxoimidazolidin-3-yl, 2,4-dioxooxazolidin-3-yl, 2,4-dioxothiazolidin-3-yl, 1,3-dioxoisoindol-2-yl, 5-oxooxadiazol-3-yl, 5-oxothiadiazol-3-yl, 3-oxopiperazin-1-yl, 2,3-dioxopiperazin-1-yl, 2,5-dioxopiperazin-1-yl and the like.

The aromatic heterocyclic group is, for example, a 5- to 7-membered monocyclic aromatic heterocyclic group containing 1 to 4 heteroatom(s) selected from an oxygen atom, a sulfur atom and a nitrogen atom as a ring-constituting atom, besides carbon atoms, or fused aromatic heterocyclic group. The fused aromatic heterocyclic group is, for example, a group where these 5- to 7-membered monocyclic aromatic heterocyclic groups and a 6-membered ring containing 1 or 2 nitrogen atom(s), a benzene ring or a 5-membered ring containing one sulfur atom are fused and the like.

Preferable examples of the aromatic heterocyclic group include 2-furyl, 3-furyl, 2-thienyl, 3-thienyl, 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 1-pyrrolyl, 2-pyrrolyl, 3-pyrrolyl, 1-imidazolyl, 2-imidazolyl, 4-imidazolyl, 5-imidazolyl, 1-pyrazolyl, 3-pyrazolyl, 4-pyrazolyl, isoxazolyl, isothiazolyl, 2-thiazolyl, 4-thiazolyl, 5-thiazolyl, 2-oxazolyl, 4-oxazolyl, 5-oxazolyl, 1,2,4-oxadiazol-5-yl, 1,3,4-oxadiazol-2-yl, 1,3,4-thiadiazol-2-yl, 1,2,4-triazol-1-yl, 1,2,4-triazol-3-yl, 1,2,3-triazol-1-yl, 1,2,3-triazol-2-yl, 1,2,3-triazol-4-yl, tetrazol-1-yl, tetrazol-5-yl, 2-quinolyl, 3-quinolyl, 4-quinolyl, 2-quinazolyl, 4-quinazolyl, 2-quinoxalyl, 2-benzofuryl, 3-benzofuryl, 2-benzothienyl, 3-benzothienyl, 2-benzoxazolyl, 2-benzothiazolyl, benzimidazol-1-yl, benzimidazol-2-yl, indol-1-yl, indol-3-yl, 1H-indazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin-2-yl, 1H-imidazo[4,5-b]pyrazin-2-yl and the like.

The substituent of the aforementioned "optionally substituted cycloalkyl group having 3 to 10 carbon atoms", "optionally substituted cycloalkenyl group having 3 to 10 carbon atoms", "optionally substituted cycloalkadienyl group having 4 to 10 carbon atoms", "optionally substituted aryl group having 6 to 14 carbon atoms" and "optionally substituted heterocyclic group" is, for example, alkyl group having 1 to 6 carbon atoms optionally having 1 to 3 substituents selected from halogen atoms (e.g., fluorine, chlorine, bromine, iodine and the like) and carbamoyl group; alkenyl group having 2 to 6 carbon atoms optionally having 1 to 3 substituents selected from halogen atoms (e.g., fluorine, chlorine, bromine, iodine and the like) and carbamoyl group; cycloalkyl group having 3 to 10 carbon atoms; aryl group having 6 to 14 carbon atoms (e.g., phenyl, naphthyl and the like); aromatic heterocyclic group (e.g., thienyl, furyl, pyridyl, oxazolyl, thiazolyl and the like); non-aromatic heterocyclic group (e.g., tetrahydrofuryl, morpholino, thiomorpholino, piperidino, pyrrolidinyl, piperazinyl and the like); aralkyl group having 7 to 13 carbon atoms; amino group optionally mono or di-substituted by alkyl group having 1 to 4 carbon atoms or acyl group having 1 to 15 carbon atoms (preferably having 2 to 8 carbon atoms) (e.g., alkylcarbonyl group and the like), such as amino, mono- or di-$C_{2-10}$ alkylcarbonylamino, $C_{1-10}$ alkoxy-carbonylamino, carbamoylamino, mono- or di-$C_{1-10}$ alkyl-carbamoylamino, $C_{6-14}$ aryl-carbonylamino, $C_{3-10}$ cycloalkyl-carbonylamino, $C_{7-13}$ aralkyloxy-carbonylamino, mono- or di-$C_{1-10}$ alkylsulfonylamino, $C_{6-14}$ arylsulfonylamino, $C_{1-6}$ alkoxy-carbamoylamino and the like; amidino group; acyl group having 2 to 8 carbon atoms (e.g., alkylcarbonyl group and the like); carbamoyl group optionally mono or di-substituted by alkyl group having 1 to 4 carbon atoms; sulfamoyl group optionally mono or di-substituted by alkyl group having 1 to 4 carbon atoms; carboxyl group; alkoxycarbonyl group having 2 to 8 carbon atoms (e.g., methoxycarbonyl, ethoxycarbonyl, isopropoxycarbonyl, tert-butoxycarbonyl and the like); hydroxy group; alkoxy group having 1 to 6 carbon atoms optionally substituted by 1 to 3 halogen atoms (e.g., fluorine, chlorine, bromine, iodine and the like); alkenyloxy group having 2 to 5 carbon atoms optionally substituted by 1 to 3 halogen atoms (e.g., fluorine, chlorine, bromine, iodine and the like); cycloalkyloxy group having 3 to 7 carbon atoms; aralkyloxy group having 7 to 13 carbon atoms; aryloxy group having 6 to 14 carbon atoms (e.g., phenyloxy, naphthyloxy and the like); thiol group; alkylthio group having 1 to 6 carbon atoms optionally substituted by 1 to 3 halogen atoms (e.g., fluorine, chlorine, bromine, iodine and the like); aralkylthio group having 7 to 13 carbon atoms; arylthio group having 6 to 14 carbon atoms (e.g., phenylthio, naphthylthio and the like); sulfo group; cyano group; azide group; nitro group; nitroso group; halogen atom (e.g., fluorine, chlorine, bromine, iodine) and the like. The number of the substituent is, for example, 1 to 3.

The "acyl group" is, for example, a group represented by the formula: —$COR^4$, —CO—$OR^4$, —$SO_2R^4$, —$SOR^4$, —$PO_3R^4R^5$, —CO—$NR^{4a}R^{5a}$ or —CS—$NR^{4a}R^{5a}$ wherein $R^4$ and $R^5$ are the same or different and each is hydrogen atom, optionally substituted hydrocarbon group or optionally substituted heterocyclic group. $R^{4a}$ and $R^{5a}$ are the same or different and each is hydrogen atom, optionally substituted hydrocarbon group or optionally substituted heterocyclic group or $R^{4a}$ and $R^{5a}$ may form, together with the adjacent nitrogen atom, an optionally substituted, nitrogen-containing heterocycle, and the like.

The "optionally substituted hydrocarbon group" for $R^4$, $R^5$, $R^{4a}$ and $R^{5a}$ is exemplified by "optionally substituted alkyl group having 1 to 10 carbon atoms", "optionally substituted alkenyl group having 2 to 10 carbon atoms", "optionally substituted alkynyl group having 2 to 10 carbon atoms", "optionally substituted cycloalkyl group having 3 to 10 carbon atoms", "optionally substituted cycloalkenyl group having 3 to 10 carbon atoms", "optionally substituted cycloalkadienyl group having 4 to 10 carbon atoms" and "optionally substituted aryl group having 6 to 14 carbon atoms", which are mentioned as the substituents for ring A; and "optionally substituted aralkyl group having 7 to 13 carbon atoms", "optionally substituted arylalkenyl group having 8 to 13 carbon atoms" and the like.

The "aralkyl group having 7 to 13 carbon atoms" of the "optionally substituted aralkyl group having 7 to 13 carbon atoms" is, for example, benzyl, phenethyl, naphthylmethyl and the like.

The "arylalkenyl group having 8 to 13 carbon atoms" of the "optionally substituted arylalkenyl group having 8 to 13 carbon atoms" is, for example, styryl and the like.

The substituent of the "optionally substituted aralkyl group having 7 to 13 carbon atoms" and "optionally substituted arylalkenyl group having 8 to 13 carbon atoms" is exemplified by that mentioned as the substituent in the aforementioned "optionally substituted cycloalkyl group having 3 to 10 carbon atoms" and the like. The number of the substituent is, for example, 1 to 3.

The "optionally substituted heterocyclic group" for $R^4$, $R^5$, $R^{4a}$ or $R^{5a}$ is exemplified by that mentioned as the substituent for ring A.

As used herein, the "nitrogen-containing heterocycle" of the "optionally substituted, nitrogen-containing heterocycle" formed by $R^{4a}$ and $R^{5a}$ together with the adjacent nitrogen atom is, for example, a 5 to 7-membered, nitrogen-containing heterocycle containing at least one nitrogen atom and optionally further containing 1 or 2 heteroatoms selected from oxygen atom, sulfur atom and nitrogen atom as a ring-constituting atom, besides carbon atoms. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 or 2 substituents at substitutable position(s). Examples of the substituent include hydroxy group, $C_{1-6}$ alkyl group optionally substituted by 1 to 3 halogen atoms (e.g., fluorine, chlorine, bromine, iodine and the like), $C_{7-13}$ aralkyl group (e.g., benzyl, diphenylmethyl and the like) and the like.

Preferable examples of the "acyl group" include formyl, carboxyl, carbamoyl, $C_{1-6}$ alkyl-carbonyl (e.g., acetyl, isobutanoyl, isopentanoyl and the like), $C_{1-6}$ alkoxy-carbonyl (e.g., methoxycarbonyl, ethoxycarbonyl, propoxycarbonyl, tert-butoxycarbonyl and the like), $C_{6-14}$ aryl-carbonyl (e.g., benzoyl, 1-naphthoyl, 2-naphthoyl and the like), $C_{6-14}$ aryloxy-carbonyl (e.g., phenyloxycarbonyl, naphthyloxycarbonyl and the like), $C_{7-13}$ aralkyloxy-carbonyl (e.g., benzyloxycarbonyl, phenethyloxycarbonyl and the like), mono- or di-($C_{1-6}$ alkyl optionally having 1 to 3 substituents selected from halogen atom and $C_{1-6}$ alkoxy-carbonyl)-carbamoyl (e.g., methylcarbamoyl, ethylcarbamoyl, dimethylcarbamoyl, diethylcarbamoyl, ethylmethylcarbamoyl, propylcarbamoyl, trifluoroethylcarbamoyl and the like), $C_{6-14}$ aryl-carbamoyl (e.g., phenylcarbamoyl and the like), $C_{3-10}$ cycloalkyl-carbamoyl (e.g., cyclopropylcarbamoyl and the like), $C_{7-13}$ aralkyl-carbamoyl (e.g., benzylcarbamoyl and the like), $C_{1-6}$ alkylsulfonyl (e.g., methylsulfonyl and the like), $C_{6-14}$ arylsulfonyl (e.g., phenylsulfonyl and the like), nitrogen-containing heterocycle-carbonyl optionally substituted by hydroxy (e.g., pyrrolidinylcarbonyl, piperidinocarbonyl and the like), $C_{1-6}$ alkylsulfinyl (e.g., methylsulfinyl and the like), $C_{1-6}$ alkoxy-carbamoyl (e.g., methoxycarbamoyl), aminocarbamoyl, hydroxycarbamoyl, thiocarbamoyl and the like.

The "optionally substituted amino group" is, for example, amino group optionally substituted by 1 or 2 substituents selected from "alkyl group having 1 to 10 carbon atoms", "alkenyl group having 2 to 10 carbon atoms", "cycloalkyl group having 3 to 10 carbon atoms", "cycloalkenyl group having 3 to 10 carbon atoms", "aryl group having 6 to 14 carbon atoms" and "acyl", each of which is optionally substituted.

As used herein, the "alkyl group having 1 to 10 carbon atoms", "alkenyl group having 2 to 10 carbon atoms", "cycloalkyl group having 3 to 10 carbon atoms", "cycloalkenyl group having 3 to 10 carbon atoms", "aryl group having 6 to 14 carbon atoms" and "acyl group" are exemplified by those mentioned as the substituent in ring A.

These "alkyl group having 1 to 10 carbon atoms", "alkenyl group having 2 to 10 carbon atoms", "alkynyl group having 2 to 10 carbon atoms", "cycloalkyl group having 3 to 10 carbon atoms", "cycloalkenyl group having 3 to 10 carbon atoms" and "aryl group having 6 to 14 carbon atoms" each optionally have 1 to 3 substituents at substitutable position(s). Such substituents are, for example, halogen atom (e.g., fluorine, chlorine, bromine, iodine and the like); alkoxycarbonyl group having 2 to 5 carbon atoms (e.g., methoxycarbonyl, ethoxycarbonyl and tert-butoxycarbonyl); alkylcarbonyl group having 2 to 5 carbon atoms; cyano group; carbamoyl group optionally substituted by 1 or 2 substituents selected from $C_{1-10}$ alkyl group (e.g., methyl, ethyl, propyl, isopropyl) and $C_{1-10}$ alkylsulfonyl group (e.g., methylsulfonyl); hydroxy group; carboxyl group; and the like.

Preferable examples of the substituted amino group include mono- or di-$C_{1-10}$ alkylamino (e.g., methylamino, dimethylamino, ethylamino, diethylamino, propylamino, dibutylamino), mono- or di-$C_{2-10}$ alkenylamino (e.g., diallylamino), mono- or di-$C_{3-10}$ cycloalkylamino (e.g., cyclohexylamino), mono- or di-$C_{2-10}$ alkylcarbonylamino (e.g., acetylamino, propionylamino, butanoylamino, isobutanoylamino, isopentanoylamino), $C_{6-14}$ aryl-carbonylamino (e.g., benzoylamino), $C_{6-14}$ arylamino (e.g., phenylamino), carbamoylamino, mono- or di-$C_{1-10}$ alkyl-carbamoylamino (e.g., methylcarbamoylamino, dimethylcarbamoylamino), $C_{1-10}$ alkoxy-carbonylamino (e.g., methoxycarbonylamino), $C_{7-13}$ aralkyloxy-carbonylamino (e.g., benzyloxycarbonylamino), $C_{3-10}$ cycloalkyl-carbonylamino (e.g., cyclopentylcarbonylamino, cyclohexylcarbonylamino), mono- or di-$C_{1-10}$ alkylsulfonylamino (e.g., methylsulfonylamino, dimethylsulfonylamino), $C_{6-14}$ arylsulfonylamino (e.g., phenylsulfonylamino), $C_{1-6}$ alkoxy-carbamoylamino (e.g., methoxycarbamoylamino), carbamoyl-$C_{1-10}$ alkylamino (e.g., carbamoylmethylamino), $C_{2-5}$ alkoxycarbonyl-$C_{1-10}$ alkylamino (e.g., methoxycarbonylmethylamino, tert-butoxycarbonylmethylamino), and the like.

The "optionally substituted hydroxy group" is, for example, hydroxy group optionally substituted by "alkyl group having 1 to 10 carbon atoms", "alkenyl group having 2 to 10 carbon atoms", "alkynyl group having 2 to 10 carbon atoms", "cycloalkyl group having 3 to 10 carbon atoms", "cycloalkenyl group having 3 to 10 carbon atoms", "aryl group having 6 to 14 carbon atoms" or "aralkyl group having 7 to 13 carbon atoms", each of which is optionally substituted.

As used herein, the "alkyl group having 1 to 10 carbon atoms", "alkenyl group having 2 to 10 carbon atoms", "alkynyl group having 2 to 10 carbon atoms", "cycloalkyl group having 3 to 10 carbon atoms", "cycloalkenyl group having 3 to 10 carbon atoms", "aryl group having 6 to 14 carbon atoms" and "aralkyl group having 7 to 13 carbon atoms" are exemplified by those mentioned as the aforementioned $R^4$ and the like.

These "alkyl group having 1 to 10 carbon atoms", "alkenyl group having 2 to 10 carbon atoms", "alkynyl group having 2 to 10 carbon atoms", "cycloalkyl group having 3 to 10 carbon atoms", "cycloalkenyl group having 3 to 10 carbon atoms", "aryl group having 6 to 14 carbon atoms" and "aralkyl group having 7 to 13 carbon atoms" each optionally have 1 to 3 substituents at substitutable position(s). Such substituents are, for example, halogen atom (e.g., fluorine, chlorine, bromine, iodine and the like); alkoxy group having 1 to 3 carbon atoms optionally substituted by 1 or 2 substituents selected from carboxyl group and alkoxycarbonyl group having 2 to 5 carbon atoms (e.g., tert-butoxycarbonyl); alkoxycarbonyl group having 2 to 5 carbon atoms (e.g., methoxycarbonyl, ethoxycarbonyl); alkylcarbonyl group having 2 to 5 carbon atoms; cyano group; carbamoyl group optionally substituted by 1 or 2 substituents selected from $C_{1-10}$ alkyl group (e.g., methyl, ethyl, propyl, isopropyl) and $C_{1-10}$ alkylsulfonyl group (e.g., methylsulfonyl); hydroxy group; cycloalkyl group having 3 to 10 carbon atoms; carboxyl group; amino group; alkylcarbonylamino group having 2 to 5 carbon atoms; aromatic heterocyclic group (e.g., furyl, thienyl, oxazolyl, thiazolyl, isoxazolyl, tetrazolyl, oxadiazolyl, thiadiazolyl) optionally substituted by 1 to 3 substituents selected from $C_{1-6}$ alkyl group (e.g., methyl, ethyl) and $C_{2-8}$ alkoxycarbonyl group (e.g., methoxycarbonyl, ethoxycarbonyl); and the like.

The substituted hydroxy group is preferably "alkoxy group having 1 to 10 carbon atoms", "alkenyloxy group having 2 to 10 carbon atoms", "alkynyloxy group having 2 to 10 carbon atoms", "cycloalkyloxy group having 3 to 10 carbon atoms", "cycloalkenyloxy group having 3 to 10 carbon atoms", "aryloxy group having 6 to 14 carbon atoms", "aralkyloxy group having 7 to 13 carbon atoms" and the like, each optionally having 1 to 3 substituents selected from halogen atom (e.g., fluorine, chlorine, bromine, iodine and the like); alkoxy group having 1 to 3 carbon atoms; alkoxycarbonyl group having 2 to 5 carbon atoms; alkylcarbonyl group having 2 to 5 carbon atoms; cyano group; carbamoyl group optionally substituted by 1 or 2 substituents selected from $C_{1-10}$ alkyl group (e.g., methyl, ethyl, propyl, isopropyl) and $C_{1-10}$ alkylsulfonyl group (e.g., methylsulfonyl); hydroxy group; carboxyl group; amino group; alkylcarbonylamino group having 2 to 5 carbon atoms; aromatic heterocyclic group (e.g., furyl, thienyl, oxazolyl, thiazolyl, isoxazolyl, tetrazolyl, oxadiazolyl, thiadiazolyl) optionally substituted by 1 to 3 substituents selected from $C_{1-6}$ alkyl group (e.g., methyl, ethyl) and $C_{2-8}$ alkoxycarbonyl group (e.g., methoxycarbonyl, ethoxycarbonyl); cycloalkyl group having 3 to 10 carbon atoms; and the like.

The "alkoxy group having 1 to 10 carbon atoms" is, for example, methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy and the like.

The "alkenyloxy group having 2 to 10 carbon atoms" is, for example, allyloxy, crotyloxy, 2-pentenyloxy, 3-hexenyloxy and the like.

The "alkynyloxy group having 2 to 10 carbon atoms" is, for example, ethynyloxy, propynyloxy, pentynyloxy and the like.

The "cycloalkyloxy group having 3 to 10 carbon atoms" is, for example, cyclobutoxy, cyclopentyloxy, cyclohexyloxy and the like.

The "cycloalkenyloxy group having 3 to 10 carbon atoms" is, for example, 2-cyclopentenyloxy, 2-cyclohexenyloxy and the like.

The "aryloxy group having 6 to 14 carbon atoms" is, for example, phenoxy, naphthyloxy and the like.

The "aralkyloxy group having 7 to 13 carbon atoms" is, for example, benzyloxy, phenethyloxy, naphthylmethyloxy and the like.

The substituted hydroxy group is more preferably "alkoxy group having 1 to 10 carbon atoms", "cycloalkyloxy group having 3 to 10 carbon atoms" or "aralkyloxy group having 7 to 13 carbon atoms", each optionally having 1 to 3 substituents selected from halogen atom (e.g., fluorine, chlorine, bromine, iodine and the like); alkoxy group having 1 to 3 carbon atoms optionally substituted by 1 or 2 substituents selected from carboxyl group and alkoxycarbonyl group having 2 to 5 carbon atoms (e.g., tert-butoxycarbonyl); alkoxycarbonyl group having 2 to 5 carbon atoms (e.g., ethoxycarbonyl); alkylcarbonyl group having 2 to 5 carbon atoms; cyano group; carbamoyl group optionally substituted by 1 or 2 substituents selected from $C_{1-10}$ alkyl group (e.g., methyl, ethyl, propyl, isopropyl) and $C_{1-10}$ alkylsulfonyl group (e.g., methylsulfonyl); hydroxy group; carboxyl group; amino group; alkylcarbonylamino group having 2 to 5 carbon atoms; aromatic heterocyclic group (e.g., furyl, thienyl, oxazolyl, thiazolyl, isoxazolyl, tetrazolyl, oxadiazolyl, thiadiazolyl) optionally substituted by 1 to 3 substituents selected from $C_{1-6}$ alkyl group (e.g., methyl, ethyl) and $C_{2-8}$ alkoxycarbonyl group (e.g., methoxycarbonyl, ethoxycarbonyl); and cycloalkyl group having 3 to 10 carbon atoms.

As the "optionally substituted thiol group", for example, thiol group optionally substituted by "alkyl group having 1 to 10 carbon atoms", "alkenyl group having 2 to 10 carbon atoms", "alkynyl group having 2 to 10 carbon atoms", "cycloalkyl group having 3 to 10 carbon atoms", "cycloalkenyl group having 3 to 10 carbon atoms", "aryl group having 6 to 14 carbon atoms" or "aralkyl group having 7 to 13 carbon atoms", each of which is optionally substituted, can be mentioned.

As used herein, as the "alkyl group having 1 to 10 carbon atoms", "alkenyl group having 2 to 10 carbon atoms", "alkynyl group having 2 to 10 carbon atoms", "cycloalkyl group having 3 to 10 carbon atoms", "cycloalkenyl group having 3 to 10 carbon atoms", "aryl group having 6 to 14 carbon atoms" and "aralkyl group having 7 to 13 carbon atoms", those exemplified for the aforementioned $R^4$ and the like can be mentioned.

These "alkyl group having 1 to 10 carbon atoms", "alkenyl group having 2 to 10 carbon atoms", "alkynyl group having 2 to 10 carbon atoms", "cycloalkyl group having 3 to 10 carbon atoms", "cycloalkenyl group having 3 to 10 carbon atoms", "aryl group having 6 to 14 carbon atoms" and "aralkyl group having 7 to 13 carbon atoms" each optionally have 1 to 3 substituents at substitutable position(s). As such substituents, for example, halogen atom (e.g., fluorine, chlorine, bromine, iodine and the like), alkoxy group having 1 to 3 carbon atoms, alkoxycarbonyl group having 2 to 5 carbon atoms, alkylcarbonyl group having 2 to 5 carbon atoms, cyano group, carbamoyl group, hydroxy group, cycloalkyl group having 3 to 10 carbon atoms, carboxyl group, amino group, alkylcarbonylamino group having 2 to 5 carbon atoms and the like can be mentioned.

The substituted thiol group is preferably "alkylthio group having 1 to 10 carbon atoms", "alkenylthio group having 2 to 10 carbon atoms", "alkynylthio group having 2 to 10 carbon atoms", "cycloalkylthio group having 3 to 10 carbon atoms", "cycloalkenylthio group having 3 to 10 carbon atoms", "arylthio group having 6 to 14 carbon atoms", "aralkylthio group having 7 to 13 carbon atoms" and the like, each optionally having 1 to 3 substituents selected from halogen atom (e.g., fluorine, chlorine, bromine, iodine and the like), alkoxy group having 1 to 3 carbon atoms, alkoxycarbonyl group having 2 to 5 carbon atoms, alkylcarbonyl group having 2 to 5 carbon atoms, cyano group, carbamoyl group, hydroxy group, carboxyl group, amino group, alkylcarbonylamino group having 2 to 5 carbon atoms and cycloalkyl group having 3 to 10 carbon atoms.

The "alkylthio group having 1 to 10 carbon atoms" is, for example, methylthio, ethylthio, propylthio, isopropylthio, butylthio, isobutylthio, sec-butylthio, tert-butylthio, pentylthio, isopentylthio, neopentylthio, hexylthio, heptylthio, nonylthio and the like.

The "alkenylthio group having 2 to 10 carbon atoms" is, for example, allylthio, crotylthio, 2-pentenylthio, 3-hexenylthio and the like.

The "alkynylthio group having 2 to 10 carbon atoms" is, for example, ethynylthio, propynylthio, pentynylthio and the like.

The "cycloalkylthio group having 3 to 10 carbon atoms" is, for example, cyclobutylthio, cyclopentylthio, cyclohexylthio and the like.

The "cycloalkenylthio group having 3 to 10 carbon atoms" is, for example, 2-cyclopentenylthio, 2-cyclohexenylthio and the like.

The "arylthio group having 6 to 14 carbon atoms" is, for example, phenylthio, naphthylthio and the like.

The "aralkylthio having 7 to 13 carbon atoms" is, for example, benzylthio, phenethylthio, naphthylmethylthio and the like.

The substituted thiol group is more preferably alkylthio group having 1 to 10 carbon atoms optionally substituted by carbamoyl group.

Preferable examples of the "substituent" of "5- to 10-membered aromatic ring" for ring A are 1) a halogen atom (e.g., fluorine, chlorine, bromine, iodine and the like);

2) a nitro group;

3) a cyano group;

4) an alkylenedioxy group having 1 to 3 carbon atoms (e.g., methylenedioxy);

5) an alkyl group having 1 to 10 carbon atoms (e.g., methyl, ethyl, propyl, butyl, pentyl) or an alkenyl group having 2 to 10 carbon atoms (e.g., ethenyl, 3-butenyl), each optionally having 1 to 3 substituents selected from halogen atom, hydroxy group, carboxyl group, alkoxycarbonyl group having 2 to 8 carbon atoms (e.g., ethoxycarbonyl), carbamoyl group, cyano group, amino group, alkylcarbonylamino group having 2 to 8 carbon atoms (e.g., acetylamino, isobutanoylamino), alkoxycarbonylamino group having 2 to 8 carbon atoms (e.g., methoxycarbonylamino, ethoxycarbonylamino), alkylsulfonylamino group having 1 to 8 carbon atoms (e.g., methylsulfonylamino), alkylcarbamoylamino group having 2 to 8 carbon atoms (e.g., methylcarbamoylamino), carboxyl-$C_{1-6}$ alkylthio (e.g., carboxylmethylthio), $C_{2-8}$ alkoxycarbonyl-$C_{1-6}$ alkylthio (e.g., ethoxycarbonylmethylthio) and carbamoyl-$C_{1-6}$ alkylthio (e.g., carbamoylmethythio);

6) an optionally substituted hydroxy group [e.g., alkoxy group having 1 to 10 carbon atoms (e.g., methoxy, ethoxy, propoxy, isopropoxy, butoxy, isobutoxy, pentyloxy), cycloalkyloxy group having 3 to 10 carbon atoms (e.g., cyclopentyloxy) or aralkyloxy group having 7 to 13 carbon atoms (e.g., benzyloxy), each optionally having 1 to 3 substituents selected from halogen atom; alkoxy group having 1 to 3 carbon atoms optionally substituted by 1 or 2 substituents selected from carboxyl group and alkoxycarbonyl group having 2 to 5 carbon atoms (e.g., tert-butoxycarbonyl) (e.g., methoxy, carboxylmethoxy, tert-butoxycarbonylmethoxy); alkoxycarbonyl group having 2 to 5 carbon atoms (e.g., methoxycarbonyl, ethoxycarbonyl); alkylcarbonyl group having 2 to 5 carbon atoms (e.g., pivaloyl); cyano group; carbamoyl group optionally substituted by 1 or 2 substituents selected from $C_{1-10}$ alkyl group (e.g., methyl, ethyl, propyl, isopropyl) and $C_{1-10}$ alkylsulfonyl group (e.g., methylsulfonyl); hydroxy group; carboxyl group; amino group; alkylcarbonylamino group having 2 to 5 carbon atoms (e.g., acetylamino); aromatic heterocyclic group (e.g., furyl, thienyl, oxazolyl, thiazolyl, isoxazolyl, tetrazolyl, oxadiazolyl, thiadiazolyl) optionally substituted by 1 to 3 substituents selected from $C_{1-6}$ alkyl group (e.g., methyl, ethyl) and $C_{2-8}$ alkoxycarbonyl group (e.g., methoxycarbonyl, ethoxycarbonyl); and cycloalkyl group having 3 to 10 carbon atoms (e.g., cyclopropyl, cyclohexyl); hydroxy group];

7) an acyl group [e.g., formyl, carboxyl, $C_{1-6}$ alkyl-carbonyl (e.g., acetyl), $C_{1-6}$ alkoxy-carbonyl (e.g., methoxycarbonyl), carbamoyl, aminocarbamoyl, hydroxycarbamoyl, mono- or di-($C_{1-6}$ alkyl optionally having 1 to 3 substituents selected from halogen atom and $C_{1-6}$ alkoxy-carbonyl (e.g., ethoxycarbonyl))-carbamoyl (e.g., methylcarbamoyl, ethylcarbamoyl, propylcarbamoyl, dimethylcarbamoyl, trifluoroethylcarbamoyl, ethoxycarbonylmethylcarbamoyl and the like), $C_{3-10}$ cycloalkyl-carbamoyl (e.g., cyclopropylcarbamoyl), $C_{7-13}$ aralkyl-carbamoyl (e.g., benzylcarbamoyl), nitrogen-containing heterocycle-carbonyl optionally substituted by hydroxy (e.g., pyrrolidinylcarbonyl, piperidinocarbonyl), $C_{1-6}$ alkylsulfonyl (e.g., methylsulfonyl), $C_{1-6}$ alkylsulfinyl (e.g., methylsulfinyl), thiocarbamoyl];

8) an optionally substituted amino group [e.g., amino, mono- or di-$C_{2-10}$ alkylcarbonylamino (e.g., acetylamino, propionylamino, isobutanoylamino, isopentanoylamino), $C_{1-10}$ alkoxy-carbonylamino (e.g., methoxycarbonylamino), carbamoylamino, mono- or di-$C_{1-10}$ alkyl-carbamoylamino (e.g., methylcarbamoylamino, dimethylcarbamoylamino), $C_{6-14}$ aryl-carbonylamino (e.g., benzoylamino), $C_{3-10}$ cycloalkyl-carbonylamino (e.g., cyclopentylcarbonylamino), $C_{7-13}$ aralkyloxy-carbonylamino (e.g., benzyloxycarbonylamino), mono- or di-$C_{1-10}$ alkylsulfonylamino (e.g., methylsulfonylamino, dimethylsulfonylamino), $C_{6-14}$ arylsulfonylamino (e.g., phenylsulfonylamino), $C_{1-6}$ alkoxy-carbamoylamino (e.g., methoxycarbamoylamino), carbamoyl-$C_{1-10}$ alkylamino (e.g., carbamoylmethylamino), $C_{2-5}$ alkoxycarbonyl-$C_{1-10}$ alkylamino (e.g., methoxycarbonylmethylamino, tert-butoxycarbonylmethylamino)];

9) an optionally substituted cycloalkyl group having 3 to 10 carbon atoms [e.g., cycloalkyl group having 3 to 10 carbon atoms (e.g., cyclopropyl, cyclobutyl) optionally having 1 to 3 substituents selected from $C_{1-6}$ alkyl group optionally substituted by 1 to 3 halogen atoms (e.g., methyl, trifluoromethyl), carboxyl group, alkoxycarbonyl group having 2 to 8 carbon atoms (e.g., methoxycarbonyl, ethoxycarbonyl, isopropoxycarbonyl), cyano group, carbamoyl group, amino group, mono- or di-$C_{2-10}$ alkylcarbonylamino group (e.g., acetylamino, isopentanoylamino), $C_{1-10}$ alkoxy-carbonylamino group (e.g., methoxycarbonylamino), carbamoylamino group, mono- or di-$C_{1-10}$ alkyl-carbamoylamino group (e.g., methylcarbamoylamino, dimethylcarbamoylamino), $C_{6-14}$ aryl-carbonylamino group (e.g., benzoylamino), $C_{3-10}$ cycloalkyl-carbonylamino group, $C_{7-13}$ aralkyloxy-carbonylamino group, mono- or di-$C_{1-10}$ alkylsulfonylamino group (e.g., methylsulfonylamino, dimethylsulfonylamino), $C_{6-14}$ arylsulfonylamino group and $C_{1-6}$ alkoxy-carbamoylamino group (e.g., methoxycarbamoylamino)];

10) an aryl group having 6 to 14 carbon atoms (e.g., phenyl);

11) an optionally substituted thiol group [e.g., alkylthio group having 1 to 10 carbon atoms optionally substituted by carbamoyl group (e.g., methylthio)];

12) an optionally substituted heterocyclic group [e.g., aromatic heterocyclic group (preferably furyl, thienyl, oxazolyl, oxadiazolyl, thiazolyl, tetrazolyl, pyridyl, pyrrolyl, triazolyl) or non-aromatic heterocyclic group (preferably dioxoisoindol-2-yl; 5-oxooxadiazol-3-yl; 5-oxothiadiazol-3-yl; 3-oxopiperazin-1-yl; 2,3-dioxopiperazin-1-yl; 2,5-dioxopiperazin-1-yl), each optionally having 1 or 2 substituents selected from $C_{1-6}$ alkyl group optionally substituted by 1 to 3 halogen atoms (e.g., methyl, trifluoromethyl), carboxyl group, alkoxycarbonyl group having 2 to 8 carbon atoms (e.g., methoxycarbonyl, ethoxycarbonyl, isopropoxycarbonyl, tert-butoxycarbonyl), cyano group, carbamoyl group, amino group, mono- or di-$C_{2-10}$ alkylcarbonylamino group (e.g., acetylamino, isopentanoylamino), $C_{1-10}$ alkoxy-carbonylamino group (e.g., methoxycarbonylamino), carbamoylamino group, mono- or di-$C_{1-10}$ alkyl-carbamoylamino group (e.g., methylcarbamoylamino, dimethylcarbamoylamino), $C_{6-14}$ aryl-carbonylamino group (e.g., benzoylamino), $C_{3-10}$ cycloalkyl-carbonylamino group, $C_{7-13}$ aralkyloxy-carbonylamino group, mono- or di-$C_{1-10}$ alkylsulfonylamino group (e.g., methylsulfonylamino, dimethylsulfonylamino), $C_{6-14}$ arylsulfonylamino group, $C_{1-6}$ alkoxy-carbamoylamino group (e.g., methoxycarbamoylamino), alkylcarbonyl group having 2 to 5 carbon atoms (e.g., acetyl) and carbamoyl-$C_{1-6}$ alkyl group (e.g., carbamoylmethyl)];

13) an amidino group;

and the like.

The number of substituents is preferably 1 to 3, more preferably 1 or 2.

The "substituent" of the "5- to 10-membered aromatic ring" for ring A is preferably 1) a halogen atom (e.g., fluorine, chlorine, bromine, iodine and the like);

2) a cyano group;

3) an alkyl group having 1 to 10 carbon atoms (preferably ethyl, propyl, butyl) or an alkenyl group having 2 to 10 carbon atoms (preferably ethenyl), each optionally having 1 to 3 substituents selected from carbamoyl group, carboxyl group and alkoxycarbonyl group having 2 to 8 carbon atoms (preferably methoxycarbonyl, ethoxycarbonyl);

4) an optionally substituted hydroxy group [preferably, alkoxy group having 1 to 10 carbon atoms (preferably methoxy, isopropoxy) optionally having 1 to 3 substituents selected from (1) carbamoyl group optionally substituted by 1 or 2 substituents selected from $C_{1-10}$ alkyl group (e.g., methyl, ethyl, propyl, isopropyl) and $C_{1-10}$ alkylsulfonyl group (e.g., methylsulfonyl); (2) carboxyl group; (3) alkoxycarbonyl group having 2 to 5 carbon atoms (preferably methoxycarbonyl); (4) aromatic heterocyclic group (e.g., furyl, thienyl, oxazolyl, thiazolyl, isoxazolyl, tetrazolyl, oxadiazolyl, thiadiazolyl) optionally substituted by 1 to 3 substituents selected from $C_{1-6}$ alkyl group (e.g., methyl, ethyl) and $C_{2-8}$ alkoxycarbonyl group (e.g., methoxycarbonyl, ethoxycarbonyl); hydroxy group; aralkyloxy group having 7 to 13 carbon atoms (preferably benzyloxy)] [more preferably, carbamoylmethoxy];

5) an acyl group [preferably $C_{1-6}$ alkyl-carbonyl (preferably acetyl), carbamoyl, mono- or di-($C_{1-6}$ alkyl optionally having 1 to 3 substituents selected from halogen atom and $C_{1-6}$ alkoxy-carbonyl)-carbamoyl (preferably methylcarbamoyl, ethylcarbamoyl, propylcarbamoyl, dimethylcarbamoyl, trifluoroethylcarbamoyl, ethoxycarbonylmethylcarbamoyl and the like), $C_{3-10}$ cycloalkyl-carbamoyl (preferably cyclopropylcarbamoyl), $C_{7-13}$ aralkyl-carbamoyl (preferably benzylcarbamoyl), nitrogen-containing heterocycle-carbonyl optionally substituted by hydroxy (preferably pyrrolidinylcarbonyl, piperidinocarbonyl), $C_{1-6}$ alkylsulfonyl (preferably methylsulfonyl), $C_{1-6}$ alkylsulfinyl (preferably methylsulfinyl), carboxyl, $C_{1-6}$ alkoxy-carbonyl (preferably methoxycarbonyl), thiocarbamoyl];

6) an optionally substituted amino group (preferably, carbamoylamino, acetylamino and the like);

7) an optionally substituted cycloalkyl group having 3 to 10 carbon atoms [preferably, cycloalkyl group having 3 to 10 carbon atoms (e.g., cyclopropyl, cyclobutyl) optionally having 1 to 3 substituents selected from carboxyl group, alkoxycarbonyl group having 2 to 8 carbon atoms and carbamoyl group];

8) an optionally substituted thiol group [preferably, alkylthio group having 1 to 10 carbon atoms optionally substituted by carbamoyl group] (preferably methylthio);

9) an optionally substituted heterocyclic group [e.g., aromatic heterocyclic group (preferably, furyl, thienyl, oxazolyl, oxadiazolyl, thiazolyl, tetrazolyl, pyridyl, pyrrolyl, triazolyl) or non-aromatic heterocyclic group (preferably, dioxoisoindol-2-yl; 5-oxooxadiazol-3-yl; 5-oxothiadiazol-3-yl; 3-oxopiperazin-1-yl; 2,3-dioxopiperazin-1-yl; 2,5-dioxopiperazin-1-yl, each optionally having 1 or 2 substituents selected from $C_{1-6}$ alkyl group optionally substituted by 1 to 3 halogen atoms, carboxyl group, alkoxycarbonyl group having 2 to 8 carbon atoms, cyano group, carbamoyl group, amino group, mono- or di-$C_{2-10}$ alkylcarbonylamino group, $C_{1-10}$ alkoxy-carbonylamino group, carbamoylamino group, mono- or di-$C_{1-10}$ alkyl-carbamoylamino group, $C_{6-14}$ aryl-carbonylamino group, $C_{3-10}$ cycloalkyl-carbonylamino group, $C_{7-13}$ aralkyloxy-carbonylamino group, mono- or di-$C_{1-10}$ alkylsulfonylamino group, $C_{6-14}$ arylsulfonylamino group, $C_{1-6}$ alkoxy-carbamoylamino group, alkylcarbonyl group having 2 to 5 carbon atoms and carbamoyl-$C_{1-6}$ alkyl group];

10) an amidino group;

and the like. The number of the substituents is preferably 1 or 2.

Among these substituents, preferred are 1) an alkyl group having 1 to 10 carbon atoms or an alkenyl group having 2 to 10 carbon atoms, each optionally having 1 to 3 substituents selected from carbamoyl group, carboxyl group and alkoxycarbonyl group having 2 to 8 carbon atoms;

2) an alkoxy group having 1 to 10 carbon atoms optionally having 1 to 3 substituents selected from (1) carbamoyl group optionally substituted by 1 or 2 substituents selected from $C_{1-10}$ alkyl group and $C_{1-10}$ alkylsulfonyl group; (2) carboxyl group; (3) alkoxycarbonyl group having 2 to 5 carbon atoms; (4) aromatic heterocyclic group (e.g., furyl, thienyl, oxazolyl, thiazolyl, isozolyl, tetrazolyl, oxadiazolyl, thiadiazolyl) optionally substituted by 1 to 3 substituents selected from $C_{1-6}$ alkyl group and $C_{2-8}$ alkoxycarbonyl group;

3) a cycloalkyl group having 3 to 10 carbon atoms optionally having 1 to 3 substituents selected from carboxyl group, alkoxycarbonyl group having 2 to 8 carbon atoms and carbamoyl group;

4) an aromatic heterocyclic group [preferably, furyl, thienyl, oxazolyl, oxadiazolyl, thiazolyl, tetrazolyl, pyridyl, pyrrolyl, triazolyl) or non-aromatic heterocyclic group (preferably, dioxoisoindol-2-yl; 5-oxooxadiazol-3-yl; 5-oxothiadiazol-3-yl; 3-oxopiperazin-1-yl; 2,3-dioxopiperazin-1-yl; 2,5-dioxopiperazin-1-yl], each optionally having 1 or 2 substituents selected from $C_{1-6}$ alkyl group optionally substituted by 1 to 3 halogen atoms, carboxyl group, alkoxycarbonyl group having 2 to 8 carbon atoms, cyano group, carbamoyl group, amino group, mono- or di-$C_{2-10}$ alkylcarbonylamino group, $C_{1-10}$ alkoxy-carbonylamino group, carbamoylamino group, mono- or di-$C_{1-10}$ alkyl-carbamoylamino group, $C_{6-14}$ arylcarbonylamino group, $C_{3-10}$ cycloalkyl-carbonylamino group, $C_{7-13}$ aralkyloxy-carbonylamino group, mono- or di-$C_{1-10}$ alkylsulfonylamino group, $C_{6-14}$ arylsulfonylamino group, $C_{1-6}$ alkoxy-carbamoylamino group, alkylcarbonyl group having 2 to 5 carbon atoms and carbamoyl-$C_{1-6}$ alkyl group;

and the like.

Ring A is preferably a benzene ring optionally having 1 or 2 substituents selected from 1) a halogen atom (e.g., fluorine, chlorine, bromine, iodine and the like);

2) a cyano group;

3) an alkyl group having 1 to 10 carbon atoms (preferably ethyl, propyl, butyl) or an alkenyl group having 2 to 10 carbon atoms (preferably ethenyl), each optionally having 1 to 3 substituents selected from carbamoyl group, carboxyl group and alkoxycarbonyl group having 2 to 8 carbon atoms (preferably methoxycarbonyl, ethoxycarbonyl);

4) an optionally substituted hydroxy group [preferably, alkoxy group having 1 to 10 carbon atoms (preferably methoxy, isopropoxy) optionally having 1 to 3 substituents selected from (1) carbamoyl group optionally substituted by 1 or 2 substituents selected from $C_{1-10}$ alkyl group (e.g., methyl, ethyl, propyl, isopropyl) and $C_{1-10}$ alkylsulfonyl group (e.g., methylsulfonyl); (2) carboxyl group; (3) alkoxycarbonyl group having 2 to 5 carbon atoms (preferably methoxycarbonyl); (4) aromatic heterocyclic group (e.g., furyl, thienyl, oxazolyl, thiazolyl, isoxazolyl, tetrazolyl, oxadiazolyl, thiadiazolyl) optionally substituted by 1 to 3 substituents selected from $C_{1-6}$ alkyl group (e.g., methyl, ethyl) and $C_{2-8}$ alkoxycarbonyl group (e.g., methoxycarbonyl, ethoxycarbonyl); hydroxy group; aralkyloxy group having 7 to 13 carbon atoms (preferably benzyloxy)] [more preferably, carbamoylmethoxy];

5) an acyl group [preferably $C_{1-6}$ alkyl-carbonyl (preferably acetyl), carbamoyl, mono- or di-($C_{1-6}$ alkyl optionally having 1 to 3 substituents selected from halogen atom and $C_{1-6}$ alkoxy-carbonyl)-carbamoyl (preferably, methylcarbamoyl, ethylcarbamoyl, propylcarbamoyl, dimethylcarbamoyl, trifluoroethylcarbamoyl, ethoxycarbonylmethylcarbamoyl and the like), $C_{3-10}$ cycloalkyl-carbamoyl (preferably cyclopropylcarbamoyl), $C_{7-13}$ aralkyl-carbamoyl (preferably benzylcarbamoyl), nitrogen-containing heterocycle-carbonyl optionally substituted by hydroxy (preferably pyrrolidinylcarbonyl, piperidinocarbonyl), $C_{1-6}$ alkylsulfonyl (preferably methylsulfonyl), $C_{1-6}$ alkylsulfinyl (preferably methylsulfinyl), carboxyl, $C_{1-6}$ alkoxy-carbonyl (preferably methoxycarbonyl), thiocarbamoyl];

6) an optionally substituted amino group (preferably, carbamoylamino, acetylamino);

7) an optionally substituted cycloalkyl group having 3 to 10 carbon atoms [preferably, cycloalkyl group having 3 to 10 carbon atoms (preferably cyclopropyl) optionally having 1 to 3 substituents selected from carboxyl group, alkoxycarbonyl group having 2 to 8 carbon atoms (preferably ethoxycarbonyl) and carbamoyl group];

8) an optionally substituted thiol group [preferably, alkylthio group having 1 to 10 carbon atoms optionally substituted by carbamoyl group (preferably methylthio)];

9) an optionally substituted heterocyclic group [preferably, an aromatic heterocyclic group (preferably, furyl, thienyl, oxazolyl, oxadiazolyl, thiazolyl, tetrazolyl, pyridyl, pyrrolyl, triazolyl) or a non-aromatic heterocyclic group (preferably, dioxoisoindol-2-yl; 5-oxooxadiazol-3-yl; 5-oxothiadiazol-3-yl; 3-oxopiperazin-1-yl; 2,3-dioxopiperazin-1-yl; 2,5-dioxopiperazin-1-yl), each optionally having 1 or 2 substituents selected from $C_{1-6}$ alkyl group optionally substituted by 1 to 3 halogen atoms (preferably methyl, trifluoromethyl), carboxyl group, alkoxycarbonyl group having 2 to 8 carbon atoms (preferably methoxycarbonyl, ethoxycarbonyl, isopropoxycarbonyl, tert-butoxycarbonyl), cyano group, carbamoyl group, amino group, mono- or di-$C_{2-10}$ alkylcarbonylamino group (e.g., acetylamino, isopentanoylamino), $C_{1-10}$ alkoxycarbonylamino group (e.g., methoxycarbonylamino), carbamoylamino group, mono- or di-$C_{1-10}$ alkyl-carbamoylamino group (e.g., methylcarbamoylamino, dimethylcarbamoylamino), $C_{6-14}$ aryl-carbonylamino group (e.g., benzoylamino), $C_{3-10}$ cycloalkyl-carbonylamino group, $C_{7-13}$ aralkyloxy-carbonylamino group, mono- or di-$C_{1-13}$ alkylsulfonylamino group (e.g., methylsulfonylamino, dimethylsulfonylamino), $C_{6-14}$ arylsulfonylamino group, $C_{1-6}$ alkoxy-carbamoylamino group (e.g., methoxycarbamoylamino), alkylcarbonyl group having 2 to 5 carbon atoms (preferably acetyl) and carbamoyl-$C_{1-6}$ alkyl group (preferably carbamoylmethyl)]; and 10) an amidino group.

As the "optionally substituted hydrocarbon group" denoted by $R^1$ or $R^2$, those exemplified for the aforementioned $R^4$ and the like can be mentioned.

As the "optionally substituted heterocyclic group" denoted by $R^1$ or $R^2$, those exemplified as the substituent for ring A can be mentioned.

$R^1$ is preferably an optionally substituted hydrocarbon group, which is exemplified by alkyl group having 1 to 10 carbon atoms, which is optionally substituted by 1 to 3 substituents selected from halogen atom, aryl group having 6 to 14 carbon atoms (e.g., phenyl, naphthyl and the like), cycloalkyl group having 3 to 10 carbon atoms (e.g., cyclopropyl and the like) and the like, and the like.

$R^1$ is more preferably an alkyl group having 1 to 10 carbon atoms which is optionally substituted by cycloalkyl group having 3 to 10 carbon atoms (e.g., cyclopropyl and the like). $R^1$ is particularly preferably an alkyl group having 3 to 10 carbon atoms and cycloalkylalkyl group having 4 to 10 carbon atoms (preferably cyclopropylmethyl), with preference given to an alkyl group having 3 to 5 carbon atoms (e.g., propyl, butyl, isobutyl, sec-butyl, tert-butyl, pentyl, isopentyl, neopentyl, 1-ethylpropyl and the like).

$R^2$ is preferably an optionally substituted hydrocarbon group. $R^2$ is more preferably an alkyl group having 1 to 10 carbon atoms (e.g., methyl, ethyl, propyl, isopropyl, butyl, isobutyl, sec-butyl, tert-butyl, pentyl, hexyl and the like), an aryl group having 6 to 14 carbon atoms (e.g., phenyl and the like) or an aralkyl group having 7 to 13 carbon atoms (e.g., benzyl, phenethyl, naphthylmethyl and the like), each optionally having 1 to 3 (preferably 1 or 2) substituents selected from halogen atom (e.g., fluorine, chlorine and the like), hydroxy group, nitro group, amino group, optionally halogenated alkyl group having 1 to 6 carbon atoms (e.g., trifluoromethyl, methyl and the like), alkoxy group having 1 to 6 carbon atoms (e.g., methoxy and the like), aromatic heterocyclic group (e.g., quinolyl, thienyl and the like) and cycloalkyl group having 3 to 10 carbon atoms (e.g., cyclopentyl and the like). $R^2$ is particularly preferably an aryl group having 6 to 14 carbon atoms (e.g., phenyl and the like) optionally having 1 or 2 substituents selected from halogen atom (e.g., fluorine, chlorine and the like) and optionally halogenated alkyl group having 1 to 6 carbon atoms (e.g., trifluoromethyl, methyl and the like).

X and Y are the same or different and each is a bond, —O—, —S—, —SO—, —SO$_2$— or —NR$^3$— wherein $R^3$ is a hydrogen atom or an optionally substituted hydrocarbon group.

As the "optionally substituted hydrocarbon group" denoted by $R^3$, those exemplified for the aforementioned $R^4$ and the like can be mentioned. Said "optionally substituted hydrocarbon group" is preferably an alkyl group having 1 to 10 carbon atoms (e.g., methyl, ethyl and the like) and the like.

X is preferably a bond.

Y is preferably a bond.

The "divalent hydrocarbon group" denoted by L is, for example, (1) $C_{1-10}$ alkylene (e.g., —CH$_2$—, —(CH$_2$)$_2$—, —(CH$_2$)$_3$—, —(CH$_2$)$_4$—, —(CH$_2$)$_5$—, —(CH$_2$)$_6$—, —CHCH$_3$—, —C(CH$_3$)$_2$—, —(CH(CH$_3$))$_2$—, —(CH$_2$)$_2$C(CH$_3$)$_2$—, —(CH$_2$)$_3$C(CH$_3$)$_2$— and the like);

(2) $C_{2-10}$ alkenylene (e.g., —CH=CH—, —CH$_2$—CH=CH—, —CH=CH—CH$_2$—, —CH=CH—CH$_2$—CH$_2$—, —C(CH$_3$)$_2$—CH=CH—, —CH$_2$—CH=CH—CH$_2$—, —CH$_2$—CH$_2$—CH=CH—, —CH=CH—CH=CH—, —CH=CH—CH$_2$—CH$_2$—CH$_2$— and the like);

(3) $C_{2-10}$ alkynylene (e.g., —C≡C—, —CH$_2$—C≡C—, —CH$_2$—C≡C—CH$_2$—CH$_2$— and the like) or the like.

The "divalent hydrocarbon group" is preferably $C_{1-10}$ alkylene, more preferably —CH$_2$—, —(CH$_2$)$_2$— and the like. Particularly, —CH$_2$— is preferable.

Preferable examples of compound (I) include the following compounds.

[Compound A]

A compound wherein ring A is a benzene ring optionally having 1 or 2 substituents selected from 1) halogen atom (e.g., fluorine, chlorine, bromine, iodine and the like);

2) cyano group;

3) alkyl group having 1 to 10 carbon atoms (preferably ethyl) or alkenyl group having 2 to 10 carbon atoms (preferably ethenyl), each optionally having 1 to 3 substituents selected from carbamoyl group, carboxyl group and alkoxycarbonyl group having 2 to 8 carbon atoms (preferably methoxycarbonyl);

4) optionally substituted hydroxy group [preferably, alkoxy group having 1 to 10 carbon atoms (preferably methoxy, isopropoxy) optionally having 1 to 3 substituents selected from carbamoyl group, carboxyl group and alkoxycarbonyl group having 2 to 5 carbon atoms (preferably methoxycarbonyl); hydroxy group; aralkyloxy group having 7 to 13 carbon atoms (preferably benzyloxy)] [more preferably, carbamoylmethoxy);

5) acyl group [preferably $C_{1-6}$ alkyl-carbonyl (preferably acetyl), carbamoyl, mono- or di-($C_{1-6}$ alkyl optionally having 1 to 3 substituents selected from halogen atom and $C_{1-6}$ alkoxy-carbonyl)-carbamoyl (preferably methylcarbamoyl, ethylcarbamoyl, propylcarbamoyl, dimethylcarbamoyl, trifluoroethylcarbamoyl, ethoxycarbonylmethylcarbamoyl and the like), $C_{3-10}$ cycloalkyl-carbamoyl (preferably cyclopropylcarbamoyl), $C_{7-13}$ aralkyl-carbamoyl (preferably benzylcarbamoyl), nitrogen-containing heterocycle-carbonyl optionally substituted by hydroxy (preferably pyrrolidinylcarbonyl, piperidinocarbonyl), $C_{1-6}$ alkylsulfonyl (preferably methylsulfonyl), $C_{1-6}$ alkylsulfinyl (preferably methylsulfinyl), carboxyl, $C_{1-6}$ alkoxy-carbonyl (preferably methoxycarbonyl), thiocarbamoyl];

6) optionally substituted amino group (preferably, carbamoylamino);

7) optionally substituted thiol group [preferably, alkylthio group having 1 to 10 carbon atoms optionally substituted by carbamoyl group (preferably methylthio)];

8) optionally substituted heterocyclic group [preferably, an aromatic heterocyclic group (preferably, furyl, thienyl, oxazolyl, oxadiazolyl, thiazolyl, tetrazolyl, pyridyl, pyrrolyl, triazolyl) or a non-aromatic heterocyclic group (preferably, dioxoisoindol-2-yl, 5-oxooxadiazol-3-yl, 5-oxothiadiazol-3-yl), each optionally having 1 or 2 substituents selected from $C_{1-6}$ alkyl group optionally substituted by 1 to 3 halogen atoms (preferably methyl, trifluoromethyl), carboxyl group, alkoxycarbonyl group having 2 to 8 carbon atoms (preferably ethoxycarbonyl), cyano group, carbamoyl group, amino group, mono- or di-$C_{2-10}$ alkylcarbonylamino group (e.g., acetylamino, isopentanoylamino), $C_{1-10}$ alkoxy-carbonylamino group (e.g., methoxycarbonylamino), carbamoylamino group, mono- or di-$C_{1-10}$ alkyl-carbamoylamino group (e.g., methylcarbamoylamino, dimethylcarbamoylamino), $C_{6-14}$ aryl-carbonylamino group (e.g., benzoylamino), $C_{3-10}$ cycloalkyl-carbonylamino group, $C_{7-13}$ aralkyloxy-carbonylamino group, mono- or di-$C_{1-10}$ alkylsulfonylamino group (e.g., methylsulfonylamino, dimethylsulfonylamino), $C_{6-14}$ arylsulfonylamino group and $C_{1-6}$ alkoxy-carbamoylamino group (e.g., methoxycarbamoylamino)]; and 9) amidino group;

$R^1$ is an alkyl group having 4 to 10 carbon atoms (preferably isobutyl) or a cycloalkylalkyl group having 4 to 10 carbon atoms (preferably cyclopropylmethyl);

$R^2$ is an alkyl group having 1 to 10 carbon atoms (e.g., methyl, ethyl, propyl, isopropyl, butyl, isobutyl, sec-butyl, tert-butyl, pentyl and the like), an aryl group having 6 to 14 carbon atoms (e.g., phenyl and the like) or an aralkyl group having 7 to 13 carbon atoms (e.g., benzyl, phenethyl, naphthylmethyl and the like), each optionally having 1 to 3 (preferably 1 or 2) substituents selected from halogen atom (e.g., fluorine, chlorine and the like), hydroxy group, nitro group, amino group, optionally halogenated alkyl group having 1 to 6 carbon atoms (e.g., trifluoromethyl, methyl and the like), alkoxy group having 1 to 6 carbon atoms (e.g., methoxy and the like), aromatic heterocyclic group (e.g., quinolyl, thienyl and the like) and cycloalkyl group having 3 to 10 carbon atoms (e.g., cyclopentyl and the like);

X is a bond;
Y is a bond; and
L is $C_{1-10}$ alkylene.

[Compound B]

A compound wherein ring A is a benzene ring optionally having 1 or 2 substituents selected from 1) halogen atom (e.g., fluorine, chlorine, bromine, iodine and the like);

2) cyano group;

3) alkyl group having 1 to 10 carbon atoms (preferably ethyl) or an alkenyl group having 2 to 10 carbon atoms (preferably ethenyl), each optionally having 1 to 3 substituents selected from carbamoyl group, carboxyl group and alkoxycarbonyl group having 2 to 8 carbon atoms (preferably methoxycarbonyl, ethoxycarbonyl);

4) optionally substituted hydroxy group [preferably, alkoxy group having 1 to 10 carbon atoms (preferably methoxy, isopropoxy) optionally having 1 to 3 substituents selected from (1) carbamoyl group optionally substituted by 1 or 2 substituents selected from $C_{1-10}$ alkyl group (e.g., methyl, ethyl, propyl, isopropyl) and $C_{1-10}$ alkylsulfonyl group (e.g., methylsulfonyl); (2) carboxyl group; (3) alkoxycarbonyl group having 2 to 5 carbon atoms (preferably methoxycarbonyl); (4) aromatic heterocyclic group (e.g., furyl, thienyl, oxazolyl, thiazolyl, isoxazolyl, tetrazolyl, oxadiazolyl, thiadiazolyl) optionally substituted by 1 to 3 substituents selected from $C_{1-6}$ alkyl group (e.g., methyl, ethyl) and $C_{2-8}$ alkoxycarbonyl group (e.g., methoxycarbonyl, ethoxycarbonyl); hydroxy group; aralkyloxy group having 7 to 13 carbon atoms (preferably benzyloxy)] [more preferably, carbamoylmethoxy];

5) acyl group [preferably $C_{1-6}$ alkyl-carbonyl (preferably acetyl), carbamoyl, mono- or di-($C_{1-6}$ alkyl optionally having 1 to 3 substituents selected from halogen atom and $C_{1-6}$ alkoxy-carbonyl)-carbamoyl (preferably methylcarbamoyl, ethylcarbamoyl, propylcarbamoyl, dimethylcarbamoyl, trifluoroethylcarbamoyl, ethoxycarbonylmethylcarbamoyl and the like), $C_{3-10}$ cycloalkyl-carbamoyl (preferably cyclopropylcarbamoyl), $C_{7-13}$ aralkyl-carbamoyl (preferably benzylcarbamoyl), nitrogen-containing heterocycle-carbonyl optionally substituted by hydroxy (preferably pyrrolidinylcarbonyl, piperidinocarbonyl), $C_{1-6}$ alkylsulfonyl (preferably methylsulfonyl), $C_{1-6}$ alkylsulfinyl (preferably methylsulfinyl), carboxyl, $C_{1-6}$ alkoxy-carbonyl (preferably methoxycarbonyl), thiocarbamoyl];

6) optionally substituted amino group (preferably, carbamoylamino, acetylamino);

7) optionally substituted thiol group [preferably, alkylthio group having 1 to 10 carbon atoms optionally substituted by carbamoyl group (preferably methylthio)];

8) optionally substituted heterocyclic group [preferably, aromatic heterocyclic group (preferably, furyl, thienyl, oxazolyl, oxadiazolyl, thiazolyl, tetrazolyl, pyridyl, pyrrolyl, triazolyl) or non-aromatic heterocyclic group (preferably, dioxoisoindol-2-yl, 5-oxooxadiazol-3-yl, 5-oxothiadiazol-3-yl), each optionally having 1 or 2 substituents selected from $C_{1-6}$ alkyl group optionally substituted by 1 to 3 halogen atoms (preferably methyl, trifluoromethyl), carboxyl group, alkoxycarbonyl group having 2 to 8 carbon atoms (preferably methoxycarbonyl, ethoxycarbonyl, isopropoxycarbonyl), cyano group, carbamoyl group, amino group, mono- or di-$C_{2-10}$ alkylcarbonylamino group (e.g., acetylamino, isopentanoylamino), $C_{1-10}$ alkoxy-carbonylamino group (e.g., methoxycarbonylamino), carbamoylamino group, mono- or di-$C_{1-10}$ alkyl-carbamoylamino group (e.g., methylcarbamoylamino, dimethylcarbamoylamino), $C_{6-14}$ aryl-carbonylamino group (e.g., benzoylamino), $C_{3-10}$ cycloalkyl-carbonylamino group, $C_{7-13}$ aralkyloxy-carbonylamino group, mono- or di-$C_{1-10}$ alkylsulfonylamino group (e.g., methylsulfonylamino, dimethylsulfonylamino), $C_{6-14}$ arylsulfonylamino group and $C_{1-6}$ alkoxy-carbamoylamino group (e.g., methoxycarbamoylamino)]; and 9) amidino group;

$R^1$ is an alkyl group having 1 to 10 carbon atoms optionally substituted by 1 to 3 substituents selected from halogen atom, aryl group having 6 to 14 carbon atoms (e.g., phenyl, naphthyl and the like), cycloalkyl group having 3 to 10 carbon atoms (e.g., cyclopropyl and the like) and the like;

$R^2$ is an alkyl group having 1 to 10 carbon atoms (e.g., methyl, ethyl, propyl, isopropyl, butyl, isobutyl, sec-butyl, tert-butyl, pentyl, hexyl), an aryl group having 6 to 14 carbon atoms (e.g., phenyl) or an aralkyl group having 7 to 13 carbon atoms (e.g., benzyl, phenethyl, naphthylmethyl), each optionally having 1 to 3 (preferably 1 or 2) substituents selected from halogen atom (e.g., fluorine, chlorine and the like), hydroxy group, nitro group, amino group, optionally halogenated alkyl group having 1 to 6 carbon atoms (e.g., trifluoromethyl, methyl and the like), alkoxy group having 1 to 6 carbon atoms (e.g., methoxy and the like), aromatic heterocyclic group (e.g., quinolyl, thienyl and the like) and cycloalkyl group having 3 to 10 carbon atoms (e.g., cyclopentyl and the like);

X is a bond;
Y is a bond; and
L is $C_{1-10}$ alkylene.

[Compound C]
A compound wherein
ring A is a benzene ring optionally having 1 or 2 substituents selected from 1) a halogen atom (e.g., fluorine, chlorine, bromine, iodine and the like);

2) a nitro group;

3) a cyano group;

4) an alkylenedioxy group having 1 to 3 carbon atoms (e.g., methylenedioxy);

5) an alkyl group having 1 to 10 carbon atoms (e.g., methyl, ethyl, propyl, butyl, pentyl) or an alkenyl group having 2 to 10 carbon atoms (e.g., ethenyl, 3-butenyl), each optionally having 1 to 3 substituents selected from halogen atom, hydroxy group, carboxyl group, alkoxycarbonyl group having 2 to 8 carbon atoms (e.g., ethoxycarbonyl), carbamoyl group, cyano group, amino group, alkylcarbonylamino group having 2 to 8 carbon atoms (e.g., acetylamino, isobutanoylamino), alkoxycarbonylamino group having 2 to 8 carbon atoms (e.g., methoxycarbonylamino, ethoxycarbonylamino), alkylsulfonylamino group having 1 to 8 carbon atoms (e.g., methylsulfonylamino), alkylcarbamoylamino group having 2 to 8 carbon atoms (e.g., methylcarbamoylamino), carboxyl-$C_{1-6}$ alkylthio (e.g., carboxylmethylthio), $C_{2-8}$ alkoxycarbonyl-$C_{1-6}$ alkylthio (e.g., ethoxycarbonylmethylthio) and carbamoyl-$C_{1-6}$ alkylthio (e.g., carbamoylmethythio);

6) an optionally substituted hydroxy group [e.g., alkoxy group having 1 to 10 carbon atoms (e.g., methoxy, ethoxy, propoxy, isopropoxy, butoxy, isobutoxy, pentyloxy), cycloalkyloxy group having 3 to 10 carbon atoms (e.g., cyclopentyloxy) or aralkyloxy group having 7 to 13 carbon atoms (e.g., benzyloxy), each optionally having 1 to 3 substituents selected from halogen atom; alkoxy group having 1 to 3 carbon atoms optionally substituted by 1 or 2 substituents selected from carboxyl group and alkoxycarbonyl group having 2 to 5 carbon atoms (e.g., tert-butoxycarbonyl) (e.g., methoxy, carboxylmethoxy, tert-butoxycarbonylmethoxy); alkoxycarbonyl group having 2 to 5 carbon atoms (e.g., methoxycarbonyl, ethoxycarbonyl); alkylcarbonyl group having 2 to 5 carbon atoms (e.g., pivaloyl); cyano group; carbamoyl group optionally substituted by 1 or 2 substituents selected from $C_{1-10}$ alkyl group (e.g., methyl, ethyl, propyl, isopropyl) and $C_{1-10}$ alkylsulfonyl group (e.g., methylsulfonyl); hydroxy group; carboxyl group; amino group; alkylcarbonylamino group having 2 to 5 carbon atoms (e.g., acetylamino); aromatic heterocyclic group (e.g., furyl, thienyl, oxazolyl, thiazolyl, isoxazolyl, tetrazolyl, oxadiazolyl, thiadiazolyl) optionally substituted by 1 to 3 substituents selected from $C_{1-6}$ alkyl group (e.g., methyl, ethyl) and $C_{2-8}$ alkoxycarbonyl group (e.g., methoxycarbonyl, ethoxycarbonyl); and cycloalkyl group having 3 to 10 carbon atoms (e.g., cyclopropyl, cyclohexyl); hydroxy group];

7) an acyl group [e.g., formyl, carboxyl, $C_{1-6}$ alkyl-carbonyl (e.g., acetyl), $C_{1-6}$ alkoxy-carbonyl (e.g., methoxycarbonyl), carbamoyl, aminocarbamoyl, hydroxycarbamoyl, mono- or di-($C_{1-6}$ alkyl optionally having 1 to 3 substituents selected from halogen atom and $C_{1-6}$ alkoxy-carbonyl (e.g., ethoxycarbonyl))-carbamoyl (e.g., methylcarbamoyl, ethylcarbamoyl, propylcarbamoyl, dimethylcarbamoyl, trifluoroethylcarbamoyl, ethoxycarbonylmethylcarbamoyl and the like), $C_{3-10}$ cycloalkyl-carbamoyl (e.g., cyclopropylcarbamoyl), $C_{7-13}$ aralkyl-carbamoyl (e.g., benzylcarbamoyl), nitrogen-containing heterocycle-carbonyl optionally substituted by hydroxy (e.g., pyrrolidinylcarbonyl, piperidinocarbonyl), $C_{1-6}$ alkylsulfonyl (e.g., methylsulfonyl), $C_{1-6}$ alkylsulfinyl (e.g., methylsulfinyl), thiocarbamoyl];

8) an optionally substituted amino group (e.g., amino, mono or di-$C_{2-10}$ alkylcarbonylamino (e.g., acetylamino, propionylamino, isobutanoylamino, isopentanoylamino), $C_{1-10}$ alkoxy-carbonylamino (e.g., methoxycarbonylamino), carbamoylamino, mono- or di-$C_{1-10}$ alkyl-carbamoylamino (e.g., methylcarbamoylamino, dimethylcarbamoylamino), $C_{6-14}$ aryl-carbonylamino (e.g., benzoylamino), $C_{3-10}$ cycloalkyl-carbonylamino (e.g., cyclopentylcarbonylamino), $C_{7-13}$ aralkyloxy-carbonylamino (e.g., benzyloxycarbonylamino), mono- or di-$C_{1-10}$ alkylsulfonylamino (e.g., methylsulfonylamino, dimethylsulfonylamino), $C_{6-14}$ arylsulfonylamino (e.g., phenylsulfonylamino), $C_{1-6}$ alkoxy-carbamoylamino (e.g., methoxycarbamoylamino), carbamoyl-$C_{1-10}$ alkylamino (e.g., carbamoylmethylamino), $C_{2-5}$ alkoxycarbonyl-$C_{1-10}$ alkylamino (e.g., methoxycarbonylmethylamino, tert-butoxycarbonylmethylamino)];

9) an optionally substituted cycloalkyl group having 3 to 10 carbon atoms [e.g., cycloalkyl group having 3 to 10 carbon atoms (e.g., cyclopropyl, cyclobutyl) optionally having 1 to 3 substituents selected from $C_{1-6}$ alkyl group optionally substituted by 1 to 3 halogen atoms (e.g., methyl, trifluoromethyl), carboxyl group, alkoxycarbonyl group having 2 to 8 carbon atoms (e.g., methoxycarbonyl, ethoxycarbonyl, isopropoxycarbonyl), cyano group, carbamoyl group, amino group, mono- or di-$C_{2-10}$ alkylcarbonylamino group (e.g., acetylamino, isopentanoylamino), $C_{1-10}$ alkoxy-carbonylamino group (e.g., methoxycarbonylamino), carbamoylamino group, mono- or di-$C_{1-10}$ alkyl-carbamoylamino group (e.g., methylcarbamoylamino, dimethylcarbamoylamino), $C_{6-14}$ aryl-carbonylamino group (e.g., benzoylamino), $C_{3-10}$ cycloalkyl-carbonylamino group, $C_{7-13}$ aralkyloxy-carbonylamino group, mono- or di-$C_{1-10}$ alkylsulfonylamino group (e.g., methylsulfonylamino, dimethylsulfonylamino), $C_{6-14}$ arylsulfonylamino group and $C_{1-6}$ alkoxy-carbamoylamino group (e.g., methoxycarbamoylamino)];

10) an aryl group having 6 to 14 carbon atoms (e.g., phenyl);

11) an optionally substituted thiol group [e.g., alkylthio group having 1 to 10 carbon atoms optionally substituted by carbamoyl group (e.g., methylthio)];

12) an optionally substituted heterocyclic group [e.g., aromatic heterocyclic group (preferably furyl, thienyl, oxazolyl, oxadiazolyl, thiazolyl, tetrazolyl, pyridyl, pyrrolyl, triazolyl) or non-aromatic heterocyclic group (preferably dioxoisoindol-2-yl; 5-oxooxadiazol-3-yl; 5-oxothiadiazol-3-yl; 3-oxopiperazin-1-yl; 2,3-dioxopiperazin-1-yl; 2,5-dioxopiperazin-1-yl), each optionally having 1 or 2 substituents selected from $C_{1-6}$ alkyl group optionally substituted by 1 to 3 halogen atoms (e.g., methyl, trifluoromethyl), carboxyl group, alkoxycarbonyl group having 2 to 8 carbon atoms (e.g., methoxycarbonyl, ethoxycarbonyl, isopropoxycarbonyl, tert-butoxycarbonyl), cyano group, carbamoyl group, amino group, mono- or di-$C_{2-10}$ alkylcarbonylamino group (e.g., acetylamino, isopentanoylamino), $C_{1-10}$ alkoxy-carbonylamino group (e.g., (methoxycarbonylamino), carbamoylamino group, mono- or di-$C_{1-10}$ alkyl-carbamoylamino group (e.g., methylcarbamoylamino, dimethylcarbamoylamino), $C_{6-14}$ aryl-carbonylamino group (e.g., benzoylamino), $C_{3-10}$ cycloalkyl-carbonylamino group, $C_{7-13}$ aralkyloxy-carbonylamino group, mono- or di-$C_{1-10}$ alkylsulfonylamino group (e.g., methylsulfonylamino, dimethylsulfonylamino), $C_{6-14}$ arylsulfonylamino group, $C_{1-6}$ alkoxy-carbamoylamino group (e.g., methoxycarbamoylamino), alkylcarbonyl group having 2 to 5 carbon atoms (e.g., acetyl) and carbamoyl-$C_{1-6}$ alkyl group (e.g., carbamoylmethyl)]; and 13) an amidino group;

$R^1$ is an alkyl group having 3 to 10 carbon atoms (preferably isobutyl) or a cycloalkylalkyl group having 4 to 10 carbon atoms (preferably cyclopropylmethyl);

$R^2$ is an alkyl group having 1 to 10 carbon atoms (e.g., methyl, ethyl, propyl, isopropyl, butyl, isobutyl, sec-butyl, tert-butyl, pentyl), an aryl group having 6 to 14 carbon atoms (e.g., phenyl) or an aralkyl group having 7 to 13 carbon atoms (e.g., benzyl, phenethyl, naphthylmethyl), each optionally having 1 to 3 (preferably 1 or 2) substituents selected from halogen atom (e.g., fluorine, chlorine and the like), hydroxy group, nitro group, amino group, optionally halogenated alkyl group having 1 to 6 carbon atoms (e.g., trifluoromethyl, methyl and the like), alkoxy group having 1 to 6 carbon atoms (e.g., methoxy and the like), aromatic heterocyclic group (e.g., quinolyl, thienyl and the like) and cycloalkyl group having 3 to 10 carbon atoms (e.g., cyclopentyl and the like);

X is a bond;
Y is a bond; and
L is $C_{1-10}$ alkylene.

[Compound D]
A compound wherein
ring A is a benzene ring optionally having 1 or 2 substituents selected from 1) an alkyl group having 1 to 10 carbon atoms or an alkenyl group having 2 to 10 carbon atoms, each optionally having 1 to 3 substituents selected from carbamoyl group, carboxyl group and alkoxycarbonyl group having 2 to 8 carbon atoms;

2) an alkoxy group having 1 to 10 carbon atoms optionally having 1 to 3 substituents selected from (1) carbamoyl group optionally substituted by 1 or 2 substituents selected from $C_{1-10}$ alkyl group and $C_{1-10}$ alkylsulfonyl group; (2) carboxyl group; (3) alkoxycarbonyl group having 2 to 5 carbon atoms; (4) aromatic heterocyclic group (e.g., furyl, thienyl, oxazolyl, thiazolyl, isoxazolyl, tetrazolyl, oxadiazolyl, thiadiazolyl) optionally substituted by 1 to 3 substituents selected from $C_{1-6}$ alkyl group and $C_{2-8}$ alkoxycarbonyl group;

3) a cycloalkyl group having 3 to 10 carbon atoms optionally having 1 to 3 substituents selected from carboxyl group, alkoxycarbonyl group having 2 to 8 carbon atoms and carbamoyl group; and 4) an aromatic heterocyclic group (preferably, furyl, thienyl, oxazolyl, oxadiazolyl, thiazolyl, tetrazolyl, pyridyl, pyrrolyl, triazolyl) or non-aromatic heterocyclic group [preferably, dioxoisoindol-2-yl; 5-oxooxadiazol-3-yl; 5-oxothiadiazol-3-yl; 3-oxopiperazin-1-yl; 2,3-dioxopiperazin-1-yl; 2,5-dioxopiperazin-1-yl], each optionally having 1 or 2 substituents selected from $C_{1-6}$ alkyl group optionally substituted by 1 to 3 halogen atoms, carboxyl group, alkoxycarbonyl group having 2 to 8 carbon atoms, cyano group, carbamoyl group, amino group, mono- or di-$C_{2-10}$ alkylcarbonylamino group, $C_{1-10}$ alkoxy-carbonylamino group, carbamoylamino group, mono- or di-$C_{1-10}$ alkyl-carbamoylamino group, $C_{6-14}$ arylcarbonylamino group, $C_{3-10}$ cycloalkyl-carbonylamino group, $C_{7-13}$ aralkyloxy-carbonylamino group, mono- or di-$C_{1-10}$ alkylsulfonylamino group, $C_{6-14}$ arylsulfonylamino group, $C_{1-6}$ alkoxy-carbamoylamino group, alkylcarbonyl group having 2 to 5 carbon atoms and carbamoyl-$C_{1-6}$ alkyl group;

$R^1$ is an alkyl group having 3 to 10 carbon atoms (preferably isobutyl) or a cycloalkylalkyl group having 4 to 10 carbon atoms (preferably cyclopropylmethyl);

$R^2$ is an aryl group having 6 to 14 carbon atoms (e.g., phenyl and the like) optionally having 1 or 2 substituents selected from halogen atom (e.g., fluorine, chlorine and the like) and optionally halogenated alkyl group having 1 to 6 carbon atoms (e.g., trifluoromethyl, methyl and the like);

X is a bond;
Y is a bond; and
L is $C_{1-10}$ alkylene (preferably —$CH_2$—).

[Compound E]
(2E)-3-[3-(aminomethyl)-2-isobutyl-4-(4-methylphenyl) quinolin-6-yl]acrylamide;
5-{[3-(aminomethyl)-2-isobutyl-4-(4-methylphenyl)quinolin-6-yl]oxy}pentanoic acid;
4-[3-(aminomethyl)-2-isobutyl-4-(4-methylphenyl)quinolin-6-yl]piperazin-2-one; and
1-[3-(aminomethyl)-2-isobutyl-4-(4-methylphenyl)quinolin-6-yl]piperazine-2,5-dione.

As a salt of compound (I), pharmacologically acceptable salt is preferable. Examples of such salt include salt with inorganic base, salt with organic base, salt with inorganic acid, salt with organic acid, salt with basic or acidic amino acid and the like.

Preferable examples of the salt with inorganic base include alkali metal salts such as sodium salt, potassium salt and the like; alkaline earth metal salts such as calcium salt, magnesium salt and the like; aluminum salt; ammonium salt and the like.

Preferable examples of the salt with organic base include a salt with trimethylamine, triethylamine, pyridine, picoline, ethanolamine, diethanolamine, triethanolamine, dicyclohexylamine, N,N-dibenzylethylenediamine or the like.

Preferable examples of the salt with inorganic acid include a salt with hydrochloric acid, hydrobromic acid, nitric acid, sulfuric acid, phosphoric acid or the like.

Preferable examples of the salt with organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid or the like.

Preferable examples of the salt with basic amino acid include a salt with arginine, lysin, ornithine or the like.

Preferable examples of the salt with acidic amino acid include a salt with aspartic acid, glutamic acid or the like.

Of the above-mentioned salts, hydrochloride and the like are preferable.

A prodrug of compound (I) is a compound that converts to compound (I) due to the reaction of enzyme, gastric acid and the like under the physiological conditions in the body. That is, a compound that converts to compound (I) by enzymatic oxidation, reduction, hydrolysis and the like, and a compound that converts to compound (I) by hydrolysis and the like by gastric acid and the like. A prodrug of compound (I) is exemplified by a compound wherein an amino group of compound (I) is acylated, alkylated, phosphorylated (e.g., compound where amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated and the like); compound wherein a hydroxy group of compound (I) is acylated, alkylated, phosphorylated, borated (e.g., compound where hydroxy group of compound (I) is acetylated, palmitoylated, propanoylated, pivaloylated, succinilated, fumarinated, alanilated, dimethylaminomethylcarbonylated and the like); compound wherein a carboxyl group of compound (I) is esterified or amidated (e.g., compound where carboxyl group of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonyethyl esterified, methylamidated and the like) and the like. These compounds can be produced from compound (I) by a method known per se.

A prodrug of compound (I) may be a compound that converts to compound (I) under physiological conditions as described in Development of pharmaceutical products, vol. 7, Molecule Design, 163-198, Hirokawa Shoten (1990).

The compound (I) may be labeled with isotope (e.g., $^3$H, $^{14}$C, $^{35}$S, $^{125}$I and the like) and the like.

The compound (I) may be an anhydride or a hydrate.

The compound (I) and a prodrug thereof (hereinafter sometimes to be simply referred to as the compound of the present invention) show low toxicity and can be used as an agent for the prophylaxis or treatment of various diseases to be mentioned later for mammals (e.g., human, mouse, rat, rabbit, dog, cat, cattle, horse, swine, simian and the like) as they are or by admixing with a pharmacologically acceptable carrier and the like to give a pharmaceutical composition.

Here, various organic or inorganic carriers conventionally used as materials for pharmaceutical preparations are used as a pharmacologically acceptable carrier, which are added as excipient, lubricant, binder, disintegrant for solid preparations; and solvent, dissolution aids, suspending agent, isotonicity agent, buffer, soothing agent and the like for liquid preparations. Where necessary, additive for pharmaceutical preparations such as preservative, antioxidant, coloring agent, sweetening agent and the like can be used.

Preferable examples of the excipient include lactose, sucrose, D-mannitol, D-sorbitol, starch, pregelatinized starch, dextrin, crystalline cellulose, low-substituted hydroxypropyl cellulose, sodium carboxymethylcellulose, powdered acacia, dextrin, pullulan, light silicic anhydride, synthetic aluminum silicate, magnesium aluminate metasilicate and the like.

Preferable examples of the lubricant include magnesium stearate, calcium stearate, talc, colloidal silica and the like.

Preferable examples of the binder include pregelatinized starch, saccharose, gelatin, powdered acacia, methylcellulose, carboxymethylcellulose, sodium carboxymethylcellulose, crystalline cellulose, sucrose, D-mannitol, trehalose, dextrin, pullulan, hydroxypropyl cellulose, hydroxypropyl methylcellulose, polyvinylpyrrolidone and the like.

Preferable examples of the disintegrant include lactose, sucrose, starch, carboxymethylcellulose, carboxymethylcellulose calcium, croscarmellose sodium, sodium carboxymethyl starch, light silicic anhydride, low-substituted hydroxypropyl cellulose and the like.

Preferable examples of the solvent include water for injection, physiological brine, Ringer's solution, alcohol, propylene glycol, polyethylene glycol, sesame oil, corn oil, olive oil, cottonseed oil and the like.

Preferable examples of the dissolution aids include polyethylene glycol, propylene glycol, D-mannitol, trehalose, benzyl benzoate, ethanol, Tris aminomethane, cholesterol, triethanolamine, sodium carbonate, sodium citrate, sodium salicylate, sodium acetate and the like.

Preferable examples of the suspending agent include surfactants such as stearyltriethanolamine, sodium lauryl sulfate, lauryl aminopropionate, lecithin, benzalkonium chloride, benzethonium chloride, monostearic glyceride and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropyl cellulose and the like; polysorbates, polyoxyethylene hydrogenated castor oil and the like.

Preferable examples of the isotonicity agent include sodium chloride, glycerol, D-mannitol, D-sorbitol, glucose and the like.

Preferable examples of the buffer include phosphate buffer, acetate buffer, carbonate buffer, citrate buffer, and the like.

Preferable examples of the soothing agent include benzyl alcohol and the like.

Preferable examples of the preservative include p-oxybenzoic acid esters, chlorobutanol, benzyl alcohol, phenethyl alcohol, dehydroacetic acid, sorbic acid and the like.

Preferable examples of the antioxidant include sulfite, ascorbate and the like.

Preferable examples of the coloring agent include water-soluble edible tar pigment (e.g., food colors such as Food Color Red Nos. 2 and 3, Food Color Yellow Nos. 4 and 5, Food Color Blue Nos. 1 and 2 and the like), water insoluble lake pigment (e.g., aluminum salt of the aforementioned water-soluble edible tar pigment and the like), natural pigments (e.g., beta carotene, chlorophil, colcothar etc.) and the like.

Preferable examples of the sweetening agent include saccharin sodium, dipotassium glycyrrhizinate, aspartame, stevia and the like.

The dosage form of the aforementioned pharmaceutical composition may be, for example, oral agents such as tablets (inclusive of sublingual tablets and orally disintegrable tablets), capsules (inclusive of soft capsules and micro capsules), granules, powders, troches, syrups, emulsions, suspensions and the like; or parenteral agents such as injections (e.g., subcutaneous injections, intravenous injections, intramuscular injections, intraperitoneal injections, drip infusions and the like), external agents (e.g., transdermal preparations, ointments and the like), suppositories (e.g., rectal suppositories, vaginal suppositories and the like), pellets, nasal preparations, pulmonary preparations (inhalations), ophthalmic preparations and the like. These may be administered safely via oral or parenteral route.

These agents may be controlled-release preparations such as rapid-release preparations and sustained-release preparations (e.g., sustained-release microcapsules).

The pharmaceutical composition can be produced according to a method conventionally used in the field of pharmaceutical preparation, such as the method described in Japan Pharmacopoeia and the like. The specific production methods of the pharmaceutical preparation are described in detail in the following.

While the content of the compound of the present invention in the pharmaceutical composition varies depending on dosage form, dose of the compound of the present invention and the like, it is, for example, about 0.1-100 wt %.

For example, an oral agent is produced by adding, to the active ingredient, excipient (e.g., lactose, sucrose, starch, D-mannitol and the like), disintegrant (e.g., carboxymethylcellulose calcium and the like), binder (e.g., pregelatinized starch, powdered acacia, carboxymethylcellulose, hydroxypropyl cellulose, polyvinylpyrrolidone and the like), lubricant (e.g., talc, magnesium stearate, polyethylene glycol 6000 and the like) and the like, compression-shaping the mixture, and where necessary, coating the same using a coating base for masking of taste, enteric property or sustained release according to a method known per se.

Examples of the coating base include a sugar-coating base, a water-soluble film coating base, an enteric film coating base, a sustained release film coating base and the like.

As a sugar-coating base, sucrose may be used, if necessary along with one or more species selected from talc, precipitated calcium carbonate, gelatin, powdered acacia, pullulan, carnauba wax and the like.

As a water-soluble film coating base, for example, cellulose polymers such as hydroxypropyl cellulose, hydroxypropyl methylcellulose, hydroxyethylcellulose, methylhydroxyethylcellulose and the like; synthetic polymers such as polyvinyl acetal diethylaminoacetate, aminoalkyl methacrylate copolymer E [Eudragit E, trade name, Rohm Pharma], polyvinylpyrrolidone and the like; polysaccharides such as pullulan and the like; and the like are used.

As a enteric film coating base, for example, cellulose polymers such as hydroxypropyl methylcellulose phthalate, hydroxypropyl methylcellulose acetate succinate, carboxymethylethylcellulose, acetic phthalic cellulose and the like; acrylic acid polymers such as methacrylic acid copolymer L [Eudragit L, trademark, Rohm Pharma], methacrylic acid copolymer LD [Eudragit L-30D55, trade name, Rohm Pharma], methacrylic acid copolymer S [Eudragit S, trade name, Rohm Pharma] and the like; naturally occurring substance such as shellac and the like; and the like are used.

As a sustained release film coating base, for example, cellulose polymers such as ethylcellulose and the like; acrylic acid polymers such as aminoalkyl methacrylate copolymer RS [Eudragit RS, trade name, Rohm Pharma], ethyl acrylate-methyl methacrylate copolymer suspension [Eudragit NE, trade name, Rohm Pharma] and the like, and the like are used.

Two or more kinds of the above-mentioned coating bases may be mixed in an appropriate ratio for use. In addition, a light shielding agent such as titanium oxide, ferric oxide and the like may be used during coating.

An injection is produced by dissolving, suspending or emulsifying an active ingredient in an aqueous solvent (e.g., distilled water, physiological saline, Ringer's solution and the like) or an oily solvent (e.g., vegetable oil such as olive oil, sesame oil, cottonseed oil, corn oil and the like, propylene glycol and the like) and the like, together with a dispersing agent (e.g., polysorbate 80, polyoxyethylene hydrogenated castor oil 60, polyethylene glycol, carboxymethylcellulose, sodium alginate and the like), preservative (e.g., methylparaben, propylparaben, benzyl alcohol, chlorobutanol, phenol and the like), isotonicity agent (e.g., sodium chloride, glycerol, D-mannitol, D-sorbitol, glucose and the like) and the like. In this step, additives such as dissolution aids (e.g., sodium salicylate, sodium acetate and the like), stabilizers (e.g., human serum albumin and the like), soothing agents (e.g., benzyl alcohol and the like) and the like may be used on demand.

The compound of the present invention and the pharmaceutical agent of the present invention show low toxicity, cause fewer side effects and can be used as an agent for the prophylaxis or treatment or diagnosis of various diseases for mammals (e.g., human, cattle, horse, dog, cat, simian, mouse, rat, especially human).

The compound of the present invention and the pharmaceutical agent of the present invention have a superior peptidase inhibitory activity and can suppress peptidase-caused degradation of a physiologically active substance such as peptide hormones, cytokines, neurotransmitters and the like.

Examples of the peptide hormones include glucagon-like peptide-1 (GLP-1), glucagon-like peptide-2 (GLP-2), GIP, growth hormone release hormone (GHRH) and the like.

Examples of the cytokines include chemokine such as RANTES and the like.

Examples of the neurotransmitters include neuropeptide Y and the like.

Examples of the peptidases include EC 3.4.11.1 (Leucyl aminopeptidase), EC 3.4.11.2 (Membrane alanine aminopeptidase), EC 3.4.11.3 (Cystinyl aminopeptidase), EC 3.4.11.4 (Tripeptide aminopeptidase), EC 3.4.11.5 (Prolyl aminopeptidase), EC 3.4.11.6 (Aminopeptidase B), EC 3.4.11.7 (Glutamyl aminopeptidase), EC 3.4.11.9 (Xaa-Pro aminopeptidase), EC 3.4.11.10 (Bacterial leucyl aminopeptidase), EC 3.4.11.13 (Clostridial aminopeptidase), EC 3.4.11.14 (Cytosol alanyl aminopeptidase), EC 3.4.11.15 (Lysyl aminopeptidase), EC 3.4.11.16 (Xaa-Trp aminopeptidase), EC 3.4.11.17 (Tryptophanyl aminopeptidase), EC 3.4.11.18 (Methionyl aminopeptidase), EC 3.4.11.19 (D-stereospecific aminopeptidase), EC 3.4.11.20 (Aminopeptidase Ey), EC 3.4.11.21 (Aspartyl aminopeptidase), EC 3.4.11.22 (Aminopeptidase I), EC 3.4.13.3 (Xaa-His dipeptidase), EC 3.4.13.4 (Xaa-Arg dipeptidase), EC 3.4.13.5 (Xaa-methyl-His dipeptidase), EC 3.4.13.7 (Glu-Glu dipeptidase), EC 3.4.13.9 (Xaa-Pro dipeptidase), EC 3.4.13.12 (Met-Xaa dipeptidase), EC 3.4.13.17 (Non-stereospecific dipeptidase), EC 3.4.13.18 (Cytosol nonspecific dipeptidase), EC 3.4.13.19 (Membrane dipeptidase), EC 3.4.13.20 (Beta-Ala-His dipeptidase), EC 3.4.14.1 (Dipeptidyl-peptidase I), EC 3.4.14.2 (Dipeptidyl-peptidase II), EC 3.4.14.4 (Dipeptidyl-peptidase III), EC 3.4.14.5 (Dipeptidyl-peptidase IV), EC 3.4.14.6 (Dipeptidyl-dipeptidase), EC 3.4.14.9 (Tripeptidyl-peptidase I), EC 3.4.14.10 (Tripeptidyl-peptidase II) and EC 3.4.14.11 (Xaa-Pro dipeptidyl-peptidase) as classified by International Union of Biochemistry and Molecular Biology (IUBMB), and the like.

Of these, EC 3.4.14.1, EC 3.4.14.2, EC 3.4.14.4, EC 3.4.14.5, EC 3.4.14.6, EC 3.4.14.9, EC 3.4.14.10 and EC 3.4.14.11 are preferable. Especially preferred is EC 3.4.14.5.

The compound of the present invention and the pharmaceutical agent of the present invention are useful as a prophylactic and therapeutic agent of diabetes (e.g., type 1 diabetes, type 2 diabetes, gestational diabetes and the like); prophylactic and therapeutic agent of hyperlipidemia (e.g., hypertriglyceridemia, hypercholesterolemia, hypoHDLemia, postprandial lipemia and the like); prophylactic and therapeutic agent of arteriosclerosis; prophylactic and therapeutic agent of impaired glucose tolerance [IGT]; an insulin secretagogue; and an agent for suppressing progress of impaired glucose tolerance into diabetes.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

The compound of the present invention and the pharmaceutical agent of the present invention can be also used as a prophylactic and therapeutic agent of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention and the pharmaceutical agent of the present invention can prevent progress of borderline type, impaired glucose tolerance, IFG (Impaired Fasting Glucose) or IFG (Impaired Fasting Glycemia) into diabetes.

The compound of the present invention and the pharmaceutical agent of the present invention can be also used as a prophylactic and therapeutic agent of, for example, diabetic complications [e.g., neuropathy, nephropathy, retinopathy, cataract, macroangiopathy, osteopenia, hyperosmolar diabetic coma, infectious disease (respiratory infection, urinary tract infection, gastrointestinal infection, dermal soft tissue infections, inferior limb infection and the like), diabetic gangrene, xerostomia, hypacusis, cerebrovascular disorder, peripheral blood circulation disorder and the like], obesity, osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, hypertension, polycystic ovary syndrome, kidney disease (e.g., diabetic nephropathy, glomerular nephritis, glomerulosclerosis, nephrotic syndrome, hypertensive nephrosclerosis, end stage kidney disease and the like), muscular dystrophy, myocardial infarction, angina pectoris, cerebrovascular accident (e.g., cerebral infarction, cerebral apoplexy), insulin resistance syndrome, Syndrome X, hyperinsulinemia, hyperinsulinemia-induced sensory disorder, tumor (e.g., leukemia, breast cancer, prostatic cancer, skin cancer and the like), irritable bowel syndrome, acute or chronic diarrhea, inflammatory diseases (e.g., chronic rheumatoid arthritis, spondylitis deformans, osteoarthritis, lumbago, gout, postoperative or traumatic inflammation, remission of tumentia, neuralgia, pharyngolaryngitis, cystitis, hepatitis (inclusive of nonalcoholic steatohepatitis), pneumonia, pancreatitis, inflammatory bowel disease, ulcerative colitis, gastric mucosal injury (inclusive of gastric mucosal injury caused by aspirin) and the like), visceral obesity syndrome and the like.

The compound of the present invention and the pharmaceutical agent of the present invention can be also used for decreasing visceral fat, suppressing visceral fat accumulation, improving glycometabolism, improving lipid metabolism, suppressing production of oxidized LDL, improving lipoprotein metabolism, improving coronary artery metabolism, prophylaxis and treatment of cardiovascular complications, prophylaxis and treatment of heart failure complications, lowering blood remnant, prophylaxis and treatment of anovulation, prophylaxis and treatment of hypertrichosis, prophylaxis and treatment of hyperandrogenemia, improving pancreatic ($\beta$ cell) function, regeneration of pancreatic ($\beta$ cell), promotion of pancreatic ($\beta$ cell) regeneration, and the like.

The compound of the present invention and the pharmaceutical agent of the present invention can be also used for secondary prophylaxis and suppression of progression of the above-mentioned various diseases (e.g., cardiovascular event such as myocardial infarction and the like).

The compound of the present invention and the pharmaceutical agent of the present invention is a glucose dependent insulin secretagogue that selectively promotes insulin secretion in hyperglycemic patients (e.g., patients showing fasting blood glucose level of not less than 126 mg/dl or 75 g oral glucose tolerance test (75 g OGTT) 2 h level of not less than 140 mg/dl and the like). Therefore, the compound of the present invention and the pharmaceutical agent of the present invention are useful as a safe prophylactic or therapeutic agent of diabetes with a low risk of vascular complications, hypoglycemia induction and the like caused by insulin.

While the dose of the compound of the present invention and the pharmaceutical agent of the present invention varies depending on the administration subject, administration route, target disease, condition and the like, the compound of the present invention as an active ingredient is generally given in a single dose of about 0.01-100 mg/kg body weight, preferably 0.05-30 mg/kg body weight, more preferably 0.1-10 mg/kg body weight, in the case of, for example, oral administration to adult diabetic patients. This dose is desirably given 1 to 3 times a day.

The compound of the present invention and the pharmaceutical agent of the present invention can be used in combination with therapeutic agents such as a therapeutic agent of diabetes, a therapeutic agent of diabetic complications, an antihyperlipemic agent, an antihypertensive agent, an antiobestic agent, a diuretic, a chemotherapeutic agent, an immunotherapeutic agent, an antithrombotic agent, a therapeutic agent of osteoporosis, an antidementia agent, an agent for improving erectile dysfunction, a therapeutic agent of incontinentia or pollakiuria and the like (hereinafter to be referred to as a combination drug). In this case, the timing of administration of the compound of the present invention or the pharmaceutical agent of the present invention and a combination drug is not limited. These may be simultaneously administered to an administration subject or administered in a staggered manner. Moreover, the compound of the present invention or the pharmaceutical agent of the present invention and a combination drug may be administered as two kinds of preparations each containing an active ingredient, or may be administered as a single preparation containing both active ingredients.

The dose of the combination drug can be determined as appropriate based on the dose clinically employed. The proportion of the compound of the present invention or the pharmaceutical agent of the present invention and combination drug can be appropriately determined depending on the administration subject, administration route, target disease, condition, combination and the like. When, for example, the administration subject is human, a combination drug is used in an amount of 0.01-100 parts by weight per 1 part by weight of the compound of the present invention or the pharmaceutical agent of the present invention.

Examples of the therapeutic agent of diabetes include insulin preparations (e.g., animal insulin preparations extracted from pancreas of cattle, swine; human insulin preparations synthesized by genetic engineering techniques using *Escherichia coli* or yeast; zinc insulin; protamine zinc insulin; fragments or derivatives of insulin (e.g., INS-1 and the like) and the like), insulin sensitizers (e.g., pioglitazone or its hydrochloride, rosiglitazone (maleate), GI-262570, Reglixane (JTT-501), Netoglitazone (MCC-555), YM-440, KRP-297, CS-011, FK-614, Ragaglitazar (NN-622), Tesaglitazar (AZ-242), BMS-298585, EML-16336, compounds described in WO99/58510 (e.g., (E)-4-[4-(5-methyl-2-phenyl-4-oxazolylmethoxy)benzyloxyimino]-4-phenylbutyric acid) and the like), PPARγ agonists, PPARγ antagonists, PPARγ/α dual agonists, α-glucosidase inhibitors (e.g., voglibose, acarbose, miglitol, emiglitate and the like), biguanides (e.g., phenformin, metformin, buformin, or a salt thereof (e.g., hydrochloride, fumarate, succinate) and the like), insulin secretagogues [sulfonylureas (e.g., tolbutamide, glibenclamide, gliclazide, chlorpropamide, tolazamide, acetohexamide, glyclopyramide, glimepiride, glipizide, glybuzole and the like), repaglinide, senaglinide, nateglinide, mitiglinide or calcium salt hydrate thereof], GLP-1 receptor agonists [e.g., GLP-1, NN-2211, AC-2993 (exendin-4), BIM-51077, Aib(8,35) hGLP-1(7,37)NH$_2$ and the like], amyrin agonists (e.g., pramlintide and the like), phosphotyrosine phosphatase inhibitors (e.g., vanadic acid and the like), dipeptidyl peptidase IV inhibitors (e.g., NVP-DPP-278, PT-100, P32/98, LAF-237, P93/01 and the like), β3 agonists (e.g., CL-316243, SR-58611-A, UL-TG-307, SB-226552, AJ-9677, BMS-196085, AZ40140 and the like), gluconeogenesis inhibitors (e.g., glycogen phosphorylase inhibitors, glucose-6-phosphatase inhibitors, glucagon antagonists, somatostatin receptor agonists and the like), SGLT (sodium-glucose cotransporter) inhibitors (e.g., T-1095 and the like) and the like.

Examples of the therapeutic agent of diabetic complications include aldose reductase inhibitors (e.g., Tolrestat, Epalrestat, Zenarestat, Zopolrestat, Minalrestat, Fidarestat, SNK-860, CT-112 and the like), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole and the like) and the like), neuranagenesis stimulators (e.g., Y-128 and the like), PKC inhibitors (e.g., LY-333531 and the like), AGE inhibitors (e.g., ALT946, pimagedine, pyratoxanthine, N-phenacylthiazolium bromide (ALT766), EXO-226 and the like), active oxygen scavengers (e.g., thioctic acid and the like), cerebral vasodilators (e.g., tiapride, mexiletine and the like), and the like.

Examples of the antihyperlipemic agent include statin compounds which are cholesterol synthesis inhibitors (e.g., cerivastatin, pravastatin, simvastatin, lovastatin, atorvastatin, fluvastatin, itavastatin and salts thereof (e.g., sodium salt, calcium salt) and the like), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzooxazepin-3-yl]acetyl]piperidine-4-acetic acid and the like) or fibrate compounds having a triglyceride lowering action (e.g., bezafibrate, clofibrate, simfibrate, clinofibrate and the like), ACAT inhibitors (e.g., Avasimibe, Eflucimibe and the like), anion exchange resins (e.g., colestyramine and the like), probucol, nicotinic acid drugs (e.g., nicomol, niceritrol and the like), ethyl icosapentate, plant sterols (e.g., soysterol, γ-oryzanol and the like) and the like.

Examples of the antihypertensive agent include angiotensin converting enzyme inhibitors (e.g., captopril, enalapril, delapril and the like), angiotensin II antagonists (e.g., candesartan cilexetil, losartan, eprosartan, valsartan, telmisartan, irbesartan, tasosartan and the like), calcium antagonists (e.g., manidipine, nifedipine, amlodipine, efonidipine, nicardipine and the like), potassium channel openers (e.g., levcromakalim, L-27152, AL 0671, NIP-121 and the like), Clonidine and the like.

Examples of the antiobestic agent include central antiobestic agents (e.g., Dexfenfluramine, fenfluramine, phentermine, Sibutramine, amfepramone, dexamphetamine, Mazindol, phenylpropanolamine, clobenzorex and the like), pancreatic lipase inhibitors (e.g., orlistat and the like), β3 agonists (e.g., CL-316243, SR-58611-A, UL-TG-307, SB-226552, AJ-9677, BMS-196085, AZ40140 and the like), peptidic anorexiants (e.g., leptin, CNTF (Ciliary Neurotropic Factor) and the like), cholecystokinin agonists (e.g., lintitript, FPL-15849 and the like) and the like.

Examples of the diuretic include xanthine derivatives (e.g., sodium salicylate and theobromine, calcium salicylate and theobromine and the like), thiazide preparations (e.g., ethiazide, cyclopenthiazide, trichloromethyazide, hydrochlorothiazide, hydroflumethiazide, benzylhydrochlorothiazide, penflutizide, polythiazide, methyclothiazide and the like), antialdosterone preparations (e.g., spironolactone, triamterene and the like), carbonate dehydrating enzyme inhibitors (e.g., acetazolamide and the like), chlorobenzenesulfonamide preparations (e.g., chlortalidone, mefruside, indapamide and the like), azosemide, isosorbide, etacrynic acid, piretanide, bumetanide, furosemide and the like.

Examples of the chemotherapeutic agent include alkylation agents (e.g., cyclophosphamide, ifosfamide and the like), metabolic antagonists (e.g., methotrexate, 5-fluorouracil or its derivative, and the like), anti-cancer antibiotics (e.g., mitomycin, adriamycin and the like), plant-derived anti-cancer agents (e.g., vincristin, vindesine, taxol and the like), cisplatin, carboplatin, etoposide and the like. Of these, furtulon and neofurtulon which are 5-fluorouracil derivatives and the like are preferable.

Examples of the immunotherapeutic agent include microorganism or bacterial components (e.g., muramyl dipeptide derivative, picibanil and the like), polysaccharides having immunity potentiating activity (e.g., lentinan, sizofiran, krestin and the like), cytokines obtained by genetic engineering techniques (e.g., interferon, interleukin (IL) and the like), colony stimulating factors (e.g., granulocytic colony stimulating factor, erythropoietin and the like) and the like, with preference given to interleukins such as IL-1, IL-2, IL-12 and the like.

Examples of the antithrombotic agent include heparin (e.g., heparin sodium, heparin calcium, dalteparin sodium and the like), warfarin (e.g., warfarin potassium and the like), anti-thrombin drugs (e.g., aragatroban and the like), thrombolytic agents (e.g., urokinase, tisokinase, alteplase, nateplase, monteplase, pamiteplase and the like), platelet aggregation inhibitors (e.g., ticlopidine hydrochloride, cilostazol, ethyl icosapentate, beraprost sodium, sarpogrelate hydrochloride and the like) and the like.

Examples of the therapeutic agent of osteoporosis include alfacalcidol, calcitriol, elcatonin, calcitonin salmon, estriol, ipriflavone, pamidronate disodium, alendronate sodium hydrate, incadronate disodium and the like.

Examples of the antidementia agent include tacrine, donepezil, rivastigmine, galantamine and the like.

Examples of the agent for improving erectile dysfunction include apomorphine, sildenafil citrate and the like.

Examples of the therapeutic agent of incontinentia or pollakiuria include flavoxate hydrochloride, oxybutynin hydrochloride, propiverine hydrochloride and the like.

Furthermore, drugs having a cachexia-improving action established in animal models and clinical situations, such as cyclooxygenase inhibitors (e.g., Indometacin and the like) [Cancer Research, vol. 49, 5935-5939, 1989], Progesterone derivatives (e.g., Megesterol acetate) [Journal of Clinical Oncology, vol. 12, 213-225, 1994], glucosteroid (e.g., dexamethasone and the like) (ibid.), metoclopramide agents (ibid.), tetrahydrocannabinol agents (ibid.), fat metabolism improving agents (e.g., eicosapentaenoic acid and the like) [British Journal of Cancer, vol. 68, 314-318, 1993], growth hormones, IGF-1, or antibodies to a cachexia-induced factor such as TNF-α, LIF, IL-6, Oncostatin M and the like, can be used in combination with the compound of the present invention or the pharmaceutical agent of the present invention.

The combination drug is preferably an insulin preparation, an insulin sensitizer, an α-glucosidase inhibitor, a biguanide, an insulin secretagogue (preferably a sulfonylurea) or the like.

Two or more of the above-mentioned combination drugs can be used in combination in an appropriate ratio. Preferable combinations in the case of using two or more combination drugs are, for example, as shown in the following.

1) an insulin secretagogue (preferably a sulfonylurea) and an α-glucosidase inhibitor;

2) an insulin secretagogue (preferably a sulfonylurea) and a biguanide;

3) an insulin secretagogue (preferably a sulfonylurea), a biguanide and an α-glucosidase inhibitor;

4) an insulin sensitizer and an a-glucosidase inhibitor;

5) an insulin sensitizer and a biguanide;

6) an insulin sensitizer, a biguanide and an α-glucosidase inhibitor.

When the compound of the present invention or the pharmaceutical agent of the present invention is used in combination with a combination drug, the amount thereof can be reduced within a safe range in consideration of counteraction of these agents. Particularly, the dose of an insulin sensitizer, an insulin secretagogue (preferably a sulfonylurea) and a biguanide can be reduced as compared with the normal dose. Therefore, an adverse effect which may be caused by these agents can be prevented safely. In addition, the dose of the therapeutic agent of diabetic complications, antihyperlipemic agent and antihypertensive agent can be reduced whereby an adverse effect which may be caused by these agents can be prevented effectively.

Hereinafter the production methods of the compound of the present invention are explained.

The compound of the present invention can be produced according to a method known per se, such as a method to be described in detail in the following, or an analogous method thereto.

Compound (I-a), which is a compound of the formula (I) wherein L is La(CH$_2$), can be produced according the following Method A or an analogous method thereto. As used herein, La denotes a bond or a divalent hydrocarbon group. As the divalent hydrocarbon group denoted by La, those exemplified for the aforementioned L can be mentioned. La is preferably a bond or C$_{1-9}$ alkylene.

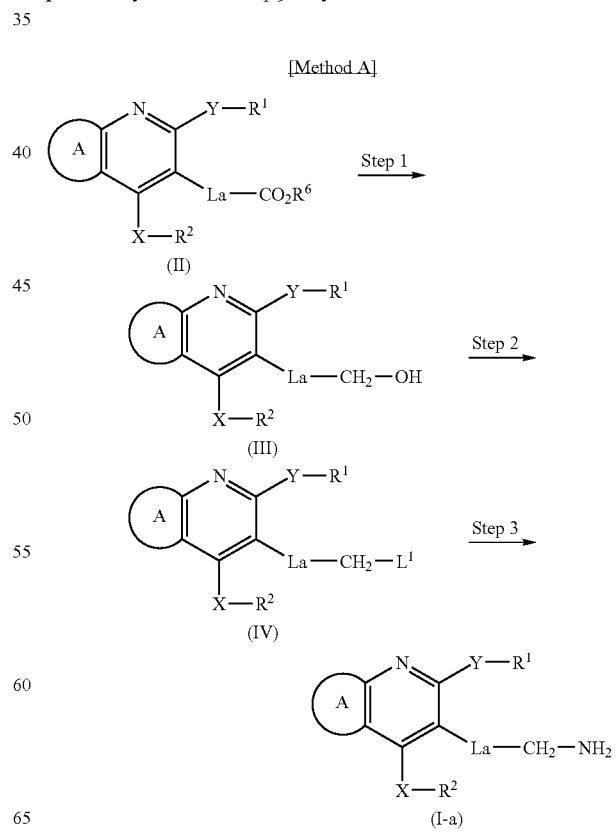

wherein $R^6$ is a hydrogen atom or an optionally substituted hydrocarbon group, $L^1$ is a leaving group, and other symbols are as defined above.

As the optionally substituted hydrocarbon group denoted by $R^6$, for example, $C_{1-6}$ alkyl (e.g., methyl, ethyl, tert-butyl), $C_{7-13}$ aralkyl (e.g., benzyl) and the like can be mentioned.

As the leaving group denoted by $L^1$, for example, halogen atom (e.g., chlorine, bromine, iodine and the like), optionally halogenated $C_{1-6}$ alkylsulfonyloxy (e.g., methanesulfonyloxy, ethanesulfonyloxy, trifluoromethanesulfonyloxy and the like), $C_{6-10}$ arylsulfonyloxy optionally having substituents, hydroxy and the like can be mentioned.

As the "substituent" of the "$C_{6-10}$ arylsulfonyloxy optionally having substituents", for example, halogen atom (e.g., chlorine, bromine, iodine and the like), optionally halogenated $C_{1-6}$ alkyl, $C_{1-6}$ alkoxy and the like can be mentioned. The number of the substituents is, for example, 1 to 3. Specific examples of the "$C_{6-10}$ arylsulfonyloxy optionally having substituents" include benzenesulfonyloxy, p-toluenesulfonyloxy, 1-naphthalenesulfonyloxy, 2-naphthalenesulfonyloxy and the like.

The "leaving group" is preferably halogen atom (e.g., chlorine, bromine, iodine and the like), methanesulfonyloxy, trifluoromethanesulfonyloxy, p-toluenesulfonyloxy and the like.

(Step 1)

In this reaction, compound (II) is subjected to reduction reaction to give compound (III).

The reduction reaction is carried out by, for example, a method comprising direct reduction in a solvent that does not adversely influence the reaction using a reducing agent (e.g., borane, lithium aluminum hydride, diisobutylaluminum hydride and the like), or a method comprising converting carboxyl group to its reactive derivative (e.g., acid halide, mixed acid anhydride, active ester, ester and the like), and then reducing with a reducing agent (e.g., sodium borohydride, lithium borohydride, lithium aluminum hydride, diisobutylaluminum hydride and the like), and the like.

The amount of the reducing agent to be used is preferably about 0.5 to about 10 molar equivalents relative to compound (II).

The solvent that does not adversely influence the reaction varies depending on the kind of the reducing agent to be used. For example, aromatic hydrocarbons such as benzene, toluene, xylene and the like; halogenated hydrocarbons such as chloroform, dichloromethane and the like; ethers such as tetrahydrofuran, 1,2-dimethoxyethane, dioxane, diethyl ether and the like; water; alcohols such as methanol, ethanol, isopropanol and the like; and the like can be mentioned. These solvents may be used in a mixture of two or more kinds thereof mixed at an appropriate ratio.

The reaction temperature is generally about −78° C. to about 150° C., preferably about −78° C. to about 100° C.

The reaction time is generally about 0.5 to about 20 hrs.

The compound (III) thus obtained can be isolated and purified by a known separation and purification means, such as concentration, concentration under reduced pressure, solvent extraction, crystallization, recrystallization, phase transfer, chromatography and the like. The compound (III) may be used as a starting material for the next reaction in a reaction mixture containing compound (III), without isolation and purification.

(Step 2)

When the leaving group denoted by $L^1$ is a halogen atom, this reaction is carried out using a halogenating agent in a solvent that does not adversely influence the reaction.

As the halogenating agent, for example, thionyl chloride, phosphorus tribromide and the like can be mentioned.

The amount of the halogenating agent to be used is preferably 1 to about 20 molar equivalents relative to compound (III).

As the solvent that does not adversely influence the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; and the like can be mentioned. These solvents may be used in a mixture of two or more kinds thereof mixed at an appropriate ratio. In addition, excess halogenating agent may be used as a solvent.

The reaction temperature is generally about −20° C. to about 150° C., preferably about 0° C. to about 100° C.

The reaction time is generally about 0.1 to about 20 hrs.

When the leaving group denoted by $L^1$ is optionally halogenated $C_{1-6}$ alkylsulfonyloxy or $C_{6-10}$ arylsulfonyloxy optionally having substituents, this reaction is carried out using a sulfonylating agent in the presence of base, in a solvent that does not adversely influence the reaction.

As the sulfonylating agent, for example, mesyl chloride, tosyl chloride, benzenesulfonyl chloride and the like can be mentioned.

As the base, for example, amines such as triethylamine, N-methylmorpholine, N,N-dimethylaniline and the like; alkali metal salts such as sodium hydrogen carbonate, sodium carbonate, potassium carbonate and the like; and the like can be mentioned.

The amount of the sulfonylating agent and the base to be used is preferably 1 to about 2 molar equivalents, relative to compound (III).

As the solvent that does not adversely influence the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; esters such as ethyl acetate and the like; and the like can be mentioned. These solvents may be used in a mixture of two or more kinds thereof mixed at an appropriate ratio.

The reaction temperature is generally about −20° C. to about 150° C., preferably about 0° C. to about 100° C.

The reaction time is generally about 0.1 to about 20 hrs.

The compound (IV) thus obtained can be isolated and purified by a known separation and purification means, such as concentration, concentration under reduced pressure, solvent extraction, crystallization, recrystallization, phase transfer, chromatography and the like. The compound (IV) may be used as a starting material for the next reaction in a reaction mixture containing compound (IV), without isolation and purification.

(Step 3)

This reaction comprises reacting compound (IV) with an aminating agent in a solvent that does not adversely influence the reaction, and subjecting, where necessary, the resulting compound to amino deprotection reaction or hydrogenolysis reaction of azide group.

As the aminating agent, for example, ammonia, hexamethylenetetramine, potassium phthalimide, di-tert-butyl imidedicarboxylate, sodium azide and the like can be mentioned.

The amount of the aminating agent to be used is preferably about 1 to about 5 molar equivalents relative to compound (IV).

As the solvent that does not influence the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; alcohols such as methanol, ethanol, isopropanol and the like; ketones such as acetone, 2-butanone and the like; amides such as N,N-dimethylformamide and the like; sulfoxides such as dimethyl sulfoxide and the like; and the like can be mentioned. These solvents may be used in a mixture of two or more kinds thereof mixed at an appropriate ratio.

The reaction temperature is generally about 0° C. to about 200° C., preferably about 20° C. to 120° C.

The reaction time is generally about 0.5 to 20 hrs.

The amino deprotection reaction and hydrogenolysis reaction of azide group are carried out according to a method known per se.

The compound (I-a) thus obtained can be isolated and purified by a known separation and purification means, such as concentration, concentration under reduced pressure, solvent extraction, crystallization, recrystallization, phase transfer, chromatography and the like.

Compound (II) used as a starting material compound in Method A can be produced according to a method known per se, such as a method described in *Synthetic Communications*, vol. 17, page 741 (1987) or a method analogous thereto.

For example, compound (II-a), which is a compound of the formula (II) wherein X and Y are each a bond, La is a bond, and $R^1$ and $R^2$ are the same or different and each is an optionally substituted hydrocarbon group, can be produced according to the following Method B.

be mentioned. These solvents may be used in a mixture of two or more kinds thereof mixed at an appropriate ratio.

As the acid catalyst, for example, Lewis acid such as aluminum chloride, zinc chloride and the like; mineral acid such as hydrochloric acid, sulfuric acid and the like; organic acid such as acetic acid, methanesulfonic acid, p-toluenesulfonic acid, polyphosphoric acid and the like; and the like can be mentioned.

The amount of the acid catalyst to be used is generally 0.1 to 10 molar equivalents, preferably 0.5 to 3 molar equivalents relative to compound (V).

The amount of the compound (X) to be used is generally 0.1 to 10 molar equivalents, preferably 1 to 3 molar equivalents, relative to compound (V).

The reaction temperature is generally 30° C. to 180° C.

The reaction time is generally 0.5 to 20 hrs.

The compound (II-a) thus obtained can be isolated and purified by a known separation and purification means, such as concentration, concentration under reduced pressure, solvent extraction, crystallization, recrystallization, phase transfer, chromatography and the like.

The compound (V) and compound (X) used as starting material compounds in Method B can be produced according to a method known per se.

Compound (I-b), which is a compound of the formula (I) wherein ring A has a substituent represented by the formula: —CO—$OR^4$ ($R^4$ is as defined above), can be also produced according to the following Method C.

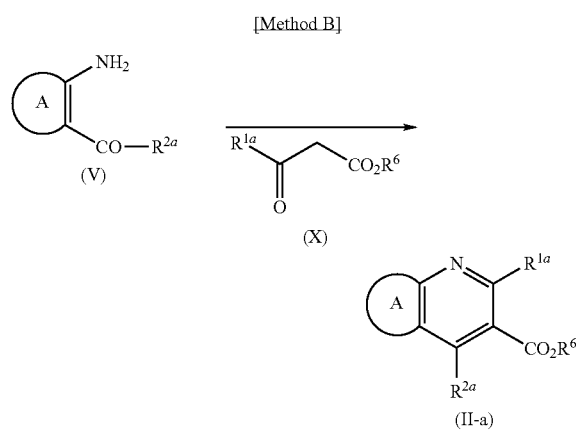

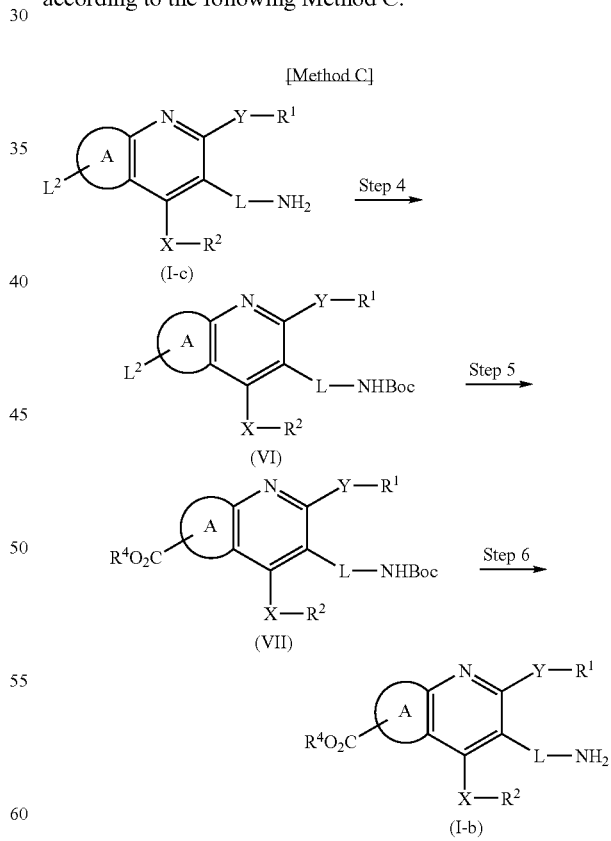

wherein $R^{1a}$ and $R^{2a}$ are the same or different and each is an optionally substituted hydrocarbon group, and other symbols are as defined above.

As the optionally substituted hydrocarbon group denoted by $R^{1a}$ or $R^{2a}$, those exemplified for the aforementioned $R^1$ and $R^2$ are used.

In this reaction, compound (V) and compound (X) are subjected to condensation reaction to give compound (II-a).

The condensation reaction is carried out according to a conventional method using an acid catalyst in, where necessary, a solvent that does not influence the reaction. In the condensation reaction, a device such as Dean-Stark trap and the like can be used.

As the solvent that does not influence the reaction, for example, halogenated hydrocarbons such as chloroform, dichloromethane and the like; aromatic hydrocarbons such as benzene, toluene and the like; ethers such as tetrahydrofuran, dioxane and the like; acetic acid, ethyl acetate and the like can wherein $L^2$ is a leaving group, Boc is a tert-butoxycarbonyl group and other symbols are as defined above.

As the leaving group denoted by $L^2$, those exemplified for the aforementioned $L^1$ can be mentioned.

(Step 4)

Compound (VI) is produced by introducing a tert-butoxycarbonyl group into compound (I-c) according to a method known per se.

The compound (VI) thus obtained can be isolated and purified by a known separation and purification means, such as concentration, concentration under reduced pressure, solvent extraction, crystallization, recrystallization, phase transfer, chromatography and the like. The compound (VI) may be used as a starting material for the next reaction in a reaction mixture containing compound (VI), without isolation and purification.

(Step 5)

This reaction is carried out in the presence of, for example, carbon monoxide, metal catalyst, reaction reagent and alcohol in a solvent that does not adversely influence the reaction.

As the metal catalyst, for example, palladium catalyst (e.g., palladium acetate) and the like can be mentioned.

The amount of the metal catalyst to be used is preferably about 0.01 to about 1 molar equivalent relative to compound (VI).

As the reaction reagent, for example, organophosphorus compound (e.g., 1,3-bis(diphenylphosphino)ferrocene), base (e.g., amines such as pyridine, triethylamine, N,N-dimethylaniline and the like) and the like can be mentioned.

The amount of the reaction reagent to be used is preferably about 1 to about 5 molar equivalents relative to compound (VI).

As the alcohol, ethanol or methanol is generally used.

The amount of the alcohol to be used is generally in excess of compound (VI).

As the solvent that does not adversely influence the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; sulfoxides such as dimethyl sulfoxide and the like; and the like can be mentioned. These solvents may be used in a mixture of two or more kinds thereof mixed at an appropriate ratio.

The reaction temperature is generally about 0° C. to about 150° C., preferably about 50° C. to about 100° C.

The reaction time is generally about 0.5 to about 20 hrs.

The compound (VII) thus obtained can be isolated and purified by a known separation and purification means, such as concentration, concentration under reduced pressure, solvent extraction, crystallization, recrystallization, phase transfer, chromatography and the like. The compound (VI) may be used as a starting material for the next reaction in a reaction mixture containing compound (VII), without isolation and purification.

(Step 6)

Compound (I-b) is produced by removing tert-butoxycarbonyl group from compound (VII) according to a method known per se.

The compound (I-b) thus obtained can be isolated and purified by a known separation and purification means, such as concentration, concentration under reduced pressure, solvent extraction, crystallization, recrystallization, phase transfer, chromatography and the like.

The compound (I-c) used as a starting material compound in Method C can be produced by, for example, the aforementioned Method A or a method analogous thereto.

The compound (I-d), which is a compound of the formula (I) wherein ring A has cyano group as a substituent, and compound (I-e), which is a compound of the formula (I) wherein ring A has carbamoyl group as a substituent, can be also produced by, for example, the following Method D.

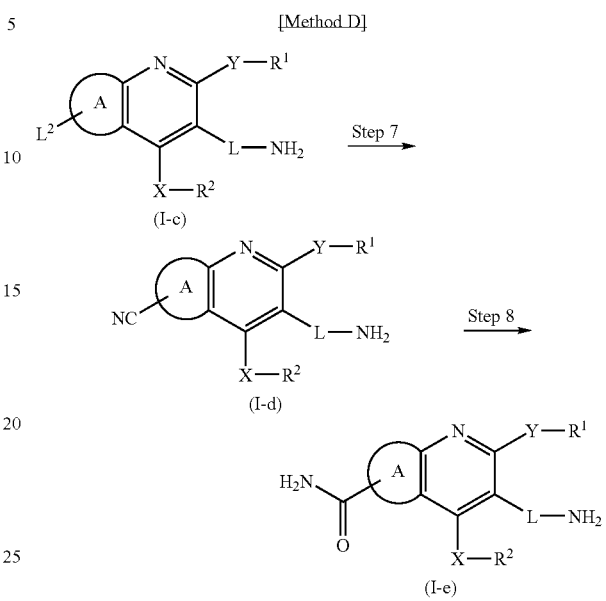

wherein the symbols in the formula are as defined above.

(Step 7)

In this reaction, compound (I-c) is reacted with a metal-cyano compound to give compound (I-d).

As the metal-cyano compound, for example, potassium cyanide, sodium cyanide, zinc cyanide and the like can be mentioned.

The amount of the metal-cyano compound to be used is generally, 1 to 100 molar equivalents, preferably 1 to 10 molar equivalents, relative to compound (I-c).

This reaction is generally carried out in a solvent that does not adversely influence the reaction.

As the solvent that does not adversely influence the reaction, for example, amides such as N,N-dimethylformamide, N,N-dimethylacetamide, N-methylpyrrolidone and the like; sulfoxides such as dimethyl sulfoxide and the like; halogenated hydrocarbons such as chloroform, dichloromethane and the like; aromatic hydrocarbons such as benzene, toluene and the like; ethers such as tetrahydrofuran, dioxane, diethyl ether, dimethoxyethane and the like; esters such as methyl acetate, ethyl acetate and the like; nitriles such as acetonitrile, propionitrile and the like; water and the like can be mentioned. These solvents may be used in a mixture of two or more kinds thereof mixed at an appropriate ratio.

This reaction may be carried out in the presence of a catalyst as necessary. As such catalyst, for example, transition metal compounds such as rhodium, palladium-carbon, tetrakis(triphenylphosphine)palladium, tetrakis(tri-(2-tolyl)phosphine)palladium, tetrakis(tri-(2-furyl)phosphine)palladium, bis(acetylacetone)nickel, dichlorobis(triphenylphosphine)nickel, bis(1,5-cyclooctadiene)nickel, bis(1,10-phenanthroline)nickel, Raney-nickel, Raney-cobalt and the like and the like can be mentioned.

The amount of the catalyst to be used is generally 0.00001 to 10 molar equivalents, preferably 0.001 to 1 molar equivalents, relative to compound (I-c).

The reaction temperature is generally −10° C. to 250° C., preferably 0° C. to 150° C.

The reaction time is generally 0.1 to 100 hrs., preferably 0.1 to 40 hrs.

The compound (I-d) thus obtained can be isolated and purified by a known separation and purification means, such as concentration, concentration under reduced pressure, solvent extraction, crystallization, recrystallization, phase transfer, chromatography and the like. The compound (I-d) may be used as a starting material for the next reaction in a reaction mixture containing compound (I-d), without isolation and purification.

(Step 8)

In this reaction, compound (I-d) is subjected to hydrolysis reaction to give compound (I-e).

The hydrolysis reaction can be generally carried out in the presence of an acid or base.

As the acid, for example, mineral acids (e.g., hydrochloric acid, hydrobromic acid, sulfuric acid, phosphoric acid and the like), carboxylic acids (e.g., formic acid, acetic acid, propionic acid etc.) and the like can be mentioned. Particularly, hydrochloric acid, sulfuric acid and the like are preferable.

As the base, for example, alkali metal salts such as lithium hydroxide, potassium hydroxide, sodium hydroxide, potassium carbonate, sodium carbonate, potassium hydrogen carbonate, sodium hydrogen carbonate and the like; alkaline earth metal salts such as calcium hydroxide, barium hydroxide and the like; amines such as trimethylamine, triethylamine, ethyldiisopropylamine, N-methylmorpholine and the like; and the like can be mentioned. Of these, potassium hydroxide, sodium hydroxide and the like are preferable.

The amount of the acid or base to be used is for example, 0.01 to 100 molar equivalents, preferably 0.1 to 50 molar equivalents, relative to compound (I-d).

The hydrolysis reaction is generally carried out in a solvent that does not adversely influence the reaction. As such solvent, for example, alcohols such as methanol, ethanol, propanol, 2-propanol, butanol, isobutanol, tert-butanol and the like; aromatic hydrocarbons such as benzene, toluene, xylene and the like; aliphatic hydrocarbons such as hexane, heptane and the like; ethers such as diethyl ether, diisopropyl ether, tert-butylmethyl ether, tetrahydrofuran, dioxane, dimethoxyethane and the like; amides such as dimethylformamide, dimethylacetamide and the like; sulfoxides such as dimethyl sulfoxide and the like; water and the like can be mentioned. These solvents may be used in a mixture of two or more kinds thereof mixed at an appropriate ratio.

The reaction temperature is generally 0° C. to 150° C., preferably 10° C. to 100° C.

The reaction time is generally 0.1 to 100 hrs., preferably 0.1 to 10 hrs.

The compound (I-e) thus obtained can be isolated and purified by a known separation and purification means, for example, concentration, concentration under reduced pressure, solvent extraction, crystallization, recrystallization, phase transfer, chromatography and the like.

Compound (I-a), which is a compound of the formula (I) wherein L is La(CH$_2$), can be also produced by the following Method E.

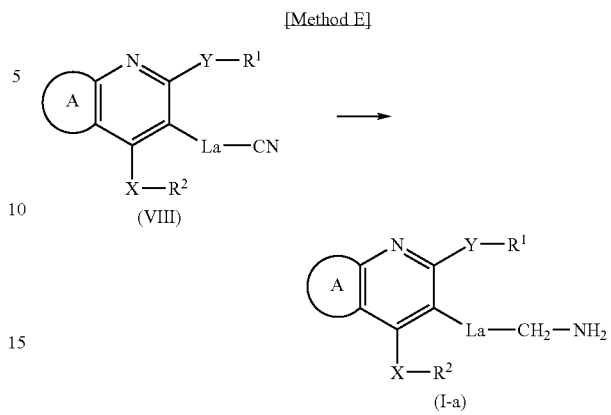

wherein the symbols in the formula are as defined above.

In this method, compound (VIII) is subjected to reduction reaction to give compound (I-a).

The reduction reaction is carried out according to a conventional method in the presence of a reducing agent and in a solvent that does not adversely influence the reaction.

As the reducing agent, for example, metal-hydrogen compounds such as sodium bis(2-methoxyethoxy)aluminum hydride, diisobutylaluminum hydride and the like; metal-hydrogen complex compounds such as sodium borohydride, sodium cyanoborohydride, lithium aluminum hydride, sodium aluminum hydride and the like; and the like can be mentioned.

The amount of the reducing agent to be used is generally 0.1 to 20 molar equivalents, relative to compound (VIII).

As the solvent that does not adversely influence the reaction, for example, alcohols such as methanol, ethanol, propanol, 2-propanol, butanol, isobutanol, tert-butanol and the like; aromatic hydrocarbons such as benzene, toluene, xylene and the like; aliphatic hydrocarbons such as hexane, heptane and the like; ethers such as diethyl ether, diisopropyl ether, tert-butylmethyl ether, tetrahydrofuran, dioxane, dimethoxyethane and the like; esters such as methyl acetate, ethyl acetate, n-butyl acetate, tert-butyl acetate and the like; amides such as dimethylformamide, dimethylacetamide, N-methylpyrrolidone and the like are used. These solvents may be used in a mixture of two or more kinds thereof mixed at an appropriate ratio.

The reaction temperature is generally −70° C. to 150° C., preferably −20° C. to 100° C.

The reaction time is generally 0.1 to 100 hrs., preferably 0.1 to 40 hrs.

The reduction reaction can be also carried out in the presence of a metal catalyst such as palladium-carbon, palladium black, palladium chloride, platinum oxide, platinum black, platinum-palladium, Raney-nickel, Raney-cobalt and the like, and a hydrogen source, in a solvent that does not adversely influence the reaction.

The amount of the metal catalyst to be used is generally 0.001 to 1000 molar equivalents, preferably 0.01 to 100 molar equivalents, relative to compound (VIII).

As the hydrogen source, hydrogen gas, formic acid, amine formate, phosphinate, hydrazine and the like can be mentioned.

As the solvent that does not adversely influence the reaction, those used in the aforementioned reduction reaction using the reducing agent can be mentioned.

The reaction temperature and the reaction time are the same as those for the aforementioned reduction reaction using a reducing agent.

This reaction may be carried out in the presence of ammonia (e.g., aqueous ammonia, ammonia-ethanol and the like) where necessary. By the reaction in the presence of ammonia, the side reaction can be suppressed and compound (I-a) can be produced in a high yield.

Compound (I-a) thus obtained can be isolated and purified by a known separation and purification means, such as concentration, concentration under reduced pressure, solvent extraction, crystallization, recrystallization, phase transfer, chromatography and the like.

Compound (VIII) used as a starting material compound in Method E can be produced according to a method known per se.

For example, compound (VIII-a), which is a compound of the formula (VIII) wherein X and Y are each a bond, La is a bond, and $R^1$ and $R^2$ are the same or different and each is an optionally substituted hydrocarbon group, can be produced according to the following Method F.

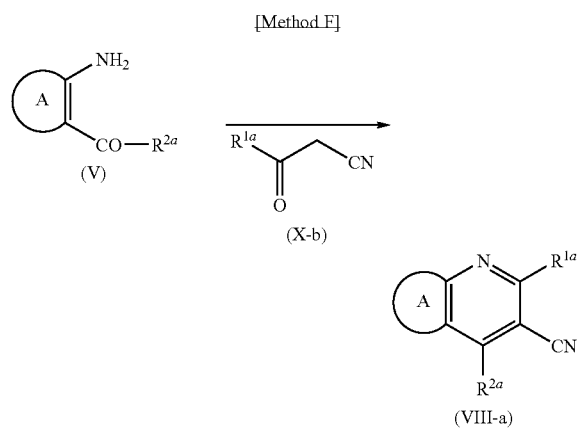

[Method F]

wherein the symbols in the formula are as defined above.

In this reaction, compound (V) and compound (X-b) are subjected to condensation reaction to give compound (VIII-a).

The condensation reaction is carried out according to a conventional method using an acid catalyst in, where necessary, a solvent that does not influence the reaction. In the condensation reaction, a device such as Dean-Stark trap and the like may be used.

As the solvent that does not influence the reaction, those used for the condensation reaction in the aforementioned Method B can be mentioned.

As the acid catalyst, those used for the condensation reaction in the aforementioned Method B can be mentioned.

The amount of the acid catalyst to be used is generally 0.1 to 10 molar equivalents, preferably 0.5 to 3 molar equivalents, relative to compound (V).

The amount of compound (X-b) to be used is generally 0.1 to 10 molar equivalents, preferably 1 to 3 molar equivalents, relative to compound (V).

The reaction temperature is generally 30° C. to 180° C.

The reaction time is generally 0.5 to 20 hrs.

Compound (VIII-a) thus obtained can be isolated and purified by a known separation and purification means, such as concentration, concentration under reduced pressure, solvent extraction; crystallization, recrystallization, phase transfer, chromatography and the like.

Compound (V) and compound (X-b) used as starting material compounds in Method F can be produced according to a method known per se.

In each of the aforementioned reactions, when the starting material compound has amino group, carboxyl group, hydroxy group or carbonyl group as a substituent, a protecting group generally known in peptide chemistry and the like may be introduced into these groups. By removing the protecting group as necessary after the reaction, the objective compound can be obtained.

The amino-protecting group includes, for example, formyl, $C_{1-6}$ alkyl-carbonyl (e.g., acetyl, propionyl and the like), $C_{1-6}$ alkoxy-carbonyl (e.g., methoxycarbonyl, ethoxycarbonyl, tert-butoxycarbonyl and the like), benzoyl, $C_{7-13}$ aralkyl-carbonyl (e.g., benzylcarbonyl and the like), $C_{7-13}$ aralkyloxy-carbonyl (e.g., benzyloxycarbonyl, 9-fluorenylmethoxycarbonyl and the like), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like. These groups are optionally substituted by 1 to 3 from halogen atoms (e.g., fluorine, chlorine, bromine, iodine and the like), $C_{1-6}$ alkoxy (e.g., methoxy, ethoxy, propoxy and the like), nitro and the like.

The carboxy-protecting group is, for example, $C_{1-6}$ alkyl (e.g., methyl, ethyl, propyl, isopropyl, butyl, tert-butyl and the like), $C_{7-13}$ aralkyl (e.g., benzyl and the like), phenyl, trityl, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like. These groups are optionally substituted by 1 to 3 halogen atoms (e.g., fluorine, chlorine, bromine, iodine and the like), $C_{1-6}$ alkoxy (e.g., methoxy, ethoxy, propoxy and the like) or nitro and the like.

The hydroxy-protecting group is, for example, $C_{1-6}$ alkyl (e.g., methyl, ethyl, propyl, isopropyl, butyl, tert-butyl and the like), phenyl, trityl, $C_{7-13}$ aralkyl (e.g., benzyl and the like), formyl, $C_{1-6}$ alkyl-carbonyl (e.g., acetyl, propionyl and the like), benzoyl, $C_{7-13}$ aralkyl-carbonyl (e.g., benzylcarbonyl and the like), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like. These groups are optionally substituted by 1 to 3 halogen atoms (e.g., fluorine, chlorine, bromine, iodine and the like), $C_{1-6}$ alkyl (e.g., methyl, ethyl, propyl and the like), $C_{1-6}$ alkoxy (e.g., methoxy, ethoxy, propoxy and the like) or nitro and the like.

The carbonyl-protecting group is, for example, cyclic acetal (e.g., 1,3-dioxane and the like), non-cyclic acetal (e.g., di-$C_{1-6}$ alkyl acetal and the like) and the like.

Introduction and removal of these protecting groups can follow a method known per se, for example, a method described in Protective Groups in Organic Synthesis, John Wiley and Sons (1980) and the like. For example, employed is a method using acid, base, UV light, hydrazine, phenyl hydrazine, sodium N-methyldithiocarbamate, tetrabutylammonium fluoride, palladium acetate, trialkylsilyl halide (e.g., trimethylsilyl iodide, trimethylsilyl bromide and the like) and the like, reduction and the like.

When the starting material compound can form a salt in each of the aforementioned reactions, the compound in the form of a salt may be used. As such salt, those exemplified above as the salt of compound (I) can be used.

When compound (I) contains an optical isomer, a stereoisomer, a positional isomer or a rotational isomer, these are also encompassed in compound (I), and can be obtained as a single product according to a synthetic method and separation method known per se. For example, when compound (I) has an optical isomer, an optical isomer resolved from this compound is also encompassed in compound (I).

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method and the like.

1) Fractional Recrystallization Method

A salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine and the like) is formed, which is separated by a fractional recrystallization method, and a free optical isomer is obtained by a neutralization step where desired.

2) Chiral Column Method

A racemate or a salt thereof is applied to a column for separation of an optical isomer (chiral column) to allow separation. In the case of a liquid chromatography, for example, a mixture of an optical isomer is applied to a chiral column such as ENANTIO-OVM (manufactured by Tosoh Corporation) or CHIRAL series (manufactured by Daicel Chemical Industries, Ltd.) and the like, and developed with water, various buffers (e.g., phosphate buffer) and organic solvents (e.g., ethanol, methanol, isopropanol, acetonitrile, trifluoroacetic acid, diethylamine and the like) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A racemic mixture is prepared into a diastereomeric mixture by chemical reaction with an optically active reagent, which is prepared into a single substance by a typical separation means (e.g., fractional recrystallization, chromatography method and the like) and the like, and subjected to a chemical treatment such as hydrolysis and the like to separate an optically active reagent moiety, whereby an optical isomer is obtained. For example, when compound (I) contains hydroxy or primary or secondary amino in a molecule, the compound and an optically active organic acid (e.g., MTPA [α-methoxy-α-(trifluoromethyl)phenylacetic acid], (−)-menthoxyacetic acid and the like) and the like are subjected to condensation reaction to give an ester form diastereomer or amide form diastereomer, respectively. When compound (I) has a carboxylic acid group, this compound and an optically active amine or an alcohol reagent are subjected to condensation reaction to give an amide form diastereomer or ester form diastereomer, respectively. The separated diastereomer is converted to an optical isomer of the original compound by acid hydrolysis or base hydrolysis reaction.

The compound (I) may be in the form of a crystal.

The crystal of compound (I) (hereinafter sometimes to be referred to as crystal of the present invention) can be produced by crystallization of compound (I) by a crystallization method known per se.

Examples of the crystallization method include crystallization from a solution, crystallization from vapor, crystallization from a molten form and the like.

The "crystallization from a solution" is typically a method including shifting a non-saturated state to supersaturated state by varying factors involved in solubility of compounds (solvent composition, pH, temperature, ionic strength, redox state and the like) or the amount of solvent. To be specific, for example, concentration method, annealing method, reaction method (diffusion method, electrolysis method), hydrothermal growth method, fusing agent method and the like can be mentioned. Examples of the solvent to be used include aromatic hydrocarbons (e.g., benzene, toluene, xylene and the like), halogenated hydrocarbons (e.g., dichloromethane, chloroform and the like), saturated hydrocarbons (e.g., hexane, heptane, cyclohexane and the like), ethers (e.g., diethyl ether, diisopropyl ether, tetrahydrofuran, dioxane and the like), nitriles (e.g., acetonitrile and the like), ketones (e.g., acetone and the like), sulfoxides (e.g., dimethyl sulfoxide and the like), acid amides (e.g., N,N-dimethylformamide and the like), esters (e.g., ethyl acetate and the like), alcohols (e.g., methanol, ethanol, isopropyl alcohol and the like), water and the like. These solvents are used alone or in combination of two or more at a suitable ratio (e.g., 1:1 to 1:100 (volume ratio)).

The "crystallization from vapor" is, for example, vaporization method (sealed tube method, gas stream method), gas phase reaction method, chemical transportation method and the like.

The "crystallization from a molten form" is, for example, normal freezing method (Czockralski method, temperature gradient method, Bridgman method), zone melting method (zone leveling method, floating zone method), special growth method (VLS method, liquid phase epitaxy method) and the like.

Preferable examples of the crystallization method include a method including dissolving compound (I) or a salt thereof in a suitable solvent (e.g., alcohols such as methanol, ethanol etc., and the like) at a temperature of 20 to 120° C. and cooling the resulting solution to a temperature not higher than the temperature of dissolution (e.g., 0 to 50° C., preferably 0 to 20° C.) and the like.

The thus-obtained crystals of the present invention can be isolated by, for example, filtration and the like.

In the present specification, the melting point refers to that measured using, for example, micromelting point measuring apparatus (Yanako, MP-500D) or DSC (differential scanning calorimetry) device (SEIKO, EXSTAR6000) and the like.

In general, melting points vary depending on measurement apparatuses, measurement conditions and the like. The crystal in the present specification may show a different melting point described in the present specification, as long as it is within general error range.

The crystal of the present invention is superior in physicochemical properties (e.g., melting point, solubility, stability and the like) and biological properties (e.g., pharmacokinetics (absorption, distribution, metabolism, excretion), efficacy expression and the like), and is extremely useful as a pharmaceutical agent.

The present invention is explained in more detail by the following Examples, Experimental Examples and Formulation Examples. These do not limit the present invention and can be modified within the range that does not deviate from the scope of the invention.

The abbreviations in Examples mean the following.

s: singlet, d: doublet, t: triplet, q: quartet, dd: double doublet, dt: double triplet, m: multiplet, bs: broad singlet, J: coupling constant, room temperature: 1-30° C.

EXAMPLES

Example 1

(6-chloro-2-isobutyl-4-phenylquinolin-3-yl)methylamine

1) To a solution of methyl 5-methyl-3-oxohexanoate (0.86 g, 5.0 mmol) and 1-amino-5-chlorobenzophenone (1.16 g, 5.0 mmol) in toluene (100 ml) was added methanesulfonic acid (0.48 g, 5.0 mmol) and the mixture was heated under reflux for 14 hrs. using a Dean-Stark trap. The reaction mixture was partitioned between ethyl acetate (100 ml) and saturated aqueous sodium hydrogen carbonate (100 ml). The organic layer was washed with saturated aqueous sodium hydrogen carbonate (50 ml) and then with saturated brine (50 ml), and dried over anhydrous magnesium sulfate. The solvent was evaporated and the residue was purified by silica gel column chromatography and crystallized from diisopropyl ether to give methyl 6-chloro-2-isobutyl-4-phenylquinoline-3-carboxylate (1.37 g, yield 77%) as pale-yellow crystals.

$^1$H-NMR (CDCl$_3$) δ: 0.99 (6H, d, J=6.6 Hz), 2.20-2.40 (1H, m), 2.88 (2H, d, J=7.4 Hz), 3.55 (3H, s), 7.32 (1H, d, J=2.2 Hz), 7.35-7.40 (1H, m), 7.45-7.55 (4H, m), 7.66 (1H, dd, J=2.2, 9.0 Hz), 8.05 (1H, d, J=9.0 Hz).

melting point: 111-112° C.

2) To a solution of methyl 6-chloro-2-isobutyl-4-phenylquinoline-3-carboxylate (0.97 g, 2.74 mmol) in toluene (20 ml) was added 1.0 M solution (6.9 ml) of diisobutylaluminum hydride in toluene under a nitrogen atmosphere at −75° C. After stirring the mixture at −75° C. for 1 hr., a solution of sodium sulfate (0.97 g) in water (10 ml) was added. The temperature of the mixture was raised to room temperature and the mixture was further stirred for 1.5 hrs. Insoluble materials were removed by filtration, and the filtrate was concentrated under reduced pressure. The residue was purified by silica gel column chromatography and crystallized from diisopropyl ether to give (6-chloro-2-isobutyl-4-phenylquinolin-3-yl)methanol (0.73 g, yield 82%) as colorless crystals.

$^1$H-NMR (CDCl$_3$) δ: 1.04 (6H, d, J=6.6 Hz), 1.58 (1H, t, J=5.7 Hz), 2.30-2.55 (1H, m), 3.05 (2H, d, J=7.3 Hz), 4.62 (2H, d, J=5.7 Hz), 7.25-7.35 (3H, m), 7.50-7.65 (4H, m), 7.90 (1H, d, J=8.8 Hz).

melting point: 130-131° C.

3) To a solution of (6-chloro-2-isobutyl-4-phenylquinolin-3-yl)methanol (0.70 g, 2.15 mmol) in toluene (15 ml) was added thionyl chloride (0.31 ml, 4.3 mmol), and the mixture was heated under reflux for 1 hr. The reaction mixture was partitioned between ethyl acetate (100 ml) and saturated aqueous sodium hydrogen carbonate (50 ml). The organic layer was washed with saturated brine (20 ml) and dried over anhydrous magnesium sulfate. The solvent was evaporated and the residue was dissolved in N,N-dimethylformamide (10 ml). Thereto was added potassium phthalimide (0.6 g, 3.2 mmol) and the mixture was stirred at room temperature for 2.5 days. The reaction mixture was partitioned between ethyl acetate (100 ml) and saturated aqueous sodium hydrogen carbonate (50 ml)-water (50 ml). The aqueous layer was extracted with ethyl acetate (50 ml) and the extract and the organic layer were combined. The mixture was washed twice with water (50 ml) and then saturated brine (50 ml), and dried over anhydrous magnesium sulfate. The solvent was evaporated and the residue was purified by silica gel column chromatography to give 2-[(6-chloro-2-isobutyl-4-phenylquinolin-3-yl)methyl]-1-H-isoindole-1,3(2H)-dione (0.55 g, yield 57%) as an orange oil.

$^1$H-NMR (CDCl$_3$) δ: 1.00 (6H, d, J=6.7 Hz), 2.25-2.40 (1H, m), 2.96 (2H, d, J=7.2 Hz), 4.91 (2H, s), 7.19 (1H, d, J=2.8 Hz), 7.20-7.25 (2H, m), 7.35-7.40 (3H, m), 7.57 (1H, dd, J=2.3, 8.9 Hz), 7.65-7.75 (4H, m), 7.95 (1H, dd, J=0.6, 8.9 Hz).

4) To a solution of 2-[(6-chloro-2-isobutyl-4-phenylquinolin-3-yl)methyl]-1H-isoindole-1,3(2H)-dione (0.54 g, 1.18 mmol) in ethanol (50 ml), being-heated under reflux, was added hydrazine monohydrate (3 ml, 62 mmol), and the mixture was heated under reflux for 2 hrs. The reaction mixture was partitioned between ethyl acetate (100 ml) and saturated aqueous sodium hydrogen carbonate (50 ml)-water (100 ml). The organic layer was washed with saturated aqueous sodium hydrogen carbonate (50 ml) and then saturated brine (20 ml), and dried over anhydrous magnesium sulfate. The solvent was evaporated and the residue was purified by silica gel column chromatography, and crystallized from n-hexane to give the title compound (0.28 g, yield 73%) as pale-yellow crystals.

$^1$H-NMR (CDCl$_3$) δ: 1.05 (6H, d, J=6.6 Hz), 1.34 (2H, bs), 2.25-2.50 (1H, m), 3.01 (2H, d, J=7.2 Hz), 3.78 (2H, s), 7.20-7.30 (3H, m), 7.50-7.60 (4H, m), 7.95 (1H, dm, J=8.9 Hz).

elemental analysis for $C_{20}H_{21}N_2Cl$
Calculated: C, 73.95; H, 6.52; N, 8.62.
Found: C, 73.73; H, 6.52; N, 8.42.
melting point: 114-116° C.

Example 2

(6-bromo-2-isobutyl-4-phenylquinolin-3-yl)methylamine

1) To a solution of methyl 5-methyl-3-oxohexanoate (2.18 g, 19.8 mmol) and 1-amino-5-bromobenzophenone (3.67 g, 13.3 mmol) in toluene (100 ml) was added methanesulfonic acid (1.28 g, 13.3 mmol), and the mixture was heated under reflux for 14 hrs. using a Dean-Stark trap. The reaction mixture was partitioned between ethyl acetate (250 ml) and saturated aqueous sodium hydrogen carbonate (200 ml). The organic layer was washed with saturated aqueous sodium hydrogen carbonate (200 ml) and then with saturated brine (100 ml), and dried over anhydrous magnesium sulfate. The solvent was evaporated and the residue was purified by silica gel column chromatography and crystallized from diisopropyl ether to give methyl 6-bromo-2-isobutyl-4-phenylquinoline-3-carboxylate (3.1 g, yield 58%) as pale-yellow crystals.

$^1$H-NMR (CDCl$_3$) δ: 0.98 (6H, d, J=6.6 Hz), 2.20-2.40 (1H, m), 2.87 (2H, d, J=7.2 Hz), 3.55 (3H, s), 7.30-7.40 (2H, m), 7.45-7.55 (3H, m), 7.71 (1H, dm, J=2.4 Hz), 7.79 (1H, dd, J=2.4, 9.0 Hz), 7.98 (1H, d, J=9.0 Hz).

melting point: 108-110° C.

2) To a solution of methyl 6-bromo-2-isobutyl-4-phenylquinoline-3-carboxylate (3.0 g, 7.5 mmol) in toluene (100 ml) was added 0.95 M solution (20 ml) of diisobutylaluminum hydride in toluene at −75° C. under a nitrogen atmosphere. After stirring the mixture at −75° C. for 1 hr., a solution of sodium sulfate (2.7 g) in water (15 ml) was added. The temperature of the mixture was raised to room temperature and the mixture was further stirred for 1 hr. Insoluble materials were removed by filtration, and the filtrate was concentrated under reduced pressure. The residue was crystallized from n-hexane, and recrystallized from n-hexane-toluene to give (6-bromo-2-isobutyl-4-phenylquinolin-3-yl)methanol (1.6 g, yield 57%) as pale-yellow crystals.

$^1$H-NMR (CDCl$_3$) δ: 1.04 (6H, d, J=6.6 Hz), 1.51 (1H, t, J=6.0 Hz), 2.30-2.50 (1H, m), 3.05 (2H, d, J=7.2 Hz), 4.60 (2H, d, J=6.0 Hz), 7.10-7.60 (6H, m), 7.72 (1H, dd, J=2.1, 9.0 Hz), 7.94 (1H, d, J=9.0 Hz).

melting point: 116-118° C.

3) To a solution of (6-bromo-2-isobutyl-4-phenylquinolin-3-yl)methanol (1.6 g, 4.2 mmol) in toluene (30 ml) was added thionyl chloride (0.61 ml, 8.4 mmol), and the mixture was heated under reflux for 30 min. The solvent was evaporated and the residue was dissolved in N,N-dimethylformamide (30 ml). Potassium phthalimide (1.2 g, 6.3 mmol) was added and the mixture was stirred at 55° C. for 1 hr. The reaction mixture was partitioned between ethyl acetate (50 ml) and water (50 ml) and the aqueous layer was extracted with ethyl acetate (50 ml). The extract and the organic layer were combined and the mixture was washed with saturated aqueous sodium hydrogen carbonate (50 ml) and then saturated brine (50 ml) and dried over anhydrous magnesium sulfate. The solvent was evaporated and toluene (20 ml)-ethyl acetate (10 ml) was added to the residue. Insoluble materials were filtered off and the filtrate was concentrated under reduced pressure. The residue was purified by silica gel column chromatography and crystallized from diisopropyl ether to give 2-[(6-bromo-2-isobutyl-4-phenylquinolin-3-yl)methyl]-1H-isoindole-1,3(2H)-dione (1.7 g, yield 82%) as pale-yellow crystals.

$^1$H-NMR (CDCl$_3$) δ: 1.01 (6H, d, J=6.6 Hz), 2.20-2.45 (1H, m), 3.00 (2H, d, J=7.2 Hz), 4.91 (2H, s), 7.15-7.25 (2H, m), 7.30-7.40 (4H, m), 7.65-7.75 (5H, m), 7.93 (1H, dm, J=8.8 Hz).

melting point: 164-165° C.

4) To a solution of 2-[(6-bromo-2-isobutyl-4-phenylquinolin-3-yl)methyl]-1H-isoindole-1,3(2H)-dione (1.7 g, 3.4 mmol) in ethanol (150 ml), being heated under reflux, was added hydrazine monohydrate (5 ml, 103 mmol), and the mixture was heated under reflux for 2 hrs. The reaction mixture was partitioned between ethyl acetate (100 ml) and saturated aqueous sodium hydrogen carbonate (250 ml). The organic layer was washed with saturated aqueous sodium hydrogen carbonate (100 ml) and then saturated brine (100 ml), and dried over anhydrous magnesium sulfate. The solvent was evaporated and the residue was purified by silica gel column chromatography, and crystallized from n-hexane-diisopropyl ether to give the title compound (0.90 g, yield 72%) as colorless crystals.

$^1$H-NMR (CDCl$_3$) δ: 1.04 (6H, d, J=6.6 Hz), 1.26 (2H, bs), 2.30-2.50 (1H, m), 3.01 (2H, d, J=7.2 Hz), 3.79 (2H, s), 7.25-7.35 (2H, m), 7.35-7.45 (1H, m), 7.50-7.60 (3H, m), 7.69 (1H, dd, J=2.1, 9.0 Hz), 7.95 (1H, dd, J=0.3, 9.0 Hz).

elemental analysis for $C_{20}H_{21}N_2Br$
Calculated: C, 65.05; H, 5.73; N, 7.59.
Found: C, 65.47; H, 5.79; N, 7.90.
melting point: 129-130° C.

Example 3

3-(aminomethyl)-2-isobutyl-4-phenylquinoline-6-carbonitrile

A solution of (6-bromo-2-isobutyl-4-phenylquinolin-3-yl)methylamine (0.20 g, 0.54 mmol) in N-methylpyrrolidone (8 ml) was stirred under a nitrogen atmosphere at 80° C. for 15 min. To the reaction mixture were added zinc cyanide (0.038 g, 0.32 mmol) and tetrakis(triphenylphosphine)palladium (0.032 g, 0.027 mmol), and the mixture was further stirred under a nitrogen atmosphere at 80° C. for 1 hr. The reaction mixture was partitioned between ethyl acetate (50 ml) and 28% aqueous ammonia (6 ml)-saturated aqueous ammonium chloride solution (22 ml)-water (22 ml). The organic layer was washed twice with 28% aqueous ammonia (6 ml)-saturated aqueous ammonium chloride solution (22 ml)-water (22 ml) and then with saturated brine (20 ml), and dried over anhydrous magnesium sulfate. The solvent was evaporated and the residue was purified by preparative HPLC and the objective fractions were combined and concentrated under reduced pressure. The residue was alkalified with saturated aqueous sodium hydrogen carbonate (50 ml) and extracted twice with ethyl acetate (50 ml). The organic layers were combined, washed with saturated brine (20 ml) and dried over anhydrous magnesium sulfate. The solvent was evaporated and the residue was crystallized from n-hexane-ethyl acetate to give the title compound (0.032 g, yield 19%) as colorless crystals.

$^1$H-NMR (CDCl$_3$) δ: 1.06 (6H, d, J=6.6 Hz), 1.40 (2H, bs), 2.30-2.55 (1H, m), 3.06 (2H, d, J=7.4 Hz), 3.82 (2H, bs), 7.20-7.35 (2H, m), 7.50-7.60 (3H, m), 7.67 (1H, d, J=1.4 Hz), 7.76 (1H, dd, J=1.4, 8.8 Hz), 8.12 (1H, d, J=8.8 Hz).

elemental analysis for $C_{21}H_{21}N_3$.
Calculated: C, 79.97; H, 6.71; N, 13.32.
Found: C, 79.49; H, 6.81; N, 13.12.
melting point: 128-130° C.

Example 4

3-(aminomethyl)-2-isobutyl-4-phenylquinoline-6-carboxamide

To a solution of 3-(aminomethyl)-2-isobutyl-4-phenylquinoline-6-carbonitrile (0.11 g, 0.35 mmol) in dimethyl sulfoxide (4 ml) was added 1N aqueous sodium hydroxide solution (2 ml) and the mixture was stirred at 80° C. for 3 hrs. The reaction mixture was partitioned between ethyl acetate (50 ml) and 1N aqueous sodium hydroxide solution (50 ml) and the aqueous layer was extracted 4 times with ethyl acetate (50 ml). The organic layers were combined and dried over anhydrous magnesium sulfate. The solvent was evaporated and the residue was purified by preparative HPLC. The objective fractions were combined and concentrated under reduced pressure. The residue was partitioned between ethyl acetate (25 ml)-tetrahydrofuran (25 ml) and 1N aqueous sodium hydroxide solution (25 ml). The organic layer was washed with saturated brine (10 ml) and dried over anhydrous magnesium sulfate. The solvent was evaporated and the residue was crystallized from diisopropyl ether-ethyl acetate to give the title compound (0.043 g, yield 37%) as pale-yellow crystals.

$^1$H-NMR (CDCl$_3$) δ: 1.05 (6H, d, J=6.6 Hz), 2.35-2.50 (1H, m), 3.05 (2H, d, J=7.1 Hz), 3.80 (2H, s), 5.64 (1H, bs), 5.94 (1H, bs), 7.25-7.35 (2H, m), 7.50-7.60 (3H, m), 7.74 (1H, dm, J=2.0 Hz), 8.01 (1H, dd, J=2.0, 8.6 Hz), 8.11 (1H, dm, J=8.6 Hz).

melting point: 128-129° C.

Example 5

Methyl 3-(aminomethyl)-2-isobutyl-4-phenylquinoline-6-carboxylate Dihydrochloride 1) To a solution of (6-bromo-2-isobutyl-4-phenylquinolin-3-yl)methylamine (1.1 g, 3.1 mmol) in ethyl acetate (50 ml) was added di-tert-butyl dicarbonate (1.0 g, 4.6 mmol), and the mixture was stirred at room temperature for 2 hrs. The reaction mixture was concentrated under reduced pressure, and the residue was purified by silica gel column chromatography, crystallized from diisopropyl ether and recrystallized from diisopropyl ether-ethyl acetate to give tert-butyl (6-bromo-2-isobutyl-4-phenylquinolin-3-yl)methylcarbamate (0.52 g, yield 36%) as colorless crystals.

$^1$H-NMR (CDCl$_3$) δ: 1.03 (6H, d, J=6.6 Hz), 1.41 (9H, s), 2.25-2.50 (1H, m), 2.96 (2H, d, J=7.2 Hz), 4.25-4.35 (3H, m), 7.20-7.30 (2H, m), 7.42 (1H, d, J=2.2 Hz), 7.50-7.60 (3H, m), 7.72 (1H, dd, J=2.2, 9.0 Hz), 7.93 (1H, d, J=9.0 Hz).

melting point: 193-194° C.

2) A mixture of tert-butyl (6-bromo-2-isobutyl-4-phenylquinolin-3-yl)methylcarbamate (0.79 g, 1.7 mmol), 1,1'-bis(diphenylphosphino)ferrocene (0.047 g, 0.084 mmol), palladium acetate (0.019 g, 0.084 mmol), triethylamine (0.26 ml, 1.9 mmol), methanol (10 ml) and tetrahydrofuran (10 ml) was stirred in a sealed tube under a 0.5 MPa carbon monoxide atmosphere at 110° C. for 3 hrs. The reaction mixture was cooled and added to a mixture of ethyl acetate (50 ml) and water (50 ml), and insoluble materials were filtered off. The organic layer was separated, washed with saturated brine (20 ml) and dried over anhydrous magnesium sulfate. The solvent was evaporated and the residue was purified by silica gel column chromatography and crystallized from diisopropyl ether-ethyl acetate to give methyl 3-{[(tert-butoxycarbonyl)amino]methyl}-2-isobutyl-4-phenylquinoline-6-carboxylate (0.71 g, yield 95%) as colorless crystals.

$^1$H-NMR (CDCl$_3$) δ: 1.05 (6H, d, J=6.6 Hz), 1.42 (9H, s), 2.30-2.55 (1H, m), 3.00 (2H, d, J=7.2 Hz), 3.87 (3H, s), 4.25-4.35 (3H, m), 7.20-7.30 (2H, m), 7.50-7.60 (3H, m), 8.06 (1H, d, J=1.8 Hz), 8.09 (1H, d, J=8.8 Hz), 8.24 (1H, dd, J=1.8, 8.8 Hz).

3) To a solution of methyl 3-{[(tert-butoxycarbonyl)amino]methyl}-2-isobutyl-4-phenylquinoline-6-carboxylate (0.10 g, 0.22 mmol) in tetrahydrofuran (2 ml) was added 4N solution of hydrogen chloride in ethyl acetate (5 ml), and the mixture was stirred at room temperature for 3 hrs. The reaction mixture was concentrated under reduced pressure, and the residue was crystallized from diisopropyl ether-ethyl acetate to give the title compound (0.084 g, yield 90%) as colorless crystals.

$^1$H-NMR (CD$_3$OD) δ: 1.16 (6H, d, J=6.6 Hz), 2.25-2.50 (1H, m), 3.44 (2H, d, J=7.7 Hz), 3.91 (3H, s), 4.34 (2H, s), 7.50-7.60 (2H, m), 7.70-7.85 (3H, m), 8.23 (1H, d, J=1.8 Hz), 8.43 (1H, d, J=9.1 Hz), 8.65 (1H, dd, J=1.8, 9.1 Hz).

melting point: 258-260° C.

Example 6

3-(aminomethyl)-2-isobutyl-4-phenylquinoline-6-carboxylic Acid Dihydrochloride

1) To a solution of methyl 3-{[(tert-butoxycarbonyl)amino]methyl}-2-isobutyl-4-phenylquinoline-6-carboxylate (0.58 g, 1.3 mmol) in tetrahydrofuran (6 ml)-methanol (6 ml) was added 1N aqueous sodium hydroxide solution (3 ml), and the mixture was stirred at 50° C. for 2 hrs. The reaction mixture was partitioned between tetrahydrofuran (50 ml)-ethyl acetate (50 ml) and 0.1N hydrochloric acid (100 ml) and the aqueous layer was extracted twice with tetrahydrofuran (25 ml)-ethyl acetate (25 ml). The organic layers were combined, washed with saturated brine (50 ml), and dried over anhydrous magnesium sulfate. The solvent was evaporated and the residue was crystallized from diisopropyl ether-ethyl acetate to give 3-{[(tert-butoxycarbonyl)amino]methyl}-2-isobutyl-4-phenylquinoline-6-carboxylic acid (0.56 g, 99%) as colorless crystals.

$^1$H-NMR (CDCl$_3$) δ: 1.05 (6H, d, J=6.6 Hz), 1.42 (9H, s), 2.30-2.55 (1H, m), 3.01 (2H, d, J=7.2 Hz), 4.25-4.40 (3H, m), 7.20-7.30 (2H, m), 7.50-7.60 (3H, m), 8.05-8.15 (2H, m), 8.27 (1H, dd, J=1.8, 8.8 Hz).

2) To a solution of 3-{[(tert-butoxycarbonyl)amino]methyl}-2-isobutyl-4-phenylquinoline-6-carboxylic acid (0.10 g, 0.23 mmol) in tetrahydrofuran (4 ml) was added 4N solution of hydrogen chloride in ethyl acetate (4 ml), and the mixture was stirred at room temperature for 4 hrs. The reaction mixture was concentrated under reduced pressure, and the residue was crystallized from diisopropyl ether-ethyl acetate to give the title compound (0.078 g, yield 82%) as colorless crystals.

$^1$H-NMR (CD$_3$OD) δ: 1.17 (6H, d, J=6.6 Hz), 2.25-2.50 (1H, m), 3.36 (2H, d, J=7.7 Hz), 4.53 (2H, s), 7.50-7.60 (2H, m), 7.70-7.85 (3H, m), 8.26 (1H, d, J=1.8 Hz), 8.44 (1H, d, J=8.8 Hz), 8.67 (1H, dd, J=1.8, 8.8 Hz).

melting point: 287-290° C. (decomp.)

Example 7

2-{[3-(aminomethyl)-4-phenyl-2-propylquinolin-6-yl]oxy}acetamide

1) To a mixture of 5-hydroxyanthranilic acid (50 g, 0.33 mol), sodium hydrogen carbonate (109 g, 1.3 mol) and water (200 ml) was added dropwise a solution of benzyl chloroformate (52 ml, 0.36 mol) in diethyl ether (200 ml) with stirring, and the mixture was stirred at room temperature for 3 hrs. The reaction mixture was acidified by adding conc. hydrochloric acid and the mixture was extracted with ethyl acetate. The extract was washed with saturated brine, and dried over anhydrous magnesium sulfate. The solvent was evaporated and the obtained crystals were washed with diisopropyl ether and hexane to give 2-{[(benzyloxy)carbonyl]amino}-5-hydroxybenzoic acid (91.6 g, yield 98%) as brown crystals.

$^1$H-NMR (DMSO-d$_6$) δ: 5.13 (2H, s), 7.00 (1H, dd, J=3.0, 9.0 Hz), 7.33-7.41 (6H, m), 8.00 (1H, d, J=9.0 Hz), 9.50 (1H, s), 10.32 (1H, s).

2) To a solution of 2-{[(benzyloxy)carbonyl]amino}-5-hydroxybenzoic acid (92 g, 0.32 mol) and N,O-dimethylhydroxyamine hydrochloride (38 g, 0.38 mol) in N,N-dimethylformamide (500 ml) was added triethylamine (53 ml, 0.40 mol), and the mixture was stirred at room temperature for 10 min. To the reaction mixture was added 1-ethyl-3-(3-dimethylaminopropyl)carbodiimide hydrochloride (73 g, 0.38 mol), and the mixture was stirred at room temperature for 6 hrs. The reaction mixture was poured into water, and the mixture was extracted with ethyl acetate. The extract was washed with saturated brine and dried over anhydrous magnesium sulfate, and the solvent was evaporated under reduced pressure. The residue was dissolved in N,N-dimethylformamide (500 ml), and tert-butyl(dimethyl)silyl chloride (48 g, 0.32 mol) and imidazole (21 g, 0.32 mol) were added. The mixture was stirred at room temperature for 6 hrs., poured into water and extracted with ethyl acetate. The extract was washed with saturated brine and dried over anhydrous magnesium sulfate. The solvent was evaporated and the residue was purified by silica gel column chromatography to give benzyl (4-{[tert-butyl(dimethyl)silyl]oxy}-2-{[methoxy(methyl)amino]carbonyl}phenyl)carbamate (91 g, yield 64%).

¹H-NMR (CDCl₃) δ: 0.28 (6H, s), 1.08 (9H, s), 3.45 (3H, s), 3.62 (3H, s), 5.28 (2H, s), 7.02 (1H, dd, J=2.6, 8.8 Hz), 7.06 (1H, d, J=2.6 Hz), 7.44-7.51 (5H, m), 8.04 (1H, d, J=8.8 Hz), 8.45 (1H, s).

3) To a solution of benzyl (4-{[tert-butyl(dimethyl)silyl]oxy}-2-{[methoxy(methyl)amino]carbonyl}phenyl)carbamate (91 g, 0.20 mol) in ethanol (250 ml)-tetrahydrofuran (250 ml) was added 5% palladium-carbon (25 g), and the mixture was stirred at room temperature under a hydrogen atmosphere for 12 hrs. The reaction mixture was filtered and the filtrate was concentrated under reduced pressure. The residue was crystallized from n-hexane to give 2-amino-5-{[tert-butyl(dimethyl)silyl]oxy}-N-methoxy-N-methylbenzamide (44 g, yield 70%) as white crystals.

¹H-NMR (CDCl₃) δ: 0.15 (6H, s), 0.97 (9H, s), 3.34 (3H, s), 3.58 (3H, s), 4.30 (2H, s), 6.60 (1H, d, J=8.4 Hz), 6.73 (1H, dd, J=2.7, 8.4 Hz), 6.87 (1H, d, J=2.7 Hz).

4) To a solution of 2-amino-5-{[tert-butyl(dimethyl)silyl]oxy}-N-methoxy-N-methylbenzamide (5.0 g, 16 mmol) in tetrahydrofuran (100 ml) was added dropwise 2.0 M solution (20 ml) of phenylmagnesium bromide in tetrahydrofuran at −78° C. The temperature of the reaction mixture was raised, and the mixture was stirred at room temperature for 30 min. Saturated aqueous ammonium chloride solution was added to the reaction mixture, and the mixture was extracted with ethyl acetate. The extract was washed with saturated brine, dried over anhydrous magnesium sulfate and concentrated under reduced pressure. The residue was purified by silica gel column to give (2-amino-5-{[tert-butyl(dimethyl)silyl]oxy}-phenyl)(phenyl)methanone (3.4 g, yield 65%) as a yellow oil.

¹H-NMR (CDCl₃) δ: 0.20 (6H, s), 1.03 (9H, s), 5.83 (2H, bs), 6.74-6.79 (1H, m), 6.99-7.02 (2H, m), 7.54-7.64 (3H, m), 7.73-7.78 (2H, m).

5) A suspension of sodium hydride (60% in oil, 18 g, 0.44 mol) in tetrahydrofuran (160 ml) was stirred at 70° C. and a solution of methyl butyrate (26 ml, 0.22 mol) and acetonitrile (23 ml, 0.44 mol) in tetrahydrofuran (50 ml) was added dropwise. The mixture was stirred at 70° C. for 8 hrs. Water was added to the reaction mixture and the mixture was filtered. The filtrate was washed with n-hexane and n-hexane-diethyl ether (1:1). The aqueous layer was separated, acidified with conc. hydrochloric acid and extracted with ethyl acetate. The extract was washed with saturated brine and dried over anhydrous magnesium sulfate. The solvent was evaporated to give 3-oxohexanenitrile (20 g, yield 82%).

¹H-NMR (CDCl₃) δ: 0.95 (3H, t, J=7.2 Hz), 1.60-1.72 (2H, m), 2.59 (2H, t, J=7.2 Hz), 3.50 (2H, s).

6) A solution of (2-amino-5-{[tert-butyl(dimethyl)silyl]oxy}-phenyl)(phenyl)methanone (2.0 g, 6.1 mmol), 3-oxohexanenitrile (0.81 g, 7.3 mmol) and methanesulfonic acid (0.59 g, 6.1 mmol) in toluene (50 ml) was stirred at 110° C. for 15 hrs. Water was added to the reaction mixture and the mixture was extracted with ethyl acetate. The extract was washed with saturated brine, and dried over anhydrous magnesium sulfate. The solvent was evaporated under reduced pressure and the residue was crystallized from disopropyl ether to give 6-hydroxy-4-phenyl-2-propylquinoline-3-carbonitrile (0.98 g, yield 56%) as pale-yellow crystals.

¹H-NMR (DMSO-d₆) δ: 1.00 (3H, t, J=7.2 Hz), 1.80-1.89 (2H, m), 3.01-3.07 (2H, m), 6.78 (1H, d, J=1.8 Hz), 7.42 (1H, dd, J=1.8, 9.3 Hz), 7.49-7.52 (2H, m), 7.60-7.65 (3H, m), 7.95 (1H, d, J=9.3 Hz), 10.19 (1H, s).

7) A suspension of 6-hydroxy-4-phenyl-2-propylquinoline-3-carbonitrile (0.98 g, 3.4 mmol), chloroacetamide (0.36 g, 3.8 mmol) and potassium carbonate (0.55 g, 4.0 mmol) in N,N-dimethylformamide (10 ml) was stirred at 60° C. for 18 hrs. Water was added to the reaction mixture and the mixture was extracted with ethyl acetate. The extract was washed with saturated brine, and dried over anhydrous magnesium sulfate. The solvent was evaporated under reduced pressure and the residue was purified by silica gel column chromatography to give 2-[(3-cyano-4-phenyl-2-propylquinolin-6-yl)oxy]acetamide (1.0 g, yield 88%) as pale-yellow crystals.

¹H-NMR (DMSO-d₆) δ: 1.00 (3H, t, J=7.5 Hz), 1.81-1.96 (2H, m), 3.08 (2H, t, J=7.5 Hz), 4.39 (2H, s), 6.86 (1H, d, J=2.7 Hz), 7.36 (1H, bs), 7.51-7.60 (3H, m), 7.60-7.66 (4H, m), 8.06 (1H, d, J=9.3 Hz).

8) A mixture of 2-[(3-cyano-4-phenyl-2-propylquinolin-6-yl)oxy]acetamide (1.0 g, 2.9 mmol), Raney-cobalt (5 ml), 25% aqueous ammonia (5 ml), methanol (5 ml) and tetrahydrofuran (5 ml) was reacted under a hydrogen atmosphere at 0.5 MPa, 70° C. for 6 hrs. The reaction mixture was filtered, and water was added to the filtrate. The mixture was extracted with ethyl acetate and the extract was washed with saturated brine and dried over anhydrous magnesium sulfate. The solvent was evaporated under reduced pressure and the residue was purified by silica gel column chromatography to give the title compound (0.62 g, yield 62%) as white crystals.

¹H-NMR (CDCl₃) δ: 1.10 (3H, t, J=7.2 Hz), 1.85-1.96 (2H, m), 3.06-3.11 (2H, m), 3.77 (2H, s), 4.33 (2H, s), 5.75 (1H, bs), 6.54 (1H, d, J=1.8 Hz), 6.55 (1H, bs), 7.25-7.33 (3H, m), 7.52-7.58 (3H, m), 8.02 (1H, d, J=9.0 Hz).

Example 8

2-{[3-(aminomethyl)-2-butyl-4-phenylquinolin-6-yl]oxy}acetamide 1) 3-oxoheptanenitrile (Synthesized according to a method similar to the method shown in Example 7(5).)

¹H-NMR (CDCl₃) δ: 0.92 (3H, t, J=7.4 Hz), 1.22-1.40 (2H, m), 1.53-1.68 (2H, m), 2.61 (2H, t, J=7.4 Hz), 3.49 (2H, s).

2) 2-butyl-6-hydroxy-4-phenylquinoline-3-carbonitrile (Synthesized according to a method similar to the method shown in Example 7(6).)

¹H-NMR (CDCl₃) δ: 0.98 (3H, t, J=7.2 Hz), 1.46-1.54 (2H, m), 1.81-1.92 (2H, m), 3.15-3.21 (2H, m), 6.91 (1H, d, J=2.7 Hz), 7.39-7.42 (3H, m), 7.51-7.56 (3H, m), 8.01 (1H, d, J=9.3 Hz), 10.19 (1H, s).

3) 2-[(2-butyl-3-cyano-4-phenylquinolin-6-yl)oxy]acetamide (Synthesized according to a method similar to the method shown in Example 7(7).)

¹H-NMR (CDCl₃) δ: 1.00 (3H, t, J=7.5 Hz), 1.48-1.60 (2H, m), 1.84-1.95 (2H, m), 3.19-3.24 (2H, m), 4.41 (2H, s), 5.65 (1H, bs), 6.52 (1H, bs), 6.92 (1H, d, J=2.7 Hz), 7.60-7.66 (2H, m), 7.50 (1H, dd, J=2.7, 8.7 Hz), 7.58-7.63 (3H, m), 8.08 (1H, d, J=8.7 Hz).

4) 2-{[3-(aminomethyl)-2-butyl-4-phenylquinolin-6-yl]oxy}acetamide (Synthesized according to a method similar to the method shown in Example 7(8).)

¹H-NMR (CDCl₃) δ: 1.00 (3H, t, J=7.4 Hz), 1.44-1.62 (2H, m), 1.84-1.90 (2H, m), 3.07-3.15 (2H, m), 3.77 (2H, s), 4.33 (2H, s), 5.68 (1H, bs), 6.55 (1H, d, J=3.0 Hz), 6.55 (1H, bs), 7.25-7.33 (3H, m), 7.52-7.57 (3H, m), 8.03 (1H, d, J=9.2 Hz).

Example 9

2-{[3-(aminomethyl)-2-pentyl-4-phenylquinolin-6-yl]oxy}acetamide 1) 3-oxooctanenitrile (Synthesized according to a method similar to the method shown in Example 7(5).)

¹H-NMR (CDCl₃) δ: 0.90 (3H, t, J=6.9 Hz), 1.25-1.34 (4H, m), 1.60-1.65 (2H, m), 2.61 (2H, t, J=6.9 Hz), 3.47 (2H, s).

2) 6-hydroxy-2-pentyl-4-phenylquinoline-3-carbonitrile (Synthesized according to a method similar to the method shown in Example 7(6).)

$^1$H-NMR (CDCl$_3$) δ: 0.89 (3H, t, J=7.2 Hz), 1.27-1.49 (4H, m), 1.82-1.91 (2H, m), 3.16 (2H, t, J=7.2 Hz), 6.66 (1H, bs), 6.92 (1H, d, J=2.7 Hz), 7.39-7.43 (3H, m), 7.52-7.54 (3H, m), 8.00 (1H, d, J=9.3 Hz).

3) 2-[(3-cyano-2-pentyl-4-phenylquinolin-6-yl)oxy]acetamide (Synthesized according to a method similar to the method shown in Example 7(7).)

$^1$H-NMR (DMSO-d$_6$) δ: 0.99 (3H, t, J=6.6 Hz), 1.45-1.55 (4H, m), 1.86-2.00 (2H, m), 3.16-3.23 (2H, m), 4.50 (2H, s), 6.96 (1H, d, J=2.6 Hz), 7.47 (1H, bs), 7.61-7.79 (6H, m), 8.05 (1H, bs), 8.18 (1H, d, J=9.0 Hz).

4) 2-{[3-(aminomethyl)-2-pentyl-4-phenylquinolin-6-yl]oxy}acetamide (Synthesized according to a method similar to the method shown in Example 7(8).)

$^1$H-NMR (CDCl$_3$) δ: 0.93 (3H, t, J=6.9 Hz), 1.39-1.54 (4H, m), 1.82-1.95 (2H, m), 3.07-3.13 (2H, m), 3.77 (2H, s), 4.33 (2H, s), 5.66 (1H, bs), 6.55 (1H, d, J=3.0 Hz), 6.55 (1H, bs), 7.25-7.29 (2H, m), 7.31 (1H, dd, J=3.0, 9.6 Hz), 7.51-7.58 (3H, m), 8.01 (1H, d, J=9.6 Hz).

Example 10

2-{[3-(aminomethyl)-2-(cyclopropylmethyl)-4-phenylquinolin-6-yl]oxy}acetamide 1) 4-cyclopropyl-3-oxobutanenitrile (Synthesized according to a method similar to the method shown in Example 7(5).)

$^1$H-NMR (CDCl$_3$) δ: 0.25-0.32 (2H, m), 0.60-0.74 (2H, m), 0.77-0.99 (1H, m), 2.56 (2H, d, J=7.5 Hz), 3.66 (2H, s).

2) 2-(cyclopropylmethyl)-6-hydroxy-4-phenylquinoline-3-carbonitrile (Synthesized according to a method similar to the method shown in Example 7 (6).)

$^1$H-NMR (DMSO-d$_6$) δ: 0.31-0.36 (2H, m), 0.48-0.54 (2H, m), 1.21-1.32 (1H, m), 3.00 (2H, d, J=6.9 Hz), 6.79 (1H, d, J=2.4 Hz), 7.42 (1H, dd, J=2.4, 9.3 Hz), 7.49-7.53 (2H, m), 7.59-7.64 (3H, m), 7.95 (1H, d, J=9.3 Hz).

3) 2-{[3-cyano-2-(cyclopropylmethyl)-4-phenylquinolin-6-yl]oxy}acetamide (Synthesized according to a method similar to the method shown in Example 7(7).)

$^1$H-NMR (DMSO-d$_6$) δ: 0.32-0.50 (2H, m), 0.51-0.55 (2H, m), 1.25-1.31 (1H, m), 3.02 (2H, d, J=6.9 Hz), 4.39 (2H, s), 6.87 (1H, d, J=2.4 Hz), 7.36 (1H, bs), 7.53-7.55 (2H, m), 7.56 (1H, bs), 7.56-7.67 (3H, m), 7.93 (1H, s), 8.06 (1H, d, J=9.6 Hz).

4) 2-{[3-(aminomethyl)-2-(cyclopropylmethyl)-4-phenylquinolin-6-yl]oxy}acetamide (Synthesized according to a method similar to the method shown in Example 7(8).)

$^1$H-NMR (CDCl$_3$) δ: 0.35-0.39 (2H, m), 0.54-0.60 (2H, m), 1.23-1.31 (1H, m), 3.08 (2H, d, J=5.6 Hz), 3.80 (2H, s), 4.33 (2H, s), 5.67 (1H, bs), 6.55 (1H, d, J=2.7 Hz), 6.56 (1H, bs), 7.26-7.30 (2H, m), 7.33 (1H, dd, J=2.7, 9.3 Hz), 7.52-7.56 (3H, m), 8.03 (1H, d, J=9.3 Hz).

Example 11

2-{[3-(aminomethyl)-2-(3-methylbutyl)-4-phenylquinolin-6-yl]oxy}acetamide 1) 6-methyl-3-oxoheptanenitrile (Synthesized according to a method similar to the method shown in Example 7(5).)

$^1$H-NMR (CDCl$_3$) δ: 0.83 (6H, d, J=5.8 Hz), 1.40-1.55 (3H, m), 2.50-2.58 (2H, m), 3.42 (2H, s).

2) 6-hydroxy-2-(3-methylbutyl)-4-phenylquinoline-3-carbonitrile (Synthesized according to a method similar to the method shown in Example 7(6).)

$^1$H-NMR (CDCl$_3$) δ: 0.98 (6H, d, J=6.3 Hz), 1.70-1.76 (4H, m), 3.14-3.20 (2H, m), 6.93 (1H, d, J=2.7 Hz), 7.38-7.44 (3H, m), 7.51-7.54 (3H, m), 8.01 (1H, d, J=9.3 Hz).

3) 2-{[3-cyano-2-(3-methylbutyl)-4-phenylquinolin-6-yl]oxy}acetamide (Synthesized according to a method similar to the method shown in Example 7(7).)

$^1$H-NMR (DMSO-d$_6$) δ: 0.95 (6H, d, J=6.3 Hz), 1.62-1.73 (3H, m), 3.06-3.12 (2H, m), 4.38 (2H, s), 6.85 (1H, d, J=3.0 Hz), 7.36 (1H, bs), 7.50-7.56 (3H, m), 7.56 (1H, bs), 7.61-7.65 (3H, m), 8.05 (1H, d, J=9.0 Hz).

4) 2-{[3-(aminomethyl)-2-(3-methylbutyl)-4-phenylquinolin-6-yl]oxy}acetamide (Synthesized according to a method similar to the method shown in Example 7(8).)

$^1$H-NMR (CDCl$_3$) δ: 1.01 (6H, d, J=6.3 Hz), 1.71-1.83 (3H, m), 3.08-3.13 (2H, m), 3.76 (2H, s), 4.32 (2H, s), 5.69 (1H, bs), 6.53 (1H, d, J=3.0 Hz), 6.54 (1H, bs), 7.24-7.26 (3H, m), 7.51-7.56 (3H, m), 8.00 (1H, d, J=9.0 Hz).

Example 12

2-{[3-(aminomethyl)-4-phenyl-2-(3,3,3-trifluoropropyl)quinolin-6-yl]oxy}acetamide 1) 6,6,6-trifluoro-3-oxohexanenitrile (Synthesized according to a method similar to the method shown in Example 7(5).)

$^1$H-NMR (CDCl$_3$) δ: 2.23-2.64 (2H, m), 2.87 (2H, t, J=6.0 Hz), 3.56 (2H, s).

2) 6-hydroxy-4-phenyl-2-(3,3,3-trifluoropropyl)quinoline-3-carbonitrile (Synthesized according to a method similar to the method shown in Example 7(6).)

$^1$H-NMR (CDCl$_3$) δ: 2.79-3.00 (2H, m), 3.43-3.53 (2H, m), 5.49 (1H, bs), 6.93 (1H, d, J=3.0 Hz), 7.40-7.47 (3H, m), 7.55-7.60 (3H, m), 8.03 (1H, d, J=9.0 Hz).

3) 2-{[3-cyano-4-phenyl-2-(3,3,3-trifluoropropyl)quinolin-6-yl]oxy}acetamide (Synthesized according to a method similar to the method shown in Example 7(7).)

$^1$H-NMR (CDCl$_3$) δ: 2.82-2.92 (2H, m), 3.46-3.52 (2H, m), 4.41 (2H, s), 5.73 (1H, bs), 6.52 (1H, bs), 6.93 (1H, d, J=3.0 Hz), 7.41-7.44 (2H, m), 7.52 (1H, dd, J=3.0, 9.0 Hz), 7.59-7.63 (3H, m), 8.0.8 (1H, d, J=9.0 Hz).

4) 2-{[3-(aminomethyl)-4-phenyl-2-(3,3,3-trifluoropropyl)quinolin-6-yl]oxy}acetamide (Synthesized according to a method similar to the method shown in Example 7(8).)

$^1$H-NMR (CDCl$_3$) δ: 2.88-2.96 (2H, m), 3.38-3.44 (2H, m), 3.77 (2H, s), 4.33 (2H, s), 5.65 (1H, bs), 6.56 (1H, d, J=2.7 Hz), 6.56 (1H, bs), 7.23-7.27 (2H, m), 7.33 (1H, dd, J=2.7, 9.3 Hz), 7.52-7.57 (3H, m), 8.05 (1H, d, J=9.3 Hz).

Example 13

2-{[3-(aminomethyl)-2-isobutyl-4-(4-methylphenyl)quinolin-6-yl]oxy}-N-methylacetamide Dihydrochloride 1) 6-hydroxy-2-isobutyl-4-(4-methylphenyl)quinoline-3-carbonitrile (Synthesized according to a method similar to the method shown in Example 7(6).)

$^1$H-NMR (CDCl$_3$) δ: 1.03 (6H, d, J=6.6 Hz), 2.30-2.38 (1H, m), 2.44 (3H, s), 3.06 (2H, d, J=7.5 Hz), 6.50 (1H, bs), 6.97 (1H, d, J=3.0 Hz), 7.25-7.43 (5H, m), 8.00 (1H, d, J=9.0 Hz).

2) A mixture of 6-hydroxy-2-isobutyl-4-(4-methylphenyl)quinoline-3-carbonitrile (10 g, 33 mmol), 25% aqueous ammonia (10 ml), Raney-cobalt (10 ml), methanol (50 ml) and tetrahydrofuran (50 ml) was stirred under a hydrogen atmosphere at 0.5 MPa, 70° C. for 8 hrs. The reaction mixture was filtered and water was added to the filtrate. The mixture was extracted with ethyl acetate, and the extract was washed with saturated brine, dried over anhydrous magnesium sulfate and concentrated under reduced pressure. The residue was dissolved in tetrahydrofuran (100 ml) and di-tert-butyl dicarbonate (7.8 g, 36 mmol) was added. The mixture was stirred at room temperature for 3 hrs. and concentrated under reduced pressure. The residue was purified by silica gel column chromatography to give tert-butyl {[6-hydroxy-2-isobutyl-4-(4-methylphenyl)quinolin-3-yl]methyl}carbamate (7.5 g, yield 54%) as pale-yellow crystals.

$^1$H-NMR (CDCl$_3$) δ: 0.97 (6H, d, J=6.6 Hz), 1.40 (9H, s), 2.22-2.27 (2H, m), 2.43 (3H, s), 2.91 (2H, d, J=7.2 Hz), 4.27 (2H, s), 6.63 (1H, d, J=3.0 Hz), 7.08 (1H, dd, J=3.0, 9.0 Hz), 7.09 (1H, bs), 7.21-7.29 (3H, m), 7.89 (1H, d, J=9.0 Hz).

3) A mixture of tert-butyl {[6-hydroxy-2-isobutyl-4-(4-methylphenyl)quinolin-3-yl]methyl}carbamate (1.5 g, 3.5 mmol), methyl bromoacetate (0.92 g, 6.0 mmol), potassium carbonate (0.55 g, 4.0 mmol) and N,N-dimethylformamide (5 ml) was stirred at room temperature for 4 hrs. Water was added to the reaction mixture and the mixture was extracted with ethyl acetate. The extract was washed with saturated brine, and dried over anhydrous magnesium sulfate. The residue was purified by silica gel column chromatography to give methyl {[3-{[(tert-butoxycarbonyl)amino]methyl}-2-isobutyl-4-(4-methylphenyl)quinolin-6-yl]oxy}acetate (1.9 g, yield 94%) as pale-yellow crystals.

$^1$H-NMR (DMSO-d$_6$) δ: 0.99 (6H, d, J=6.6 Hz), 1.35 (9H, s), 2.26-2.32 (1H, m), 2.43 (3H, s), 3.09-3.10 (2H, m), 3.60 (3H, s), 4.12 (2H, s), 6.54 (1H, s), 7.12 (1H, s), 7.29 (2H, d, J=7.8 Hz), 7.46 (2H, d, J=7.8 Hz), 7.55-7.77 (1H, m), 8.48-8.51 (1H, m).

4) To a solution of methyl {[3-{[(tert-butoxycarbonyl)amino]methyl}-2-isobutyl-4-(4-methylphenyl)quinolin-6-yl]oxy}acetate (1.6 g, 3.2 mmol) in tetrahydrofuran (5 ml)-methanol (5 ml) was added 1N aqueous sodium hydroxide solution (10 ml), and the mixture was stirred at room temperature for 3 hrs. The reaction mixture was acidified with 1N hydrochloric acid and the mixture was extracted with ethyl acetate. The extract was washed with saturated brine, and dried over anhydrous magnesium sulfate. The solvent was evaporated under reduced pressure and the residue was crystallized from diisopropyl ether to give {[3-{[(tert-butoxycarbonyl)amino]methyl}-2-isobutyl-4-(4-methylphenyl)quinolin-6-yl]oxy}acetic acid (1.3 g, yield 85%) as pale-yellow crystals.

$^1$H-NMR (DMSO-d$_6$) δ: 1.05 (6H, d, J=6.6 Hz), 1.40 (9H, s), 2.29-2.31 (1H, m), 2.48 (3H, s), 3.36 (2H, s), 4.35 (2H, s), 4.53 (2H, s), 4.89 (1H, bs), 6.71 (1H, s), 7.12-7.13 (2H, m), 7.27-7.40 (3H, m), 8.57 (1H, d, J=8.1 Hz).

5) To a solution of {[3-{[(tert-butoxycarbonyl)amino]methyl}-2-isobutyl-4-(4-methylphenyl)quinolin-6-yl]oxy}acetic acid (0.48 g, 1.0 mmol) in N,N-dimethylformamide (10 ml) were added 1-ethyl-3(3-dimethylaminopropyl)carbodiimide hydrochloride (0.23 g, 1.2 mmol), 1-hydroxy-1H-benzotriazole (0.16 g, 1.2 mmol) and 1.0 M solution of methylamine in tetrahydrofuran (2 ml) and the mixture was stirred at room temperature for 12 hrs. Water was added to the reaction mixture and the mixture was extracted with ethyl acetate. The extract was washed with 1N hydrochloric acid and saturated brine, and dried over anhydrous magnesium sulfate and concentrated under reduced pressure. The residue was purified by silica gel column chromatography to give tert-butyl {[2-isobutyl-6-[2-(methylamino)-2-oxoethoxy]-4-(4-methylphenyl)quinolin-3-yl]methyl}carbamate (0.27 g, yield 55%) as pale-yellow crystals.

$^1$H-NMR (CDCl$_3$) δ: 1.00 (6H, d, J=6.6 Hz), 1.41 (9H, s), 2.30-2.33 (1H, m), 2.49 (3H, s), 2.88-2.98 (5H, m), 4.28-4.34 (4H, m), 6.58-6.59 (1H, m), 6.60 (1H, bs), 7.07 (2H, d, J=8.1 Hz), 7.32 (2H, d, J=8.1 Hz), 7.33-7.34 (1H, m), 8.02 (1H, d, J=9.0 Hz).

6) To a solution of tert-butyl {[2-isobutyl-6-[2-(methylamino)-2-oxoethoxy]-4-(4-methylphenyl)quinolin-3-yl]methyl}carbamate (0.26 g, 0.53 mmol) in ethyl acetate (5 ml) was added 4N solution of hydrogen chloride in ethyl acetate (2 ml), and the mixture was stirred at room temperature for 3 hrs. The reaction mixture was concentrated under reduced pressure and crystallized from diisopropyl ether to give the title compound (0.20 g, yield 79%) as pale-yellow crystals.

$^1$H-NMR (DMSO-d$_6$) δ: 0.99 (6H, d, J=6.6 Hz), 2.26-2.30 (1H, m), 2.46 (3H, s), 2.58 (3H, s), 3.18 (2H, s), 3.97 (2H, s), 4.42 (2H, s), 6.64 (1H, s), 7.32 (2H, d, J=8.4 Hz), 7.44 (2H, d, J=8.4 Hz), 7.72-7.73 (1H, m), 8.07-8.08 (1H, m), 8.41 (3H, bs).

Example 14

2-{[3-(aminomethyl)-2-isobutyl-4-(4-methylphenyl)quinolin-6-yl]oxy}-N-isopropylacetamide Dihydrochloride 1) tert-butyl {[2-isobutyl-6-[2-(isopropylamino)-2-oxoethoxy]-4-(4-methylphenyl)quinolin-3-yl]methyl}carbamate (Synthesized according to a method similar to the method shown in Example 13(5).)

$^1$H-NMR (CDCl$_3$) δ: 1.02 (6H, d, J=6.6 Hz), 1.18 (6H, d, J=6.6 Hz), 1.41 (9H, s), 2.32-2.39 (1H, m), 2.49 (3H, s), 2.92 (2H, d, J=7.2 Hz), 4.09-4.18 (1H, m), 4.28 (4H, s), 6.37-6.38 (1H, m), 6.58 (1H, d, J=2.7 Hz), 7.08 (2H, d, J=7.8 Hz), 7.30-7.36 (3H, m), 7.98 (1H, d, J=9.0 Hz).

2) 2-{[3-(aminomethyl)-2-isobutyl-4-(4-methylphenyl)quinolin-6-yl]oxy}-N-isopropylacetamide dihydrochloride (Synthesized according to a method similar to the method shown in Example 13(6).)

$^1$H-NMR (DMSO-d$_6$) δ: 1.00 (12H, d, J=6.6 Hz), 2.28-2.30 (1H, m), 2.45 (3H, s), 3.23 (2H, s), 3.79-3.84 (1H, m), 3.97 (2H, s), 4.40 (2H, s), 6.60 (2H, s), 7.33 (2H, d, J=6.9 Hz), 7.44 (2H, d, J=6.9 Hz), 7.72-7.73 (1H, m), 7.92 (1H, s), 8.47 (3H, bs).

Example 15

2-{[3-(aminomethyl)-2-isobutyl-4-(4-methylphenyl)quinolin-6-yl]oxy}-N-(methylsulfonyl)Acetamide Dihydrochloride 1) To a solution of {[3-{[(tert-butoxycarbonyl)amino]methyl}-2-isobutyl-4-(4-methylphenyl)quinolin-6-yl]oxy}acetic acid (0.25 g, 0.52 mmol) in N,N-dimethylformamide (5 ml) was added di(N-succinimidyl) carbonate (0.42 g, 2.6 mmol), and the mixture was stirred at room temperature for 1 hr. To the reaction mixture were added methanesulfonamide (0.25 g, 2.6 mmol) and 1,8-diazabicyclo[5.4.0]-7-undecene (0.40 ml, 2.6 mmol), and the mixture was stirred at 100° C. for 5 hrs. The reaction mixture was cooled to room temperature and water was poured thereinto. The mixture was extracted with ethyl acetate and the extract was washed with saturated brine, and dried over anhydrous magnesium sulfate. The solvent was evaporated and the residue was crystallized from n-hexane-diisopropyl ether to give tert-butyl [(2-isobutyl-4-(4-methylphenyl)-6-{2-[(methylsulfonyl)amino]-2-oxoethoxy}quinolin-3-yl)methyl]carbamate (0.29 g, yield 98%) as pale-yellow crystals.

$^1$H-NMR (CDCl$_3$) δ: 1.02 (6H, d, J=6.6 Hz), 1.41 (9H, s), 2.33-2.38 (1H, m), 2.50 (3H, s), 2.85-2.90 (2H, m), 3.32 (3H, s), 4.31-4.32 (2H, m), 4.48 (2H, s), 6.62 (1H, s), 7.10-7.13 (2H, m), 7.35-7.39 (3H, m), 8.02 (1H, s), 8.17 (1H, bs).

2) 2-{[3-(aminomethyl)-2-isobutyl-4-(4-methylphenyl)quinolin-6-yl]oxy}-N-(methylsulfonyl)acetamide dihydrochloride (Synthesized according to a method similar to the method shown in Example 13(6).)

$^1$H-NMR (DMSO-d$_6$) δ: 0.99 (6H, d, J=6.6 Hz), 2.26-2.30 (1H, m), 2.45 (3H, s), 3.17 (3H, s), 3.17-3.18 (2H, m), 3.97-3.99 (2H, m), 4.67 (2H, s), 6.56 (1H, d, J=2.4 Hz), 7.32 (2H, d, J=8.7 Hz), 7.45 (2H, d, J=8.7 Hz), 7.72-7.74 (2H, m), 8.42 (3H, bs).

Example 16

3-(aminomethyl)-2-isobutyl-4-(4-methylphenyl)quinolin-6-ol Dihydrochloride (Synthesized According to a Method Similar to the Method Shown in Example 13(6)

$^1$H-NMR (DMSO-d$_6$) δ: 1.00 (6H, d, J=6.3 Hz), 2.20-2.31 (1H, m), 2.45 (3H, s), 3.29 (2H, s), 3.97-3.99 (2H, m), 6.66 (1H, s), 7.37 (2H, d, J=7.8 Hz), 7.46 (2H, d, J=7.5 Hz), 7.61-7.64 (1H, m), 8.45 (1H, s), 8.57 (3H, bs), 10.69 (1H, bs).

Example 17

Methyl {[3-(aminomethyl)-2-isobutyl-4-(4-methylphenyl)quinolin-6-yl]oxy}acetate Dihydrochloride (Synthesized According to a Method Similar to the Method Shown in Example 13(6)

$^1$H-NMR (DMSO-d$_6$) δ: 1.00 (6H, d, J=6.6 Hz), 2.24-2.32 (1H, m), 2.46 (3H, s), 3.25 (2H, s), 3.59 (3H, s), 3.97-3.99 (2H, m), 4.75 (2H, s), 6.49 (1H, s), 7.33 (2H, d, J=7.5 Hz), 7.45 (2H, d, J=7.5 Hz), 7.72-7.75 (2H, m), 8.39-8.42 (1H, m), 8.56 (3H, bs).

Example 18

{[3-(aminomethyl)-2-isobutyl-4-(4-methylphenyl)quinolin-6-yl]oxy}acetic Acid Dihydrochloride (Synthesized According to a Method Similar to the Method Shown in Example 13(6)

$^1$H-NMR (DMSO-d$_6$) δ: 1.00 (6H, d, J=6.6 Hz), 2.20-2.31 (1H, m), 2.45 (3H, s), 3.20 (2H, s), 3.97-3.99 (2H, m), 4.64 (2H, s), 6.57 (1H, d, J=2.7 Hz), 7.32 (2H, d, J=8.1 Hz), 7.40 (2H, d, J=8.1 Hz), 7.72 (1H, bs), 8.46 (3H, bs).

Example 19

(2E)-3-[3-(aminomethyl)-2-isobutyl-4-(4-methylphenyl)quinolin-6-yl]acrylamide Dihydrochloride 1) To a solution of tert-butyl {[6-hydroxy-2-isobutyl-4-(4-methylphenyl)quinolin-3-yl]methyl}carbamate (1.5 g, 3.6 mmol) in N,N-dimethylformamide (10 ml) was added sodium hydride (60% in oil, 0.21 g, 5.4 mmol) under ice-cooling, and the mixture was stirred for 10 min. To the reaction mixture was added N-phenylbis(trifluoromethanesulfonimide) (1.9 g, 5.4 mmol), and the mixture was stirred at room temperature for 30 min. Water was added to the reaction mixture and the mixture was extracted with ethyl acetate. The extract was washed with saturated brine, and dried over anhydrous magnesium sulfate. The solvent was evaporated under reduced pressure and the residue was crystallized from diisopropyl ether to give 3-{[(tert-butoxycarbonyl)amino]methyl}-2-isobutyl-4-(4-methylphenyl)quinolin-6-yl trifluoromethanesulfonate (1.5 g, yield 75%) as pale-yellow crystals.

$^1$H-NMR (CDCl$_3$) δ: 1.01 (6H, d, J=6.6 Hz), 1.41 (9H, s), 2.33-2.420 (1H, m), 2.49 (3H, s), 2.97-3.01 (2H, m), 4.33 (2H, s), 7.12 (2H, d, J=8.0 Hz), 7.25 (1H, d, J=3.0 Hz), 7.36 (2H, d, J=8.0 Hz), 7.52 (1H, dd, J=3.0, 7.4 Hz), 8.13 (1H, d, J=7.4 Hz).

2) To a solution of 3-{[(tert-butoxycarbonyl)amino]methyl}-2-isobutyl-4-(4-methylphenyl)quinolin-6-yl trifluoromethanesulfonate (1.5 g, 2.8 mmol) in N,N-dimethylformamide (10 ml) were added dichlorobistriphenylphosphine palladium (0.021 g, 0.030 mmol), triethylamine (4.2 ml, 30 mmol) and ethyl acrylate (0.65 ml, 6.0 mmol) and the mixture was stirred at 70° C. for 6 hrs. Water was added to the reaction mixture and the mixture was extracted with ethyl acetate. The extract was washed with saturated brine, and dried over anhydrous magnesium sulfate. The solvent was evaporated under reduced pressure and the residue was purified by silica gel column chromatography to give ethyl (2E)-3-[3-{[(tert-butoxycarbonyl)amino]methyl}-2-isobutyl-4-(4-methylphenyl)quinolin-6-yl]acrylate (0.87 g, yield 62%) as pale-yellow crystals.

$^1$H-NMR (CDCl$_3$) δ: 1.05 (6H, d, J=6.6 Hz), 1.32 (3H, t, J=7.2 Hz), 1.41 (9H, s), 2.34-2.39 (1H, m), 2.51 (3H, s), 4.25 (2H, q, J=7.2 Hz), 4.33-4.36 (4H, m), 6.41 (1H, d, J=15.9 Hz), 7.12 (2H, d, J=7.8 Hz), 7.36 (2H, d, J=7.8 Hz), 7.41 (1H, s), 7.63 (1H, d, J=15.9 Hz), 7.89-7.91 (1H, m), 8.13-8.14 (1H, m).

3) To a solution of ethyl (2E)-3-[3-{[(tert-butoxycarbonyl)amino]methyl}-2-isobutyl-4-(4-methylphenyl)quinolin-6-yl]acrylate (0.62 g, 1.3 mmol) in tetrahydrofuran (5 ml)-methanol (5 ml) was added 1N aqueous sodium hydroxide solution (5 ml), and the mixture was stirred at room temperature for 12 hrs. The mixture was acidified with 1N hydrochloric acid and extracted with ethyl acetate. The extract was washed with saturated brine, and dried over anhydrous magnesium sulfate. The solvent was evaporated under reduced pressure and the residue was crystallized from diisopropyl ether to give (2E)-3-[3-{[(tert-butoxycarbonyl)amino]methyl}-2-isobutyl-4-(4-methylphenyl)quinolin-6-yl]acrylic acid (0.41 g, yield 70%) as pale-yellow crystals.

$^1$H-NMR (CDCl$_3$) δ: 1.13 (6H, d, J=6.6 Hz), 1.41 (9H, s), 2.36-2.39 (1H, m), 2.52 (3H, s), 3.15 (2H, s), 4.35 (2H, s), 4.30-4.40 (1H, m), 6.43 (1H, d, J=15.6 Hz), 7.14 (2H, d, J=8.1 Hz), 7.26 (1H, s), 7.28 (2H, d, J=8.1 Hz), 7.45 (1H, s), 7.70 (1H, d, J=15.6 Hz), 7.93 (1H, s).

4) To a solution of (2E)-3-[(3-{[(tert-butoxycarbonyl)amino]methyl}-2-isobutyl-4-(4-methylphenyl)quinolin-6-yl]acrylic acid (0.30 g, 0.63 mmol) in N,N-dimethylformamide (10 ml) were added 1-ethyl-3-(3-dimethylaminopropyl)carbodiimide hydrochloride (0.23 g, 1.2 mmol) and 1-hydroxy-1H-benzotriazole ammonium salt (0.18 g, 1.2 mmol) and the mixture was stirred at room temperature for 12 hrs. Water was added to the reaction mixture and the mixture was extracted with ethyl acetate. The extract was washed with 1N hydrochloric acid and saturated brine, dried over anhydrous magnesium sulfate and concentrated under reduced pressure. The residue was purified by silica gel column chromatography to give tert-butyl {[6-[(1E)-3-amino-3-oxoprop- 1-en-1-yl]-2-isobutyl-4-(4-methylphenyl)quinolin-3-yl]methyl}carbamate (0.25 g, yield 83%) as pale-yellow crystals.

$^1$H-NMR (CDCl$_3$) δ: 1.03 (6H, d, J=6.6 Hz), 1.41 (9H, s), 2.35-2.39 (1H, m), 2.50 (3H, s), 2.97 (2H, d, J=7.2 Hz), 4.32 (2H, s), 5.49 (2H, bs), 6.42 (1H, d, J=15.6 Hz), 7.11 (2H, d, J=8.1 Hz), 7.33-7.37 (3H, m), 7.58 (1H, d, J=15.6 Hz), 7.82 (1H, dd, J=2.1, 8.1 Hz), 8.04 (1H, d, J=8.7 Hz).

5) (2E)-3-[3-(aminomethyl)-2-isobutyl-4-(4-methylphenyl)quinolin-6-yl]acrylamide Dihydrochloride (Synthesized According to a Method Similar to the Method Shown in Example 13(6)

$^1$H-NMR (DMSO-d$_6$) δ: 0.98 (6H, d, J=6.6 Hz), 2.28-2.30 (1H, m), 2.43 (3H, s), 3.18-3.19 (2H, m), 3.94-3.96 (2H, m), 6.60 (1H, d, J=15.6 Hz), 7.11-7.12 (1H, m), 7.35-7.45 (5H, m), 7.56 (1H, d, J=15.6 Hz), 7.60-7.62 (1H, m), 8.13-8.14 (1H, m), 8.45 (3H, bs).

Example 20

(2E)-3-[3-(aminomethyl)-2-isobutyl-4-(4-methylphenyl)quinolin-6-yl]acrylic Acid Dihydrochloride (Synthesized According to a Method Similar to the Method Shown in Example 13(6)

$^1$H-NMR (DMSO-d$_6$) δ: 1.01 (6H, d, J=6.6 Hz), 2.24-2.39 (1H, m), 2.46 (3H, s), 3.09 (2H, s), 3.96-3.99 (2H, m), 6.52 (1H, d, J=15.9 Hz), 7.33 (2H, d, J=8.1 Hz), 7.43-7.46 (3H, m), 7.56 (1H, d, J=15.9 Hz), 8.16-8.26 (2H, m), 8.36 (3H, bs).

Example 21

Ethyl (2E)-3-[3-(aminomethyl)-2-isobutyl-4-(4-methylphenyl)quinolin-6-yl]acrylate Dihydrochloride (Synthesized According to a Method Similar to the Method Shown in Example 13(6)

$^1$H-NMR (DMSO-d$_6$) δ: 1.00 (6H, d, J=6.6 Hz), 1.22 (3H, t, J=7.2 Hz), 2.31-2.34 (1H, m), 2.46 (3H, s), 3.21 (2H, s), 3.97 (2H, s), 4.15 (2H, q, J=7.2 Hz), 6.67 (1H, d, J=15.9 Hz), 7.36 (2H, d, J=7.8 Hz), 7.45 (2H, d, J=7.8 Hz), 7.52 (1H, s), 7.65 (1H, d, J=15.9 Hz), 8.36 (2H, s), 8.52 (3H, bs).

Example 22

Ethyl 4-({[3-(aminomethyl)-2-isobutyl-4-(4-methylphenyl)quinolin-6-yl]oxy}methyl)-2-furoate Dihydrochloride 1) To a solution of tert-butyl {[6-hydroxy-2-isobutyl-4-(4-methylphenyl)quinolin-3-yl]methyl}carbamate (0.40 g, 0.95 mmol) in N,N-dimethylformamide (10 ml) were added potassium carbonate (0.28 g, 2.0 mmol) and ethyl 5-chloromethyl-2-furancarboxylate (0.38 g, 2.0 mmol) and the mixture was stirred at room temperature for 6 hrs. Water was added to the reaction mixture and the mixture was extracted with ethyl acetate. The extract was washed with saturated brine, and dried over anhydrous magnesium sulfate. The solvent was evaporated under reduced pressure and the residue was purified by silica gel column chromatography to give ethyl 4-({[3-{[(tert-butoxycarbonyl)amino]methyl}-2-isobutyl-4-(4-methylphenyl)quinolin-6-yl]oxy}methyl)-2-furoate (0.43 g, yield 80%) as pale-yellow crystals.

$^1$H-NMR (CDCl$_3$) δ: 1.09 (6H, d, J=6.0 Hz), 1.37 (3H, t, J=7.2 Hz), 1.40 (9H, s), 2.35-2.39 (1H, m), 2.52 (3H, s), 4.35 (2H, s), 4.35 (2H, q, J=7.2 Hz), 4.38 (2H, s), 4.92 (2H, s), 6.40 (1H, d, J=3.6 Hz), 6.72 (1H, s), 7.11-7.16 (3H, m), 7.39-7.41 (2H, m).

2) ethyl 4-({[3-(aminomethyl)-2-isobutyl-4-(4-methylphenyl)quinolin-6-yl]oxy}methyl)-2-furoate Dihydrochloride (Synthesized According to a Method Similar to the Method Shown in Example 13(6)

$^1$H-NMR (DMSO-d$_6$) δ: 1.01 (6H, d, J=6.0 Hz), 1.26 (3H, t, J=6.9 Hz), 2.26-2.30 (1H, m), 2.46 (3H, s), 3.28 (2H, s), 3.99 (2H, s), 4.25 (2H, q, J=6.9 Hz), 5.14 (2H, s), 6.53-6.56 (1H, m), 6.74-6.75 (1H, m), 7.24 (1H, d, J=3.3 Hz), 7.35 (2H, d, J=7.5 Hz), 7.45 (2H, d, J=7.5 Hz), 7.81-7.84 (1H, m), 8.51 (1H, s), 8.58 (3H, bs).

Example 23

({2-isobutyl-4-(4-methylphenyl)-6-[(2-methyl-1,3-thiazol-4-yl)methoxy]quinolin-3-yl}methyl)amine Dihydrochloride 1) To a solution of tert-butyl {[6-hydroxy-2-isobutyl-4-(4-methylphenyl)quinolin-3-yl]methyl}carbamate (0.40 g, 0.95 mmol) in N,N-dimethylformamide (10 ml) were added potassium carbonate (0.28 g, 2.0 mmol), 4-(chloromethyl)-2-methyl-1,3-thiazole hydrochloride (0.37 g, 2.0 mmol) and triethylamine (0.31 ml, 2.2 mmol) and the mixture was stirred at room temperature for 6 hrs. Water was added to the reaction mixture and the mixture was extracted with ethyl acetate. The extract was washed with saturated brine, dried over anhydrous magnesium sulfate and concentrated under reduced pressure. The residue was purified by silica gel column chromatography to give tert-butyl ({2-isobutyl-4-(4-methylphenyl)-6-[(2-methyl-1,3-thiazol-4-yl)methoxy]quinolin-3-yl}methyl)carbamate (0.32 g, yield 63%) as pale-yellow crystals.

$^1$H-NMR (CDCl$_3$) δ: 1.11 (6H, d, J=6.6 Hz), 1.40 (9H, s), 2.35-2.40 (1H, m), 2.53 (3H, s), 2.70 (3H, s), 3.50-3.53 (2H, m), 4.36 (2H, s), 4.39 (1H, bs), 5.02 (2H, s), 6.80 (1H, s), 7.09 (1H, s), 7.15 (2H, d, J=7.5 Hz), 7.42 (2H, d, J=7.5 Hz), 7.63 (1H, dd, J=2.7, 9.3 Hz), 9.10 (1H, d, J=9.3 Hz).

2) ({2-isobutyl-4-(4-methylphenyl)-6-[(2-methyl-1,3-thiazol-4-yl)methoxy]quinolin-3-yl}methyl)amine Dihydrochloride (Synthesized According to a Method Similar to the Method Shown in Example 13(6)

$^1$H-NMR (DMSO-d$_6$) δ: 1.01 (6H, d, J=6.6 Hz), 2.16-2.30 (1H, m), 2.46 (3H, s), 2.60 (3H, s), 3.35-3.38 (2H, m), 3.99 (2H, s), 5.08 (2H, s), 6.82 (2H, s), 7.35-7.39 (3H, m), 7.44-7.47 (2H, m), 7.88-7.89 (1H, m), 8.63 (3H, bs).

Example 24

{[6-[(3,5-dimethylisoxazol-4-yl)methoxy]2-isobutyl-4-(4-methylphenyl)quinolin-3-yl]methyl}amine Dihydrochloride 1) To a solution of tert-butyl {([6-hydroxy-2-isobutyl-4-(4-methylphenyl)quinolin-3-yl]methyl}carbamate (0.40 g, 0.95 mmol) in N,N-dimethylformamide (10 ml) were added potassium carbonate (0.28 g, 2.0 mmol) and 4-(chloromethyl)-3,5-dimethylisoxazole (0.29 g, 2.0 mmol) and the mixture was stirred at room temperature for 6 hrs. Water was added to the reaction mixture and the mixture was extracted with ethyl acetate. The extract was washed with saturated brine, dried over anhydrous magnesium sulfate and concentrated under reduced pressure. The residue was purified by silica gel column chromatography to give tert-butyl {[(6-[(3,5-dimethylisoxazol-4-yl)methoxy]-2-isobutyl-4-(4-methylphenyl)quinolin-3-yl]methyl}carbamate (0.38 g, yield 75%) as pale-yellow crystals.

¹H-NMR (CDCl₃) δ: 1.11 (6H, d, J=6.6 Hz), 1.39 (9H, s), 2.17 (3H, s), 2.24 (3H, s), 2.31-2.41 (1H, m), 2.53 (3H, s), 3.49-3.52 (2H, m), 4.35-4.38 (2H, m), 4.47 (1H, bs), 4.72 (2H, s), 6.70 (1H, d, J=2.7 Hz), 7.18 (2H, d, J=8.1 Hz), 7.46 (2H, d, J=8.1 Hz), 7.57 (1H, dd, J=2.7, 9.0 Hz), 9.12 (1H, d, J=9.0 Hz).

2) {[6-[(3,5-dimethylisoxazol-4-yl)methoxy]-2-isobutyl-4-(4-methylphenyl)quinolin-3-yl]methyl}amine dihydrochloride (Synthesized According to a Method Similar to the Method Shown in Example 13(6)

¹H-NMR (DMSO-d₆) δ: 1.00 (6H, d, J=6.6 Hz), 2.08 (3H, s), 2.18 (3H, s), 2.25-2.29 (1H, m), 2.46 (3H, s), 3.23-3.24 (2H, m), 3.94-3.99 (2H, m), 4.89 (2H, s), 6.68 (1H, d, J=2.7 Hz), 7.35 (2H, d, J=8.1 Hz), 7.45 (2H, d, J=8.1 Hz), 7.73-7.75 (1H, m), 8.49 (3H, bs).

Example 25

(2-isobutyl-6-methoxy-4-phenylquinolin-3-yl)methylamine 1) 2-isobutyl-6-methoxy-4-phenylquinoline-3-carbonitrile (Synthesized according to a method similar to a the method shown in Example 7(6).)

¹H-NMR (CDCl₃) δ: 1.06 (6H, d, J=6.6 Hz), 2.25-2.50 (1H, m), 3.09 (2H, d, J=7.3 Hz), 3.74 (3H, s), 6.84 (1H, d, J=2.9 Hz), 7.40-7.50 (2H, m), 7.44 (1H, d, J=2.9 Hz), 7.55-7.65 (3H, m), 8.03 (1H, d, J=9.5 Hz).

melting point: 107-109° C.

2) To a mixture of 2-isobutyl-6-methoxy-4-phenylquinoline-3-carbonitrile (1.00 g, 3.16 mmol), 25% aqueous ammonia (4 ml), tetrahydrofuran (30 ml) and methanol (50 ml) was added Raney-nickel (1 ml) and the mixture was stirred under a hydrogen atmosphere at 0.5 MPa, room temperature for 6 hrs. The reaction mixture was filtered, and the filtrate was concentrated under reduced pressure. The residue was purified by silica gel column chromatography and recrystallized from n-hexane-ethyl acetate to give the title compound (0.44 g, yield 44%) as colorless crystals.

¹H-NMR (CDCl₃) δ: 1.04 (6H, d, J=6.6 Hz), 1.49 (2H, bs), 2.25-2.45 (1H, m), 2.53 (2H, d, J=7.3 Hz), 3.66 (3H, s), 3.77 (2H, s), 6.51 (1H, d, J=2.7 Hz), 7.25-7.35 (3H, m), 7.45-7.60 (3H, m), 8.06 (1H, d, J=9.5 Hz).

elemental analysis for $C_{21}H_{24}N_2O$.

Calculated: C, 78.71; H, 7.55; N, 8.74

Found: C, 78.70; H, 7.65; N, 8.66.

melting point: 73-76° C.

Example 26

2-{[3-(aminomethyl)-4-(2-fluorophenyl)-2-isobutylquinolin-6-yl]oxy}acetamide Dihydrochloride 1) 6-bromo-4-(2-fluorophenyl)-2-isobutylquinoline-3-carbonitrile (Synthesized according to a method similar to the method shown in Example 7(6).)

¹H-NMR (CDCl₃) δ: 1.06 (6H, d, J=6.6 Hz), 2.30-2.50 (1H, m), 3.12 (2H, d, J=7.2 Hz), 7.30-7.45 (3H, m), 7.55-7.70 (2H, m), 7.89 (1H, dd, J=2.1, 8.9 Hz), 8.02 (1H, d, J=8.9 Hz).

melting point: 128-129° C.

2) Palladium acetate (0.015 g, 0.65 mmol) and racemic-2,2'-bis(diphenylphosphino)-1,1'-binaphthyl (0.12 g, 0.19 mmol) were added to toluene (10 ml) under a nitrogen atmosphere and the mixture was stirred at 40° C. for 30 min. The reaction mixture was cooled to room temperature and 6-bromo-4-(2-fluorophenyl)-2-isobutylquinoline-3-carbonitrile (0.50 g, 1.30 mmol), tert-butanol (0.25 ml, 2.61 mmol) and sodium tert-butoxide (0.188 g, 1.96 mmol) were added, and the mixture was stirred under a nitrogen atmosphere at 90° C. for 1 hr. The reaction mixture was cooled and 0.1N hydrochloric acid (10 ml) was added and the mixture was stirred at room temperature for 30 min. Toluene (50 ml) was added to the reaction mixture. The organic layer was washed with water (10 ml), and dried over anhydrous magnesium sulfate. The solvent was evaporated under reduced pressure, and the residue was purified by silica gel column chromatography and crystallized from n-hexane to give 6-tert-butoxy-4-(2-fluorophenyl)-2-isobutylquinoline-3-carbonitrile (0.40 g; yield 82%) as pale-yellow crystals.

¹H-NMR (CDCl₃) δ: 1.06 (6H, d, J=6.6 Hz), 1.34 (9H, s), 2.25-2.50 (1H, m), 3.06 (2H, d, J=7.0 Hz), 7.00-7.10 (1H, m), 7.25-7.40 (3H, m), 7.50 (1H, dd, J=2.6, 9.2 Hz), 7.55-7.65 (1H, m), 8.04 (1H, d, J=9.2 Hz).

melting point: 127-129° C.

3) To a solution of 6-tert-butoxy-4-(2-fluorophenyl)-2-isobutylquinoline-3-carbonitrile (0.22 g, 0.58 mmol) in tetrahydrofuran (1 ml) was added trifluoroacetic acid (5 ml), and the mixture was stirred at room temperature for 30 min. The reaction mixture was concentrated and the obtained crude crystals were recrystallized from n-hexane-ethyl acetate to give 4(2-fluorophenyl)-6-hydroxy-2-isobutylquinoline-3-carbonitrile (0.17 g, yield 92%) as pale-yellow crystals.

¹H-NMR (CDCl₃) δ: 1.04 (6H, d, J=7.0 Hz), 2.25-2.45 (1H, m), 3.09 (2H, d, J=7.3 Hz), 6.19 (1H, bs), 6.75-6.85 (1H, m), 7.20-7.40 (3H, m), 7.43 (1H, dd, J=2.6, 9.2 Hz), 7.45-7.65 (1H, m), 8.04 (1H, d, J=9.2 Hz).

melting point: 256-257° C.

4) 2-{[3-cyano-4-(2-fluorophenyl)-2-isobutylquinolin-6-yl]oxy}acetamide (Synthesized According to a Method Similar to the Method Shown in Example 7(7)

¹H-NMR (CDCl₃) δ: 1.06 (6H, d, J=6.6 Hz), 2.25-2.50 (1H, m), 3.11 (2H, d, J=7.3 Hz), 4.43 (2H, s), 5.69 (1H, bs), 6.51 (1H, bs), 6.75-6.85 (1H, m), 7.25-7.45 (3H, m), 7.52 (1H, dd, J=2.9, 9.4 Hz), 7.55-7.70 (1H, m), 8.11 (1H, d, J=9.4 Hz).

melting point: 163-165° C.

5) To a mixture of 2-{[3-cyano-4-(2-fluorophenyl)-2-isobutylquinolin-6-yl]oxy}acetamide (0.11 g, 0.29 mmol), 25% aqueous ammonia (2 ml), tetrahydrofuran (2 ml) and methanol (10 ml) was added Raney-nickel (1 ml), and the mixture was stirred under a hydrogen (0.5 MPa) atmosphere at room temperature for 6 hrs. The reaction mixture was filtered, and the filtrate was partitioned between ethyl acetate (50 ml) and 10% aqueous potassium carbonate solution (25 ml). The organic layer was washed with saturated brine (10 ml) and dried over anhydrous magnesium sulfate. The solvent was evaporated under reduced pressure and the residue was purified by silica gel column chromatography to give a colorless oil. This was dissolved in ethyl acetate (2 ml) and 4N solution of hydrogen chloride in ethyl acetate (1 ml) was added. The reaction mixture was concentrated and the obtained crude crystals were recrystallized from diisopropyl ether-methanol to give the title compound (0.078 g, yield 59%) as pale-yellow crystals.

¹H-NMR (DMSO-d₆) δ: 1.02 (6H, dd, J=6.6, 7.5 Hz), 2.25-2.40 (1H, m), 3.05-3.20 (2H, m), 3.75-3.95 (1H, m), 4.05-4.25 (1H, m), 4.39 (2H, s), 6.59 (1H, bs), 7.37 (1H, bs), 7.45-7.80 (6H, m), 8.20-8.35 (1H, m), 8.46 (3H, bs).

melting point: 212° C. (decomp.)

Example 27

2-{[3-(aminomethyl)-2-isobutyl-4-phenylquinolin-6-yl]oxy}acetamide Dihydrochloride 1) To a solution of (2-isobutyl-6-methoxy-4-phenylquinolin-3-yl)methylamine (0.50 g, 1.57 mmol) in dichloromethane (10 ml) was added 1.0 M solution (3.9 ml) of boron tribromide in dichloromethane, and the mixture was stirred at room temperature for 20 hrs. To the reaction mixture were added ethyl acetate (100 ml) and saturated aqueous sodium hydrogen carbonate (50 ml) and the mixture was stirred at room temperature for 17 hrs. The organic layer was separated, washed twice with saturated aqueous sodium hydrogen carbonate (20 ml) and once with saturated brine (10 ml), and dried over anhydrous magnesium sulfate. The solvent was evaporated under reduced pressure and the residue was dissolved in tetrahydrofuran (10 ml). Di-tert-butyl dicarbonate (0.37 ml, 1.6 mmol) was added and the mixture was stirred at room temperature for 1 hr. The reaction mixture was partitioned between ethyl acetate (100 ml) and saturated brine (20 ml). The organic layer was dried over anhydrous magnesium sulfate, and the solvent was evaporated under reduced pressure. The obtained crude crystals were recrystallized from toluene-ethyl acetate to give tert-butyl (6-hydroxy-2-isobutyl-4-phenylquinolin-3-yl)methylcarbamate (0.53 g, yield 83%) as colorless crystals.

$^1$H-NMR (DMSO-d$_6$) δ: 0.97 (6H, d, J=6.6 Hz), 1.37 (9H, s), 2.25-2.45 (1H, m), 2.75 (2H, d, J=7.0 Hz), 3.54 (2H, d, J=4.4 Hz), 6.46 (1H, d, J=2.6 Hz), 7.00 (1H, t, J=4.4 Hz), 7.10-7.25 (2H, m), 7.30-7.60 (4H, m), 7.82 (1H, d, J=9.2 Hz), 9.69 (1H, s).

melting point: 225° C. (decomp.)

2) tert-butyl [6-(2-amino-2-oxoethoxy)-2-isobutyl-4-phenylquinolin-3-yl]methylcarbamate (Synthesized According to a Method Similar to the Method Shown in Example 7(7)

$^1$H-NMR (CDCl$_3$) δ: 1.03 (6H, d, J=7.0 Hz), 1.41 (9H, s), 2.25-2.50 (1H, m), 2.92 (2H, d, J=7.3 Hz), 4.25-4.35 (3H, m), 4.33 (2H, s), 5.63 (1H, bs), 6.55 (1H, bs), 6.57 (1H, d, J=2.6 Hz), 7.15-7.25 (2H, m), 7.40 (1H, dd, J=2.6, 9.2 Hz), 7.50-7.60 (3H, m), 8.03 (1H, d, J=9.2 Hz).

melting point: 201-202° C.

3) To a solution of tert-butyl [6-(2-amino-2-oxoethoxy)-2-isobutyl-4-phenylquinolin-3-yl]methylcarbamate (0.10 g, 0.21 mmol) in tetrahydrofuran (5 ml) was added trifluoroacetic acid (5 ml), and the mixture was stirred at room temperature for 2 hrs. The reaction mixture was partitioned between ethyl acetate (50 ml) and 10% aqueous potassium carbonate solution (100 ml). The aqueous layer was separated and extracted twice with ethyl acetate-isopropanol (10:1, 25 ml). The organic layer and the extract were combined and washed with saturated brine (10 ml), and dried over anhydrous magnesium sulfate. The solvent was evaporated under reduced pressure and the residue was purified by silica gel column chromatography to give a colorless oil. The obtained colorless oil was dissolved in ethyl acetate (2 ml) and 4N solution of hydrogen chloride in ethyl acetate (1 ml) was added. The reaction mixture was concentrated and the obtained residue was crystallized from diisopropyl ether-methanol to give the title compound (0.062 g, yield 67%) as pale-yellow crystals.

$^1$H-NMR (DMSO-d$_6$) δ: 1.03 (6H, d, J=6.4 Hz), 2.20-2.40 (1H, m), 3.20 (2H, d, J=7.3 Hz), 3.98 (2H, d, J=5.3 Hz), 4.38 (2H, s), 6.62 (1H, d, J=2.5 Hz), 7.36 (1H, bs), 7.40-7.50 (2H, m), 7.59 (1H, bs), 7.60-7.70 (3H, m), 7.71 (1H, d, J=11.1 Hz), 8.25-8.40 (1H, m), 8.48 (3H, bs).

melting point: 256-257° C.

Example 28

2-{[3-(aminomethyl)-2-isobutyl-4-(4-methylphenyl)quinolin-6-yl]oxy}acetamide 1) 2-{[3-cyano-2-isobutyl-4-(4-methylphenyl)quinolin-6-yl]oxy}acetamide (Synthesized according to a method similar to the method shown in Example 7(7).)

$^1$H-NMR (CDCl$_3$) δ: 1.05 (6H, d, J=6.6 Hz), 2.30-2.50 (1H, m), 2.51 (3H, s), 3.04 (2H, d, J=7.3 Hz), 4.42 (2H, s), 5.71 (1H, bs), 6.53 (1H, bs), 6.96 (1H, d, J=2.9 Hz), 7.25-7.45 (4H, m), 7.50 (1H, dd, J=2.9, 9.2 Hz), 8.08 (1H, d, J=9.2 Hz).

melting point: 184-186° C.

2) 2-{[3-(aminomethyl)-2-isobutyl-4-(4-methylphenyl)quinolin-6-yl]oxy}acetamide (Synthesized according to a method similar to the method shown in Example 25(2).)

$^1$H-NMR (CDCl$_3$) δ: 1.04 (6H, d, J=6.6 Hz), 1.60 (2H, bs), 2.25-2.45 (1H, m), 2.50 (3H, s), 2.99 (2H, d, J=7.3 Hz), 3.78 (2H, s), 4.34 (2H, s), 5.68 (1H, bs), 6.58 (1H, bs), 6.59 (1H, d, J=2.9 Hz), 7.15 (2H, d, J=8.1 Hz), 7.25-7.40 (3H, m), 8.01 (1H, d, J=9.2 Hz).

melting point: 175-177° C.

Example 29

Methyl 3-(aminomethyl)-4-(2-fluorophenyl)-2-isobutylquinoline-6-carboxylate 1) methyl 3-cyano-4-(2-fluorophenyl)-2-isobutylquinoline-6-carboxylate (Synthesized according to a method similar to the method shown in Example 5(2).)

$^1$H-NMR (CDCl$_3$) δ: 1.07 (6H, d, J=6.6 Hz), 2.30-2.55 (1H, m), 3.16 (2H, d, J=7.3 Hz), 3.92 (3H, s), 7.33 (1H, d, J=8.4 Hz), 7.35-7.45 (2H, m), 7.55-7.70 (1H, m), 8.18 (1H, d, J=8.8 Hz), 8.25-8.35 (1H, m), 8.41 (1H, dd, J=1.8, 8.8 Hz).

melting point: 96-97° C.

2) methyl 3-(aminomethyl)-4-(2-fluorophenyl)-2-isobutylquinoline-6-carboxylate (Synthesized according to a method similar to the method shown in Example 25(2).)

$^1$H-NMR (CDCl$_3$) δ: 1.06 (6H, dd, J=1.1, 6.6 Hz), 1.62 (2H, bs), 2.35-2.55 (1H, m), 3.06 (2H, d, J=7.3 Hz), 3.81 (2H, s), 3.88 (3H, s), 7.20-7.40 (3H, m), 7.50-7.65 (1H, m), 8.00-8.05 (1H, m), 8.10 (1H, d, J=8.8 Hz), 8.24 (1H, dd, J=1.8, 8.8 Hz).

elemental analysis for $C_{22}H_{23}FN_2O_2$

Calculated: C, 72.11; H, 6.33; N, 7.64.

Found: C, 72.04; H, 6.32; N, 7.50.

melting point: 138-139° C.

Example 30

[6-(benzyloxy)-2-isobutyl-4-(4-methylphenyl)quinolin-3-yl]methylamine

1) To a solution of 6-hydroxy-2-isobutyl-4-(4-methylphenyl)quinoline-3-carbonitrile (1.5 g, 4.7 mmol) and benzyl bromide (0.61 g, 5.1 mmol) in N,N-dimethylformamide (10 ml) was added potassium carbonate (0.71 g, 5.1 mmol), and the mixture was stirred at room temperature for 17 hrs. The reaction mixture was partitioned between ethyl acetate (50 ml) and water (100 ml). The aqueous layer was separated and extracted with ethyl acetate (50 ml). The organic layer and the extract were combined and the mixture was washed with saturated brine (50 ml) and dried over anhydrous magnesium sulfate. The solvent was evaporated under reduced pressure and the residue was purified by silica gel column chromatography, and crystallized from n-hexane-ethyl acetate to give 6-(benzyloxy)-2-isobutyl-4-(4-methylphenyl)quinoline-3-carbonitrile (1.7 g, yield 91%) as pale-yellow crystals.

$^1$H-NMR (CDCl$_3$) δ: 1.04 (6H, d, J=6.6 Hz), 2.25-2.45 (1H, m), 2.50 (3H, s), 3.07 (2H, d, J=7.0 Hz), 5.00 (2H, s), 6.98 (1H, d, J=2.8 Hz), 7.20-7.45 (9H, m), 7.52 (1H, dd, J=2.8, 9.2 Hz), 8.03 (1H, d, J=9.2 Hz).

melting point: 137-138° C.

2) [6-(benzyloxy)-2-isobutyl-4-(4-methylphenyl)quinolin-3-yl]methylamine (Synthesized according to a method similar to the method shown in Example 25(2).)

$^1$H-NMR (CDCl$_3$) δ: 1.03 (6H, d, J=6.6 Hz), 1.49 (2H, bs), 2.20-2.50 (1H, m), 2.50 (3H, s), 2.97 (2H, d, J=7.3 Hz), 3.77 (2H, s), 4.91 (2H, s), 6.62 (1H, d, J=2.9 Hz), 7.07 (2H, d, J=8.1 Hz), 7.25-7.40 (8H, m), 8.05 (1H, d, J=9.2 Hz).

elemental analysis for C$_{28}$H$_{30}$N$_2$O

Calculated: C, 81.91; H, 7.37; N, 6.82.

Found: C, 81.79; H, 7.18; N, 6.64.

melting point: 119-120° C.

Example 31

3-(aminomethyl)-4-(2-fluorophenyl)-2-isobutylquinoline-6-carboxylic Acid Dihydrochloride 1) methyl 3-{[(tert-butoxycarbonyl)amino]methyl}-4-(2-fluorophenyl)-2-isobutylquinoline-6-carboxylate (Synthesized according to a method similar to the method shown in Example 5(1).)

$^1$H-NMR (CDCl$_3$) δ: 1.05 (6H, dd, J=2.6, 6.6 Hz), 1.43 (9H, s), 2.35-2.55 (1H, m), 2.99 (2H, d, J=8.4 Hz), 3.88 (3H, s), 4.10-4.25 (1H, m), 4.35-4.55 (2H, m), 7.15-7.40 (3H, m), 7.50-7.65 (1H, m), 8.03 (1H, d, J=1.8 Hz), 8.11 (1H, d, J=8.9 Hz), 8.26 (1H, dd, J=1.8, 8.9 Hz).

melting point: 151-153° C.

2) 3-{[(tert-butoxycarbonyl)amino]methyl}-4-(2-fluorophenyl)-2-isobutylquinoline-6-carboxylic acid (Synthesized according to a method similar to the method shown in Example 6(1).)

$^1$H-NMR (CDCl$_3$) δ: 1.04 (6H, dd, J=3.8, 6.6 Hz), 1.43 (9H, s), 2.30-2.50 (1H, m), 3.01 (2H, d, J=7.3 Hz), 4.10-4.25 (1H, m), 4.40-4.55 (2H, m), 7.20-7.40 (3H, m), 7.50-7.60 (1H, m), 8.10 (1H, d, J=1.8 Hz), 8.17 (1H, d, J=9.0 Hz), 8.30 (1H, dd, J=1.8, 9.0 Hz).

melting point: 214-216° C.

3) 3-(aminomethyl)-4-(2-fluorophenyl)-2-isobutylquinoline-6-carboxylic acid dihydrochloride (Synthesized according to a method similar to the method shown in Example 13(6).)

$^1$H-NMR (CD$_3$OD) δ: 1.16 (6H, dd, J=6.6, 9.6 Hz), 2.20-2.50 (1H, m), 3.35 (2H, d, J=7.5 Hz), 4.15-4.50 (2H, m), 7.45-7.70 (3H, m), 7.75-7.90 (1H, m), 8.20-8.30 (1H, m), 8.40-8.50 (1H, m), 8.60-8.75 (1H, m).

melting point: 256-259° C.

Example 32

3-(aminomethyl)-4-(2-fluorophenyl)-2-isobutylquinoline-6-carboxamide 1) tert-butyl [6-(aminocarbonyl)-4-(2-fluorophenyl)-2-isobutylquinolin-3-yl]methylcarbamate (Synthesized according to a method similar to the method shown in Example 19(4).)

$^1$H-NMR (CDCl$_3$) δ: 1.05 (6H, d, J=6.6 Hz), 1.43 (9H, s), 2.35-2.50 (1H, m), 2.99 (2H, dd, J=2.5, 7.1 Hz), 4.10-4.25 (2H, m), 4.40-4.55 (2H, m), 5.58 (1H, bs), 5.96 (1H, bs), 7.15-7.40 (2H, m), 7.55 (1H, dd, J=2.1, 7.9 Hz), 7.79 (1H, d, J=1.8 Hz), 8.03 (1H, dd, J=1.8, 8.8 Hz), 8.15 (1H, d, J=8.8 Hz).

melting point: 247-248° C.

2) A mixture of tert-butyl [6-(aminocarbonyl)-4-(2-fluorophenyl)-2-isobutylquinolin-3-yl]methylcarbamate (0.32 g, 0.70 mmol) and trifluoroacetic acid (4 ml) was stirred at room temperature for 1 hr. The reaction mixture was concentrated under reduced pressure and the residue was partitioned between ethyl acetate-tetrahydrofuran (1:1, 50 ml) and 10% aqueous potassium carbonate solution (50 ml). The organic layer was washed with saturated brine (15 ml) and dried over anhydrous magnesium sulfate. The solvent was evaporated under reduced pressure and the residue was purified by silica gel column chromatography. The obtained crude crystals were recrystallized from n-hexane-ethyl acetate to give the title compound (0.15 g, yield 61%) as colorless crystals.

$^1$H-NMR (CDCl$_3$) δ: 1.06 (6H, dd, J=1.5, 6.7 Hz), 1.58 (2H, bs), 2.35-2.55 (1H, m), 3.06 (2H, d, J=7.2 Hz), 3.81 (2H, d, J=1.3 Hz), 5.80 (1H, bs), 6.03 (1H, bs), 7.20-7.40 (3H, m), 7.50-7.60 (1H, m), 7.70-7.80 (1H, m), 8.00 (1H, dd, J=1.9, 8.8 Hz), 8.12 (1H, d, J=8.8 Hz).

melting point: 285° C. (decomp.)

Example 33

2-{[3-(aminomethyl)-2-isobutyl-4-thien-2-ylquinolin-6-yl]oxy}acetamide

1) To a solution of 2-bromothiophene (2.7 g, 16 mmol) in dimethyl ether (30 ml) was added dropwise 1.6 M solution (8.9 ml) of n-butyllithium in n-hexane at −78° C. The reaction mixture was stirred at −78° C. for 30 min. and a solution of 2-amino-5-{[tert-butyl(dimethyl)silyl]oxy}-N-methoxy-N-methylbenzamide (2.0 g, 6.4 mmol) in tetrahydrofuran (10 ml) was added dropwise. The reaction mixture was stirred at −78° C. for 30 min. and 0.1N hydrochloric acid was added. The mixture was extracted with ethyl acetate and the extract was washed with saturated brine, dried over anhydrous magnesium sulfate and concentrated under reduced pressure. The residue was purified by silica gel column chromatography to give (2-amino-5-{[tert-butyl(dimethyl)silyl]oxy}phenyl)(thien-2-yl)methanone (0.98 g, yield 46%) as a yellow oil.

$^1$H-NMR (CDCl$_3$) δ: 0.16 (6H, s), 0.96 (9H, s), 5.32 (2H, bs), 6.64 (1H, d, J=8.8 Hz), 6.89 (1H, dd, J=2.7, 8.8 Hz), 7.14 (1H, dd, J=3.7, 4.8 Hz), 7.21 (1H, d, J=2.7 Hz), 7.59 (1H, dd, J=1.1, 3.7 Hz), 7.67 (1H, dd, J=1.1, 4.8 Hz).

2) 6-hydroxy-2-isobutyl-4-thien-2-ylquinoline-3-carbonitrile (Synthesized according to a method similar to the method shown in Example 7(6).)

$^1$H-NMR (CDCl$_3$) δ: 1.03 (6H, d, J=6.6 Hz), 2.15-2.50 (1H, m), 3.06 (2H, d, J=7.3 Hz), 6.43 (1H, bs), 7.15-7.35 (3H, m), 7.43 (1H, dd, J=2.9, 9.2 Hz), 7.60 (1H, dd, J=1.1, 5.1 Hz), 8.02 (1H, d, J=9.2 Hz).

melting point: 240° C. (decomp.)

3) 2-[(3-cyano-2-isobutyl-4-thien-2-ylquinolin-6-yl)oxy]acetamide (Synthesized according to a method similar to the method shown in Example 7(7).)

$^1$H-NMR (CDCl$_3$) δ: 1.05 (6H, d, J=6.6 Hz), 2.30-2.50 (1H, m), 3.09 (2H, d, J=7.4 Hz), 4.50 (2H, s), 5.68 (1H, bs), 6.54 (1H, bs), 7.20-7.35 (2H, m), 7.38 (1H, dd, J=1.1, 3.6 Hz), 7.52 (1H, dd, J=2.8, 9.2 Hz), 7.69 (1H, dd, J=1.1, 5.1 Hz), 8.08 (1H, d, J=9.2 Hz).

melting point: 198-200° C.

4) 2-{[3-(aminomethyl)-2-isobutyl-4-thien-2-ylquinolin-6-yl]oxy}acetamide (Synthesized according to a method similar to the method shown in Example 25(2).)

¹H-NMR (CDCl₃) δ: 1.04 (6H, d, J=6.6 Hz), 1.50 (2H, bs), 2.25-2.50 (1H, m), 2.99 (2H, d, J=7.2 Hz), 3.87 (2H, s), 4.41 (2H, s), 5.67 (1H, bs), 6.57 (1H, bs), 6.67 (1H, d, J=2.8 Hz), 7.00-7.10 (1H, m), 7.20-7.25 (1H, m), 7.34 (1H, dd, J=2.6, 9.0 Hz), 7.56 (1H, d, J=5.1 Hz), 8.01 (1H, d, J=9.0 Hz).

elemental analysis for $C_{20}H_{23}N_3O_2S$

Calculated: C, 65.01; H, 6.27; N, 11.37.

Found: C, 65.19; H, 6.50; N, 11.19.

melting point: 156-157° C.

Example 34

2-{[3-(aminomethyl)-4-(4-fluorophenyl)-2-isobutylquinolin-6-yl]oxy}acetamide 1) (2-amino-5-{[tert-butyl(dimethyl)silyl]oxy}phenyl)(4-fluorophenyl)methanone (Synthesized according to a method similar to the method shown in Example 7(4).)

¹H-NMR (CDCl₃) δ: 0.10 (6H, s), 0.93 (9H, s), 5.63 (2H, bs), 6.65 (1H, d, J=9.2 Hz), 6.80-6.95 (2H, m), 7.05-7.20 (2H, m), 7.60-7.75 (2H, m).

2) 4-(4-fluorophenyl)-6-hydroxy-2-isobutylquinoline-3-carbonitrile (Synthesized according to a method similar to the method shown in Example 7(6).)

¹H-NMR (CDCl₃) δ: 1.04 (6H, d, J=6.6 Hz), 2.15-2.45 (1H, m), 3.07 (2H, d, J=7.2 Hz), 5.87 (1H, bs), 6.89 (1H, d, J=2.6 Hz), 7.10-7.50 (5H, m), 8.04 (1H, d, J=9.2 Hz).

melting point: 246-249° C.

3) 2-{[3-cyano-4-(4-fluorophenyl)-2-isobutylquinolin-6-yl]oxy}acetamide (Synthesized according to a method similar to the method shown in Example 7(7).)

¹H-NMR (CDCl₃) δ: 1.05 (6H, d, J=6.6 Hz), 2.30-2.50 (1H, m), 3.10 (2H, d, J=7.4 Hz), 4.43 (2H, s), 5.68 (1H, bs), 6.51 (1H, bs), 6.90 (1H, d, J=2.9 Hz), 7.25-7.50 (4H, m), 7.52 (1H, dd, J=2.9, 9.2 Hz), 8.11 (1H, d, J=9.2 Hz).

melting point: 153-154° C.

4) 2-{[3-(aminomethyl)-4-(4-fluorophenyl)-2-isobutylquinolin-6-yl]oxy}acetamide (Synthesized according to a method similar to the method shown in Example 7(8).)

¹H-NMR (CDCl₃) δ: 1.04 (6H, d, J=6.6 Hz), 1.54 (2H, bs), 2.25-2.40 (1H, m), 2.99 (2H, d, J=7.2 Hz), 3.77 (2H, s), 4.36 (2H, s), 5.63 (1H, bs), 6.54 (1H, bs), 6.54 (1H, d, J=2.8 Hz), 7.20-7.30 (4H, m), 7.33 (1H, dd, J=2.8, 9.2 Hz), 8.03 (1H, d, J=9.2 Hz).

melting point: 142-143° C.

Example 35

2-{[3-(aminomethyl)-2-isobutyl-4-(3-methylphenyl)quinolin-6-yl]oxy}acetamide

1) To a solution of 2-amino-5-{[tert-butyl(dimethyl)silyl]oxy}-N-methoxy-N-methylbenzamide (2.0 g, 6.4 mmol) in diethyl ether (50 ml) was added dropwise 1.0 M solution of m-tolylmagnesium bromide in tetrahydrofuran (30 ml, 30 mmol) under ice-cooling over 30 min. Ice water (250 g) was added to the reaction mixture and the mixture was extracted with ethyl acetate. The extract was washed with saturated brine, dried over anhydrous magnesium sulfate and concentrated under reduced pressure. The residue was purified by silica gel column chromatography to give (2-amino-5-{[tert-butyl(dimethyl)silyl]oxy}phenyl)(3-methylphenyl)methanone as a mixture. To a solution of the obtained mixture (1.4 g) of (2-amino-5-{[tert-butyl(dimethyl)silyl]oxy}phenyl)(3-methylphenyl)methanone and 5-methyl-3-oxohexanenitrile (0.60 g, 4.7 mmol) in toluene (50 ml) was added methanesulfonic acid (0.38 g, 4.0 mmol), and the mixture was heated under reflux for 6 hrs. The reaction mixture was partitioned between ethyl acetate (100 ml) and saturated aqueous sodium hydrogen carbonate (100 ml), and the organic layer was washed with saturated brine (50 ml) and dried over anhydrous magnesium sulfate. The solvent was evaporated under reduced pressure and the obtained crude crystals were recrystallized from n-hexane-ethyl acetate to give 6-hydroxy-2-isobutyl-4-(3-methylphenyl)quinoline-3-carbonitrile (0.73 g, yield 36%) as pale-yellow crystals.

¹H-NMR (DMSO-d₆) δ: 0.99 (6H, d, J=6.6 Hz), 2.20-2.35 (1H, m), 2.43 (3H, s), 2.96 (2H, d, J=7.3 Hz), 6.81 (1H, d, J=2.6 Hz), 7.25-7.60 (5H, m), 7.97 (1H, d, J=9.2 Hz), 10.20 (1H, s).

melting point: 275° C. (decomp.)

2) 2-{[3-cyano-2-isobutyl-4-(3-methylphenyl)quinolin-6-yl]oxy}acetamide (Synthesized according to a method similar to the method shown in Example 7(7).)

¹H-NMR (CDCl₃) δ: 1.05 (6H, d, J=6.8 Hz), 2.25-2.45 (1H, m), 2.48 (3H, s), 3.10 (2H, d, J=7.2 Hz), 4.41 (2H, s), 5.64 (1H, bs), 6.53 (1H, bs), 6.93 (1H, d, J=2.8 Hz), 7.15-7.55 (5H, m), 8.09 (1H, d, J=9.2 Hz).

melting point: 123-125° C.

3) 2-{[3-(aminomethyl)-2-isobutyl-4-(3-methylphenyl)quinolin-6-yl]oxy}acetamide (Synthesized according to a method similar to the method shown in Example 7(8).)

¹H-NMR (CDCl₃) δ: 1.04 (6H, d, J=6.6 Hz), 1.60 (2H, bs), 2.30-2.45 (1H, m), 2.45 (3H, s), 2.99 (2H, d, J=7.4 Hz), 3.78 (2H, bs), 4.34 (2H, s), 5.63 (1H, bs), 6.57 (1H, d, J=2.6 Hz), 6.60 (1H, bs), 7.05 (1H, d, J=7.2 Hz), 7.25-7.40 (1H, m), 7.32 (2H, dd, J=2.6, 9.2 Hz), 7.40-7.50 (1H, m), 8.01 (1H, d, J=9.2 Hz).

melting point: 98-101° C.

Example 36

2-{[3-(aminomethyl)-2-isobutyl-4-(2-methylphenyl)quinolin-6-yl]oxy}acetamide 1) 6-hydroxy-2-isobutyl-4-(2-methylphenyl)quinoline-3-carbonitrile (Synthesized according to a method similar to the method shown in Example 7(4).)

¹H-NMR (DMSO-d₆) δ: 0.99 (6H, dd, J=4.6, 6.6 Hz), 1.96 (3H, s), 2.15-2.35 (1H, m), 2.97 (2H, d, J=7.1 Hz), 6.56 (1H, d, J=2.7 Hz), 7.28 (1H, d, J=7.3 Hz), 7.35-7.55 (4H, m), 7.98 (1H, d, J=9.0 Hz), 10.19 (1H, s).

melting point: 254-256° C.

2) 2-{[3-cyano-2-isobutyl-4-(2-methylphenyl)quinolin-6-yl]oxy}acetamide (Synthesized according to a method similar to the method shown in Example 7(7).)

¹H-NMR (CDCl₃) δ: 1.05 (6H, d, J=6.6 Hz), 2.04 (3H, s), 2.25-2.45 (1H, m), 3.11 (2H, d, J=7.4 Hz), 4.37 (2H, s), 5.66 (1H, bs), 6.51 (1H, bs), 6.66 (1H, d, J=2.8 Hz), 7.10-7.20 (1H, m), 7.35-7.55 (4H, m), 8.11 (1H, d, J=9.2 Hz).

melting point: 175-177° C.

3) 2-{[3-(aminomethyl)-2-isobutyl-4-(2-methylphenyl)quinolin-6-yl]oxy}acetamide (Synthesized according to a method similar to the method shown in Example 7(8).)

¹H-NMR (CDCl₃) δ: 1.04 (6H, dd, J=6.6, 11 Hz), 1.45 (2H, bs), 1.93 (3H, s), 2.30-2.45 (1H, m), 3.01 (2H, dd, J=2.1, 7.3 Hz), 3.60 (1H, d, J=13.4 Hz), 3.85 (1H, d, J=13.4 Hz), 4.32

(2H, s), 5.73 (1H, bs), 6.43 (1H, d, J=2.8 Hz), 6.56 (1H, bs), 7.10-7.15 (1H, m), 7.30-7.50 (4H, m), 8.03 (1H, d, J=9.2 Hz).

melting point: 135-137° C.

Example 37

2-{[3-(aminomethyl)-2-isobutyl-4-thien-3-ylquinolin-6-yl]oxy}acetamide 1) (2-amino-5-{[tert-butyl(dimethyl)silyl]oxy}phenyl)(thien-3-yl)methanone (Synthesized according to a method similar to the method shown in Example 33(1).)

$^1$H-NMR (CDCl$_3$) δ: 0.13 (6H, s), 0.95 (9H, s), 5.53 (2H, bs), 6.63 (1H, d, J=8.8 Hz), 6.88 (1H, dd, J=2.9, 8.8 Hz), 7.09 (1H, d, J=2.9 Hz), 7.36 (1H, dd, J=2.9, 5.1 Hz), 7.48 (1H, dd, J=1.5, 5.1 Hz), 7.80 (1H, dd, J=1.5, 2.9 Hz).

2) 6-hydroxy-2-isobutyl-4-thien-3-ylquinoline-3-carbonitrile (Synthesized according to a method similar to the method shown in Example 7(6).)

$^1$H-NMR (CDCl$_3$) δ: 1.04 (6H, d, J=6.8 Hz), 2.25-2.45 (1H, m), 3.07 (2H, d, J=7.4 Hz), 5.67 (1H, bs), 7.10 (1H, d, J=2.8 Hz), 7.28 (1H, dd, J=1.5, 4.9 Hz), 7.42 (1H, dd, J=2.8, 9.2 Hz), 7.50-7.65 (2H, m), 8.03 (1H, d, J=9.2 Hz).

melting point: 257-259° C.

3) 2-[(3-cyano-2-isobutyl-4-thien-3-ylquinolin-6-yl)oxy]acetamide (Synthesized according to a method similar to the method shown in Example 7(7).)

$^1$H-NMR (CDCl$_3$) δ: 1.05 (6H, d, J=6.6 Hz), 2.30-2.45 (1H, m), 3.09 (2H, d, J=7.4 Hz), 4.48 (2H, s), 5.64 (1H, bs), 6.53 (1H, bs), 7.12 (1H, d, J=2.8 Hz), 7.29 (1H, dd, J=1.9, 4.5 z), 7.51 (1H, dd, J=2.8, 9.2 Hz), 7.60-7.70 (2H, m), 8.08 (1H, d, J=9.2 Hz).

melting point: 213-214° C.

4) 2-{[3-(aminomethyl)-2-isobutyl-4-thien-3-ylquinolin-6-yl]oxy}acetamide (Synthesized according to a method similar to the method shown in Example 25(2).)

$^1$H-NMR (CDCl$_3$) δ: 1.04 (6H, d, J=6.6 Hz), 1.51 (2H, bs), 2.30-2.45 (1H, m), 2.98 (2H, d, J=7.2 Hz), 3.75-3.85 (2H, m), 4.40 (2H, s), 5.63 (1H, bs), 6.57 (1H, bs), 6.69 (1H, d, J=2.8 Hz), 7.09 (1H, dd, J=1.1, 4.9 Hz), 7.25-7.40 (2H, m), 7.58 (1H, dd, J=3.0, 4.9 Hz), 8.01 (1H, d, J=9.2 Hz).

melting point: 144-147° C.

Example 38

2-{[3-(aminomethyl)-4-(3-fluorophenyl)-2-isobutylquinolin-6-yl]oxy}acetamide 1) (2-amino-5-{[tert-butyl(dimethyl)silyl]oxy}phenyl)(3-fluorophenyl)methanone (Synthesized according to a method similar to the method shown in Example 7(4).)

$^1$H-NMR (CDCl$_3$) δ: 0.09 (6H, s), 0.92 (9H, s), 5.75 (2H, bs), 6.66 (1H, d, J=8.4 Hz), 6.80-6.95 (2H, m), 7.15-7.25 (1H, m), 7.30-7.50 (3H, m).

2) 4-(3-fluorophenyl)-6-hydroxy-2-isobutylquinoline-3-carbonitrile (Synthesized according to a method similar to the method shown in Example 7(6).)

$^1$H-NMR (DMSO-d$_6$) δ: 1.05 (6H, d, J=6.6 Hz), 2.25-2.45 (1H, m), 3.08 (2H, d, J=7.4 Hz), 5.46 (1H, bs), 6.88 (1H, d, J=2.8 Hz), 7.10-7.35 (3H, m), 7.43 (1H, dd, J=2.8, 9.2 Hz), 7.50-7.65 (1H, m), 8.05 (1H, d, J=9.2 Hz).

melting point: 273-276° C.

3) 2-{[3-cyano-4-(3-fluorophenyl)-2-isobutylquinolin-6-yl]oxy}acetamide (Synthesized according to a method similar to the method shown in Example 7(7).)

$^1$H-NMR (CDCl$_3$) δ: 1.06 (6H, d, J=6.6 Hz), 2.30-2.50 (1H, m), 3.10 (2H, d, J=7.3 Hz), 4.43 (2H, s), 5.74 (1H, bs), 6.52 (1H, bs), 6.88 (1H, d, J=2.8 Hz), 7.10-7.40 (3H, m), 7.52 (1H, dd, J=2.8, 9.2 Hz), 7.55-7.65 (1H, m), 8.11 (1H, d, J=9.2 Hz).

melting point: 186-194° C.

4) 2-{[3-(aminomethyl)-4-(3-fluorophenyl)-2-isobutylquinolin-6-yl]oxy}acetamide (Synthesized according to a method similar to the method shown in Example 25(2).)

$^1$H-NMR (CDCl$_3$) δ: 1.04 (6H, d, J=6.6 Hz), 1.51 (2H, bs), 2.25-2.50 (1H, m), 3.00 (2H, d, J=7.2 Hz), 3.78 (2H, s), 4.36 (2H, s), 5.62 (1H, bs), 6.53 (1H, d, J=2.8 Hz), 6.55 (1H, bs), 6.90-7.30 (3H, m), 7.34 (1H, dd, J=2.8, 9.2 Hz), 7.45-7.60 (1H, m), 8.03 (1H, d, J=9.2 Hz).

elemental analysis for $C_{22}H_{24}N_3O_2F$ $H_2O$

Calculated: C, 66.15; H, 6.56; N, 10.52.

Found: C, 65.92; H, 6.43; N, 10.31.

melting point: 106-109° C.

Example 39

2-{[3-(aminomethyl)-4-(2-fluorophenyl)-2-isobutylquinolin-6-yl]oxy}propanamide

1) To a mixture of 6-tert-butoxy-4-(2-fluorophenyl)-2-isobutylquinoline-3-carbonitrile (2.0 g, 5.3 mmol), 25% aqueous ammonia (6 ml), tetrahydrofuran (25 ml) and methanol (100 ml) was added Raney-nickel (4 ml), and the mixture was stirred under a hydrogen (0.5 MPa) atmosphere at room temperature for 7 hrs. The reaction mixture was filtered, and the filtrate was concentrated under reduced pressure. Trifluoroacetic acid (10 ml) was added to the residue and the mixture was stirred at room temperature for 30 min. The reaction mixture was concentrated under reduced pressure and the residue was partitioned between ethyl acetate-isopropanol (4:1, 125 ml) and 10% aqueous potassium carbonate solution (200 ml). The aqueous layer was separated and extracted with ethyl acetate-isopropanol (4:1, 125 ml). The organic layer and the extract were combined, washed with saturated brine, and dried over anhydrous magnesium sulfate. The solvent was evaporated under reduced pressure and tetrahydrofuran (50 ml) was added to dissolve the residue. Di-tert-butyl dicarbonate (1.7 g, 7.9 mmol) was added and the mixture was stirred at room temperature for 17 hrs. The reaction mixture was concentrated under reduced pressure and the obtained crude crystals were recrystallized from toluene to give tert-butyl [4-(2-fluorophenyl)-6-hydroxy-2-isobutylquinolin-3-yl]methylcarbamate (2.0 g, yield 90%) as pale-yellow crystals.

$^1$H-NMR (CDCl$_3$) δ: 1.02 (6H, d, J=6.6 Hz), 1.42 (9H, s), 2.25-2.40 (1H, m), 2.92 (2H, dd, J=2.9, 7.3 Hz), 4.10-4.20 (1H, m), 4.35-4.50 (1H, m), 4.43 (1H, s), 5.38 (1H, bs), 6.55 (1H, d, J=2.5 Hz), 7.10-7.35 (4H, m), 7.45-7.55 (1H, m), 7.98 (1H, d, J=9.0 Hz).

2) To a solution of tert-butyl [4-(2-fluorophenyl)-6-hydroxy-2-isobutylquinolin-3-yl]methylcarbamate (0.20 g, 0.47 mmol) and 2-chloropropionamide (0.076 g, 0.71 mmol) in N,N-dimethylformamide (20 ml) was added potassium carbonate (0.098 g, 0.71 mmol), and the mixture was stirred at 75° C. for 24 hrs. The reaction mixture was partitioned between ethyl acetate (100 ml) and 0.1N hydrochloric acid (150 ml). The aqueous layer was separated and extracted with ethyl acetate (100 ml). The organic layer and the extract were combined and the mixture was washed with saturated brine (100 ml) and dried over anhydrous magnesium sulfate. The solvent was evaporated and the residue was purified by silica gel column chromatography and crystallized from diisopropyl ether-ethyl acetate to give tert-butyl [6-(2-amino-1-methyl-2-oxoethoxy)-4-(2-fluorophenyl)-2-isobutylquinolin-3-yl]methylcarbamate (0.15 g, yield 65%) as pale-yellow crystals.

3) To tert-butyl [6-(2-amino-1-methyl-2-oxoethoxy)-4-(2-fluorophenyl)-2-isobutylquinolin-3-yl]methylcarbamate (0.12 g, 0.24 mmol) was added 4N solution of hydrogen chloride in 1,4-dioxane (5 ml) and the mixture was stirred at room temperature for 30 min. The reaction mixture was partitioned between ethyl acetate-isopropanol (4:1, 125 ml) and 10% aqueous potassium carbonate solution (100 ml). The organic layer was dried over anhydrous magnesium sulfate, and the solvent was evaporated under reduced pressure. The residue was purified by silica gel column chromatography to give the title compound (0.070 g, yield 73%) as a colorless powder.

$^1$H-NMR (CDCl$_3$) δ: 1.04 (6H, dd, J=1.3, 6.7 Hz), 1.45 (2H, bs), 1.51 (3H, d, J=6.6 Hz), 2.30-2.50 (1H, m), 3.00 (2H, d, J=7.2 Hz), 3.79 (2H, s), 4.45-4.65 (1H, m), 5.40 (1H, bs), 6.35 (1H, bs), 6.50-6.60 (1H, m), 7.15-7.40 (4H, m), 7.45-7.60 (1H, m), 8.03 (1H, d, J=9.2 Hz).

Example 40

2-{[3-(aminomethyl)-2-(2,2-dimethylpropyl)-4-phenylquinolin-6-yl]oxy}acetamide 1) 6-bromo-2-(2,2-dimethylpropyl)-4-phenylquinoline-3-carbonitrile (Synthesized according to a method similar to the method shown in Example 7(6).)

$^1$H-NMR (CDCl$_3$) δ: 1.11 (9H, s), 3.18 (2H, s), 7.42-7.47 (2H, m), 7.58-7.65 (3H, m), 7.78 (1H, d, J=2.2 Hz), 7.87 (1H, dd, J=2.2, 8.6 Hz), 8.01 (1H, d, J=8.6 Hz).

melting point: 163-164° C.

elemental analysis for C$_{21}$H$_{19}$N$_2$Br

Calculated: C, 66.50; H, 5.05; N, 7.38.

Found: C, 66.50; H, 4.95; N, 7.13.

2) 6-tert-butoxy-2-(2,2-dimethylpropyl)-4-phenylquinoline-3-carbonitrile (Synthesized according to a method similar to the method shown in Example 26(2).)

$^1$H-NMR (CDCl$_3$) δ: 1.12 (9H, s), 1.33 (9H, s), 3.17 (2H, s), 7.13 (1H, d, J=2.4 Hz), 7.42-7.62 (6H, m), 8.03 (1H, d, J=9.2 Hz).

melting point: 129-130° C.

3) 2-(2,2-dimethylpropyl)-6-hydroxy-4-phenylquinoline-3-carbonitrile (Synthesized according to a method similar to the method shown in Example 26(3).)

$^1$H-NMR (CDCl$_3$) δ: 1.16 (9H, s), 3.39 (2H, s), 7.15 (1H, d, J=2.6 Hz), 7.45-7.50 (2H, m), 7.61-7.73 (4H, m), 8.58 (1H, d, J=9.2 Hz), 9.67 (1H, bs).

melting point: 181-182° C.

4) 2-{[3-cyano-2-(2,2-dimethylpropyl)-4-phenylquinolin-6-yl]oxy}acetamide (Synthesized according to a method similar to the method shown in Example 7(7).)

$^1$H-NMR (CDCl$_3$) δ: 1.19 (9H, s), 3.17 (2H, s), 4.41 (2H, s), 5.69 (1H, bs), 6.52 (1H, bs), 6.92 (1H, d, J=2.8 Hz), 7.41-7.48 (2H, m), 7.51 (1H, dd, J=2.8, 9.0 Hz), 7.57-7.64 (3H, m), 8.11 (1H, d, J=9.0 Hz).

melting point: 184-185° C.

elemental analysis for C$_{23}$H$_{23}$N$_3$O$_2$

Calculated: C, 73.79; H, 6.21; N, 11.25.

Found: C, 73.76; H, 6.10; N, 11.06.

5) 2-{[3-(aminomethyl)-2-(2,2-dimethylpropyl)-4-phenylquinolin-6-yl]oxy}acetamide (Synthesized according to a method similar to the method shown in Example 25(2).)

$^1$H-NMR (CDCl$_3$) δ: 1.08 (9H, s), 1.34 (2H, bs), 3.07 (2H, s), 3.84 (2H, s), 4.33 (2H, s), 5.73 (1H, bs), 6.54 (1H, d, J=2.7 Hz), 6.55 (1H, bs), 7.25-7.30 (2H, m), 7.31 (1H, dd, J=2.7, 9.0 Hz), 7.51-7.57 (3H, m), 8.02 (1H, d, J=9.0 Hz).

melting point: 152-154° C.

elemental analysis for C$_{23}$H$_{27}$N$_3$O$_2$

Calculated: C, 73.18; H, 7.21; N, 11.13.

Found: C, 72.91; H, 7.24; N, 10.83.

Example 41

2-{[3-(aminomethyl)-2-benzyl-4-phenylquinolin-6-yl]oxy}acetamide 1) 2-benzyl-6-hydroxy-4-phenylquinoline-3-carbonitrile (Synthesized according to a method similar to the method shown in Example 7(6).)

$^1$H-NMR (CDCl$_3$) δ: 4.50 (2H, s), 6.91 (1H, d, J=2.6 Hz), 7.13-7.50 (12H, m), 8.02 (1H, d, J=8.8 Hz).

melting point: 235.5-236° C.

elemental analysis for C$_{23}$H$_{16}$N$_2$O.

Calculated: C, 82.12; H, 4.79; N, 8.33.

Found: C, 82.88; H, 4.76; N, 8.08.

2) 2-[(2-benzyl-3-cyano-4-phenylquinolin-6-yl)oxy]acetamide (Synthesized according to a method similar to the method shown in Example 7(7).)

$^1$H-NMR (CDCl$_3$) δ: 4.40 (2H, s), 4.56 (2H, s), 5.63 (1H, bs), 6.50 (1H, bs), 6.91 (1H, d, J=3.0 Hz), 7.19-7.43 (6H, m), 7.49-7.62 (5H, m), 8.14 (1H, d, J=9.2 Hz).

melting point: 178-179° C.

elemental analysis for C$_{25}$H$_{19}$N$_3$O$_2$

Calculated: C, 76.32; H, 4.87; N, 10.68.

Found: C, 76.06; H, 4.66; N, 10.52.

3) 2-{[3-(aminomethyl)-2-benzyl-4-phenylquinolin-6-yl]oxy}acetamide (Synthesized according to a method similar to the method shown in Example 25(2) to give the title compound (0.29 g, yield 74%) as white crystals.)

$^1$H-NMR (CDCl$_3$) δ: 1.32 (2H, bs), 3.68 (2H, s), 4.33 (2H, s), 4.56 (2H, s), 5.83 (1H, bs), 6.56 (1H, d, J=3.0 Hz), 6.58 (1H, bs), 7.15-7.30 (7H, m), 7.34 (1H, dd, J=3.0, 9.0 Hz), 7.45-7.54 (3H, m), 8.08 (1H, d, J=9.0 Hz).

melting point: 180.5-182° C.

Example 42

2-{[3-(aminomethyl)-2-(cyclopentylmethyl)-4-phenylquinolin-6-yl]oxy}acetamide 1) 2-(cyclopentylmethyl)-6-hydroxy-4-phenylquinoline-3-carbonitrile (Synthesized according to a method similar to the method shown in Example 7(6).)

$^1$H-NMR (CDCl$_3$) δ: 1.26-1.80 (8H, m), 2.35-2.51 (1H, m), 3.18 (2H, d, J=7.4 Hz), 6.93 (1H, d, J=2.6 Hz), 7.33-7.53 (6H, m), 7.60 (1H, bs), 7.99 (1H, d, J=9.2 Hz).

melting point: 238-238.5° C.

2) 2-{[3-cyano-2-(cyclopentylmethyl)-4-phenylquinolin-6-yl]oxy}acetamide (Synthesized according to a method similar to the method shown in Example 7(7).)

$^1$H-NMR (CDCl$_3$) δ: 1.34-1.86 (8H, m), 2.45-2.60 (1H, m), 3.23 (2H, d, J=7.4 Hz), 4.41 (2H, s), 5.89 (1H, bs), 6.53 (1H, bs), 6.92 (1H, d, J=3.0 Hz), 7.42-7.54 (3H, m), 7.57-7.65 (3H, m), 8.09 (1H, d, J=9.2 Hz).

melting point: 178-179° C.

elemental analysis for C$_{24}$H$_{23}$N$_3$O$_2$

Calculated: C, 74.78; H, 6.01; N, 10.90.

Found: C, 74.55; H, 6.05; N, 10.66.

3) 2-{[3-(aminomethyl)-2-(cyclopentylmethyl)-4-phenylquinolin-6-yl]oxy}acetamide (Synthesized according to a method similar to the method shown in Example 25(2).)

¹H-NMR (CDCl₃) δ: 1.31-1.88 (8H, m), 2.44-2.57 (1H, m), 3.13 (2H, d, J=7.2 Hz), 3.78 (2H, s), 4.32 (2H, s), 5.70 (1H, bs), 6.53 (1H, bs), 6.54 (1H, d, J=2.7 Hz), 7.22-7.28 (3H, m), 7.31 (1H, dd, J=2.7, 9.0 Hz), 7.47-7.57 (3H, m), 8.00 (1H, d, J=9.0 Hz).

melting point: 159-160° C.

elemental analysis for $C_{24}H_{27}N_3O_2$

Calculated: C, 74.01; H, 6.99; N, 10.79.

Found: C, 73.79; H, 7.10; N, 10.56.

Example 43

2-{[3-(aminomethyl)-2,4-diphenylquinolin-6-yl]oxy}acetamide 1) 6-hydroxy-2,4-diphenylquinoline-3-carbonitrile (Synthesized according to a method similar to the method shown in Example 7 (6).)

¹H-NMR (CDCl₃) δ: 6.85 (1H, d, J=2.8 Hz), 7.51 (1H, dd, J=2.8, 9.2 Hz), 7.55-7.70 (8H, m), 7.87-7.94 (2H, m), 8.08 (1H, d, J=9.2 Hz), 10.37 (1H, s).

melting point: 321-322° C.

2) 2-[(3-cyano-2,4-diphenylquinolin-6-yl)oxy]acetamide (Synthesized according to a method similar to the method shown in Example 7(7).)

¹H-NMR (CDCl₃) δ: 4.43 (2H, s), 5.81 (1H, bs), 6.52 (1H, bs), 6.95 (1H, d, J=2.8 Hz), 7.47-7.66 (9H, m), 7.93-8.01 (2H, m), 8.22 (1H, d, J=9.2 Hz).

melting point: 210.5-211° C.

3) 2-{[3-(aminomethyl)-2,4-diphenylquinolin-6-yl]oxy}acetamide (Synthesized according to a method similar to the method shown in Example 25(2).)

¹H-NMR (CDCl₃) δ: 1.16 (2H, bs), 3.74 (2H, s), 4.36 (2H, s), 5.84 (1H, bs), 6.55 (1H, bs), 6.63 (1H, d, J=2.8 Hz), 7.33-7.41 (3H, m), 7.44-7.60 (6H, m), 7.47-7.57 (3H, m), 7.64-7.70 (2H, m), 8.12 (1H, d, J=9.0 Hz).

melting point: 205-207° C.

Example 44

Methyl 3-(aminomethyl)-2-isobutyl-4-(4-methylphenyl) quinoline-6-carboxylate Dihydrochloride 1) To a solution of tert-butyl [6-hydroxy-2-isobutyl-4-(4-methylphenyl)quinolin-3-yl]methylcarbamate (12.6 g, 30 mmol) in N,N-dimethylformamide (100 ml) was added sodium hydride (60% in oil, 1.8 g, 45 mmol) at 0° C. and the mixture was stirred at 0° C. for 30 min. N-Phenyltrifluoromethanesulfonimide (16.0 g, 45 mmol) was added at 0° C., and the mixture was stirred at room temperature for 1 hr. The reaction mixture was poured into water and extracted with ethyl acetate. The extract was washed with saturated brine, and dried over anhydrous magnesium sulfate. The solvent was evaporated under reduced pressure and the residue was purified by silica gel column chromatography to give tert-butyl [2-isobutyl-4-(4-methylphenyl)-6-trifluoromethanesulfonyloxy-quinolin-3-yl]methylcarbamate (12.2 g, yield 74%) as colorless crystals.

2) A mixture of tert-butyl [2-isobutyl-4-(4-methylphenyl)-6-trifluoromethanesulfonyloxy-quinolin-3-yl]methylcarbamate (12.16 g, 22 mmol), 1,1'-bis(diphenylphosphino)ferrocene (0.61 g, 1.1 mmol), palladium acetate (0.25 g, 1.1 mmol), triethylamine (3.4 ml, 24.2 mmol), methanol (30 ml) and tetrahydrofuran (50 ml) was stirred in a sealed tube under a 0.5 MPa carbon monoxide atmosphere at 100° C. for 3 hrs. The reaction mixture was poured into water and extracted with ethyl acetate. The extract was washed with saturated brine, and dried over anhydrous magnesium sulfate. The solvent was evaporated under reduced pressure and the residue was purified by silica gel column chromatography to give methyl 3-{[(tert-butoxycarbonyl)amino]methyl}-2-isobutyl-4-(4-methylphenyl)quinoline-6-carboxylate (6.84 g, yield 67%) as colorless crystals.

¹H-NMR (CDCl₃) δ: 1.04 (6H, d, J=6.3 Hz), 1.42 (9H, s), 2.14-2.27 (1H, m), 2.49 (3H, s), 2.99 (2H, d, J=7.2 Hz), 3.87 (3H, s), 4.25-4.40 (3H, m), 7.13 (2H, d, J=7.8 Hz), 7.35 (2H, d, J=7.8 Hz), 8.06-8.10 (2H, m), 8.23 (1H, dd, J=2.1, 8.7 Hz).

melting point: 192.5-193.5° C.

3) To methyl 3-{[(tert-butoxycarbonyl)amino]methyl}-2-isobutyl-4-(4-methylphenyl)quinoline-6-carboxylate (0.10 g, 0.22 mmol) was added 4N solution of hydrogen chloride in 1,4-dioxane (5 ml), and the mixture was stirred at room temperature for 1 hr. The reaction mixture was concentrated under reduced pressure, and the residue was crystallized from ethyl acetate to give methyl 3-(aminomethyl)-2-isobutyl-4-(4-methylphenyl)quinoline-6-carboxylate dihydrochloride (0.12 g, yield 92%) as white crystals.

¹H-NMR (DMSO-d₆) δ: 1.04 (6H, d, J=6.6 Hz), 2.31-2.44 (1H, m), 2.49 (3H, s), 3.20 (2H, d, J=6.6 Hz), 3.83 (3H, s), 3.99 (2H, d, J=5.1 Hz), 7.38 (2H, d, J=8.0 Hz), 7.47 (2H, d, J=8.0 Hz), 7.98 (1H, s), 8.30-8.37 (2H, m), 8.55 (3H, bs).

melting point: 261-263° C.

Example 45

3-(aminomethyl)-2-isobutyl-4-(4-methylphenyl)quinoline-6-carboxylic Acid Dihydrochloride 1) 3-{[(tert-butoxycarbonyl)amino]methyl}-2-isobutyl-4-(4-methylphenyl)quinoline-6-carboxylic acid (Synthesized according to a method similar to the method shown in Example 6(1).)

¹H-NMR (CDCl₃) δ: 1.05 (6H, d, J=6.3 Hz), 1.41 (9H, s), 2.30-2.49 (4H, m), 3.18 (2H, bs), 4.35 (2H, d, J=5.1 Hz), 4.49 (1H, bs), 7.15 (2H, d, J=7.5 Hz), 7.33-7.38 (3H, m), 8.19 (1H, m), 8.28-8.41 (2H, m).

melting point: 276-277° C.

2) 3-(aminomethyl)-2-isobutyl-4-(4-methylphenyl)quinoline-6-carboxylic acid dihydrochloride (Synthesized according to a method similar to the method shown in Example 44(3).)

¹H-NMR (DMSO-d₆) δ: 1.04 (6H, d, J=6.3 Hz), 2.28-2.44 (1H, m), 2.49 (3H, s), 3.27 (2H, d, J=6.9 Hz), 4.02 (2H, d, J=5.4 Hz), 7.41 (2H, d, J=8.0 Hz), 7.49 (2H, d, J=8.0 Hz), 8.00 (1H, d, J=1.5 Hz), 8.34-8.45 (2H, m), 8.62 (3H, bs).

melting point: 284-286° C.

Example 46

3-(aminomethyl)-2-isobutyl-4-(4-methylphenyl)quinoline-6-carboxamide Dihydrochloride 1) tert-butyl {[6-(aminocarbonyl)-2-isobutyl-4-(4-methylphenyl)quinolin-3-yl]methyl}carbamate (Synthesized according to a method similar to the method shown in Example 19(4).)

¹H-NMR (CDCl₃) δ: 1.02 (6H, d, J=6.3 Hz), 1.41 (9H, s), 2.29-2.48 (1H, m), 2.52 (3H, s), 3.49 (2H, d, J=6.6 Hz), 4.37 (2H, d, J=5.1 Hz), 5.26 (1H, bs), 5.84 (1H, s), 7.23 (2H, d, J=7.8 Hz), 7.39 (2H, d, J=7.8 Hz), 8.08 (2H, bs), 8.55 (1H, d, J=9.0 Hz), 8.79 (1H, d, J=9.0 Hz.

melting point: 206-208° C.

2) 3-(aminomethyl)-2-isobutyl-4-(4-methylphenyl)quinoline-6-carboxamide dihydrochloride (Synthesized according to a method similar to the method shown in Example 44(3).)

$^1$H-NMR (DMSO-$d_6$) δ: 1.03 (6H, d, J=6.0 Hz), 2.32-2.49 (4H, m), 3.17 (2H, bs), 3.99 (2H, d, J=7.8 Hz), 7.36 (2H, d, J=7.8 Hz), 7.47 (2H, d, J=7.8 Hz), 7.59 (1H, bs), 7.89 (1H, bs), 8.21-8.33 (3H, m), 8.42 (3H, bs).

melting point: 194-196° C.

Example 47

Ethyl 2-[3-(aminomethyl)-2-isobutyl-4-(4-methylphenyl)quinolin-6-yl]-1,3-thiazole-4-carboxylate 1) A mixture of tert-butyl [2-isobutyl-4-(4-methylphenyl)-6-trifluoromethanesulfonyloxy-quinolin-3-yl]methylcarbamate (2.76 g, 5.0 mmol), boron bispinacolate (1.52 g, 6.0 mmol), [1,1'-bis(diphenylphosphino)ferrocene]dichloropalladium-dichloromethane (1:1) complex (0.11 g, 0.15 mmol), potassium acetate (1.47 g, 7.5 mmol) and dimethyl sulfoxide (30 ml) was stirred under an argon atmosphere at 100° C. for 2 hrs. The reaction mixture was poured into water and extracted with ethyl acetate. The extract was washed with saturated brine, and dried over anhydrous magnesium sulfate. The solvent was evaporated under reduced pressure and a mixture of the residue, 2-chlorothiazole (0.96 g, 5.0 mmol), tetrakis(triphenylphosphine)palladium (0.58 g, 0.5 mmol), potassium carbonate (3.46 g, 25 mmol), ethanol (5 ml), toluene (30 ml) and water (5 ml) was stirred under an argon atmosphere at 100° C. for 10 hrs. The reaction mixture was poured into water and extracted with ethyl acetate. The extract was washed with saturated brine, and dried over anhydrous magnesium sulfate. The solvent was evaporated under reduced pressure and the residue was purified by silica gel column chromatography to give ethyl 2-[3-{[(tert-butoxycarbonyl)amino]methyl}-2-isobutyl-4-(4-methylphenyl)quinolin-6-yl]-1,3-thiazole-4-carboxylate as a mixture. To a solution of the obtained mixture in tetrahydrofuran (4 ml) was added 4N solution of hydrogen chloride in 1,4-dioxane (4 ml), and the mixture was stirred at room temperature for 4 hrs. The reaction mixture was concentrated under reduced pressure, poured into 5% aqueous potassium carbonate solution (100 ml) and extracted with ethyl acetate. The extract was washed with saturated brine, and dried over anhydrous magnesium sulfate. The solvent was evaporated under reduced pressure and the residue was purified by silica gel column chromatography to give ethyl 2-[3-(aminomethyl)-2-isobutyl-4-(4-methylphenyl)quinolin-6-yl]-1,3-thiazole-4-carboxylate (0.08 g, yield 15%) as white crystals.

$^1$H-NMR (CDCl$_3$) δ: 1.04 (6H, d, J=6.6 Hz), 1.39 (2H, bs), 1.42 (3H, t, J=7.0 Hz), 2.35-2.50 (4H, m), 3.03 (2H, d, J=7.5 Hz), 3.81 (2H, s), 4.42 (2H, q, J=7.0 Hz), 7.21 (2H, d, J=7.8 Hz), 7.36 (2H, d, J=7.8 Hz), 7.84 (1H, d, J=1.8 Hz), 8.09 (1H, s), 8.11 (1H, d, J=8.7 Hz), 8.33 (1H, dd, J=1.8, 8.7 Hz).

melting point: 150-152° C.

Example 48

2-[3-(aminomethyl)-2-isobutyl-4-(4-methylphenyl)quinolin-6-yl]-1,3-thiazole-4-carboxylic Acid Dihydrochloride 1) A mixture of tert-butyl [2-isobutyl-4-(4-methylphenyl)-6-trifluoromethanesulfonyloxy-quinolin-3-yl]methylcarbamate (0.50 g, 0.90 mmol), boron bispinacolate (0.25 g, 1.0 mmol), [1,1'-bis(diphenylphosphino)ferrocene]dichloropalladium-dichloromethane (1:1) complex (0.020 g, 0.027 mmol), potassium acetate (0.27 g, 2.7 mmol) and dimethyl sulfoxide (20 ml) was stirred under an argon atmosphere at 100° C. for 15 min. The reaction mixture was poured into water and extracted with ethyl acetate. The extract was washed with saturated brine, and dried over anhydrous magnesium sulfate. The solvent was evaporated under reduced pressure and a mixture of the residue, 2-chlorothiazole (0.17 g, 0.90 mmol), tetrakis(triphenylphosphine)palladium (0.10 g, 0.090 mmol), potassium carbonate (0.63 g, 4.5 mmol), ethanol (4 ml), toluene (20 ml) and water (4 ml) was stirred under an argon atmosphere at 100° C. for 17 hrs. The reaction mixture was poured into water and extracted with ethyl acetate. The extract was washed with saturated brine, and dried over anhydrous magnesium sulfate. The solvent was evaporated under reduced pressure and the residue was purified by silica gel column chromatography. The obtained mixture was dissolved in tetrahydrofuran-methanol (1:1, 8 ml) and 1N aqueous sodium hydroxide solution (2 ml) was added. The mixture was stirred at room temperature for 15 min. 1N Hydrochloric acid (50 ml) was added to the reaction mixture and the mixture was extracted with ethyl acetate-tetrahydrofuran (1:1, 100 ml). The extract was washed with saturated brine, and dried over anhydrous magnesium sulfate. The solvent was evaporated under reduced pressure and the residue was purified by silica gel column chromatography to give 2-[3-{[(tert-butoxycarbonyl)amino]methyl}-2-isobutyl-4-(4-methylphenyl)quinolin-6-yl]-1,3-thiazole-4-carboxylic acid (0.17 g, yield 36%) as pale-yellow crystals.

$^1$H-NMR (CDCl$_3$) δ: 1.05 (6H, d, J=6.6 Hz), 1.43 (9H, s), 2.25-2.50 (1H, m), 2.50 (3H, s), 3.03 (2H, d, J=7.2 Hz), 4.33 (2H, d, J=4.4 Hz), 4.41 (1H, bs), 7.18 (2H, d, J=7.7 Hz), 7.37 (2H, d, J=7.7 Hz), 7.80-7.95 (1H, m), 8.10-8.25 (1H, m), 8.20 (1H, s), 8.32 (1H, dd, J=2.2, 9.1 Hz).

2) 2-[3-(aminomethyl)-2-isobutyl-4-(4-methylphenyl)quinolin-6-yl]-1,3-thiazole-4-carboxylic acid dihydrochloride (Synthesized according to a method similar to the method shown in Example 44(3).)

$^1$H-NMR (CD$_3$OD) δ: 1.16 (6H, d, J=6.6 Hz), 2.25-2.45 (1H, m), 2.56 (3H, s), 3.28 (2H, d, J=7.0 Hz), 4.33 (2H, s), 7.44 (2H, d, J=8.1 Hz), 7.60 (2H, d, J=8.1 Hz), 8.15 (1H, d, J=1.9 Hz), 8.41 (1H, d, J=8.9 Hz), 8.46 (1H, s), 8.76 (1H, dd, J=1.9, 8.9 Hz).

Example 49

2-[3-(aminomethyl)-2-isobutyl-4-(4-methylphenyl)quinolin-6-yl]-1,3-thiazole-4-carboxamide Dihydrochloride 1) tert-butyl [6-[4-(aminocarbonyl)-1,3-thiazol-2-yl]-2-isobutyl-4-(4-methylphenyl)quinolin-3-yl]methylcarbamate (Synthesized according to a method similar to the method shown in Example 19(4).)

$^1$H-NMR (DMSO-$d_6$) δ: 1.00 (6H, d, J=6.6 Hz), 1.39 (9H, s), 2.30-2.55 (1H, m), 2.46 (3H, s), 2.85 (2H, d, J=6.6 Hz), 4.08 (2H, d, J=4.5 Hz), 7.17 (1H, t, J=4.5 Hz), 7.30-7.45 (4H, m), 7.67 (1H, bs), 7.76 (1H, d, J=2.2 Hz), 7.84 (1H, bs), 8.12 (1H, d, J=8.8 Hz), 8.23 (1H, s), 8.42 (1H, dd, J=2.2, 8.8 Hz).

melting point: 256-258° C.

2) 2-[3-(aminomethyl)-2-isobutyl-4-(4-methylphenyl)quinolin-6-yl]-1,3-thiazole-4-carboxamide dihydrochloride (Synthesized according to a method similar to the method shown in Example 27(3).)

$^1$H-NMR (DMSO-$d_6$) δ: 1.05 (6H, d, J=6.6 Hz), 2.30-2.40 (1H, m), 2.43 (3H, s), 3.00-3.10 (2H, m), 3.95-4.05 (2H, m), 7.35-7.45 (2H, m), 7.49 (2H, d, J=8.2 Hz), 7.68 (1H, bs), 7.75-7.80 (1H, m), 7.85 (1H, bs), 8.15-8.25 (1H, m), 8.26 (1H, s), 8.35 (3H, bs), 8.45-8.60 (1H, m).

melting point: 212° C. (decomp.)

Example 50

Isopropyl 2-[3-(aminomethyl)-2-isobutyl-4-(4-methylphenyl)quinolin-6-yl]-1,3-thiazole-4-carboxylate Dihydrochloride 1) To a mixture of 2-[3-{[(tert-butoxycarbonyl)amino]methyl}-2-isobutyl-4-(4-methylphenyl)quinolin-6-yl]-1,3-thiazole-4-carboxylic acid (0.26 g, 0.5 mmol), n-tributylphosphine (0.25 ml, 1.0 mmol), isopropanol (0.5 ml) and tetrahydrofuran (10 ml) was added 1,1-(azodicarbonyl)dipiperidine (0.25 g, 1.0 mmol), and the mixture was stirred at room temperature for 2 hrs. Precipitated crystals were removed and the solvent was evaporated. The residue was purified by silica gel column chromatography to give isopropyl 2-[3-{[(tert-butoxycarbonyl)amino]methyl}-2-isobutyl-4-(4-methylphenyl)quinolin-6-yl]-1,3-thiazole-4-carboxylate (0.20 g, yield 71%) as white crystals.

$^1$H-NMR (CDCl$_3$) δ: 1.05 (6H, d, J=6.6 Hz), 1.39 (6H, d, J=6.3 Hz), 1.42 (9H, s), 2.34-2.45 (1H, m), 2.49 (3H, s), 2.98 (2H, d, J=7.2 Hz), 4.28-4.37 (3H, m), 5.20-5.33 (1H, m), 7.16 (2H, d, J=7.8 Hz), 7.35 (2H, d, J=7.8 Hz), 7.88 (1H, d, J=2.0 Hz), 8.06 (1H, s), 8.11 (1H, d, J=9.0 Hz), 8.33 (1H, dd, J=2.0, 9.0 Hz).

melting point: 190.5-191° C.

2) isopropyl 2-[3-(aminomethyl)-2-isobutyl-4-(4-methylphenyl)quinolin-6-yl]-1,3-thiazole-4-carboxylate dihydrochloride (Synthesized according to a method similar to the method shown in Example 44(3).)

$^1$H-NMR (DMSO-d$_6$) δ: 1.06 (6H, d, J=6.6 Hz), 1.32 (6H, d, J=6.2 Hz), 2.29-2.46 (1H, m), 2.60 (3H, s), 3.24 (2H, d, J=7.0 Hz), 4.03 (2H, d, J=7.0 Hz), 5.02-5.21 (1H, m), 7.44 (2H, d, J=8.2 Hz), 7.51 (2H, d, J=8.2 Hz), 7.95 (1H, s), 8.43-8.49 (2H, m), 8.55 (1H, m), 8.60 (3H, bs).

melting point: 233-235° C.

Example 51

{[6-(benzyloxy)-4-butyl-2-isobutylquinolin-3-yl]methyl}amine Dihydrochloride

1) To a solution of 2-amino-5-{[tert-butyl(dimethyl)silyl]oxy}-N-methoxy-N-methylbenzamide (4.97 g, 16.0 mmol) in tetrahydrofuran (50 ml) was added dropwise slowly 1.6 M solution (20 ml) of n-butyllithium in n-hexane at −78° C., and after the completion of the dropwise addition, the mixture was stirred at −78° C. for 30 min. The reaction mixture was poured into water and extracted with ethyl acetate. The extract was washed with saturated brine, and dried over anhydrous magnesium sulfate. The solvent was evaporated under reduced pressure and the residue was purified by silica gel column chromatography to give 1-(2-amino-5-{[tert-butyl(dimethyl)silyl]oxy}phenyl)pentan-1-one (3.45 g, yield 70%) as a pale-yellow oil.

$^1$H-NMR (CDCl$_3$) δ: 0.18 (6H, s), 0.95 (3H, t, J=7.2 Hz), 0.99 (9H, s), 1.27-1.50 (2H, m), 1.62-1.77 (2H, m), 2.87 (2H, t, J=7.3 Hz), 5.93 (2H, bs), 7.56 (1H, d, J=8.8 Hz), 6.85 (1H, dd, J=2.8, 8.8 Hz), 7.18 (1H, d, J=2.8 Hz).

2) methyl 4-butyl-6-hydroxy-2-isobutylquinoline-3-carboxylate (Synthesized according to a method similar to the method shown in Example 1(1).)

$^1$H-NMR (CDCl$_3$) δ: 0.83-0.92 (9H, m), 1.33-1.45 (2H, m), 1.58-1.68 (2H, m), 2.08-2.21 (1H, m), 2.79 (2H, d, J=7.2 Hz), 2.81-2.87 (2H, m), 3.96 (3H, s), 7.25 (1H, dd, J=2.7, 9.0 Hz), 7.34 (1H, d, J=2.7. Hz), 7.85 (1H, d, J=9.0 Hz), 9.52 (1H, bs).

melting point: 169-169.5° C.

elemental analysis for C$_{19}$H$_{25}$NO$_3$

Calculated: C, 72.35; H, 7.99; N, 4.44.

Found: C, 72.11; H, 7.94; N, 4.56.

3) methyl 6-(benzyloxy)-4-butyl-2-isobutylquinoline-3-carboxylate (Synthesized according to a method similar to the method shown in Example 30(1).)

$^1$H-NMR (CDCl$_3$) δ: 0.97 (3H, t, J=7.0 Hz), 1.02 (6H, d, J=6.2 Hz), 1.37-1.68 (2H, m), 2.20-2.38 (1H, m), 3.00 (2H, t, J=7.2 Hz), 3.28 (2H, d, J=6.2 Hz), 4.03 (3H, s), 5.29 (2H, s), 7.32-7.49 (6H, m), 7.70 (1H, d, J=8.0 Hz), 9.12 (1H, d, J=8.0 Hz).

melting point: 154-155° C.

4) [6-(benzyloxy)-4-butyl-2-isobutylquinolin-3-yl]methanol (Synthesized according to a method similar to the method shown in Example 1(2).)

$^1$H-NMR (CDCl$_3$) δ: 0.95-0.99 (9H, m), 1.42-1.61 (4H, m), 1.78 (1H, bs), 2.15-2.29 (1H, m), 2.89 (2H, d, J=6.9 Hz), 3.06 (2H, t, J=6.9 Hz), 4.88 (2H, d, J=5.1 Hz), 5.21 (2H, s), 7.24-7.40 (5H, m), 7.46-7.49 (2H, m), 7.91 (1H, d, J=9.0 Hz).

melting point: 121-122° C.

5) To a solution of [6-(benzyloxy)-4-butyl-2-isobutylquinolin-3-yl]methanol (1.43 g, 3.8 mmol) in tetrahydrofuran (20 ml) were added triethylamine (0.64 ml, 4.6 mmol) and methanesulfonyl chloride (0.36 ml, 4.6 mmol) and the mixture was stirred at 0° C. for 1 hr. The reaction mixture was poured into water and extracted with ethyl acetate. The extract was washed with saturated brine, and dried over anhydrous magnesium sulfate. The solvent was evaporated under reduced pressure and the residue was dissolved in N,N-dimethylformamide (30 ml). Potassium phthalimide (1.41 g, 7.6 mmol) was added, and the mixture was stirred at room temperature for 6 hrs. The reaction mixture was poured into water and extracted with ethyl acetate. The extract was washed with saturated brine, and dried over anhydrous magnesium sulfate. The solvent was evaporated under reduced pressure and the residue was purified by silica gel column chromatography to give 2-{[6-(benzyloxy)-4-butyl-2-isobutylquinolin-3-yl]methyl}-1H-isoindole-1,3(2H)-dione (1.81 g, yield 94%) as white crystals.

$^1$H-NMR (CDCl$_3$) δ: 0.80 (3H, t, J=6.8 Hz), 1.08 (6H, d, J=6.2 Hz), 1.26-1.46 (4H, m), 2.20-2.36 (1H, m), 3.21 (2H, bs), 3.62 (2H, d, J=7.0 Hz), 5.09 (2H, s), 5.25 (2H, s), 7.31-7.43 (6H, m), 7.65 (1H, d, J=6.6 Hz), 7.73-7.86 (4H, m), 9.11 (1H, d, J=6.6 Hz).

melting point: 166-168° C.

6) To a solution of 2-{[6-(benzyloxy)-4-butyl-2-isobutylquinolin-3-yl]methyl}-1H-isoindole-1,3(2H)-dione (1.75 g, 3.5 mmol) in ethanol (50 ml), being heated under reflux, was added hydrazine monohydrate (0.5 ml, 10.5 mmol), and the mixture was heated under reflux for 1 hr. The reaction mixture was poured into water and extracted with ethyl acetate. The extract was washed with saturated brine, and dried over anhydrous magnesium sulfate. The solvent was evaporated under reduced pressure and the residue was dissolved in tetrahydrofuran (20 ml). Di-tert-butyl dicarbonate (0.96 ml, 4.2 mmol) was added, and the mixture was stirred at room temperature for 1 hr. The reaction mixture was poured into water and extracted with ethyl acetate. The extract was washed with saturated brine, and dried over anhydrous magnesium sulfate. The solvent was evaporated under reduced pressure and the residue was purified by silica gel column chromatography to give tert-butyl {[6-(benzyloxy)-4-butyl-2-isobutylquinolin-3-yl]methyl}carbamate (1.32 g, yield 79%) as white crystals.

¹H-NMR (CDCl₃) δ: 0.94-0.99 (9H, m), 1.43-1.56 (13H, m), 2.16-2.30 (1H, m), 2.83 (2H, d, J=7.2 Hz), 2.95-3.00 (2H, m), 4.43 (1H, bs), 4.52 (2H, d, J=4.5 Hz), 5.21 (2H, s), 7.23 (1H, d, J=2.7 Hz), 7.29-7.41 (4H, m), 7.45-7.49 (2H, m), 7.91 (1H, d, J=9.3 Hz).

elemental analysis for C₃₀H₄₀N₂O₃
Calculated: C, 75.59; H, 8.46; N, 5.88.
Found: C, 75.45; H, 8.18; N, 5.74.
melting point: 131-132° C.

7) {[6-(benzyloxy)-4-butyl-2-isobutylquinolin-3-yl]methyl}amine Dihydrochloride (Synthesized according to a method similar to the method shown in Example 44(3).)

¹H-NMR (DMSO-d₆) δ: 0.94 (3H, t, J=7.0 Hz), 0.97 (6H, d, J=6.6 Hz), 1.37-1.61 (4H, m), 2.06-2.44 (1H, m), 3.21-3.39 (4H, m), 4.31 (2H, d, J=4.8 Hz), 5.46 (2H, s), 7.31-7.46 (3H, m), 7.52-7.57 (2H, m), 7.66 (1H, d, J=2.2 Hz), 7.85 (1H, d, J=8.2 Hz), 8.53 (1H, d, J=8.2 Hz), 8.80 (3H, bs).

melting point: 211-213° C.

Example 52

3-(aminomethyl)-4-butyl-2-isobutylquinolin-6-ol Dihydrochloride

1) A suspension of {[6-(benzyloxy)-4-butyl-2-isobutylquinolin-3-yl]methyl}amine (0.95 g, 2.0 mmol) and 5% palladium-carbon (1.0 g) in tetrahydrofuran (20 ml)-ethanol (20 ml) was stirred under a hydrogen atmosphere at room temperature for 6 hrs. The reaction mixture was filtered, and the filtrate was evaporated. The residue was crystallized from ethyl acetate-diisopropyl ether to give tert-butyl [(4-butyl-6-hydroxy-2-isobutylquinolin-3-yl)methyl]carbamate (0.68 g, yield 88%) as white crystals.

¹H-NMR (CDCl₃) δ: 0.96 (3H, t, J=6.9 Hz), 1.05 (6H, d, J=6.3 Hz), 1.45 (9H, s), 1.52-1.69 (4H, m), 2.16-2.32 (1H, m), 3.18 (2H, t, J=6.0 Hz), 3.32 (2H, d, J=6.6 Hz), 4.60 (2H, s), 5.46 (1H, bs), 7.57 (1H, s), 7.66 (1H, d, J=8.6 Hz), 8.39 (1H, d, J=8.6 Hz), 10.01 (1H, bs).

melting point: 198-200° C.

2) 3-(aminomethyl)-4-butyl-2-isobutylquinolin-6-ol dihydrochloride (Synthesized according to a method similar to the method shown in Example 44(3).)

¹H-NMR (DMSO-d₆) δ: 0.97-1.01 (9H, m), 1.52-1.63 (4H, m), 2.08-2.21 (1H, m), 3.19-3.29 (4H, m), 4.31 (2H, d, J=4.8 Hz), 7.64 (1H, s), 7.70 (1H, d, J=8.4 Hz), 8.46 (1H, d, J=8.4 Hz), 8.76 (3H, bs), 11.06 (1H, bs).

melting point: 243-244° C.

Example 53

2-{[3-(aminomethyl)-4-butyl-2-isobutylquinolin-6-yl]oxy}acetamide Dihydrochloride 1) tert-butyl {[6-(2-amino-2-oxoethoxy)-4-butyl-2-isobutylquinolin-3-yl]methyl}carbamate (Synthesized according to a method similar to the method shown in Example 7(7).)

¹H-NMR (CDCl₃) δ: 0.97-1.04 (9H, m), 1.48-1.75 (13H, m), 2.15-2.34 (1H, m), 2.86 (2H, d, J=7.0 Hz), 3.05 (2H, t, J=7.5 Hz), 4.46 (1H, bs), 4.55 (2H, d, J=4.0 Hz), 4.63 (2H, s), 5.77 (1H, bs), 6.61 (1H, bs), 7.24 (1H, d, J=2.4 Hz), 7.35 (1H, dd, J=2.4, 9.0 Hz), 7.97 (1H, d, J=9.0 Hz).

melting point: 205.5-207° C.

2) 2-{[3-(aminomethyl)-4-butyl-2-isobutylquinolin-6-yl]oxy}acetamide dihydrochloride (Synthesized according to a method similar to the method shown in Example 44(3).)

¹H-NMR (DMSO-d₆) δ: 0.97-0.99 (9H, m), 1.53-1.63 (4H, m), 2.08-2.24 (1H, m), 3.26-3.34 (4H, m), 4.33 (2H, d, J=4.5 Hz), 4.78 (2H, s), 7.50 (1H, bs), 7.61 (1H, d, J=2.1 Hz), 7.79 (1H, bs), 7.84 (1H, dd, J=2.1, 9.3 Hz), 8.55 (1H, d, J=9.3 Hz), 8.79 (3H, bs).

melting point: 218-220° C.

Example 54

{[6-(benzyloxy)-4-hexyl-2-isobutylquinolin-3-yl]methyl}amine Dihydrochloride 1) 1-(2-amino-5-{[tert-butyl(dimethyl)silyl]oxy}phenyl)heptan-1-one (Synthesized according to a method similar to the method shown in Example 51(1).)

¹H-NMR (CDCl₃) δ: 0.18 (6H, s), 0.83-0.87 (3H, m), 0.99 (9H, s), 1.23-1.43 (6H, m), 1.65-1.75 (2H, m), 2.86 (2H, t, J=9.0 Hz), 5.93 (2H, bs), 6.55 (1H, d, J=8.8 Hz), 6.84 (1H, dd, J=2.8, 8.8 Hz), 7.17 (1H, d, J=2.8 Hz).

2) methyl 4-hexyl-6-hydroxy-2-isobutylquinoline-3-carboxylate (Synthesized according to a method similar to the method shown in Example 1(1).)

¹H-NMR (CDCl₃) δ: 0.88 (3H, t, J=7.5 Hz), 0.91 (6H, d, J=6.6 Hz), 1.22-1.42 (6H, m), 1.58-1.72 (2H, m), 2.05-2.21 (1H, m), 2.78-2.89 (4H, m), 3.96 (3H, s), 7.24 (1H, dd, J=2.6, 9.2 Hz), 7.36 (1H, d, J=2.6 Hz), 7.84 (1H, d, J=9.2 Hz), 9.82 (1H, bs).

melting point: 142-143° C.

elemental analysis for C₂₁H₂₉NO₃
Calculated: C, 73.44; H, 8.51; N, 4.08.
Found: C, 73.23; H, 8.26; N, 4.00.

3) methyl 6-(benzyloxy)-4-hexyl-2-isobutylquinoline-3-carboxylate (Synthesized according to a method similar to the method shown in Example 30(1).)

¹H-NMR (CDCl₃) δ: 0.92 (3H, t, J=6.8 Hz), 1.02 (6H, d, J=6.6 Hz), 1.26-1.48 (6H, m), 1.55-1.66 (2H, m), 2.23-2.36 (1H, m), 3.00 (2H, t, J=8.1 Hz), 3.27 (2H, d, J=7.5 Hz), 4.03 (3H, s), 5.29 (2H, s), 7.35-7.48 (6H, m), 7.70 (1H, dd, J=2.5, 9.3 Hz), 9.12 (1H, d, J=9.3 Hz).

melting point: 122-123° C.

4) [6-(benzyloxy)-4-hexyl-2-isobutylquinolin-3-yl]methanol (Synthesized according to a method similar to the method shown in Example 1(2).)

¹H-NMR (CDCl₃) δ: 0.92 (3H, t, J=6.6 Hz), 0.96 (6H, d, J=6.6 Hz), 1.30-1.37 (4H, m), 1.42-1.62 (4H, m), 1.87 (1H, bs), 2.14-2.28 (1H, m), 2.88 (2H, d, J=7.2 Hz), 3.05 (2H, t, J=8.1 Hz), 4.88 (2H, s), 5.20 (2H, s), 7.24 (1H, d, J=2.7 Hz), 7.30-7.42 (4H, m), 7.46-7.48 (2H, m), 7.91 (1H, d, J=9.3 Hz).

melting point: 82-83° C.

elemental analysis for C₂₇H₃₅NO₂
Calculated: C, 79.96; H, 8.70; N, 3.45.
Found: C, 79.90; H, 8.49; N, 3.30.

5) 2-{[6-(benzyloxy)-4-hexyl-2-isobutylquinolin-3-yl]methyl}-1H-isoindole-1,3(2H)-dione (Synthesized according to a method similar to the method shown in Example 51(5).)

¹H-NMR (CDCl₃) δ: 0.83 (3H, t, J=7.0 Hz), 0.96 (6H, d, J=6.6 Hz), 1.04-1.24 (4H, m), 1.30-1.39 (4H, m), 2.12-2.25 (1H, m), 3.06 (2H, d, J=7.5 Hz), 3.09 (2H, d, J=7.5 Hz), 5.07 (2H, s), 5.19 (2H, s), 7.23 (1H, d, J=2.7 Hz), 7.27-7.47 (6H, m), 7.67-7.80 (4H, m), 7.92 (1H, d, J=9.3 Hz).

melting point: 140-140.5° C.

6) tert-butyl {[6-(benzyloxy)-4-hexyl-2-isobutylquinolin-3-yl]methyl}carbamate (Synthesized according to a method similar to the method shown in Example 51(6).)

$^1$H-NMR (CDCl$_3$) δ: 0.92 (3H, t, J=6.6 Hz), 0.98 (6H, d, J=6.9 Hz), 1.26-1.64 (17H, m), 2.13-2.35 (1H, m), 2.84 (2H, d, J=7.4 Hz), 2.98 (2H, t, J=7.7 Hz), 4.41 (1H, bs), 4.52 (2H, d, J=6.6 Hz), 5.21 (2H, s), 7.24 (1H, d, J=2.8 Hz), 7.29-7.51 (6H, m), 7.92 (1H, d, J=9.2 Hz).

elemental analysis for C$_{32}$H$_{44}$N$_2$O$_3$

Calculated: C, 76.15; H, 8.79; N, 5.55.

Found: C, 76.16; H, 8.59; N, 5.39.

melting point: 125.5-126° C.

7) {[6-(benzyloxy)-4-hexyl-2-isobutylquinolin-3-yl]methyl}amine dihydrochloride (Synthesized according to a method similar to the method shown in Example 44(3).)

$^1$H-NMR (DMSO-d$_6$) δ: 0.89 (3H, t, J=6.6 Hz), 0.97 (6H, d, J=6.6 Hz), 1.30 (4H, bs), 1.49 (4H, bs), 2.09-2.22 (1H, m), 3.22-3.36 (4H, m), 4.30 (2H, d, J=5.1 Hz), 5.44 (2H, s), 7.32-7.54 (4H, m), 7.66 (1H, s), 7.84 (1H, d, J=9.6 Hz), 8.51 (1H, bs), 8.77 (3H, bs).

melting point: 195-197° C.

Example 55

3-(aminomethyl)-4-hexyl-2-isobutylquinolin-6-ol Dihydrochloride 1) tert-butyl [(4-hexyl-6-hydroxy-2-isobutylquinolin-3-yl)methyl]carbamate (Synthesized according to a method similar to the method shown in Example 52(1).)

$^1$H-NMR (CDCl$_3$) δ: 0.86 (3H, t, J=6.3 Hz), 1.06 (6H, d, J=6.0 Hz), 1.24-1.35 (4H, m), 1.46-1.69 (13H, m), 2.18-2.29 (1H, m), 3.16 (2H, t, J=6.5 Hz), 3.30 (2H, bs), 4.59 (2H, bs), 5.31 (1H, bs), 7.52 (1H, bs), 7.70 (1H, bs), 8.38 (1H, bs).

melting point: 173-175° C.

2) 3-(aminomethyl)-4-hexyl-2-isobutylquinolin-6-ol dihydrochloride (Synthesized according to a method similar to the method shown in Example 44(3).)

$^1$H-NMR (DMSO-d$_6$) δ: 0.89 (3H, t, J=7.2 Hz), 0.98 (6H, d, J=6.6 Hz), 1.26-1.39 (4H, m), 1.49-1.65 (4H, m), 2.09-2.21 (1H, m), 3.19-3.29 (4H, m), 4.32 (2H, d, J=5.1 Hz), 7.64 (1H, d, J=1.4 Hz), 7.71 (1H, dd, J=1.4, 9.0 Hz), 8.48 (1H, d, J=9.0 Hz), 8.78 (3H, bs), 11.07 (1H, bs).

melting point: 257-258° C.

Example 56

Ethyl 2-(3-(aminomethyl)-4-(4-methylphenyl)-2-neopentyl-6-quinolinyl)-1,3-thiazole-4-carboxylate Dihydrochloride 1) 6-hydroxy-4-(4-methylphenyl)-2-neopentyl-3-quinolinecarbonitrile (Synthesized according to a method similar to the method shown in Example 7(6).)

$^1$H-NMR (CDCl$_3$) δ: 1.09 (9H, s), 2.45 (3H, bs), 3.13 (2H, s), 6.22 (1H, bs), 6.95 (1H, d, J=2.7 Hz), 7.30 (2H, d, J=8.1 Hz), 7.35 (2H, d, J=8.1 Hz), 7.39 (1H, dd, J=2.7, 9.0 Hz), 8.02 (1H, dd, J=1.8, 8.7 Hz).

2) tert-butyl (6-hydroxy-4-(4-methylphenyl)-2-neopentyl-3-quinolinyl)methylcarbamate (Synthesized according to a method similar to the method shown in Example 13(2).)

$^1$H-NMR (CDCl$_3$) δ: 1.04 (9H, s), 1.39 (9H, s), 2.44 (3H, s), 3.00 (2H, s), 4.23 (3H, bs), 6.62 (1H, bs), 6.90 (1H, bs), 7.09 (2H, d, J=7.8 Hz), 7.19-7.23 (3H, m), 7.92 (1H, d, J=9.3 Hz).

3) tert-butyl [4-(4-methylphenyl)-2-neopentyl-6-trifluoromethanesulfonyloxy-quinolin-3-yl]methylcarbamate (Synthesized according to a method similar to the method shown in Example 19(1).)

$^1$H-NMR (CDCl$_3$) δ: 1.09 (9H, s), 1.40 (9H, s), 2.49 (3H, s), 3.07 (2H, s), 4.30 (1H, bs), 4.38 (2H, d, J=5.1 Hz), 7.12 (2H, d, J=7.8 Hz), 7.21 (1H, d, J=2.7 Hz), 7.36 (2H, d, J=7.8 Hz), 7.52 (1H, dd, J=2.7, 9.3 Hz), 8.13 (1H, d, J=9.3 Hz).

4) A mixture of tert-butyl [4-(4-methylphenyl)-2-neopentyl-6-trifluoromethanesulfonyloxy-quinolin-3-yl]methylcarbamate (3.97 g, 7.0 mmol), boron bispinacolate (3.55 g, 14.0 mmol), [1,1'-bis(diphenylphosphino)ferrocene]dichloropalladium-dichloromethane (1:1) complex (0.15 g, 0.21 mmol), potassium acetate (2.06 g, 21 mmol) and dimethyl sulfoxide (50 ml) was stirred under an argon atmosphere at 100° C. for 2 hrs. The reaction mixture was poured into water and extracted with ethyl acetate. The extract was washed with saturated brine, and dried over anhydrous magnesium sulfate. The solvent was evaporated under reduced pressure, and a mixture of the residue, 2-chlorothiazole (2.68 g, 14.0 mmol), tetrakis(triphenylphosphine)palladium (0.80 g, 0.7 mmol), potassium carbonate (2.90 g, 21 mmol), ethanol (5 ml), toluene (30 ml) and water (5 ml) was stirred under an argon atmosphere at 100° C. for 10 hrs. The reaction mixture was poured into water and extracted with ethyl acetate. The extract was washed with saturated brine, and dried over anhydrous magnesium sulfate. The solvent was evaporated under reduced pressure and the residue was purified by silica gel column chromatography to give ethyl 2-[3-[[(tert-butoxycarbonyl)amino]methyl]-4-(4-methylphenyl)-2-neopentyl-6-quinolinyl]-1,3-thiazole-4-carboxylate (3.02 g, yield 75%) as white crystals.

$^1$H-NMR (CDCl$_3$) δ: 1.11 (9H, s), 1.40-1.44 (12H, m), 2.49 (3H, s), 3.06 (2H, s), 4.36 (3H, bs), 4.43 (2H, q, J=6.9 Hz), 7.17 (2H, d, J=7.8 Hz), 7.36 (2H, d, J=7.8 Hz), 7.86 (1H, d, J=2.1 Hz), 8.11 (1H, s), 8.12 (1H, d, J=8.7 Hz), 8.36 (1H, dd, J=2.1, 8.7 Hz).

5) ethyl 2-(3-(aminomethyl)-4-(4-methylphenyl)-2-neopentyl-6-quinolinyl)-1,3-thiazole-4-carboxylate dihydrochloride (Synthesized according to a method similar to the method shown in Example 44(3).)

$^1$H-NMR (DMSO-d$_6$) δ: 1.10 (9H, s), 1.32 (3H, t, J=7.2 Hz), 2.50 (3H, s), 3.23 (2H, bs), 4.07 (2H, bs), 4.31 (2H, q, J=7.2 Hz), 7.42 (2H, d, J=7.8 Hz), 7.50 (2H, d, J=7.8 Hz), 7.91 (1H, bs), 8.43 (5H, bs), 8.58 (1H, s).

Example 57

2-(3-(aminomethyl)-4-(4-methylphenyl)-2-neopentyl-6-quinolinyl)-1,3-thiazole-4-carboxylic Acid Dihydrochloride 1) 2-[3-[[(tert-butoxycarbonyl)amino]methyl]-4-(4-methylphenyl)-2-neopentyl-6-quinolinyl]-1,3-thiazole-4-carboxylic acid (Synthesized according to a method similar to the method shown in Example 6(1).)

$^1$H-NMR (CDCl$_3$) δ: 1.11 (9H, s), 1.41 (9H, s), 2.50 (3H, s), 3.10 (2H, s), 4.38 (2H, s), 7.18 (2H, d, J=7.7 Hz), 7.37 (2H, d, J=7.7 Hz), 7.86 (1H, d, J=2.0 Hz), 8.18 (1H, d, J=9.0 Hz), 8.21 (1H, s), 8.31 (1H, dd, J=2.0, 9.0 Hz).

2) 2-(3-(aminomethyl)-4-(4-methylphenyl)-2-neopentyl-6-quinolinyl)-1,3-thiazole-4-carboxylic acid dihydrochloride (Synthesized according to a method similar to the method shown in Example 44(3).)

$^1$H-NMR (DMSO-d$_6$) δ: 1.10 (9H, s), 2.50 (3H, s), 3.17 (2H, bs), 4.06 (2H, bs), 7.39-7.51 (4H, m), 7.89-7.93 (1H, m), 8.31-8.54 (6H, m).

Example 58

2-(3-(aminomethyl)-4-(4-methylphenyl)-2-neopentyl-6-quinolinyl)-1,3-thiazole-4-carboxamide Dihydrochloride

1) tert-butyl [6-[4-(aminocarbonyl)-1,3-thiazol-2-yl]-4-(4-methylphenyl)-2-neopentyl-3-quinolinyl]methylcarbamate (Synthesized according to a method similar to the method shown in Example 19(4).)

$^1$H-NMR (CDCl$_3$) δ: 1.19 (9H, s), 1.40 (9H, s), 2.52 (3H, s), 3.24 (2H, bs), 4.43 (2H, bs), 5.73 (1H, bs), 7.17-7.25 (4H, m), 7.46 (2H, d, J=7.8 Hz), 7.89 (1H, d, J=1.8 Hz), 8.17 (1H, s), 8.46 (1H, d, J=8.7 Hz), 8.06 (1H, s).

2) 2-(3-(aminomethyl)-4-(4-methylphenyl)-2-neopentyl-6-quinolinyl)-1,3-thiazole-4-carboxamide dihydrochloride (Synthesized according to a method similar to the method shown in Example 44(3).)

$^1$H-NMR (DMSO-d$_6$) δ: 1.11 (9H, s), 2.50 (3H, s), 3.24 (2H, bs), 4.07 (2H, d, J=5.4 Hz), 7.35 (1H, bs), 7.42 (2H, d, J=7.8 Hz), 7.50 (2H, d, J=7.8 Hz), 7.70 (1H, bs), 7.80 (1H, s), 7.88 (1H, bs), 8.29 (1H, s), 8.43 (3H, bs), 8.60 (1H, s).

Example 59

2-((3-(aminomethyl)-4-(4-methylphenyl)-2-neopentyl-6-quinolinyl)oxy)acetamide

1) 2-[[3-cyano-4-(4-methylphenyl)-2-neopentyl-6-quinolinyl]oxy]acetamide (Synthesized according to a method similar to the method shown in Example 7(7).)

$^1$H-NMR (CDCl$_3$) δ: 1.11 (9H, s), 2.51 (3H, s), 3.17 (2H, s), 4.42 (2H, s), 5.71 (1H, bs), 6.55 (1H, bs), 6.96 (1H, d, J=3.0 Hz), 7.33 (2H, d, J=8.1 Hz), 7.40 (2H, d, J=8.1 Hz), 7.50 (1H, dd, J=3.0, 9.0 Hz), 8.10 (1H, d, J=9.0 Hz).

2) 2-((3-(aminomethyl)-4-(4-methylphenyl)-2-neopentyl-6-quinolinyl)oxy)acetamide (Synthesized according to a method similar to the method shown in Example 7(8).)

$^1$H-NMR (CDCl$_3$) δ: 1.08 (9H, s), 1.37 (2H, bs), 2.50 (3H, s), 3.06 (2H, s), 3.84 (2H, s), 4.34 (2H, s), 5.67 (1H, bs), 6.57 (1H, d, J=2.7 Hz), 7.15 (2H, d, J=8.1 Hz), 7.26-7.35 (4H, m), 8.00 (1H, d, J=9.3 Hz).

Example 60

{[2-isobutyl-4-(4-methylphenyl)-6-(2H-tetrazol-5-ylmethoxy)quinolin-3-yl]methyl}amine Dihydrochloride

1) A mixture of tert-butyl {[6-hydroxy-2-isobutyl-4-(4-methylphenyl)quinolin-3-yl]methyl}carbamate (2.5 g, 5.9 mmol), bromoacetonitrile (0.5 ml, 7.2 mmol), potassium carbonate (1.0 g, 7.2 mmol) and N,N-dimethylformamide (10 ml) was stirred at room temperature for 12 hrs. Water was added to the reaction mixture and the mixture was extracted with ethyl acetate. The extract was washed with saturated brine, dried over anhydrous magnesium sulfate and concentrated under reduced pressure. The residue was purified by silica gel column chromatography to give tert-butyl {[6-(cyanomethoxy)-2-isobutyl-4-(4-methylphenyl)quinolin-3-yl]methyl}carbamate (1.4 g, yield 52%) as pale-yellow crystals.

$^1$H-NMR (CDCl$_3$) δ: 1.01 (6H, d, J=6.6 Hz), 1.41 (9H, s), 2.30-2.39 (1H, m), 2.47 (3H, s), 2.94 (2H, d, J=6.9 Hz), 4.30 (3H, s), 4.64 (2H, s), 6.70 (1H, d, J=2.7 Hz), 7.14 (2H, d, J=7.8 Hz), 7.33-7.36 (3H, m), 8.02 (1H, d, J=9.0 Hz).

2) To a solution of tert-butyl {[6-(cyanomethoxy)-2-isobutyl-4-(4-methylphenyl)quinolin-3-yl]methyl}carbamate (0.46 g, 1.0 mmol) and sodium azide (0.13 g, 2.0 mmol) in dimethyl sulfoxide (10 ml) was added ammonium chloride (0.22 g, 4.0 mmol), and the mixture was stirred at 70° C. for 24 hrs. Water was added to the reaction mixture and the mixture was extracted with ethyl acetate. The extract was washed with saturated brine, dried over anhydrous magnesium sulfate and concentrated under reduced pressure. The residue was crystallized from diisopropyl ether to give tert-butyl {[2-isobutyl-4-(4-methylphenyl)-6-(2H-tetrazol-5-ylmethoxy)quinolin-3-yl]methyl}carbamate (0.47 g, yield 93%) as pale-yellow crystals.

$^1$H-NMR (CDCl$_3$) δ: 0.94 (6H, d, J=6.6 Hz), 1.39 (9H, s), 2.17-2.19 (1H, m), 2.50 (3H, s), 3.06-3.07 (2H, m), 4.31-4.34 (3H, m), 5.36 (2H, s), 6.48 (1H, d, J=2.4 Hz), 6.68-6.69 (1H, m), 6.97 (2H, d, J=7.8 Hz), 7.35 (2H, d, J=7.8 Hz), 7.36-7.37 (1H, m).

3) {[2-isobutyl-4-(4-methylphenyl)-6-(2H-tetrazol-5-ylmethoxy)quinolin-3-yl]methyl}amine dihydrochloride (Synthesized according to a method similar to the method shown in Example 13(6).)

$^1$H-NMR (DMSO-d$_6$) δ: 0.86 (6H, d, J=6.0 Hz), 2.17-2.25 (1H, m), 2.33 (3H, s), 2.98 (2H, s), 3.83 (2H, s), 5.32 (2H, s), 6.60 (1H, s), 7.14 (2H, d, J=8.1 Hz), 7.30 (2H, d, J=8.1 Hz), 7.62 (2H, s), 8.20 (4H, m).

Example 61

3-({[3-(aminomethyl)-2-isobutyl-4-(4-methylphenyl)quinolin-6-yl]oxy}methyl)-1,2,4-oxadiazol-5(4H)-one Dihydrochloride

1) A mixture of tert-butyl {[6-(cyanomethoxy)-2-isobutyl-4-(4-methylphenyl)quinolin-3-yl]methyl}carbamate (0.46 g, 1.0 mmol), hydroxyammonium chloride (0.21 g, 3.0 mmol), sodium carbonate (0.43 g, 4.0 mmol) and ethanol (10 ml) was stirred at 70° C. for 17 hrs. Water was added to the reaction mixture and the mixture was extracted with ethyl acetate. The extract was washed with saturated brine, dried over anhydrous magnesium sulfate and concentrated under reduced pressure. The residue was dissolved in tetrahydrofuran (10 ml). 1,1'-Carbonylbis-1H-imidazole (0.32 g, 2.0 mmol) was added and the mixture was stirred at 70° C. for 24 hrs. Water was added to the reaction mixture and the mixture was extracted with ethyl acetate. The extract was washed with saturated brine, dried over anhydrous magnesium sulfate and concentrated under reduced pressure. The residue was purified by silica gel column chromatography to give tert-butyl ({2-isobutyl-4-(4-methylphenyl)-6-[(5-oxo-4,5-dihydro-1,2,4-oxadiazol-3-yl)methoxy]quinolin-3-yl}methyl)carbamate (0.18 g, yield 35%) as pale-yellow crystals.

$^1$H-NMR (CDCl$_3$) δ: 0.99 (6H, d, J=6.6 Hz), 1.41 (9H, s), 2.21-2.24 (1H, m), 2.50 (3H, s), 2.96-2.97 (1H, m), 4.30-4.31 (1H, m), 4.33 (1H, bs), 4.85 (2H, s), 6.56 (1H, s), 6.71-6.73 (1H, m), 7.08 (2H, d, J=9.0 Hz), 7.38 (2H, d, J=9.0 Hz), 7.56-7.58 (1H, m).

2) 3-({[3-(aminomethyl)-2-isobutyl-4-(4-methylphenyl)quinolin-6-yl]oxy}methyl)-1,2,4-oxadiazol-5(4H)-one Dihydrochloride (Synthesized According to a Method Similar to the Method Shown in Example 13(6)

$^1$H-NMR (DMSO-d$_6$) δ: 1.14 (6H, d, J=6.6 Hz), 2.44-2.48 (1H, m), 2.59 (3H, s), 3.18 (2H, s), 4.10-4.11 (2H, m), 5.17

(2H, s), 6.84 (1H, s), 7.42 (2H, d, J=8.1 Hz), 7.56 (2H, d, J=8.1 Hz), 7.75-7.79 (1H, m), 8.37 (4H, bs).

Example 62

Methyl 5-[3-(aminomethyl)-2-isobutyl-4-(4-methylphenyl)quinolin-6-yl]-2-furoate Dihydrochloride 1) methyl 5-[3-{[(tert-butoxycarbonyl)amino]methyl}-2-isobutyl-4-(4-methylphenyl)quinolin-6-yl]-2-furoate (Synthesized according to a method similar to the method shown in Example 56(1).)

$^1$H-NMR (CDCl$_3$) δ: 1.04 (6H, d, J=6.6 Hz), 1.42 (9H, s), 2.36-2.39 (1H, m), 2.50 (3H, s), 3.00 (2H, d, J=6.9 Hz), 3.89 (3H, s), 4.32 (3H, s), 6.66 (1H, d, J=3.3 Hz), 7.16 (2H, d, J=7.5 Hz), 7.20 (1H, d, J=3.3 Hz), 7.36 (2H, d, J=7.5 Hz), 7.68 (1H, s), 8.10-8.14 (2H, m).

2) methyl 5-[3-(aminomethyl)-2-isobutyl-4-(4-methylphenyl)quinolin-6-yl]-2-furoate dihydrochloride (Synthesized according to a method similar to the method shown in Example 13(6).)

$^1$H-NMR (DMSO-d$_6$) δ: 1.01 (6H, d, J=6.6 Hz), 2.34-2.36 (1H, m), 2.48 (3H, s), 3.16 (2H, s), 3.78 (3H, s), 3.98 (3H, s), 7.26 (1H, d, J=3.6 Hz), 7.39-7.40 (3H, m), 7.47 (2H, d, J=7.8 Hz), 7.66 (1H, s), 8.50 (3H, bs).

Example 63

5-[3-(aminomethyl)-2-isobutyl-4-(4-methylphenyl)quinolin-6-yl]-2-furoic Acid Dihydrochloride 1) 5-[3-{[(tert-butoxycarbonyl)amino]methyl}-2-isobutyl-4-(4-methylphenyl)quinolin-6-yl]-2-furoic acid (Synthesized according to a method similar to the method shown in Example 6(1).)

$^1$H-NMR (CDCl$_3$) δ: 1.09 (6H, d, J=6.3 Hz), 1.42 (9H, s), 2.22-2.26 (1H, m), 2.52 (3H, s), 3.32 (2H, s), 4.35 (2H, s), 4.82 (1H, bs), 6.68 (1H, d, J=3.3 Hz), 7.20-7.23 (3H, m), 7.41-7.43 (2H, m), 7.67 (1H, s), 8.12-8.13 (1H, m), 8.55-8.58 (1H, m).

2) 5-[3-(aminomethyl)-2-isobutyl-4-(4-methylphenyl)quinolin-6-yl]-2-furoic acid dihydrochloride (Synthesized according to a method similar to the method shown in Example 13(6).)

$^1$H-NMR (DMSO-d$_6$) δ: 1.02 (6H, d, J=6.6 Hz), 2.35-2.38 (1H, m), 2.48 (3H, s), 3.06 (2H, s), 3.95 (3H, s), 7.19 (1H, d, J=3.6 Hz), 7.30-7.37 (3H, m), 7.47 (2H, d, J=7.8 Hz), 7.64 (1H, s), 8.50 (3H, bs).

Example 64

5-[3-(aminomethyl)-2-isobutyl-4-(4-methylphenyl)quinolin-6-yl]-2-furamide 1) tert-butyl {[6-[5-(aminocarbonyl)-2-furyl]-2-isobutyl-4-(4-methylphenyl)quinolin-3-yl]methyl}carbamate (Synthesized according to a method similar to the method shown in Example 19(4).)

$^1$H-NMR (CDCl$_3$) δ: 1.03 (6H, d, J=6.6 Hz), 1.42 (9H, s), 2.31-2.35 (1H, m), 2.51 (3H, s), 3.14-3.16 (2H, m), 4.33 (2H, d, J=4.8 Hz), 4.79 (1H, bs), 5.74 (1H, bs), 6.37 (1H, bs), 6.70 (1H, d, J=3.6 Hz), 7.19-7.22 (3H, m), 7.39 (2H, d, J=8.1 Hz), 7.61 (1H, s), 7.82-7.85 (1H, m), 8.07-8.11 (1H, m).

2) To a solution of tert-butyl {[6-[5-(aminocarbonyl)-2-furyl]-2-isobutyl-4-(4-methylphenyl)quinolin-3-yl]methyl}carbamate (0.5 g, 1.0 mmol) in ethyl acetate (5 ml) was added 4N solution of hydrogen chloride in ethyl acetate (2 ml), and the mixture was stirred at room temperature for 3 hrs. The reaction mixture was concentrated under reduced pressure and the residue was crystallized from diisopropyl ether. The obtained crystals were dissolved in ethyl acetate (5 ml) and triethylamine (1 ml) was added. Water was added to the reaction mixture and the mixture was extracted with ethyl acetate. The extract was washed with saturated brine, dried over anhydrous magnesium sulfate and concentrated under reduced pressure. The residue was crystallized from diisopropyl ether to give 5-[3-(aminomethyl)-2-isobutyl-4-(4-methylphenyl)quinolin-6-yl]-2-furamide (0.29 g, yield 71%) as white crystals.

$^1$H-NMR (CDCl$_3$) δ: 1.05 (6H, d, J=6.6 Hz), 2.41-2.44 (1H, m), 2.50 (3H, s), 3.02 (2H, d, J=7.2 Hz), 3.81 (2H, s), 6.67 (1H, d, J=3.9 Hz), 7.20-7.23 (3H, m), 7.36 (2H, d, J=7.8 Hz), 7.60 (1H, s), 7.95-7.99 (1H, m), 8.09-8.12 (1H, m).

Example 65

2-{[3-(aminomethyl)-4-(4-methylphenyl)-2-propylquinolin-6-yl]oxy}acetamide Dihydrochloride 1) 6-hydroxy-4-(4-methylphenyl)-2-propylquinoline-3-carbonitrile (Synthesized according to a method similar to the method shown in Example 7(6).)

$^1$H-NMR (CDCl$_3$) δ: 1.07 (3H, t, J=7.5 Hz), 1.81-2.03 (2H, m), 2.46 (3H, s), 3.12-3.17 (2H, m), 6.99 (1H, d, J=2.7 Hz), 7.33-7.35 (4H, m), 7.45 (1H, dd, J=2.7 Hz, 9.0 Hz), 7.97 (1H, d, J=9.0 Hz), 8.49 (1H, bs).

2) tert-butyl {[6-hydroxy-4-(4-methylphenyl)-2-propylquinolin-3-yl]methyl}carbamate (Synthesized according to a method similar to the method shown in Example 13(2).)

$^1$H-NMR (CDCl$_3$) δ: 1.02 (3H, t, J=7.2 Hz), 1.40 (9H, s), 1.75-1.82 (2H, m), 2.42 (3H, s), 2.97-3.02 (2H, m), 4.27-4.28 (1H, m), 4.33 (1H, bs), 6.66 (1H, d, J=2.7 Hz), 7.07 (2H, d, J=7.5 Hz), 7.23-7.27 (3H, m), 7.85 (1H, d, J=9.6 Hz).

3) tert-butyl {[6-(2-amino-2-oxoethoxy)-4-(4-methylphenyl)-2-propylquinolin-3-yl]methyl}carbamate (Synthesized according to a method similar to the method shown in Example 23(1).)

$^1$H-NMR (CDCl$_3$) δ: 1.12 (3H, t, J=7.2 Hz), 1.41 (9H, s), 1.90-1.94 (2H, m), 2.51 (3H, s), 3.23-3.24 (2H, m), 4.34 (1H, bs), 4.35 (1H, bs), 5.64 (1H, bs), 6.60 (1H, bs), 6.63 (1H, d, J=2.7 Hz), 7.12 (2H, d, J=8.1 Hz), 7.37 (2H, d, J=8.1 Hz), 7.41 (2H, s).

4) 2-{[3-(aminomethyl)-4-(4-methylphenyl)-2-propylquinolin-6-yl]oxy}acetamide dihydrochloride (Synthesized according to a method similar to the method shown in Example 13(6).)

$^1$H-NMR (DMSO-d$_6$) δ: 0.92 (3H, t, J=7.2 Hz), 1.69-1.77 (2H, m), 2.31 (3H, s), 3.02 (2H, s), 3.82-3.83 (2H, m), 4.21 (2H, s), 6.49 (1H, s), 7.17 (2H, d, J=7.8 Hz), 7.19 (1H, s), 7.29 (2H, d, J=7.8 Hz), 7.43-7.50 (2H, m), 8.04-8.10 (1H, m), 8.48 (3H, bs).

Example 66

Ethyl 2-[3-(aminomethyl)-4-(4-methylphenyl)-2-propylquinolin-6-yl]-1,3-thiazole-4-carboxylate Dihydrochloride 1) ethyl 2-[3-{[(tert-butoxycarbonyl)amino]methyl}-4-(4-methylphenyl)-2-propylquinolin-6-yl]-1,3-thiazole-4-carboxylate (Synthesized according to a method similar to the method shown in Example 56(4).)

$^1$H-NMR (CDCl$_3$) δ: 1.11 (3H, t, J=7.2 Hz), 1.42 (3H, t, J=7.2 Hz), 1.56 (9H, s), 1.87-1.95 (2H, m), 2.50 (3H, s), 3.05-3.11 (2H, m), 4.33-4.39 (3H, m), 4.42 (2H, q, J=7.2 Hz), 7.17 (2H, d, J=8.1 Hz), 7.36 (2H, d, J=8.1 Hz), 7.87 (1H, d, J=1.8 Hz), 8.11 (1H, s), 8.13 (1H, d, J=9.0 Hz), 8.36 (1H, dd, J=1.8 Hz, 9.0 Hz).

2) ethyl 2-[3-(aminomethyl)-4-(4-methylphenyl)-2-propylquinolin-6-yl]-1,3-thiazole-4-carboxylate dihydrochloride (Synthesized according to a method similar to the method shown in Example 13(6).)

$^1$H-NMR (DMSO-d$_6$) δ: 1.12 (3H, t, J=7.2 Hz), 1.34 (3H, t, J=7.2 Hz), 1.91-2.01 (2H, m), 2.53 (3H, s), 3.14-3.16 (2H, m), 4.01-4.02 (2H, m), 4.32 (2H, q, J=7.2 Hz), 7.39 (2H, d, J=8.1 Hz), 7.51 (2H, d, J=8.1 Hz), 7.92 (1H, s), 8.20-8.23 (1H, m), 8.34 (3H, bs), 8.35-8.38 (1H, m), 8.59 (1H, s).

Example 67

2-[3-(aminomethyl)-4-(4-methylphenyl)-2-propylquinolin-6-yl]-1,3-thiazole-4-carboxylic Acid Dihydrochloride 1) 2-[3-{[(tert-butoxycarbonyl)amino]methyl}-4-(4-methylphenyl)-2-propylquinolin-6-yl]-1,3-thiazole-4-carboxylic acid (Synthesized according to a method similar to the method shown in Example 6(1).)

$^1$H-NMR (CDCl$_3$) δ: 1.12 (3H, t, J=7.2 Hz), 1.43 (9H, s), 1.88-1.94 (2H, m), 2.51 (3H, s), 3.13-3.14 (2H, m), 4.34 (2H, s), 4.36 (1H, bs), 7.17 (2H, d, J=8.1 Hz), 7.38 (2H, d, J=8.1 Hz), 7.88 (1H, s), 8.22 (2H, s), 8.28-8.29 (1H, m).

2) 2-[3-(aminomethyl)-4-(4-methylphenyl)-2-propylquinolin-6-yl]-1,3-thiazole-4-carboxylic acid dihydrochloride (Synthesized according to a method similar to the method shown in Example 13(6).)

$^1$H-NMR (DMSO-d$_6$) δ: 1.01 (3H, t, J=7.2 Hz), 1.80-1.91 (2H, m), 2.41 (3H, s), 3.05-3.10 (2H, m), 3.91 (2H, s), 7.29 (2H, d, J=8.1 Hz), 7.41 (2H, d, J=8.1 Hz), 7.81 (1H, s), 8.13-8.16 (1H, m), 8.25-8.28 (1H, m), 8.28 (3H, bs), 8.42 (1H, s).

Example 68

2-[3-(aminomethyl)-2-propyl-4-(4-methylphenyl) quinolin-6-yl]-1,3-thiazole-4-carboxamide Dihydrochloride 1) tert-butyl {[6-[4-(aminocarbonyl)-1,3-thiazol-2-yl]-4-(4-methylphenyl)-2-propylquinolin-3-yl]methyl}carbamate (Synthesized according to a method similar to the method shown in Example 7(7).)

$^1$H-NMR (CDCl$_3$) δ: 1.19 (3H, t, J=7.2 Hz), 1.42 (9H, s), 1.98-20.9 (2H, m), 2.55 (3H, s), 3.58-3.64 (2H, m), 4.41-4.43 (2H, m), 4.89 (1H, bs), 5.85 (1H, bs), 7.27 (2H, d, J=8.1 Hz), 7.48 (2H, d, J=8.1 Hz), 7.91 (1H, s), 8.18 (1H, s), 8.47-8.51 (1H, m), 9.07-9.10 (1H, m).

2) 2-[3-(aminomethyl)-4-(4-methylphenyl)-2-propylquinolin-6-yl]-1,3-thiazole-4-carboxamide dihydrochloride (Synthesized according to a method similar to the method shown in Example 13(6).)

$^1$H-NMR (DMSO-d$_6$) δ: 1.23 (3H, t, J=7.2 Hz), 2.04-2.08 (2H, m), 2.63 (3H, s), 3.28 (2H, t, J=7.5 Hz), 4.12-4.13 (2H, m), 7.52 (2H, d, J=7.8 Hz), 7.62 (2H, d, J=7.8 Hz), 7.90 (1H, d, J=1.5 Hz), 8.33 (1H, d, J=9.0 Hz), 8.39 (1H, s), 8.42 (3H, bs), 8.61 (1H, dd, J=1.5 Hz, 9.0 Hz).

Example 69

2-{[3-(aminomethyl)-2-(cyclopropylmethyl)-4-(4-methylphenyl)quinolin-6-yl]oxy}acetamide Dihydrochloride 1) 6-hydroxy-2-(cyclopropylmethyl)-4-(4-methylphenyl)quinoline-3-carbonitrile (Synthesized according to a method similar to the method shown in Example 7(6).)

$^1$H-NMR (CDCl$_3$) δ: 0.39-0.45 (2H, m), 0.49-0.58 (2H, m), 1.29-1.38 (1H, m), 2.46 (3H, s), 3.10 (2H, d, J=7.2 Hz), 6.99 (1H, d, J=2.7 Hz), 7.25-7.43 (5H, m), 8.03 (1H, d, J=9.3 Hz).

2) tert-butyl {[6-hydroxy-2-(cyclopropylmethyl)-4-(4-methylphenyl)quinolin-3-yl]methyl}carbamate (Synthesized according to a method similar to the method shown in Example 13(2).)

$^1$H-NMR (DMSO-d$_6$) δ: 0.00-0.01 (2H, m), 0.23-0.25 (2H, m), 1.10 (9H, s), 2.16 (3H, s), 2.54-2.56 (2H, m), 3.74-3.75 (2H, m), 6.24 (1H, d, J=2.4 Hz), 6.77 (1H, bs), 6.95 (1H, dd, J=2.4 Hz, 9.0 Hz), 7.01 (2H, d, J=8.1 Hz), 7.69 (2H, d, J=8.1 Hz), 7.57 (1H, d, J=9.0 Hz), 9.42 (1H, s).

3) tert-butyl {[6-(2-amino-2-oxoethoxy)-2-(cyclopropylmethyl)-4-(4-methylphenyl)quinolin-3-yl]methyl}carbamate (Synthesized according to a method similar to the method shown in Example 23(1).)

$^1$H-NMR (CDCl$_3$) δ: 0.55-0.58 (4H, m), 1.39 (9H, s), 1.52-1.55 (1H, m), 2.52 (3H, s), 3.29-3.31 (2H, m), 4.35 (2H, s), 4.35-4.37 (2H, m), 4.37 (1H, bs), 5.65 (1H, bs), 6.64 (1H, bs), 6.65 (1H, s), 7.14 (2H, d, J=7.8 Hz), 7.39 (2H, d, J=7.8 Hz), 7.38-7.39 (1H, m), 7.49-7.50 (1H, m).

4) 2-{[3-(aminomethyl)-2-(cyclopropylmethyl)-4-(4-methylphenyl)quinolin-6-yl]oxy}acetamide dihydrochloride (Synthesized according to a method similar to the method shown in Example 13(6).)

$^1$H-NMR (DMSO-d$_6$) δ: 0.25-0.32 (4H, m), 1.86-1.92 (1H, m), 2.22 (3H, s), 3.11 (2H, s), 3.73-3.78 (2H, m), 4.16 (2H, s), 6.47 (1H, s), 7.12-7.15 (3H, m), 7.20-7.23 (2H, m), 7.18 (1H, s), 7.55-7.57 (1H, m), 8.34 (4H, bs).

Example 70

Ethyl (2E)-3-[3-(aminomethyl)-4-(4-methylphenyl)-2-propylquinolin-6-yl]acrylate Dihydrochloride 1) 3-{[(tert-butoxycarbonyl)amino]methyl}-4-(4-methylphenyl)-2-propylquinolin-6-yl trifluoromethanesulfonate was synthesized according to a method similar to that shown in Example 19(1), and subsequently, ethyl (2E)-3-[3-{[(tert-butoxycarbonyl)amino]methyl}-4-(4-methylphenyl)-2-propylquinolin-6-yl]acrylate was synthesized according to a method similar to that shown in Example 19(2).

$^1$H-NMR (CDCl$_3$) δ: 1.09 (3H, t, J=7.2 Hz), 1.32 (3H, t, J=7.2 Hz), 1.42 (9H, s), 1.85-1.93 (2H, m), 2.50 (3H, s), 3.04-3.10 (2H, m), 4.24 (2H, q, J=7.2 Hz), 4.25-4.40 (3H, m), 6.40 (1H, d, J=15.9 Hz), 7.12 (2H, d, J=7.8 Hz), 7.34 (1H, d, J=2.1 Hz), 7.35 (2H, d, J=7.8 Hz), 7.63 (1H, d, J=15.9 Hz), 7.62 (1H, dd, J=2.1 Hz, 8.7 Hz), 8.05 (1H, d, J=8.7 Hz).

2) ethyl (2E)-3-[3-(aminomethyl)-4-(4-methylphenyl)-2-propylquinolin-6-yl]acrylate dihydrochloride (Synthesized according to a method similar to the method shown in Example 13(6).)

$^1$H-NMR (DMSO-d$_6$) δ: 1.07 (3H, t, J=7.2 Hz), 1.23 (3H, t, J=7.2 Hz), 1.82-1.92 (2H, m), 2.47 (3H, s), 3.21 (2H, bs), 3.96-3.98 (2H, m), 4.16 (2H, q, J=7.2 Hz), 6.65 (1H, d, J=15.9

Hz), 7.34 (2H, d, J=8.1 Hz), 7.44 (2H, d, J=8.1 Hz), 7.48 (1H, bs), 7.65 (1H, d, J=15.9 Hz), 8.19 (1H, bs), 8.30 (1H, bs), 8.46 (3H, bs).

Example 71

(2E)-3-[3-(aminomethyl)-4-(4-methylphenyl)-2-propylquinolin-6-yl]acrylic Acid Dihydrochloride 1) (2E)-3-[3-{[(tert-butoxycarbonyl)amino]methyl}-4-(4-methylphenyl)-2-propylquinolin-6-yl]acrylic acid (Synthesized according to a method similar to the method shown in Example 70(1).)

$^1$H-NMR (CDCl$_3$) δ: 1.12 (3H, t, J=7.8 Hz), 1.42 (9H, s), 1.86-1.96 (2H, m), 2.51 (3H, s), 3.22 (2H, bs), 4.33-4.35 (2H, m), 4.46 (1H, bs), 6.43 (1H, d, J=15.6 Hz), 7.14 (2H, d, J=8.1 Hz), 7.38 (2H, d, J=8.1 Hz), 7.44 (1H, s), 7.70 (1H, d, J=15.6 Hz), 7.89-7.92 (1H, m).

2) (2E)-3-[3-(aminomethyl)-4-(4-methylphenyl)-2-propylquinolin-6-yl]acrylic acid dihydrochloride (Synthesized according to a method similar to the method shown in Example 13(6).)

$^1$H-NMR (DMSO-d$_6$) δ: 0.89 (3H, t, J=7.2 Hz), 1.65-1.75 (2H, m), 2.29 (3H, s), 2.96 (2H, bs), 3.78-3.82 (2H, m), 6.35 (1H, d, J=15.6 Hz), 7.14 (2H, d, J=7.8 Hz), 7.24 (1H, s), 7.28 (2H, d, J=7.8 Hz), 7.37 (1H, d, J=15.6 Hz), 7.89-7.94 (1H, m), 8.02-8.06 (1H, m), 8.14 (3H, bs).

Example 72

(2E)-3-[3-(aminomethyl)-4-(4-methylphenyl)-2-propylquinolin-6-yl]acrylamide Dihydrochloride 1) tert-butyl {[6-[1E)-3-amino-3-oxoprop-1-en-1-yl]-4-(4-methylphenyl)-2-propylquinolin-3-yl]methyl}carbamate (Synthesized according to a method similar to the method shown in Example 19(4).)

$^1$H-NMR (CDCl$_3$) δ: 1.14 (3H, t, J=7.2 Hz), 1.42 (9H, s), 1.94-2.03 (2H, m), 2.53 (3H, s), 3.37-3.41 (2H, m), 4.36 (2H, s), 4.93 (1H, bs), 6.65 (1H, d, J=15.9 Hz), 7.18 (2H, d, J=7.8 Hz), 7.34 (2H, d, J=7.8 Hz), 7.40 (1H, s), 7.42 (1H, d, J=15.9 Hz), 7.95-7.99 (1H, m), 8.42 (1H, bs).

2) (2E)-3-[3-(aminomethyl)-4-(4-methylphenyl)-2-propylquinolin-6-yl]acrylamide dihydrochloride (Synthesized according to a method similar to the method shown in Example 13(6).)

$^1$H-NMR (DMSO-d$_6$) δ: 1.23 (3H, t, J=7.2 Hz), 1.99-2.09 (2H, m), 2.62 (3H, s), 3.41 (2H, bs), 4.12-4.14 (2H, m), 6.78 (1H, d, J=15.9 Hz), 7.33 (1H, bs), 7.51 (2H, d, J=7.8 Hz), 7.50-7.52 (1H, m), 7.61 (2H, d, J=7.8 Hz), 7.82 (1H, bs), 8.31-8.32 (1H, m), 8.45-8.46 (1H, m), 8.14 (3H, bs).

Example 73

3-[3-(aminomethyl)-2-isobutyl-4-(4-methylphenyl)quinolin-6-yl]propanamide Dihydrochloride 1) To a solution of tert-butyl {[6-[(1E)-3-amino-3-oxoprop-1-en-1-yl]-2-isobutyl-4-(4-methylphenyl)-quinolin-3-yl]methyl}carbamate (250 mg, 0.53 mmol) in methanol (5 ml) and tetrahydrofuran (5 ml) was added 5% palladium-carbon (0.10 g), and the mixture was stirred under a hydrogen atmosphere at room temperature for 12 hrs. The reaction mixture was filtered, and the filtrate was concentrated under reduced pressure. The residue was crystallized from diisopropyl ether to give tert-butyl {[6-(3-amino-3-oxopropyl)-2-isobutyl-4-(4-methylphenyl)quinolin-3-yl]methyl}carbamate (204 mg, yield 81%) as white crystals.

$^1$H-NMR (CDCl$_3$) δ: 1.03 (6H, d, J=6.6 Hz), 1.41 (9H, s), 2.31-2.39 (1H, m), 2.49 (3H, s), 2.46 (2H, t, J=7.8 Hz), 3.00 (2H, t, J=7.8 Hz), 3.00-3.03 (2H, m), 4.31 (2H, s), 5.28 (1H, bs), 5.40 (1H, bs), 7.12 (2H, d, J=8.1 Hz), 7.12-7.15 (1H, m), 7.35 (2H, d, J=8.1 Hz), 7.55-7.61 (1H, m), 8.17 (1H, bs).

2) 3-[3-(aminomethyl)-2-isobutyl-4-(4-methylphenyl)quinolin-6-yl]propanamide dihydrochloride (Synthesized according to a method similar to the method shown in Example 13(6).)

$^1$H-NMR (DMSO-d$_6$) δ: 0.84 (6H, d, J=6.6 Hz), 2.11-2.17 (1H, m), 2.15 (2H, t, J=7.2 Hz), 2.30 (3H, s), 2.71 (2H, t, J=7.2 Hz), 3.09 (2H, s), 3.82-3.88 (2H, m), 6.57 (1H, bs), 7.03 (1H, s), 7.09 (1H, bs), 7.20 (2H, d, J=7.8 Hz), 7.29 (2H, d, J=7.8 Hz), 7.55-7.76 (1H, m), 8.27-8.33 (1H, m), 8.32 (3H, bs).

Example 74

Ethyl (2E)-3-[3-(aminomethyl)-2-(cyclopropylmethyl)-4-(4-methylphenyl)quinolin-6-yl]acrylate Dihydrochloride 1) ethyl (2E)-3-[3-{[(tert-butoxycarbonyl)amino]methyl}-2-(cyclopropylmethyl)-4-(4-methylphenyl)quinolin-6-yl]acrylate (Synthesized according to a method similar to the method shown in Example 19(2).)

$^1$H-NMR (CDCl$_3$) δ: 0.35-0.38 (2H, m), 0.54-0.57 (2H, m), 1.32 (3H, t, J=7.2 Hz), 1.55-1.56 (1H, m), 1.56 (9H, s), 2.50 (3H, s), 3.05 (2H, d, J=6.6 Hz), 4.23 (2H, q, J=7.2 Hz), 4.25-4.40 (3H, m), 6.39 (1H, d, J=16.2 Hz), 7.13 (2H, d, J=7.8 Hz), 7.35 (1H, d, J=2.1 Hz), 7.38 (2H, d, J=7.8 Hz), 7.65 (1H, d, J=16.2 Hz), 7.85 (1H, dd, J=2.1 Hz, 8.7 Hz), 8.05 (1H, d, J=8.7 Hz).

2) ethyl (2E)-3-[3-(aminomethyl)-2-(cyclopropylmethyl)-4-(4-methylphenyl)quinolin-6-yl]acrylate dihydrochloride (Synthesized according to a method similar to the method shown in Example 13(6).)

$^1$H-NMR (DMSO-d$_6$) δ: 0.18-0.26 (2H, m), 0.30-0.35 (2H, m), 1.02 (3H, t, J=7.2 Hz), 1.12-1.19 (1H, m), 2.26 (3H, s), 2.95-2.99 (2H, m), 3.74-3.79 (2H, m), 3.95 (2H, q, J=7.2 Hz), 6.45 (1H, d, J=15.9 Hz), 7.13 (2H, d, J=7.8 Hz), 7.24 (2H, d, J=7.8 Hz), 7.26-7.28 (1H, m), 7.43 (1H, d, J=15.9 Hz), 8.01-8.03 (1H, m), 8.08-8.09 (1H, m), 8.19 (3H, bs).

Example 75

(2E)-3-[3-(aminomethyl)-2-(cyclopropylmethyl)-4-(4-methylphenyl)quinolin-6-yl]acrylic Acid Dihydrochloride 1) (2E)-3-[3-{[(tert-butoxycarbonyl)amino]methyl}-2-(cyclopropylmethyl)-4-(4-methylphenyl)quinolin-6-yl]acrylic acid (Synthesized according to a method similar to the method shown in Example 19(3).)

$^1$H-NMR (CDCl$_3$) δ: 0.55-0.60 (4H, m), 1.25-1.36 (1H, m), 1.41 (9H, s), 2.53 (3H, s), 3.45 (2H, bs), 4.38 (2H, bs), 4.72 (1H, bs), 6.44 (1H, d, J=15.9 Hz), 7.18 (2H, d, J=7.8 Hz), 7.41 (2H, d, J=7.8 Hz), 7.47 (1H, s), 7.65 (1H, d, J=15.9 Hz), 7.86-7.90 (1H, m).

2) (2E)-3-[3-(aminomethyl)-2-(cyclopropylmethyl)-4-(4-methylphenyl)quinolin-6-yl]acrylic acid dihydrochloride (Synthesized according to a method similar to the method shown in Example 13(6).)

$^1$H-NMR (DMSO-d$_6$) δ: 0.18-0.21 (2H, m), 0.22-0.33 (2H, m), 1.02-1.53 (1H, m), 2.24 (3H, s), 2.96 (2H, s), 3.75-3.76

(2H, m), 6.30 (1H, d, J=15.9 Hz), 7.12 (2H, d, J=7.8 Hz), 7.20 (2H, d, J=7.8 Hz), 7.22 (1H, s), 7.35 (1H, d, J=15.9 Hz), 8.02 (1H, s), 8.17 (4H, bs).

Example 76

(2E)-3-[3-(aminomethyl)-2-(cyclopropylmethyl)-4-(4-methylphenyl)quinolin-6-yl]acrylamide Dihydrochloride 1) tert-butyl {[6-[(1E)-3-amino-3-oxoprop-1-en-1-yl]-2-(cyclopropylmethyl)-4-(4-methylphenyl)quinolin-3-yl]methyl}carbamate (Synthesized according to a method similar to the method shown in Example 19 (4).)

$^1$H-NMR (CDCl$_3$) δ: 0.53-0.67 (4H, m), 1.21-1.34 (1H, m), 1.41 (9H, s), 2.54 (3H, s), 3.42-3.45 (2H, m), 4.41 (2H, s), 4.93 (1H, bs), 6.79 (1H, d, J=15.9 Hz), 7.24 (2H, d, J=7.8 Hz), 7.36 (2H, d, J=7.8 Hz), 7.41 (1H, s), 7.51 (1H, d, J=15.9 Hz), 7.95-7.98 (1H, m), 8.73 (1H, bs).

2) (2E)-3-[3-(aminomethyl)-2-(cyclopropylmethyl)-4-(4-methylphenyl)quinolin-6-yl]acrylamide dihydrochloride (Synthesized according to a method similar to the method shown in Example 13(6).)

$^1$H-NMR (DMSO-d$_6$) δ: 0.18 (2H, bs), 0.30-0.33 (2H, m), 1.14-1.18 (1H, m), 2.25 (3H, s), 2.98 (2H, bs), 3.77 (2H, s), 6.40 (1H, d, J=15.9 Hz), 6.94 (1H, bs), 7.15 (2H, d, J=7.8 Hz), 7.14-7.16 (1H, m), 7.25 (2H, d, J=7.8 Hz), 7.42 (1H, bs), 7.88 (1H, bs), 7.95-7.98 (1H, m), 8.22 (3H, bs).

Example 77

Methyl 3-(aminomethyl)-4-(2,6-difluorophenyl)-2-isobutylquinoline-6-carboxylate 1) 4-Bromoaniline (14.9 g, 86.5 mmol) was heated to 120° C. and 2,6-difluorobenzoyl chloride (36.7 g, 208 mmol) was added. The temperature of the mixture was raised to 180° C. and zinc chloride (14.2 g, 104 mmol) was added. The temperature of the mixture was raised to 205° C. and the mixture was stirred for 3 hrs. The reaction mixture was cooled to 150° C., and 4N hydrochloric acid (100 ml) was added, and the mixture was heated under reflux for 15 min. The supernatant was removed, 4N hydrochloric acid (100 ml) was added to the residue, and the mixture was heated under reflux for 15 min. The supernatant was removed and the residue was dissolved in acetic acid (85 ml). Conc. hydrochloric acid (85 ml) was added at 120° C. and the mixture was heated under reflux for 12 hrs. The reaction mixture was concentrated under reduced pressure and 1N aqueous sodium hydroxide solution (200 ml) was added to the residue. The mixture was extracted with ethyl acetate, and the extract was washed with 1N hydrochloric acid and saturated brine and dried over anhydrous magnesium sulfate. The solvent was evaporated under reduced pressure and the residue was purified by silica gel column chromatography to give a crude product of (2-amino-5-bromophenyl)(2,6-difluorophenyl)methanone (7.8 g). To a solution of the crude product (5.2 g) and 5-methyl-3-oxohexanenitrile (2.1 g, 17 mmol) in toluene (100 ml) was added methanesulfonic acid (1.6 g, 17 mmol) and the mixture was heated under reflux for 17 hrs. The reaction mixture was washed with saturated aqueous sodium hydrogen carbonate and saturated brine, and dried over anhydrous magnesium sulfate. The solvent was evaporated under reduced pressure and the residue was purified by silica gel column chromatography to give 6-bromo-4-(2,6-difluorophenyl)-2-isobutylquinoline-3-carbonitrile (1.6 g, yield 4.6%) as a yellow solid.

$^1$H-NMR (CDCl$_3$) δ: 1.06 (6H, d, J=6.6 Hz), 2.30-2.50 (1H, m), 3.12 (2H, d, J=7.4 Hz), 7.15-7.25 (2H, m), 7.55-7.70 (2H, m), 7.91 (1H, dd, J=2.1, 9.1 Hz), 8.03 (1H, d, J=9.1 Hz).

2) methyl 3-cyano-4-(2,6-difluorophenyl)-2-isobutylquinoline-6-carboxylate (Synthesized according to a method similar to the method-shown in Example 5(2).)

$^1$H-NMR (CDCl$_3$) δ: 1.08 (6H, d, J=6.6 Hz), 2.30-2.50 (1H, m), 3.17 (2H, d, J=7.2 Hz), 3.94 (3H, s), 7.15-7.25 (2H, m), 7.55-7.70 (1H, m), 8.21 (1H, d, J=8.8 Hz), 8.20-8.30 (1H, m), 8.43 (1H, dd, J=1.8, 8.8 Hz).

melting point: 125-126° C.

3) methyl 3-(aminomethyl)-4-(2,6-difluorophenyl)-2-isobutylquinoline-6-carboxylate (Synthesized according to a method similar to the method shown in Example 25(2).)

$^1$H-NMR (CDCl$_3$) δ: 1.06 (6H, d, J=6.6 Hz), 1.50 (2H, bs), 2.35-2.55 (1H, m), 3.07 (2H, d, J=7.4 Hz), 3.82 (2H, s), 3.89 (3H, s), 7.15 (2H, dd, J=7.0, 8.5 Hz), 7.45-7.65 (1H, m), 8.01 (1H, s), 8.12 (1H, d, J=8.8 Hz), 8.26 (1H, dd, J=1.9, 8.8 Hz).

Example 78

N-[3-(aminomethyl)-2-isobutyl-4-(4-methylphenyl)-6-quinolinyl]acetamide Dihydrochloride 1) A mixture of 3-{[(tert-butoxycarbonyl)amino]methyl}-2-isobutyl-4-(4-methylphenyl)quinoline-6-carboxylic acid (Example 45(1)) (2.24 g, 5.0 mmol), diphenylphosphoryl azide (1.3 ml, 6.0 mmol), triethylamine (0.84 ml, 6.0 mmol) and N,N-dimethylformamide (20 ml) was stirred at room temperature for 1 hr. The reaction mixture was poured into water and extracted with ethyl acetate. The extract was washed with saturated brine, and dried over anhydrous magnesium sulfate. The solvent was evaporated under reduced pressure and toluene (30 ml) was added to the residue. The mixture was heated under reflux for 1 hr. The obtained mixture was cooled to room temperature and 9-fluorenylmethanol (1.47 g, 7.5 mmol) was added. The mixture was heated under reflux for 12 hrs. The reaction mixture was poured into water and extracted with ethyl acetate. The extract was washed with saturated brine, and dried over anhydrous magnesium sulfate. The solvent was evaporated under reduced pressure and the residue was purified by silica gel column chromatography to give 9H-fluoren-9-ylmethyl 3-[[(tert-butoxycarbonyl)amino]methyl]-2-isobutyl-4-(4-methylphenyl)-6-quinolinylcarbamate (1.45 g, yield 45%) as an amorphous form.

$^1$H-NMR (CDCl$_3$) δ: 1.02 (6H, d, J=6.6 Hz), 1.41 (9H, s), 2.30-2.46 (4H, m), 2.93 (2H, d, J=7.2 Hz), 4.03-4.21 (3H, m), 4.25 (2H, d, J=4.8 Hz), 4.32 (1H, bs), 4.49 (2H, d, J=6.6 Hz), 6.76 (1H, bs), 7.07-7.12 (3H, m), 7.25-7.41 (5H, m), 7.53-7.62 (3H, m), 7.73-7.77 (3H, m), 7.99 (1H, d, J=9.0 Hz).

2) To a solution of 9H-fluoren-9-ylmethyl 3-[[(tert-butoxycarbonyl)amino]methyl]-2-isobutyl-4-(4-methylphenyl)-6-quinolinylcarbamate (1.28 g, 2.0 mmol) in N,N-dimethylformamide (20 ml) was added piperidine (1 ml), and the mixture was stirred at room temperature for 1 hr. The reaction mixture was poured into water and extracted with ethyl acetate. The extract was washed with saturated brine, and dried over anhydrous magnesium-sulfate. The solvent was evaporated under reduced pressure and the residue was purified by silica gel column chromatography to give tert-butyl [6-amino-2-isobutyl-4-(4-methylphenyl)-3-quinolinyl]methylcarbamate (0.81 g, yield 96.4%).

$^1$H-NMR (CDCl$_3$) δ: 1.01 (6H, d, J=6.6 Hz), 1.41 (9H, s), 2.24-2.38 (1H, m), 2.46 (3H, s), 2.89 (2H, d, J=7.2 Hz), 3.75

(2H, bs), 4.23 (2H, d, J=5.1 Hz), 4.31 (1H, bs), 6.37 (1H, d, J=2.4 Hz), 7.06-7.11 (3H, m), 7.30 (2H, d, J=7.8 Hz), 7.86 (1H, d, J=8.7 Hz).

3) To a solution of tert-butyl [6-amino-2-isobutyl-4-(4-methylphenyl)-3-quinolinyl]methylcarbamate (0.21 g, 0.5 mmol) in tetrahydrofuran (10 ml) were added acetyl chloride (0.04 ml, 0.6 mmol) and triethylamine (0.08 ml, 0.6 mmol) and the mixture was stirred at room temperature for 2 hrs. The reaction mixture was poured into water and extracted with ethyl acetate. The extract was washed with saturated brine, and dried over anhydrous magnesium sulfate. The solvent was evaporated under reduced pressure and the residue was purified by silica gel column chromatography to give tert-butyl [6-(acetylamino)-2-isobutyl-4-(4-methylphenyl)-3-quinolinyl]methylcarbamate (0.19 g, yield 83%) as white crystals.

$^1$H-NMR (CDCl$_3$) δ: 1.02 (6H, d, J=6.6 Hz), 1.41 (9H, s), 2.28-2.42 (1H, m), 2.66 (3H, s), 2.94 (2H, d, J=7.5 Hz), 4.27-4.33 (3H, m), 7.12 (2H, d, J=7.8 Hz), 7.32-7.34 (3H, m), 7.90 (1H, dd, J=2.1, 9.0 Hz), 8.02 (1H, d, J=9.0 Hz).

4) N-[3-(aminomethyl)-2-isobutyl-4-(4-methylphenyl)-6-quinolinyl]acetamide dihydrochloride (Synthesized according to a method similar to the method shown in Example 44(3).)

$^1$H-NMR (DMSO-d$_6$) δ: 1.02 (6H, d, J=6.3 Hz), 2.03 (3H, s), 2.24-2.37 (1H, m), 2.48 (3H, bs), 3.25 (2H, bs), 3.99 (2H, d, J=5.1 Hz), 7.36 (2H, d, J=7.8 Hz), 7.47 (2H, d, J=7.8 Hz), 7.80 (1H, bs), 8.22 (1H, d, J=2.4 Hz), 8.35-8.49 (4H, m), 10.52 (1H, s).

Example 79

Ethyl 2-[3-(aminomethyl)-4-(4-methylphenyl)-2-propylquinolin-6-yl]cyclopropanecarboxylate Dihydrochloride 1) To a suspension of sodium hydride (60% in oil, 120 mg, 3 mmol) in dimethyl sulfoxide (10 ml) was added trimethylsulfoxonium bromide (605 mg, 3.5 mmol), and the mixture was stirred at room temperature for 30 min. To the reaction mixture was added ethyl (2E)-3-[3-{[(tert-butoxycarbonyl)amino]methyl}-4-(4-methylphenyl)-2-propylquinolin-6-yl]acrylate (0.73 g, 1.5 mmol) and the mixture was stirred at room temperature for 1 hr. Saturated aqueous ammonium chloride solution was poured into the reaction mixture and the mixture was extracted with ethyl acetate. The extract was washed with saturated brine, dried over anhydrous magnesium sulfate and concentrated under reduced pressure. The residue was crystallized from diisopropyl ether to give ethyl 2-[3-{[(tert-butoxycarbonyl)amino]methyl}-4-(4-methylphenyl)-2-propylquinolin-6-yl]cyclopropane-1-carboxylate (0.61 g, yield 81%) as white crystals.

$^1$H-NMR (CDCl$_3$) δ: 1.08 (3H, t, J=7.2 Hz), 1.26 (3H, t, J=7.2 Hz), 1.41 (9H, s), 1.53-1.60 (2H, m), 1.83-1.91 (3H, m), 2.47-2.54 (1H, m), 2.48 (3H, s), 3.01-3.06 (2H, m), 4.14 (2H, q, J=7.2 Hz), 4.29 (2H, s), 4.32 (1H, bs), 7.06-7.12 (3H, m), 7.24-7.27 (1H, m), 7.33 (2H, d, J=7.8 Hz), 7.96 (1H, d, J=8.7 Hz).

2) ethyl 2-[3-(aminomethyl)-4-(4-methylphenyl)-2-propylquinolin-6-yl]cyclopropanecarboxylate dihydrochloride (Synthesized according to a method similar to the method shown in Example 13(6).)

$^1$H-NMR (DMSO-d$_6$) δ: 0.84 (3H, t, J=7.2 Hz), 0.94 (3H, t, J=7.2 Hz), 1.08-1.20 (1H, m), 1.22-1.28 (1H, m), 1.60-1.64 (3H, m), 1.67-1.72 (1H, m), 2.24 (3H, s), 2.86 (2H, t, J=7.5 Hz), 2.98 (2H, bs), 3.74 (2H, s), 3.85 (2H, q, J=7.2 Hz), 6.94 (1H, s), 7.10 (2H, d, J=7.8 Hz), 7.23 (2H, d, J=7.8 Hz), 7.41-7.42 (1H, m), 7.95 (1H, s), 8.18 (3H, bs).

Example 80

2-[3-(aminomethyl)-4-(4-methylphenyl)-2-propylquinolin-6-yl]cyclopropanecarboxylic Acid Dihydrochloride 1) 2-[3-{[(tert-butoxycarbonyl)amino]methyl}-4-(4-methylphenyl)-2-propylquinolin-6-yl]cyclopropane-1-carboxylic acid (Synthesized according to a method similar to the method shown in Example 6(1).)

$^1$H-NMR (CDCl$_3$) δ: 1.14 (3H, t, J=7.2 Hz), 1.36-1.40 (2H, m), 1.40 (9H, s), 1.66-1.69 (1H, m), 1.86-1.94 (3H, m), 2.53 (3H, s), 2.53-2.62 (1H, m), 3.50-3.53 (2H, m), 4.37 (2H, s), 4.41 (1H, bs), 7.13-7.16 (3H, m), 7.41-7.43 (3H, m).

2) 2-[3-(aminomethyl)-4-(4-methylphenyl)-2-propylquinolin-6-yl]cyclopropanecarboxylic acid dihydrochloride (Synthesized according to a method similar to the method shown in Example 13(6).)

$^1$H-NMR (DMSO-d$_6$) δ: 1.13 (3H, t, J=7.2 Hz), 1.37-1.42 (1H, m), 1.48-1.55 (1H, m), 1.89-2.00 (3H, m), 2.52-2.55 (1H, m), 2.53 (3H, s), 3.35 (2H, s), 4.03 (2H, s), 7.26 (1H, s), 7.41-7.44 (2H, m), 7.51 (2H, d, J=7.5 Hz), 7.76 (1H, s), 8.39 (1H, bs), 8.61 (3H, bs).

Example 81

2-[3-(aminomethyl)-4-(4-methylphenyl)-2-propylquinolin-6-yl]cyclopropanecarboxamide Dihydrochloride 1) tert-butyl {[6-[2-(aminocarbonyl)cyclopropyl]-4-(4-methylphenyl)-2-propylquinolin-3-yl]methyl}carbamate (Synthesized according to a method similar to the method shown in Example 19(4).)

$^1$H-NMR (CDCl$_3$) δ: 1.16 (3H, t, J=6.9 Hz), 1.26-1.33 (1H, m), 1.40 (9H, s), 1.63-1.70 (1H, m), 1.91-2.01 (2H, m), 2.04-2.12 (1H, m), 2.47-2.54 (2H, m), 2.53 (3H, s), 3.53-3.57 (2H, m), 4.38 (2H, s), 4.66 (1H, bs), 5.88 (1H, bs), 6.86 (1H, bs), 7.17 (2H, d, J=7.8 Hz), 7.27 (1H, d, J=9.0 Hz), 7.43-7.46 (3H, m), 8.55 (1H, d, J=9.0 Hz).

2) 2-[3-(aminomethyl)-4-(4-methylphenyl)-2-propylquinolin-6-yl]cyclopropanecarboxamide dihydrochloride (Synthesized according to a method similar to the method shown in Example 13(6).)

$^1$H-NMR (DMSO-d$_6$) δ: 0.84 (3H, t, J=6.9 Hz), 0.92-0.97 (1H, m), 1.09-1.16 (1H, m), 1.58-1.68 (3H, m), 2.02-2.08 (1H, m), 2.24 (3H, s), 3.06 (2H, s), 3.75-3.78 (2H, m), 6.73 (1H, bs), 6.89 (1H, bs), 7.13 (2H, d, J=7.8 Hz), 7.40 (1H, s), 7.40-7.48 (1H, m), 8.09 (1H, bs), 8.29 (3H, bs).

Example 82

3-[3-(aminomethyl)-4-(4-methylphenyl)-2-propylquinolin-6-yl]propanamide Dihydrochloride 1) tert-butyl {[6-(3-amino-3-oxopropyl)-4-(4-methylphenyl)-2-propylquinolin-3-yl]methyl}carbamate (Synthesized according to a method similar to the method shown in Example 73(1).)

$^1$H-NMR (CDCl$_3$) δ: 1.18 (3H, t, J=7.2 Hz), 1.40 (9H, s), 1.93-1.98 (2H, m), 2.53 (3H, s), 2.55 (2H, t, J=7.5 Hz), 3.05 (2H, t, J=7.5 Hz), 3.55-3.59 (2H, m), 4.38 (2H, d, J=5.7 Hz), 4.61 (1H, bs), 5.32 (1H, bs), 6.08 (1H, bs), 7.17 (2H, d, J=8.4 Hz), 7.30 (1H, s), 7.43 (2H, d, J=8.4 Hz), 7.87 (1H, d, J=9.0 Hz), 8.93 (1H, d, J=9.0 Hz).

2) 3-[3-(aminomethyl)-4-(4-methylphenyl)-2-propylquinolin-6-yl]propanamide dihydrochloride (Synthesized according to a method similar to the method shown in Example 13(6).)

$^1$H-NMR (DMSO-d$_6$) δ: 1.07 (3H, t, J=7.2 Hz), 1.80-1.92 (2H, m), 2.30 (2H, t, J=7.5 Hz), 2.47 (3H, s), 2.86 (2H, t, J=7.5 Hz), 3.19 (2H, bs), 3.97 (2H, bs), 6.75 (1H, s), 7.14 (1H, s), 7.28 (1H, s), 7.31 (2H, d, J=8.1 Hz), 7.45 (2H, d, J=8.1 Hz), 7.80 (1H, bs), 8.14 (1H, bs), 8.32 (3H, bs).

Example 83

3-[3-(aminomethyl)-2-(cyclopropylmethyl)-4-(4-methylphenyl)quinolin-6-yl]propanamide Dihydrochloride 1) tert-butyl {[6-(3-amino-3-oxopropyl)-2-(cyclopropylmethyl)-4-(4-methylphenyl)quinolin-3-yl]methyl}carbamate (Synthesized according to a method similar to the method shown in Example 73(1).)

$^1$H-NMR (CDCl$_3$) δ: 0.35-0.42 (2H, m), 0.52-0.57 (2H, m), 1.21-1.36 (1H, m), 1.40 (9H, s), 2.47 (2H, t, J=8.1. Hz), 2.49 (3H, s), 2.99 (2H, t, J=8.1 Hz), 3.06-3.09 (2H, m), 4.31-4.36 (3H, m), 5.32 (2H, bs), 7.09-7.13 (3H, m), 7.33 (2H, d, J=7.8 Hz), 7.53 (1H, d, J=8.4 Hz), 8.05 (1H, bs).

2) 3-[3-(aminomethyl)-2-(cyclopropylmethyl)-4-(4-methylphenyl)quinolin-6-yl]-propanamide dihydrochloride (Synthesized according to a method similar to the method shown in Example 13(6).)

$^1$H-NMR (DMSO-d$_6$) δ: 0.48-0.55 (2H, m), 0.59-0.62 (2H, m), 1.26-1.35 (1H, m), 2.32 (2H, t, J=7.5 Hz), 2.47 (3H, s), 2.89 (2H, t, J=7.5 Hz), 3.42 (2H, d, J=6.0 Hz), 4.06 (2H, s), 6.75 (1H, bs), 7.26 (1H, s), 7.27 (1H, bs), 7.39 (2H, d, J=7.8 Hz), 7.48 (2H, d, J=7.8 Hz), 8.01 (1H, bs), 8.62 (4H, bs).

Example 84

1-{2-[3-(aminomethyl)-2-isobutyl-4-(4-methylphenyl)-6-quinolinyl]-1,3-thiazol-4-yl}ethanone Dihydrochloride 1) A mixture of 2-[3-{[(tert-butoxycarbonyl)amino]methyl}-2-isobutyl-4-(4-methylphenyl)-6-quinolinyl]-1,3-thiazole-4-carboxylic acid (0.27 g, 0.5 mmol), N,O-dimethylhydroxylamine hydrochloride (0.06 g, 0.6 mmol), ethyl-3(3-dimethylaminopropyl)carbodiimide hydrochloride (0.12 g, 0.6 mmol), 1-hydroxy-1H-benzotriazole (0.09 g, 0.6 mmol), triethylamine (0.08 ml, 0.6 mmol) and N,N-dimethylformamide (10 ml) was stirred at room temperature for 2 hrs. The reaction mixture was poured into water and extracted with ethyl acetate. The extract was washed with saturated brine, and dried over anhydrous magnesium sulfate. The solvent was evaporated under reduced pressure and the residue was crystallized from diisopropyl ether to give tert-butyl {[2-isobutyl-6-(4-{[methoxy(methyl)amino]carbonyl}-1,3-thiazol-2-yl)-4-(4-methylphenyl)quinolin-3-yl]methyl}carbamate (0.24 g, yield 85%) as white crystals.

$^1$H-NMR (CDCl$_3$) δ: 1.11 (6H, d, J=6.6 Hz), 1.41 (9H, s), 2.35-2.47 (1H, m), 2.52 (3H, s), 3.40 (5H, bs), 3.71 (3H, s), 4.39 (2H, d, J=5.1 Hz), 4.47 (1H, bs), 7.20-7.22 (3H, m), 7.42 (2H, d, J=7.8 Hz), 8.05 (2H, bs), 8.34 (1H, d, J=8.7 Hz).

2) To a suspension of tert-butyl {[2-isobutyl-6-(4-{[methoxy(methyl)amino]carbonyl}-1,3-thiazol-2-yl)-4-(4-methylphenyl)quinolin-3-yl]methyl}carbamate (0.23 g, 0.4 mmol) in tetrahydrofuran (10 ml) was added dropwise 3.0 M methylmagnesium bromide (0.4 ml, 1.2 mmol) at 0° C. After the completion of the dropwise addition, the mixture was stirred at 0° C. for 1 hr. The reaction mixture was poured into water and extracted with ethyl acetate. The extract was washed with saturated brine, and dried over anhydrous magnesium sulfate. The solvent was evaporated under reduced pressure and the residue was purified by silica gel column chromatography to give tert-butyl [6-(4-acetyl-1,3-thiazol-2-yl)-2-isobutyl-4-(4-methylphenyl)-3-quinolinyl]methylcarbamate (0.20 g, yield 95%) as white crystals.

$^1$H-NMR (CDCl$_3$) δ: 1.05 (6H, d, J=6.6 Hz), 1.43 (9H, s), 2.34-2.48 (1H, m), 2.50 (3H, s), 2.70 (3H, s), 2.99 (2H, d, J=6.9 Hz), 4.34 (3H, bs), 7.18 (2H, d, J=7.8 Hz), 7.37 (2H, d, J=7.8 Hz), 7.86 (1H, d, J=1.8 Hz), 8.08 (1H, s), 8.15 (1H, d, J=8.7 Hz), 8.12 (1H, dd, J=1.8, 8.7 Hz).

3) 1-{2-[3-(aminomethyl)-2-isobutyl-4-(4-methylphenyl)-6-quinolinyl]-1,3-thiazol-4-yl}ethanone dihydrochloride (Synthesized according to a method similar to the method shown in Example 13(6).)

$^1$H-NMR (DMSO-d$_6$) δ: 1.02 (6H, d, J=6.0 Hz), 2.31-2.46 (1H, m), 2.48 (3H, s), 2.57 (3H, s), 3.13 (2H, d, J=6.3 Hz), 4.00 (2H, d, J=5.4 Hz), 7.41 (2H, d, J=7.8 Hz), 7.48 (2H, d, J=7.8 Hz), 7.88 (1H, d, J=2.1 Hz), 8.31-8.56 (5H, m), 8.57 (1H, s).

Example 85

3-(aminomethyl)-2-isobutyl-4-(4-methylphenyl)-6-quinolinecarbonitrile Dihydrochloride 1) A mixture of tert-butyl [4-(4-methylphenyl)-2-isobutyl-6-trifluoromethanesulfonyloxy-quinolin-3-yl]methylcarbamate (3.87 g, 7.0 mmol), zinc cyanide (0.49 g, 4.2 mmol), tetrakis(triphenylphosphine)palladium (0.40 g, 0.35 mmol) and 1-methyl-2-pyrrolidone (40 ml) was stirred under an argon atmosphere at 80° C. for 2 hrs. The reaction mixture was poured into water and extracted with ethyl acetate. The extract was washed with saturated brine and dried over anhydrous magnesium sulfate. The solvent was evaporated under reduced pressure and the residue was purified by silica gel column chromatography to give tert-butyl [6-cyano-2-isobutyl-4-(4-methylphenyl)-3-quinolinyl]methylcarbamate (2.18 g, yield 72%) as white crystals.

$^1$H-NMR (CDCl$_3$) δ: 1.03 (6H, d, J=6.6 Hz), 1.42 (9H, s), 2.34-2.47 (1H, m), 2.50 (3H, s), 3.00 (2H, d, J=7.2 Hz), 4.34 (3H, bs), 7.11 (2H, d, J=7.8 Hz), 7.37 (2H, d, J=7.8 Hz), 7.72 (1H, d, J=1.8 Hz), 7.77 (1H, dd, J=1.8, 8.7 Hz), 8.12 (1H, d, J=8.7 Hz).

2) 3-(aminomethyl)-2-isobutyl-4-(4-methylphenyl)-6-quinolinecarbonitrile Dihydrochloride (Synthesized according to a method similar to the method shown in Example 13(6).)

$^1$H-NMR (DMSO-d$_6$) δ: 1.03 (6H, d, J=6.6 Hz), 2.34-2.45 (1H, m), 2.48 (3H, s), 3.14 (2H, bs), 3.99 (2H, d, J=5.1 Hz), 7.38 (2H, d, J=7.8 Hz), 7.46 (2H, d, J=7.8 Hz), 7.69 (1H, s), 8.14 (1H, d, J=8.4 Hz), 8.30 (1H, d, J=8.7 Hz), 8.59 (3H, bs).

Example 86

N-(3-(aminomethyl)-2-isobutyl-4-(4-methylphenyl)-6-quinolinyl)methanesulfonamide Dihydrochloride 1) To a solution of tert-butyl [6-amino-2-isobutyl-4-(4-methylphenyl)-3-quinolinyl]methylcarbamate (0.21 g, 0.5 mmol) in tetrahydrofuran (10 ml) were added dropwise methanesulfonyl chloride (0.05 ml, 0.6 mmol) and triethylamine (0.08 ml, 0.6 mmol) and the mixture was stirred at room temperature for 2 hrs. The reaction mixture was poured into water and extracted with ethyl acetate. The extract was washed with saturated brine, and dried over anhydrous magnesium sulfate. The solvent was evaporated under reduced pressure and the residue was purified by silica gel column chromatography to give tert-butyl [2-isobutyl-4-(4-methylphenyl)-6-[(methylsulfonyl)amino]-3-quinolinyl]methylcarbamate (0.21 g, yield 84%) as white crystals.

$^1$H-NMR (CDCl$_3$) δ: 1.02 (6H, d, J=6.6 Hz), 1.42 (9H, s), 2.29-2.43 (1H, m), 2.48 (3H, s), 2.95 (3H, s), 2.96 (2H, d, J=7.8 Hz), 4.30 (3H, bs), 6.46 (1H, bs), 7.00 (1H, d, J=2.4 Hz), 7.11 (2H, d, J=7.8 Hz), 7.34 (2H, d, J=7.8 Hz), 7.63 (1H, dd, J=2.4, 9.0 Hz), 8.06 (1H, d, J=9.0 Hz).

2) N-[3-(aminomethyl)-2-isobutyl-4-(4-methylphenyl)-6-quinolinyl]methanesulfonamide dihydrochloride (Synthesized according to a method similar to the method shown in Example 13(6).)

$^1$H-NMR (DMSO-d$_6$) δ: 1.02 (6H, d, J=6.6 Hz), 2.24-2.37 (1H, m), 2.47 (3H, s), 3.02 (3H, s), 3.28 (2H, bs), 3.99 (2H, bs), 7.24 (1H, d, J=1.8 Hz), 7.38 (2H, d, J=7.8 Hz), 7.47 (2H, d, J=7.8 Hz), 7.92 (1H, d, J=9.3 Hz), 8.40-8.61 (4H, m), 10.41 (1H, bs).

Example 87

1-[3-(aminomethyl)-2-isobutyl-4-(4-methylphenyl)-6-quinolinyl]ethanone Dihydrochloride 1) tert-butyl [2-isobutyl-6-{[methoxy(methyl)amino]carbonyl}-4-(4-methylphenyl)quinolin-3-yl]methylcarbamate (Synthesized according to a method similar to the method shown in Example 84(1).)

$^1$H-NMR (CDCl$_3$) δ: 1.13 (6H, d, J=6.3 Hz), 1.40 (9H, s), 2.36-2.52 (4H, m), 3.33 (3H, s), 3.45 (3H, s), 3.54 (2H, bs), 4.41 (2H, d, J=5.4 Hz), 4.48 (1H, bs), 7.17-7.20 (3H, m), 7.42 (2H, d, J=7.8 Hz), 7.83 (1H, s), 8.14 (1H, d, J=8.7 Hz).

2) tert-butyl [6-acetyl-2-isobutyl-4-(4-methylphenyl)-3-quinolinyl]methylcarbamate (Synthesized according to a method similar to the method shown in Example 84 (2).)

$^1$H-NMR (CDCl$_3$) δ: 1.04 (6H, d, J=6.6 Hz), 1.42 (9H, s), 2.34-2.46 (1H, m), 2.50 (3H, s), 2.51 (3H, s), 2.99 (2H, d, J=6.9 Hz), 4.34 (3H, bs), 7.15 (2H, d, J=8.0 Hz), 7.36 (2H, d, J=8.0 Hz), 7.96 (1H, d, J=2.0 Hz), 8.10 (1H, d, J=8.8 Hz), 8.20 (1H, dd, J=2.0, 8.8 Hz).

3) 1-[3-(aminomethyl)-2-isobutyl-4-(4-methylphenyl)-6-quinolinyl]ethanone dihydrochloride (Synthesized according to a method similar to the method shown in Example 13(6).)

$^1$H-NMR (DMSO-d$_6$) δ: 1.03 (6H, d, J=6.6 Hz), 2.34-2.51 (1H, m), 2.49 (3H, s), 2.54 (3H, s), 3.13 (2H, bs), 3.99 (2H, d, J=5.4 Hz), 7.38 (2H, d, J=8.0 Hz), 7.47 (2H, d, J=8.0 Hz), 7.90 (1H, s), 8.24-8.46 (5H, m).

Example 88

Ethyl 2-[3-(aminomethyl)-2-isobutyl-4-(4-methylphenyl)-6-quinolinyl]cyclopropanecarboxylate Dihydrochloride 1) ethyl 2-[3-{[(tert-butoxycarbonyl)amino]methyl}-2-isobutyl-4-(4-methylphenyl)-6-quinolinyl]cyclopropanecarboxylate (Synthesized according to a method similar to the method shown in Example 79(1).)

$^1$H-NMR (CDCl$_3$) δ: 1.01 (6H, d, J=6.9 Hz), 1.26 (3H, t, J=7.2 Hz), 1.42 (9H, s), 1.54-1.60 (1H, m), 1.83-1.91 (1H, m), 2.31-2.39 (1H, m), 2.49-2.54 (5H, m), 2.94 (2H, d, J=7.5 Hz), 4.14 (2H, q, J=7.2 Hz), 4.29 (3H, bs), 7.08 (1H, d, J=1.8 Hz), 7.11 (2H, d, J=7.8 Hz), 7.26 (1H, dd, J=1.8, 9.0 Hz), 7.33 (2H, d, J=7.8 Hz), 7.97 (1H, d, J=9.0 Hz).

2) ethyl 2-[3-(aminomethyl)-2-isobutyl-4-(4-methylphenyl)-6-quinolinyl]cyclopropanecarboxylate dihydrochloride (Synthesized according to a method similar to the method shown in Example 13(6).)

$^1$H-NMR (DMSO-d$_6$) δ: 1.01 (6H, d, J=6.0 Hz), 1.18 (3H, t, J=7.2 Hz), 1.33-1.42 (1H, m), 1.46-1.53 (1H, m), 1.93-2.03 (1H, m), 2.26-2.38 (1H, m), 2.48-2.58 (4H, m), 3.16 (2H, bs), 3.98 (2H, d, J=4.8 Hz), 4.07 (2H, q, J=7.2 Hz), 7.18 (1H, bs), 7.35 (2H, d, J=7.2 Hz), 7.46 (2H, d, J=7.2 Hz), 7.65 (1H, bs), 8.22 (1H, bs), 8.39 (3H, bs).

Example 89

2-[3-(aminomethyl)-2-isobutyl-4-(4-methylphenyl)-6-quinolinyl]cyclopropanecarboxylic Acid Dihydrochloride 1) 2-[3-{[(tert-butoxycarbonyl)amino]methyl}-2-isobutyl-4-(4-methylphenyl)-6-quinolinyl]cyclopropanecarboxylic acid (Synthesized according to a method similar to the method shown in Example 6(1).)

$^1$H-NMR (CDCl$_3$) δ: 1.01 (6H, d, J=6.3 Hz), 1.31-1.38 (1H, m), 1.42 (9H, s), 1.59-1.66 (1H, m), 1.84-1.90 (3H, m), 2.26-2.40 (1H, m), 2.49 (3H, s), 2.56-2.61 (1H, m), 2.96 (2H, d, J=7.2 Hz), 4.29 (3H, bs), 7.08 (1H, d, J=2.0 Hz), 7.11 (2H, d, J=7.2 Hz), 7.27 (1H, dd, J=2.0, 8.7 Hz), 7.33 (2H, d, J=7.2 Hz), 8.00 (1H, d, J=8.7 Hz).

2) 2-[3-(aminomethyl)-2-isobutyl-4-(4-methylphenyl)-6-quinolinyl]cyclopropanecarboxylic acid dihydrochloride (Synthesized according to a method similar to the method shown in Example 13(6).)

$^1$H-NMR (DMSO-d$_6$) δ: 1.01 (6H, d, J=5.4 Hz), 1.28-1.37 (1H, m), 1.41-1.49 (1H, m), 1.80-1.88 (1H, m), 2.27-2.37 (1H, m), 2.48 (4H, m), 3.19 (2H, bs), 3.98 (2H, bs), 7.18 (1H, bs), 7.36 (2H, d, J=7.5 Hz), 7.46 (2H, d, J=7.5 Hz), 7.68 (1H, bs), 8.26 (1H, bs), 8.43 (3H, bs).

Example 90

2-[3-(aminomethyl)-2-isobutyl-4-(4-methylphenyl)-6-quinolinyl]cyclopropanecarboxamide Dihydrochloride 1) tert-butyl {[6-[2-(aminocarbonyl)cyclopropyl]-2-isobutyl-4-(4-methylphenyl)-3-quinolinyl]methyl}carbamate (Synthesized according to a method similar to the method shown in Example 19(4).)

$^1$H-NMR (CDCl$_3$) δ: 1.01 (6H, d, J=6.6 Hz), 1.22-1.29 (1H, m), 1.42 (9H, s), 1.57-1.67 (1H, m), 2.28-2.42 (2H, m), 2.49-2.54 (5H, m), 2.95 (2H, d, J=7.2 Hz), 4.29 (3H, bs), 5.32 (1H, bs), 5.58 (1H, bs), 7.09-7.12 (3H, m), 7.25 (1H, dd, J=1.8, 8.7 Hz), 7.33 (2H, d, J=7.8 Hz), 7.97 (1H, d, J=8.7 Hz).

2) 2-[3-(aminomethyl)-2-isobutyl-4-(4-methylphenyl)-6-quinolinyl]cyclopropanecarboxamide dihydrochloride (Synthesized according to a method similar to the method shown in Example 13(6).)

$^1$H-NMR (DMSO-d$_6$) δ: 1.02 (6H, d, J=6.6 Hz), 1.15-1.24 (1H, m), 1.32-1.40 (1H, m), 1.83-1.91 (1H, m), 2.25-2.37 (2H, m), 2.48 (3H, s), 3.23 (1H, bs), 3.33 (1H, bs), 4.02 (2H, bs), 7.00 (1H, bs), 7.13-7.17 (1H, m), 7.36-7.40 (2H, m), 7.47 (2H, d, J=6.6 Hz), 7.64-7.78 (2H, m), 8.44-8.60 (4H, m).

Example 91

Ethyl (2E)-3-[3-(aminomethyl)-4-(4-methylphenyl)-2-neopentyl-6-quinolinyl]acrylate Dihydrochloride 1) ethyl (2E)-3-[3-{[(tert-butoxycarbonyl)amino]methyl}-4-(4-methylphenyl)-2-neopentyl-6-quinolinyl]acrylate (Synthesized according to a method similar to the method shown in Example 70(1).)

$^1$H-NMR (DMSO-$d_6$) δ: 1.09 (9H, s), 1.32 (3H, t, J=7.2 Hz), 1.41 (9H, s), 2.50 (3H, s), 3.06 (2H, s), 4.24 (2H, q, J=7.2 Hz), 4.35 (3H, bs), 6.41 (1H, d, J=16.0 Hz), 7.12 (2H, d, J=7.8 Hz), 7.35 (2H, d, J=7.8 Hz), 7.38 (1H, d, J=1.6 Hz), 7.64 (1H, d, J=16.0 Hz), 7.84 (1H, dd, J=1.6, 8.8 Hz), 8.04 (1H, d, J=8.8 Hz).

2) ethyl (2E)-3-[3-(aminomethyl)-4-(4-methylphenyl)-2-neopentyl-6-quinolinyl]acrylate dihydrochloride (Synthesized according to a method similar to the method shown in Example 13(6).)

$^1$H-NMR (DMSO-$d_6$) δ: 1.08 (9H, s), 1.24 (3H, t, J=7.2 Hz), 2.48 (3H, s), 3.21 (2H, bs), 4.17 (2H, q, J=7.2 Hz), 6.68 (1H, d, J=15.9 Hz), 7.35 (2H, d, J=8.1 Hz), 7.45-7.52 (3H, m), 7.66 (1H, d, J=15.9 Hz), 8.19-8.34 (5H, m).

Example 92

Methyl [3-(aminomethyl)-2-isobutyl-4-(4-methylphenyl)-6-quinolinyl]ethylcarbamate Dihydrochloride 1) A mixture of tert-butyl [6-(3-amino-3-oxopropyl)-2-isobutyl-4-(4-methylphenyl)quinolin-3-yl]methylcarbamate (2.38 g, 5.0 mmol), 4N aqueous sodium hydroxide solution (12.5 ml, 50 mmol) and ethanol (20 ml) was stirred at 80° C. for 2 hrs. The reaction mixture was poured into water, neutralized with 1N hydrochloric acid and extracted with ethyl acetate. The extract was washed with saturated brine, and dried over anhydrous magnesium sulfate. The solvent was evaporated under reduced pressure and the residue was purified by silica gel column chromatography to give 3-[3-{[(tert-butoxycarbonyl)amino]methyl}-2-isobutyl-4-(4-methylphenyl)quinolin-6-yl]propanoic acid (2.01 g, yield 84%) as white crystals.

$^1$H-NMR (CDCl$_3$) δ: 1.09 (6H, d, J=6.6 Hz), 1.39 (9H, s), 2.27-2.43 (1H, m), 2.51 (3H, s), 2.64 (2H, t, J=7.2 Hz), 3.01 (2H, t, J=7.2 Hz), 3.40 (2H, s), 4.36 (2H, d, J=5.1 Hz), 4.54 (1H, bs), 7.14 (2H, d, J=7.8 Hz), 7.22-7.26 (2H, m), 7.40 (2H, d, J=7.8 Hz), 7.71 (1H, d, J=8.1 Hz), 8.72 (1H, bs).

2) A mixture of 3-[3-{[(tert-butoxycarbonyl)amino]methyl}-2-isobutyl-4-(4-methylphenyl)quinolin-6-yl]propanoic acid (0.38 g, 0.8 mmol), diphenylphosphoryl azide (0.22 ml, 1.0 mmol), triethylamine (0.14 ml, 1.0 mmol) and N,N-dimethylformamide (10 ml) was stirred at room temperature for 2 hrs. The reaction mixture was poured into water and extracted with ethyl acetate. The extract was washed with saturated brine, and dried over anhydrous magnesium sulfate. The solvent was evaporated under reduced pressure. Toluene (20 ml) was added to the residue and the mixture was heated under reflux for 1 hr. The obtained mixture was cooled to room temperature and methanol (1 ml) was added, and the mixture was heated under reflux for 12 hrs. The reaction mixture was poured into water and extracted with ethyl acetate. The extract was washed with saturated brine, and dried over anhydrous magnesium sulfate. The solvent was evaporated under reduced pressure and the residue was purified by silica gel column chromatography. The obtained oil was dissolved in ethyl acetate (5 ml), and 4N solution of hydrogen chloride in dioxane (5 ml) was added. The mixture was stirred at room temperature for 2 hrs. The reaction mixture was concentrated under reduced pressure to give methyl [3-(aminomethyl)-2-isobutyl-4-(4-methylphenyl)-6-quinolinyl]ethylcarbamate dihydrochloride (0.06 g, yield 85%) as an amorphous form.

$^1$H-NMR (DMSO-$d_6$) δ: 1.02 (6H, d, J=6.3 Hz), 2.28-2.37 (1H, m), 2.48 (3H, s), 2.79 (2H, t, J=6.8 Hz), 3.13-3.26 (4H, m), 3.46 (3H, s), 4.01 (2H, s), 7.12-7.16 (2H, m), 7.36 (2H, d, J=8.0 Hz), 7.47 (2H, d, J=8.0 Hz), 7.88 (1H, d, J=9.3 Hz), 8.35 (1H, bs), 8.46 (3H, bs).

Example 93

N-{2-[3-(aminomethyl)-2-isobutyl-4-(4-methylphenyl)-6-quinolinyl]ethyl}-N'-methylurea Dihydrochloride Synthesized according to a method similar to the method shown in Example 92(2).

$^1$H-NMR (DMSO-$d_6$) δ: 1.03 (6H, d, J=6.3 Hz), 2.23-2.36 (1H, m), 2.49 (3H, s), 2.80 (2H, t, J=6.8 Hz), 3.18 (2H, t, J=6.8 Hz), 3.45 (2H, bs), 3.57 (3H, s), 4.04 (2H, bs), 7.23 (1H, s), 7.43 (2H, d, J=8.0 Hz), 7.49 (2H, d, J=8.0 Hz), 8.04 (1H, d, J=8.4 Hz), 8.66-8.74 (4H, m).

Example 94

[3-(aminomethyl)-2-isobutyl-4-(4-methylphenyl)-6-quinolinyl]methanol Dihydrochloride 1) To a solution of 3-{[(tert-butoxycarbonyl)amino]methyl}-2-isobutyl-4-(4-methylphenyl)quinoline-6-carboxylic acid (4.48 g, 10 mmol) in tetrahydrofuran (50 ml) were added dropwise ethyl chlorocarbonate (1.6 ml, 15-mmol) and N-methylmorpholine (1.6 ml, 15 mmol) at 0° C., and after the completion of the dropwise addition, the mixture was stirred at 0° C. for 10 min. Sodium tetrahydroborate (1.32 g, 35 mmol) and methanol (10 ml) were added to the reaction mixture and the mixture was stirred at room temperature for 6 hrs. The reaction mixture was poured into water and extracted with ethyl acetate. The extract was washed with saturated brine, and dried over anhydrous magnesium sulfate. The solvent was evaporated under reduced pressure and the residue was crystallized from tetrahydrofuran-diisopropyl ether to give tert-butyl [6-(hydroxymethyl)-2-isobutyl-4-(4-methylphenyl)quinolin-3-yl]methylcarbamate (2.42 g, yield 55%) as white crystals.

$^1$H-NMR (CDCl$_3$) δ: 1.02 (6H, d, J=6.6 Hz), 1.42 (9H, s), 1.73 (1H, bs), 2.30-2.44 (1H, m), 2.48 (3H, s), 2.96 (2H, d, J=7.2 Hz), 4.30 (3H, bs), 4.71 (2H, bs), 7.12 (2H, d, J=8.0 Hz), 7.26 (1H, d, J=1.8 Hz), 7.33 (2H, d, J=8.0 Hz), 7.67 (1H, dd, J=1.8, 8.7 Hz), 8.05 (1H, d, J=8.7 Hz).

2) [3-(aminomethyl)-2-isobutyl-4-(4-methylphenyl)-6-quinolinyl]methanol dihydrochloride (Synthesized according to a method similar to the method shown in Example 13(6).)

$^1$H-NMR (DMSO-$d_6$) δ: 1.03 (6H, d, J=6.6 Hz), 2.26-2.41 (1H, m), 2.48 (3H, s), 3.32 (2H, bs), 4.02 (2H, bs), 4.61 (3H, bs), 7.33-7.40 (3H, m), 7.48 (2H, d, J=7.8 Hz), 7.96 (1H, d, J=7.8 Hz), 8.43-8.56 (4H, m).

Example 95

N-{2-[3-(aminomethyl)-2-isobutyl-4-(4-methylphenyl)-6-quinolinyl]ethyl}acetamide Dihydrochloride 1) A mixture of 3-[3-{[(tert-butoxycarbonyl)amino]methyl}-2-isobutyl-4-(4-methylphenyl)quinolin-6-yl]propanoic acid (1.90 g, 4.0 mmol), diphenylphosphoryl azide (1.3 ml, 6.0 mmol), triethylamine (0.80 ml, 6.0 mmol) and N,N-dimethylformamide (20 ml) was stirred at room temperature for 2 hrs. The reaction mixture was poured into water and extracted with ethyl acetate. The extract was washed with saturated brine, and dried over anhydrous magnesium sulfate. The solvent was evaporated under reduced pressure and toluene (30 ml) was added to the residue. The mixture was heated under reflux for 1 hr. and the obtained mixture was cooled to room temperature. Benzyl alcohol (3 ml) was added, and the mixture was heated under reflux for 12 hrs. The reaction mixture was poured into water and extracted with ethyl acetate. The extract was washed with saturated brine and dried over anhydrous magnesium sulfate. The solvent was evaporated under reduced pressure and the residue was purified by silica gel column chromatography to give benzyl 2-[3-{[(tert-butoxycarbonyl)amino]methyl}-2-isobutyl-4-(4-methylphenyl)quinolin-6-yl]ethylcarbamate (0.83 g, yield 35%) as an amorphous form.

$^1$H-NMR (CDCl$_3$) δ: 1.02 (6H, d, J=6.6 Hz), 1.42 (9H, s), 2.29-2.42 (1H, m), 2.47 (3H, s), 2.83 (2H, t, J=6.9 Hz), 2.96 (2H, d, J=7.2 Hz), 3.41 (2H, q, J=6.9 Hz), 4.28 (3H, bs), 4.68 (1H, bs), 5.05 (2H, s), 7.08-7.10 (3H, m), 7.26-7.36 (7H, m), 7.49 (1H, d, J=8.6 Hz), 8.00 (1H, d, J=8.6 Hz).

2) A suspension of benzyl 2-[3-{[(tert-butoxycarbonyl)amino]methyl}-2-isobutyl-4-(4-(methylphenyl)quinolin-6-yl]ethylcarbamate (0.70 g, 1.2 mmol) and 5% palladium-carbon (0.5 g) in tetrahydrofuran (10 ml)-ethanol (10 ml) was stirred under a hydrogen atmosphere at room temperature for 2 hrs. The reaction mixture was filtered, and the filtrate was evaporated to give tert-butyl [6-(2-aminoethyl)-2-isobutyl-4-(4-methylphenyl)quinolin-3-yl]methylcarbamate (0.48 g, yield 90%) as an amorphous form.

$^1$H-NMR (CDCl$_3$) δ: 1.02 (6H, d, J=6.6 Hz), 1.41 (9H, s), 2.27-2.40 (1H, m), 2.48 (3H, s), 2.76 (2H, t, J=6.9 Hz), 2.90-2.97 (4H, m), 4.29 (3H, bs), 7.09-7.13 (3H, m), 7.33 (2H, d, J=8.1 Hz), 8.51 (1H, dd, J=2.0, 8.6 Hz), 8.00 (1H, d, J=8.6 Hz).

3) tert-Butyl [6-[2-(acetylamino)ethyl]-2-isobutyl-4-(4-methylphenyl)quinolin-3-yl]methylcarbamate was synthesized by a method similar to the method shown in Example 78(3), and subsequently, N-{2-[3-(aminomethyl)-2-isobutyl-4-(4-methylphenyl)-6-quinolinyl]ethyl}acetamide dihydrochloride was synthesized by a method similar to the method shown in Example 44(3).

$^1$H-NMR (DMSO-d$_6$) δ: 1.02 (6H, d, J=6.6 Hz), 1.69 (3H, s), 2.25-2.38 (1H, m), 2.48 (3H, s), 2.77 (2H, t, J=7.5 Hz), 3.17-3.20 (2H, m), 3.99 (2H, bs), 4.30 (2H, bs), 7.10-7.21 (1H, m), 7.34 (2H, d, J=7.2 Hz), 7.46 (2H, d, J=7.2 Hz), 7.83-7.88 (1H, m), 8.25-8.40 (4H, m).

Example 96

N-{2-[3-(aminomethyl)-2-isobutyl-4-(4-methylphenyl)-6-quinolinyl]ethyl}methanesulfonamide Dihydrochloride tert-Butyl (2-isobutyl-4-(4-methylphenyl)-6-{2-[(methylsulfonyl)amino]ethyl}quinolin-3-yl)methylcarbamate was synthesized by a method similar to the method shown in Example 78(3), and subsequently, N-{2-[3-(aminomethyl)-2-isobutyl-4-(4-methylphenyl)-6-quinolinyl]ethyl}methanesulfonamide dihydrochloride was synthesized by a method similar to the method shown in Example 44(3).

$^1$H-NMR (DMSO-d$_6$) δ: 1.03 (6H, d, J=6.6 Hz), 2.26 (1H, m), 2.48 (3H, s), 2.80 (3H, s), 2.87 (2H, t, J=6.9 Hz), 3.13-3.19 (2H, m), 3.29 (2H, bs), 4.02 (2H, bs), 7.05 (1H, bs), 7.25 (1H, bs), 7.39 (2H, d, J=7.8 Hz), 7.47 (2H, d, J=7.8 Hz), 7.96 (1H, d, J=7.5 Hz), 8.39-8.53 (4H, m).

Example 97

Ethyl 6-{[3-(aminomethyl)-2-isobutyl-4-(4-methylphenyl)quinolin-6-yl]oxy}hexanoate Dihydrochloride 1) ethyl 6-{[3-{[(tert-butoxycarbonyl)amino]methyl}-2-isobutyl-4-(4-methylphenyl)quinolin-6-yl]oxy}hexanoate (Synthesized according to a method similar to the method shown in Example 13(3).)

$^1$H-NMR (CDCl$_3$) δ: 1.12 (6H, d, J=6.6 Hz), 1.25 (3H, t, J=7.2 Hz), 1.40 (9H, s), 1.43-1.53 (2H, m), 1.61-1.81 (2H, m), 2.29-2.43 (3H, m), 2.52 (3H, s), 3.51 (2H, d, J=7.5 Hz), 3.83 (2H, t, J=6.0 Hz), 4.12 (2H, q, J=7.2 Hz), 4.37 (3H, bs), 6.64 (1H, d, J=2.4 Hz), 7.16 (2H, d, J=7.6 Hz), 7.44 (2H, d, J=7.6 Hz), 7.53 (1H, dd, J=2.4, 9.3 Hz), 9.09 (1H, d, J=9.3 Hz).

2) ethyl 6-{[3-(aminomethyl)-2-isobutyl-4-(4-methylphenyl)quinolin-6-yl]oxy}hexanoate dihydrochloride (Synthesized according to a method similar to the method shown in Example 13(6).)

$^1$H-NMR (DMSO-d$_6$) δ: 1.02 (6H, d, J=6.3 Hz), 1.16 (3H, t, J=7.2 Hz), 1.30-1.40 (2H, m), 1.63-1.71 (2H, m), 2.25-2.35 (3H, m), 2.47 (3H, s), 3.25 (2H, bs), 3.88 (2H, t, J=5.7 Hz), 4.00-4.07 (4H, m), 6.62 (1H, bs), 7.39 (2H, d, J=7.5 Hz), 7.47 (2H, d, J=7.5 Hz), 7.71 (1H, bs), 8.51 (4H, bs).

Example 98

6-{[3-(aminomethyl)-2-isobutyl-4-(4-methylphenyl)quinolin-6-yl]oxy}hexanoic Acid Dihydrochloride 1) 6-{[3-{[(tert-butoxycarbonyl)amino]methyl}-2-isobutyl-4-(4-methylphenyl)quinolin-6-yl]oxy}hexanoic acid (Synthesized according to a method similar to the method shown in Example 13(4).)

$^1$H-NMR (CDCl$_3$) δ: 1.07 (6H, d, J=6.6 Hz), 1.40 (9H, s), 1.42-1.53 (2H, m), 1.61-1.79 (2H, m), 2.29-2.41 (3H, m), 2.50 (3H, s), 3.26 (2H, bs), 3.82 (2H, t, J=6.2 Hz), 4.32 (2H, d, J=4.8 Hz), 4.41 (1H, bs), 6.61 (1H, d, J=2.7 Hz), 7.15 (2H, d, J=8.0 Hz), 7.37-7.44 (3H, m), 8.54-8.62 (1H, m).

2) 6-{[3-(aminomethyl)-2-isobutyl-4-(4-methylphenyl)quinolin-6-yl]oxy}hexanoic acid dihydrochloride (Synthesized according to a method similar to the method shown in Example 13(6).)

$^1$H-NMR (DMSO-d$_6$) δ: 1.03 (6H, d, J=6.3 Hz), 1.30-1.40 (2H, m), 1.45-1.55 (2H, m), 1.63-1.72 (2H, m), 2.20 (2H, t, J=7.2 Hz), 2.23-2.34 (1H, m), 2.48 (3H, s), 3.35 (2H, d, J=6.9 Hz), 3.89 (2H, t, J=6.3 Hz), 3.99 (2H, bs), 6.65 (1H, d, J=2.4 Hz), 7.42 (2H, d, J=7.8 Hz), 7.49 (2H, d, J=7.8 Hz), 7.78 (1H, d, J=8.4 Hz), 8.56-8.65 (4H, m).

Example 99

6-{[3-(aminomethyl)-2-isobutyl-4-(4-methylphenyl)quinolin-6-yl]oxy}hexanamide Dihydrochloride 1) tert-butyl [6-[(6-amino-6-oxohexyl)oxy]-2-isobutyl-4-(4-methylphenyl)quinolin-3-yl]methylcarbamate
(Synthesized according to a method similar to the method shown in Example 19(4).)
$^1$H-NMR (CDCl$_3$) δ: 1.11 (6H, d, J=6.6 Hz), 1.40 (9H, s), 1.43-1.53 (2H, m), 1.61-1.85 (4H, m), 2.27 (2H, t, J=7.3 Hz), 2.32-2.43 (1H, m), 2.52 (3H, s), 3.49 (2H, d, J=7.5 Hz), 3.83 (2H, t, J=5.8 Hz), 4.37 (2H, bs), 4.54 (1H, bs), 5.69 (1H, bs), 5.84 (1H, bs), 6.65 (1H, d, J=2.1 Hz), 7.18 (2H, d, J=7.7 Hz), 7.44 (2H, d, J=7.7 Hz), 7.53 (1H, dd, J=2.1, 9.2 Hz), 9.01 (1H, d, J=9.2 Hz).

2) 6-{[3-(aminomethyl)-2-isobutyl-4-(4-methylphenyl)quinolin-6-yl]oxy}hexanamide dihydrochloride
(Synthesized according to a method similar to the method shown in Example 13(6).)
$^1$H-NMR (DMSO-d$_6$) δ: 1.03 (6H, d, J=6.6 Hz), 1.30-1.38 (2H, m), 1.44-1.53 (2H, m), 1.63-1.72 (2H, m), 2.04 (2H, t, J=7.2 Hz), 2.23-2.33 (1H, m), 2.48 (3H, s), 3.41 (2H, d, J=7.2 Hz), 3.90 (2H, t, J=6.3 Hz), 4.04 (2H, bs), 6.67 (1H, d, J=2.7 Hz), 7.44 (2H, d, J=8.1 Hz), 7.50 (2H, d, J=8.1 Hz), 7.84 (1H, dd, J=2.7, 9.3 Hz), 8.66-8.69 (4H, m).

Example 100 tert-butyl N-[3-(aminomethyl)-2-isobutyl-4-(4-methylphenyl)quinolin-6-yl]glycinate 1) 6-bromo-2-isobutyl-4-(4-methylphenyl)quinoline-3-carbonitrile
(Synthesized according to a method similar to the method shown in Example 7(6).)
$^1$H-NMR (CDCl$_3$) δ: 1.05 (6H, d, J=6.8 Hz), 2.30-2.50 (1H, m), 2.50 (3H, s), 3.10 (2H, d, J=7.4 Hz), 7.34 (2H, d, J=8.2 Hz), 7.42 (2H, d, J=8.2 Hz), 7.80-7.90 (2H, m), 7.99 (1H, d, J=9.0 Hz).

2) tert-butyl N-[3-cyano-2-isobutyl-4-(4-methylphenyl)quinolin-6-yl]glycinate
(Synthesized according to a method similar to the method shown in Example 26(2).)
$^1$H-NMR (CDCl$_3$) δ: 1.03 (6H, d, J=6.6 Hz), 1.44 (9H, s), 2.25-2.40 (1H, m), 2.49 (3H, s), 3.04 (2H, d, J=7.2 Hz), 3.71 (2H, d, J=5.2 Hz), 4.61 (1H, t, J=5.2 Hz), 6.45 (1H, d, J=2.6 Hz), 7.22 (1H, dd, J=2.6, 9.0 Hz), 7.30-7.40 (4H, m), 7.92 (1H, d, J=9.0 Hz).

3) tert-butyl N-[3-(aminomethyl)-2-isobutyl-4-(4-methylphenyl)quinolin-6-yl]glycinate
(Synthesized according to a method similar to the method shown in Example 25(2).)
$^1$H-NMR (CDCl$_3$) δ: 1.02 (6H, d, J=6.6 Hz), 1.44 (11H, bs), 2.25-2.40 (1H, m), 2.48 (3H, s), 2.93 (2H, d, J=7.4 Hz), 3.65 (2H, s), 3.72 (2H, s), 4.40 (1H, t, J=5.5 Hz), 6.13 (1H, d, J=2.6 Hz), 7.06 (1H, dd, J=2.6, 9.0 Hz), 7.15 (2H, d, J=7.9 Hz), 7.32 (2H, d, J=7.9 Hz), 7.87 (1H, d, J=9.0 Hz).
melting point: 134-135° C.

Example 101

1-[3-(aminomethyl)-2-isobutyl-4-(4-methylphenyl)quinolin-6-yl]piperazine-2,3-dione 1) Palladium acetate (0.030 g, 0.13 mmol) and racemic-2,2'-bis(diphenylphosphino)-1,1'-binaphthyl (0.25 g, 0.40 mmol) were added to toluene (20 ml) under a nitrogen atmosphere and the mixture was stirred at 40° C. for 30 min. The reaction mixture was cooled to room temperature and 6-bromo-2-isobutyl-4-(4-methylphenyl)quinoline-3-carbonitrile (1.0 g, 2.6 mmol), ethylenediamine (0.44 ml, 6.6 mmol) and sodium tert-butoxide (0.35 g, 3.7 mmol) were added. The mixture was stirred under a nitrogen atmosphere at 80° C. for 2 hrs. The reaction mixture was cooled and partitioned between ethyl acetate and saturated aqueous sodium hydrogen carbonate. The aqueous layer was extracted with ethyl acetate. The organic layer and the extract were combined, and the mixture was washed with saturated brine and dried over anhydrous magnesium sulfate. The solvent was evaporated under reduced pressure and the residue was dissolved in tetrahydrofuran (100 ml). Di-tert-butyl dicarbonate (0.73 ml, 3.2 mmol) was added and the mixture was stirred at room temperature for 1 hr. The reaction mixture was concentrated under reduced pressure and the residue was purified by silica gel column chromatography to give tert-butyl 2-{[3-cyano-2-isobutyl-4-(4-methylphenyl)quinolin-6-yl]amino}ethylcarbamate (0.85 g, yield 70%) as a pale-yellow powder.
$^1$H-NMR (CDCl$_3$) δ: 1.03 (6H, d, J=6.6 Hz), 1.43 (9H, s), 2.25-2.40 (1H, m), 2.48 (3H, s), 3.03 (2H, d, J=7.4 Hz), 3.15 (2H, q, J=5.5 Hz), 3.36 (2H, q, J=5.5 Hz), 4.57 (1H, bs), 4.74 (1H, bs), 6.49 (1H, d, J=2.5 Hz), 7.18 (1H, dd, J=2.5, 9.1 Hz), 7.30-7.40 (4H, m), 7.89 (1H, d, J=9.1 Hz).

2) tert-butyl [6-({2-[(tert-butoxycarbonyl)amino]ethyl}amino)-2-isobutyl-4-(4-methylphenyl)quinolin-3-yl]methylcarbamate (Synthesized according to a method similar to the method shown in Example 39(1).)
$^1$H-NMR (CDCl$_3$) δ: 1.01 (6H, d, J=6.6 Hz), 1.41 (9H, s), 1.43 (9H, s), 2.20-2.40 (1H, m), 2.46 (3H, s), 2.89 (2H, d, J=7.2 Hz), 3.10 (2H, q, J=5.3 Hz), 3.30 (2H, q, J=5.3 Hz), 4.20-4.25 (3H, m), 4.31 (1H, bs), 4.72 (1H, bs), 6.17 (1H, d, J=2.5 Hz), 7.05 (1H, dd, J=2.5, 9.0 Hz), 7.11 (2H, d, J=7.8 Hz), 7.30 (2H, d, J=7.8 Hz), 7.85 (1H, d, J=9.0 Hz).

3) To a solution of tert-butyl [6-({2-[(tert-butoxycarbonyl)amino]ethyl}amino)-2-isobutyl-4-(4-methylphenyl)quinolin-3-yl]methylcarbamate (0.50 g, 0.89 mmol) in ethyl acetate (50 ml) was added saturated aqueous sodium hydrogen carbonate (50 ml), and the mixture was vigorously stirred at room temperature. Ethyl chloroglyoxylate (0.30 g, 2.2 mmol) was added dropwise to the obtained mixture and the mixture was vigorously stirred for 30 min. The organic layer was separated, washed with saturated brine and dried over anhydrous magnesium sulfate. The solvent was evaporated under reduced pressure and the residue was purified by silica gel column chromatography to give ethyl {{2-[(tert-butoxycarbonyl)amino]ethyl}[3-{[(tert-butoxycarbonyl)amino]methyl}-2-isobutyl-4-(4-methylphenyl)quinolin-6-yl]amino}(oxo)acetate (0.53 g, yield 90%) as a white powder.
$^1$H-NMR (CDCl$_3$) δ: 0.93 (3H, t, J=7.1 Hz), 1.03 (6H, d, J=6.6 Hz), 1.33 (9H, s), 1.42 (9H, s), 2.30-2.45 (1H, m), 2.48 (3H, s), 2.98 (2H, d, J=7.4 Hz), 3.31 (2H, q, J=6.0 Hz), 3.85-3.90 (2H, m), 3.90 (2H, q, J=7.1 Hz), 4.25-4.35 (3H, m), 4.75 (1H, bs), 7.08 (1H, d, J=7.9 Hz), 7.14 (2H, d, J=2.1 Hz), 7.30 (2H, d, J=7.9 Hz), 7.56 (1H, dd, J=2.1, 8.9 Hz), 7.85 (1H, d, J=8.9 Hz).

4) 1-[3-(aminomethyl)-2-isobutyl-4-(4-methylphenyl)quinolin-6-yl]piperazine-2,3-dione
(Synthesized according to a method similar to the method shown in Example 32(2).)
$^1$H-NMR (DMSO-d$_6$) δ: 1.02 (6H, d, J=6.6 Hz), 1.66 (2H, bs), 2.30-2.45 (1H, m), 2.46 (3H, s), 3.01 (2H, d, J=7.2 Hz), 3.55-3.65 (2H, m), 3.80 (2H, s), 3.85-3.90 (2H, m), 7.16 (2H, d, J=8.0 Hz), 7.18 (1H, d, J=2.3 Hz), 7.32 (2H, d, J=8.0 Hz), 7.57 (1H, dd, J=2.3, 9.0 Hz), 8.06 (1H, d, J=9.0 Hz), 8.08 (1H, bs).

melting point: 229-233° C.

Example 102

3-(aminomethyl)-4-(2,6-difluorophenyl)-2-isobutylquinoline-6-carboxamide 1) methyl 3-{[(tert-butoxycarbonyl)amino]methyl}-4-(2,6-difluorophenyl)-2-isobutylquinoline-6-carboxylate (Synthesized according to a method similar to the method shown in Example 5(1).)

$^1$H-NMR (CDCl$_3$) δ: 1.05 (6H, d, J=6.6 Hz), 1.42 (9H, s), 2.35-2.50 (1H, m), 2.99 (2H, d, J=7.2 Hz), 3.90 (3H, s), 4.33 (2H, d, J=5.5 Hz), 4.49 (1H, t, J=4.5 Hz), 7.05-7.20 (2H, m), 7.45-7.65 (1H, m), 8.02 (1H, s), 8.13 (1H, d, J=8.8 Hz), 8.28 (1H, dd, J=1.8, 8.8 Hz).

2) 3-{[(tert-butoxycarbonyl)amino]methyl}-4-(2,6-difluorophenyl)-2-isobutylquinoline-6-carboxylic acid (Synthesized according to a method similar to the method shown in Example 6(1).)

$^1$H-NMR (CDCl$_3$) δ: 1.05 (6H, d, J=6.6 Hz), 1.43 (9H, s), 2.35-2.50 (1H, m), 3.02 (2H, d, J=7.2 Hz), 4.35 (2H, d, J=5.3 Hz), 4.51 (1H, t, J=4.7 Hz), 7.05-7.20 (2H, m), 7.50-7.65 (1H, m), 8.09 (1H, s), 8.19 (1H, d, J=8.8 Hz), 8.32 (1H, dd, J=1.8, 8.8 Hz).

3) tert-butyl [6-(aminocarbonyl)-4-(2,6-difluorophenyl)-2-isobutylquinolin-3-yl]methylcarbamate (Synthesized according to a method similar to the method shown in Example 19(4).)

$^1$H-NMR (CD$_3$OD) δ: 1.06 (6H, d, J=6.6 Hz), 1.38 (9H, s), 2.20-2.40 (1H, m), 3.03 (2H, d, J=7.4 Hz), 4.30 (2H, s), 6.65 (1H, t, J=5.1 Hz), 7.15-7.30 (2H, m), 7.55-7.75 (1H, m), 7.90-7.95 (1H, m), 8.12 (1H, d, J=8.7 Hz), 8.17 (1H, dd, J=1.7, 8.7 Hz).

4) 3-(aminomethyl)-4-(2,6-difluorophenyl)-2-isobutylquinoline-6-carboxamide (Synthesized according to a method similar to the method shown in Example 32(2).)

$^1$H-NMR (CD$_3$OD) δ: 1.06 (6H, d, J=6.6 Hz), 2.25-2.45 (1H, m), 3.10 (2H, d, J=7.2 Hz), 3.86 (2H, s), 7.05-7.35 (3H, m), 7.60-7.75 (1H, m), 8.13 (1H, d, J=8.7 Hz), 8.18 (1H, dd, J=1.7, 8.7 Hz).

melting point: 165-171° C.

Example 103

4-[3-(aminomethyl)-2-isobutyl-4-(4-methylphenyl)quinolin-6-yl]piperazin-2-one

1) Palladium acetate (0.014 g, 0.063 mmol) and racemic-2,2'-bis(diphenylphosphino)-1,1'-binaphthyl (0.12 g, 0.19 mmol) were added to 1,4-dioxane (30 ml) under a nitrogen atmosphere, and the mixture was stirred at 40° C. for 30 min. The reaction mixture was cooled to room temperature and 6-bromo-2-isobutyl-4-(4-methylphenyl)quinoline-3-carbonitrile (0.50 g, 1.3 mmol), 2-piperazinone (0.50 ml, 5.0 mmol) and cesium carbonate (0.57 g, 1.8 mmol) were added. The mixture was stirred under a nitrogen atmosphere at 80° C. for 2 days. The reaction mixture was cooled and partitioned between ethyl acetate and water, and the aqueous layer was extracted with ethyl acetate. The organic layer and the extract were combined, washed with saturated brine and dried over anhydrous magnesium sulfate. The solvent was evaporated under reduced pressure and the residue was purified by silica gel column chromatography to give 2-isobutyl-4-(4-methylphenyl)-6-(3-oxopiperazin-1-yl)quinoline-3-carbonitrile (0.35 g, yield 71%) as a yellow powder.

$^1$H-NMR (CDCl$_3$) δ: 1.04 (6H, d, J=6.6 Hz), 2.25-2.45 (1H, m), 2.50 (3H, s), 3.07 (2H, d, J=7.4 Hz), 3.45-3.60 (4H, m), 3.81 (2H, s), 6.22 (1H, s), 6.83 (1H, d, J=2.8 Hz), 7.30-7.45 (4H, m), 7.53 (1H, dd, J=2.7, 9.4 Hz), 8.04 (1H, d, J=9.4 Hz).

2) 4-[3-(aminomethyl)-2-isobutyl-4-(4-methylphenyl)quinolin-6-yl]piperazin-2-one (Synthesized according to a method similar to the method shown in Example 25(2).)

$^1$H-NMR (CDCl$_3$) δ: 1.03 (6H, d, J=6.6 Hz), 1.55 (2H, bs), 2.25-2.40 (1H, m), 2.49 (3H, s), 2.97 (2H, d, J=7.2 Hz), 3.35-3.45 (2H, m), 3.45-3.55 (2H, m), 3.73 (2H, s), 3.75 (2H, s), 6.21 (1H, d, J=10.9 Hz), 6.50 (1H, d, J=2.8 Hz), 7.15 (2H, d, J=7.8 Hz), 7.33 (2H, d, J=7.8 Hz), 7.37 (1H, dd, J=2.8, 9.2 Hz), 7.99 (1H, d, J=9.2 Hz).

melting point: 155-157° C.

Example 104

N$^2$-[3-(aminomethyl)-2-isobutyl-4-(4-methylphenyl)quinolin-6-yl]glycinamide

1) Trifluoroacetic acid (3 ml) was added to tert-butyl N-[3-(aminomethyl)-2-isobutyl-4-(4-methylphenyl)quinolin-6-yl]glycinate (0.52 g, 1.2 mmol) and the mixture was stirred at room temperature for 1 hr. The reaction mixture was concentrated under reduced pressure, and ethyl acetate (50 ml), tetrahydrofuran (50 ml) and saturated aqueous sodium hydrogen carbonate (20 ml) were added to the residue. Di-tert-butyl dicarbonate (0.41 ml, 1.8 mmol) was added to the obtained mixture and the mixture was stirred at room temperature for 3 hrs. The organic layer was separated, washed with saturated brine and dried over anhydrous magnesium sulfate. The solvent was evaporated under reduced pressure and the residue was crystallized from diisopropyl ether to give N-[3-{[(tert-butoxycarbonyl)amino]methyl}-2-isobutyl-4-(4-methylphenyl)quinolin-6-yl]glycine (0.47 g, yield 83%) as a yellow powder.

$^1$H-NMR (CD$_3$OD) δ: 1.02 (6H, d, J=6.6 Hz), 1.42 (9H, s), 2.10-2.25 (1H, m), 2.46 (3H, s), 2.87 (2H, d, J=7.2 Hz), 3.56 (2H, s), 4.14 (2H, s), 6.17 (1H, d, J=2.5 Hz), 7.21 (2H, d, J=7.7 Hz), 7.24 (1H, dd, J=2.5, 9.0 Hz), 7.36 (2H, d, J=7.7 Hz), 7.79 (1H, d, J=9.0 Hz).

2) N-[3-{[(tert-butoxycarbonyl)amino]methyl}-2-isobutyl-4-(4-methylphenyl)quinolin-6-yl]glycinamide (Synthesized according to a method similar to the method shown in Example 19(4).)

$^1$H-NMR (CD$_3$OD) δ: 1.00 (6H, d, J=6.6 Hz), 1.42 (9H, s), 2.10-2.30 (1H, m), 2.44 (3H, s), 2.84 (2H, d, J=7.2 Hz), 3.59 (2H, s), 4.12 (2H, s), 6.20 (1H, d, J=2.6 Hz), 7.10-7.25 (3H, m), 7.34 (2H, d, J=7.9 Hz), 7.80 (1H, d, J=9.0 Hz).

3) N$^2$-[3-(aminomethyl)-2-isobutyl-4-(4-methylphenyl)quinolin-6-yl]glycinamide (Synthesized according to a method similar to the method shown in Example 32(2).)

$^1$H-NMR (CD$_3$OD) δ: 1.01 (6H, d, J=6.6 Hz), 2.05-2.55 (1H, m), 2.46 (3H, s), 2.94 (2H, d, J=7.4 Hz), 3.39 (2H, s), 3.73 (2H, s), 6.16 (1H, d, J=2.7 Hz), 7.19 (1H, dd, J=2.7, 9.0 Hz), 7.20 (2H, d, J=7.9 Hz), 7.38 (2H, d, J=7.9 Hz), 7.80 (1H, d, J=9.0 Hz).

Example 105

1-[3-(aminomethyl)-2-isobutyl-4-(4-methylphenyl) quinolin-6-yl]piperazine-2,5-dione Dihydrochloride 1) tert-butyl N-[3-{[(tert-butoxycarbonyl)amino]methyl}-2-isobutyl-4-(4-methylphenyl)quinolin-6-yl]glycinate (Synthesized according to a method similar to the method shown in Example 5(1).)

$^1$H-NMR (CDCl$_3$) δ: 1.01 (6H, d, J=6.6 Hz), 1.41 (9H, s), 1.44 (9H, s), 2.20-2.40 (1H, m), 2.48 (3H, s), 2.89 (2H, d, J=7.4 Hz), 3.65 (2H, d, J=5.3 Hz), 4.22 (2H, d, J=4.9 Hz), 4.30 (1H, bs), 4.42 (1H, t, J=4.9 Hz), 6.14 (1H, d, J=2.5 Hz), 7.08 (1H, dd, J=2.5, 9.0 Hz), 7.11 (2H, d, J=8.0 Hz), 7.31 (2H, d, J=8.0 Hz), 7.87 (1H, d, J=9.0 Hz).

2) To a mixture of N-[(benzyloxy)carbonyl]glycine (0.78 g, 3.8 mmol), N,N-dimethylformamide (0.1 ml) and tetrahydrofuran (20 ml) was added dropwise oxalyl chloride (0.33 ml, 3.7 mmol) under ice-cooling. The mixture was stirred under ice-cooling for 1 hr. to give a crude product of N-[(benzyloxy)carbonyl]glycyl chloride. To a mixture of tert-butyl N-[3-{[(tert-butoxycarbonyl)amino]methyl}-2-isobutyl-4-(4-methylphenyl)quinolin-6-yl]glycinate (0.40 g, 0.75 mmol), pyridine (0.3 ml, 3.7 mmol) and tetrahydrofuran (100 ml) was added dropwise the crude product. The obtained mixture was stirred for 1 hr. and 4-dimethylaminopyridine (0.01 g, 0.82 mmol) was added, and the mixture was stirred at room temperature for 2 days. The reaction mixture was partitioned between ethyl acetate and water. The organic layer was washed successively with water, saturated aqueous sodium hydrogen carbonate and saturated brine, and dried over anhydrous magnesium sulfate. The solvent was evaporated under reduced pressure and the residue was purified by silica gel column chromatography to give tert-butyl N-[(benzyloxy)carbonyl]glycyl-N-[3-{[(tert-butoxycarbonyl)amino]methyl}-2-isobutyl-4-(4-methylphenyl)quinolin-6-yl]glycinate (0.47 g, yield 87%) as a white powder.

$^1$H-NMR (CDCl$_3$) δ: 1.04 (6H, d, J=6.8 Hz), 1.37 (9H, s), 1.42 (9H, s), 2.25-2.45 (1H, m), 2.46 (3H, s), 3.00 (2H, d, J=7.4 Hz), 3.69 (2H, d, J=4.3 Hz), 4.22 (2H, s), 4.25-4.40 (3H, m), 5.04 (2H, s), 5.60 (1H, t, J=4.3 Hz), 7.11 (2H, d, J=7.9 Hz), 7.25-7.40 (8H, m), 7.60 (1H, dd, J=2.1, 8.9 Hz), 8.11 (1H, d, J=8.9 Hz).

3) A mixture of tert-butyl N-[(benzyloxy)carbonyl]glycyl-N-[3-{[(tert-butoxycarbonyl)amino]methyl}-2-isobutyl-4-(4-methylphenyl)quinolin-6-yl]glycinate (0.45 g, 0.62 mmol), 10% palladium-carbon (0.04 g) and ethanol (100 ml) was stirred under a hydrogen atmosphere at room temperature for one day. The reaction mixture was filtered, and the filtrate was heated under reflux for 17 hrs. The reaction mixture was concentrated under reduced pressure, and the residue was purified by silica gel column chromatography and crystallized from ethyl acetate to give tert-butyl [6-(2,5-dioxopiperazin-1-yl)-2-isobutyl-4-(4-methylphenyl)quinolin-3-yl]methylcarbamate (0.16 g, yield 44%) as pale-yellow crystals.

$^1$H-NMR (CDCl$_3$) δ: 1.02 (6H, d, J=6.8 Hz), 1.42 (9H, s), 2.25-2.45 (1H, m), 2.48 (3H, s), 2.98 (2H, d, J=7.2 Hz), 4.16 (2H, s), 4.28 (2H, s), 4.25-4.35 (3H, m), 6.13 (1H, s), 7.12 (2H, d, J=7.8 Hz), 7.14 (1H, d, J=2.3 Hz), 7.34 (2H, d, J=7.8 Hz), 7.62 (1H, dd, J=2.3, 9.0 Hz), 8.11 (1H, d, J=9.0 Hz).

4) 1-[3-(aminomethyl)-2-isobutyl-4-(4-methylphenyl) quinolin-6-yl]piperazine-2,5-dione dihydrochloride (Synthesized according to a method similar to the method shown in Example 44(3).)

$^1$H-NMR (DMSO-d$_6$) δ: 1.03 (6H, d, J=6.6 Hz), 2.25-2.40 (1H, m), 2.46 (3H, s), 3.13 (2H, d, J=7.0 Hz), 3.92 (2H, s), 3.98 (2H, d, J=5.5 Hz), 4.21 (2H, s), 7.23 (1H, d, J=1.9 Hz), 7.34 (2H, d, J=7.9 Hz), 7.45 (2H, d, J=7.9 Hz), 7.88 (1H, d, J=8.8 Hz), 8.24 (1H, dd, J=1.9, 8.8 Hz), 8.30 (1H, bs), 8.35 (3H, bs).

melting point: 249° C. (decomp.)

Example 106

[2-isobutyl-4-(4-methylphenyl)-6-(2H-tetrazol-5-yl) quinolin-3-yl]methylamine Dihydrochloride 1) A mixture of tert-butyl [6-cyano-2-isobutyl-4-(4-methylphenyl)quinolin-3-yl]methylcarbamate (0.60 g, 1.4 mmol), sodium azide (0.18 g, 2.8 mmol), ammonium chloride (0.30 g, 3.6 mmol) and dimethyl sulfoxide (810 ml) was stirred at 70° C. for 2 days. The reaction mixture was partitioned between ethyl acetate and 0.1N hydrochloric acid. The organic layer was washed with saturated brine, dried over anhydrous magnesium sulfate and concentrated under reduced pressure. The residue was crystallized from n-hexane-ethyl acetate to give tert-butyl [2-isobutyl-4-(4-methylphenyl)-6-(2H-tetrazol-5-yl)quinolin-3-yl]methylcarbamate (0.38 g, yield 57%) as a white powder.

$^1$H-NMR (DMSO-d$_6$) δ: 1.00 (6H, d, J=6.4 Hz), 1.39 (9H, s), 2.25-2.45 (1H, m), 2.47 (3H, s), 2.86 (2H, d, J=7.0 Hz), 4.07 (2H, d, J=4.3 Hz), 7.09 (1H, t, J=4.3 Hz), 7.35 (2H, d, J=8.1 Hz), 7.41 (2H, d, J=8.1 Hz), 8.05 (1H, d, J=1.8 Hz), 8.18 (1H, d, J=8.7 Hz), 8.28 (1H, dd, J=1.8, 8.7 Hz).

2) [2-isobutyl-4-(4-methylphenyl)-6-(2H-tetrazol-5-yl) quinolin-3-yl]methylamine dihydrochloride (Synthesized according to a method similar to the method shown in Example 44(3).)

$^1$H-NMR (DMSO-d$_6$) δ: 1.05 (6H, d, J=6.8 Hz), 2.30-2.50 (1H, m), 2.49 (3H, s), 3.08 (2H, d, J=7.0 Hz), 4.00 (2H, d, J=5.5 Hz), 7.38 (2H, d, J=7.8 Hz), 7.49 (2H, d, J=7.8 Hz), 8.08 (1H, d, J=1.5 Hz), 8.29 (1H, d, J=8.8 Hz), 8.33 (3H, bs), 8.43 (1H, dd, J=1.9, 8.8 Hz).

Example 107 tert-butyl 4-[3-(aminomethyl)-2-isobutyl-4-(4-methylphenyl)quinolin-6-yl]piperazine-1-carboxylate 1) 2-isobutyl-4-(4-methylphenyl)-6-piperazin-1-ylquinoline-3-carbonitrile (Synthesized according to a method similar to the method shown in Example 26(2).)

$^1$H-NMR (CDCl$_3$) δ: 1.04 (6H, d, J=6.8 Hz), 2.25-2.45 (1H, m), 2.49 (3H, s), 2.95-3.05 (4H, m), 3.06 (2H, d, J=7.4 Hz), 3.10-3.20 (4H, m), 6.87 (1H, d, J=2.7 Hz), 7.30-7.45 (4H, m), 7.58 (1H, dd, J=2.7, 9.3 Hz), 7.99 (1H, d, J=9.3 Hz).

2) tert-butyl 4-[3-cyano-2-isobutyl-4-(4-methylphenyl) quinolin-6-yl]piperazine-1-carboxylate (Synthesized according to a method similar to the method shown in Example 5(1).)

$^1$H-NMR (CDCl$_3$) δ: 1.04 (6H, d, J=6.6 Hz), 1.47 (9H, s), 2.25-2.45 (1H, m), 2.50 (3H, s), 3.06 (2H, d, J=7.4 Hz), 3.11 (4H, t, J=5.0 Hz), 3.56 (4H, t, J=5.0 Hz), 6.87 (1H, d, J=2.6 Hz), 7.30-7.45 (4H, m), 7.57 (1H, dd, J=2.6, 9.3 Hz), 8.00 (1H, d, J=9.3 Hz).

3) tert-butyl 4-[3-(aminomethyl)-2-isobutyl-4-(4-methylphenyl)quinolin-6-yl]piperazine-1-carboxylate (Synthesized according to a method similar to the method shown in Example 25(2).)

¹H-NMR (CDCl₃) δ: 1.03 (6H, d, J=6.6 Hz), 1.46 (9H, s), 1.49 (2H, bs), 2.25-2.45 (1H, m), 2.49 (3H, s), 2.96 (2H, d, J=7.2 Hz), 3.01 (4H, t, J=5.1 Hz), 3.53 (4H, t, J=5.1 Hz), 3.75 (2H, s), 6.53 (1H, d, J=2.7 Hz), 7.16 (2H, d, J=7.9 Hz), 7.33 (2H, d, J=7.9 Hz), 7.40 (1H, dd, J=2.7, 9.2 Hz), 7.95 (1H, d, J=9.2 Hz).

Example 108

3-[3-(aminomethyl)-2-isobutyl-4-(4-methylphenyl)quinolin-6-yl]-1,2,4-oxadiazol-5(4H)-one Dihydrochloride 1) To a mixture of tert-butyl [6-cyano-2-isobutyl-4-(4-methylphenyl)quinolin-3-yl]methylcarbamate (3.0 g, 7.0 mmol), hydroxylamine hydrochloride (0.73 g, 11 mmol) and ethanol (75 ml) was added sodium tert-butoxide (1.2 g, 11 mmol), and the mixture was stirred at 70° C. for 6 hrs. The precipitate was filtered off and the filtrate was concentrated under reduced pressure. The residue was partitioned between ethyl acetate-tetrahydrofuran and water and the organic layer was washed with saturated brine. The organic layer was dried over anhydrous magnesium sulfate and the solvent was evaporated under reduced pressure to give tert-butyl [6-[(Z)-amino(hydroxyimino)methyl]-2-isobutyl-4-(4-methylphenyl)quinolin-3-yl]methylcarbamate (2.5 g, yield 79%) as a white powder.

¹H-NMR (CDCl₃) δ: 1.03 (6H, d, J=6.6 Hz), 1.43 (9H, s), 2.25-2.45 (1H, m), 2.47 (3H, s), 2.96 (2H, d, J=7.2 Hz), 4.29 (2H, d, J=4.7 Hz), 4.49 (1H, t, J=4.7 Hz), 4.75 (2H, bs), 7.12 (2H, d, J=7.6 Hz), 7.33 (2H, d, J=7.6 Hz), 7.40-7.50 (1H, m), 7.80-7.95 (1H, m), 8.10 (1H, d, J=8.7 Hz).

2) To a solution of tert-butyl [6-[(Z)-amino(hydroxyimino)methyl]-2-isobutyl-4-(4-methylphenyl)quinolin-3-yl]methylcarbamate (0.25 g, 0.54 mmol) in tetrahydrofuran (10 ml)-ethyl acetate (10 ml) was added N,N-carbonyldiimidazole (0.26 g, 1.6 mmol), and the mixture was heated under reflux for 3 hrs. The reaction mixture was partitioned between ethyl acetate and 0.1M aqueous citric acid solution. The organic layer was washed with saturated brine and dried over anhydrous magnesium sulfate. The solvent was evaporated under reduced pressure and the residue was crystallized from n-hexane-ethyl acetate to give tert-butyl [2-isobutyl-4-(4-methylphenyl)-6-(5-oxo-4,5-dihydro-1,2,4-oxadiazol-3-yl)quinolin-3-yl]methylcarbamate (0.24 g, yield 90%) as a white powder.

¹H-NMR (DMSO-d₆) δ: 0.99 (6H, d, J=6.6 Hz), 1.38 (9H, s), 2.30-2.50 (1H, m), 2.45 (3H, s), 2.85 (2H, d, J=6.8 Hz), 4.05 (2H, d, J=4.2 Hz), 7.08 (1H, t, J=4.2 Hz), 7.31 (2H, d, J=8.0 Hz), 7.38 (2H, d, J=8.0 Hz), 7.81 (1H, d, J=1.9 Hz), 8.03 (1H, dd, J=1.9, 8.8 Hz), 8.14 (1H, d, J=8.8 Hz), 13.21 (1H, bs)

3) 3-[3-(aminomethyl)-2-isobutyl-4-(4-methylphenyl)quinolin-6-yl]-1,2,4-oxadiazol-5(4H)-one (Synthesized according to a method similar to the method shown in Example 25(2).)

¹H-NMR (DMSO-d₆) δ: 1.04 (6H, d, J=6.6 Hz), 2.30-2.45 (1H, m), 2.49 (3H, s), 3.08 (2H, d, J=7.2 Hz), 3.97 (2H, d, J=5.3 Hz), 7.34 (2H, d, J=7.9 Hz), 7.46 (2H, d, J=7.9 Hz), 7.83 (1H, d, J=1.8 Hz), 8.16 (1H, dd, J=1.8, 8.9 Hz), 8.25 (1H, d, J=8.9 Hz), 8.36 (3H, bs), 13.33 (1H, bs).

Example 109

2-{5-[3-(aminomethyl)-2-isobutyl-4-(4-methylphenyl)quinolin-6-yl]-2H-tetrazol-2-yl}acetamide Dihydrochloride 1) A mixture of tert-butyl [2-isobutyl-4-(4-methylphenyl)-6-(2H-tetrazol-5-yl)quinolin-3-yl]methylcarbamate (0.16 g, 0.33 mmol), 2-chloroacetamide (0.047 g, 0.50 mmol), potassium carbonate (0.070 g, 0.50 mmol) and N,N-dimethylformamide (5 ml) was stirred at 80° C. for 3 hrs. The reaction mixture was partitioned between ethyl acetate-tetrahydrofuran and water and the aqueous layer was extracted with ethyl acetate. The organic layer and the extract were combined and washed successively with water and saturated brine, and dried over anhydrous magnesium sulfate. The solvent was evaporated under reduced pressure and the residue was purified by silica gel column chromatography to give tert-butyl [6-[2-(2-amino-2-oxoethyl)-2H-tetrazol-5-yl]-2-isobutyl-4-(4-methylphenyl)quinolin-3-yl]methylcarbamate (0.12 g, yield 69%) as a pale-yellow powder.

¹H-NMR (CDCl₃) δ: 1.05 (6H, d, J=6.6 Hz), 1.42 (9H, s), 2.25-2.50 (1H, m), 2.50 (3H, s), 3.00 (2H, d, J=7.2 Hz), 4.25-4.40 (3H, m), 5.37 (2H, s), 5.57 (1H, bs), 5.91 (1H, bs), 7.15-7.20 (2H, m), 7.30-7.40 (2H, m), 8.10-8.20 (2H, m), 8.35-8.40 (1H, m).

2) 2-{5-[3-(aminomethyl)-2-isobutyl-4-(4-methylphenyl)quinolin-6-yl]-2H-tetrazol-2-yl}acetamide dihydrochloride (Synthesized according to a method similar to the method shown in Example 44(3).)

¹H-NMR (DMSO-d₆) δ: 1.05 (6H, d, J=6.6 Hz), 2.35-2.50 (1H, m), 2.50 (3H, s), 3.07 (2H, d, J=7.0 Hz), 3.99 (2H, d, J=5.3 Hz), 5.48 (2H, s), 7.38 (2H, d, J=7.8 Hz), 7.49 (2H, d, J=7.8 Hz), 7.54 (1H, bs), 7.90 (1H, bs), 8.04 (1H, d, J=1.8 Hz), 8.27 (1H, d, J=8.8 Hz), 8.29 (3H, bs), 8.44 (1H, dd, J=1.8, 8.8 Hz).

Example 110

Methyl N-[3-(aminomethyl)-2-isobutyl-4-(4-methylphenyl)quinolin-6-yl]glycinate To a solution of tert-butyl N-[3-cyano-2-isobutyl-4-(4-methylphenyl)quinolin-6-yl]glycinate (3.0 g, 7.0 mmol) in tetrahydrofuran (10 ml) was added trifluoroacetic acid (820 ml), and the mixture was stirred at room temperature for 6 hrs. The reaction mixture was concentrated under reduced pressure and the residue was partitioned between ethyl-acetate and water. The aqueous layer was extracted with ethyl acetate. The organic layer and the extract were combined, washed with saturated brine and dried over anhydrous magnesium sulfate. The solvent was evaporated under reduced pressure and the residue (3.0 g) was dissolved in N,N-dimethylformamide (10 ml). Thereto were added methyl iodide (1.5 g, 5.3 mmol) and potassium carbonate (0.73 g, 5.3 mmol) and the mixture was stirred at room temperature for 2 days. The reaction mixture was partitioned between ethyl acetate and water, and the aqueous layer was extracted with ethyl acetate. The organic layer and the extract were combined, washed successively with 0.1 M aqueous citric acid solution, saturated aqueous sodium hydrogen carbonate and saturated brine, and dried over anhydrous magnesium sulfate. The solvent was evaporated under reduced pressure and the residue was purified by silica gel column chromatography to give methyl N-[3-cyano-2-isobutyl-4-(4-methylphenyl)quinolin-6-yl]glycinate (1.6 g, yield 79%) as a pale-yellow powder. Subsequently, methyl N-[3-(aminomethyl)-2-isobutyl-4-(4- methylphenyl)quinolin-6-yl]glycinate (1.0 g, yield 62%, pale-yellow powder) was synthesized by a method similar to the method shown in Example 25(2).

$^1$H-NMR (CDCl$_3$) δ: 1.02 (6H, d, J=6.6 Hz), 1.44 (2H, bs), 2.20-2.40 (1H, m), 2.48 (3H, s), 2.94 (2H, d, J=7.2 Hz), 3.73 (3H, s), 3.74 (2H, s), 3.77 (2H, d, J=5.5 Hz), 4.41 (1H, t, J=5.5 Hz), 6.14 (1H, d, J=2.6 Hz), 7.07 (1H, dd, J=2.6, 9.0 Hz), 7.10-7.20 (2H, m), 7.32 (2H, d, J=7.7 Hz), 7.88 (1H, d, J=9.0 Hz).

Example 111

Ethyl 4-{[3-(aminomethyl)-2-isobutyl-4-(4-methylphenyl)-6-quinolinyl]oxy}butanoate p-toluenesulfonic Acid Salt 1) A mixture of tert-butyl {[6-hydroxy-2-isobutyl-4-(4-methylphenyl)quinolin-3-yl]methyl}carbamate (2.7 g, 6.3 mmol), ethyl 4-bromobutanoate (1.4 g, 7.0 mmol), potassium carbonate (0.97 g, 7.0 mmol) and N,N-dimethylformamide (30 ml) was stirred at 50° C. for 3 hrs. Water was added to the reaction mixture and the mixture was extracted with ethyl acetate. The extract was washed successively with 1N hydrochloric acid, saturated aqueous sodium hydrogen carbonate and saturated brine, dried over anhydrous magnesium sulfate and concentrated under reduced pressure. The residue was purified by silica gel column chromatography to give ethyl 4-{[3-{[(tert-butoxycarbonyl)amino]methyl}-2-isobutyl-4-(4-ethylphenyl)quinolin-6-yl]oxy}butanoate (2.2 g, yield 67%) as crystals.

$^1$H-NMR (CDCl$_3$) δ: 1.02 (6H, d, J 6.6 Hz), 1.23 (3H, t, J=7.2 Hz), 1.41 (9H, s), 2.00-2.09 (2H, m), 2.29-2.38 (1H, m), 2.47 (2H, t, J=6.0 Hz), 2.47 (3H, s), 2.92 (2H, d, J=7.2 Hz), 3.85 (2H, t, J=5.9 Hz), 4.12 (2H, q, J=7.2 Hz), 4.26 (2H, d, J=4.0 Hz), 4.28 (1H, bs), 6.56 (1H, d, J=2.6 Hz), 7.11 (2H, d, J=7.9 Hz), 7.27-7.33 (3H, m), 7.95 (1H, d, J=9.0 Hz).

2) To a solution of ethyl 4-{[3-{[(tert-butoxycarbonyl)amino]methyl}-2-isobutyl-4-(4-methylphenyl)quinolin-6-yl]oxy}butanoate (0.2 g, 0.37 mmol) in ethyl acetate (10 ml) was added 4N solution of hydrogen chloride in ethyl acetate (10 ml), and the mixture was stirred at room temperature for 3 hrs. The reaction mixture was concentrated under reduced pressure and saturated aqueous sodium hydrogen carbonate was added to neutralize the residue. The obtained mixture was extracted with ethyl acetate and the extract was washed with saturated brine, dried over anhydrous magnesium sulfate, and concentrated under reduced pressure to give ethyl 4-{[3-(aminomethyl)-2-isobutyl-4-(4-methylphenyl)-6-quinolinyl]oxy}butanoate (0.12 g) as an oil. The oil and p-toluenesulfonic acid monohydrate (57 mg, 0.25 mmol) were dissolved in ethanol (10 ml) and the mixture was concentrated under reduced pressure. The residue was crystallized from diethyl ether to give the title compound (0.11 g, yield 50%) as colorless crystals.

$^1$H-NMR (DMSO-d$_6$) δ: 1.01 (6H, d, J=6.6 Hz), 1.14 (3H, t, J=7.0 Hz), 1.88-1.96 (2H, m), 2.28 (3H, s), 2.33-2.42 (3H, m), 2.46 (3H, s), 2.91 (2H, d, J=7.0 Hz). 3.84 (2H, t, J=6.0 Hz), 3.94 (2H, s), 4.02 (2H, q, J=7.0 Hz), 6.50 (1H, d, J=2.6 Hz), 7.10 (2H, d, J=7.7 Hz), 7.27 (2H, d, J=7.9 Hz), 7.42-7.48 (5H, m), 7.95 (1H, d, J=9.2 Hz), 7.99 (3H, s).

elemental analysis for C$_{34}$H$_{42}$N$_2$O$_6$S

Calculated: C, 67.30; H, 6.98; N, 4.62.

Found: C, 67.21; H, 6.91; N, 4.69.

Example 112

4-{[3-(aminomethyl)-2-isobutyl-4-(4-methylphenyl)-6-quinolinyl]oxy}butanoic Acid Dihydrochloride 1) To a solution of ethyl {[3-{[(tert-butoxycarbonyl)amino]methyl}-2-isobutyl-4-(4-methylphenyl)quinolin-6-yl]oxy}butanoate (1.8 g, 3.4 mmol) in tetrahydrofuran (20 ml)-ethanol (20 ml) was added 2N aqueous sodium hydroxide solution (4 ml), and the mixture was stirred at room temperature for 3 hrs. The reaction mixture was acidified with 1N hydrochloric acid and the mixture was extracted with ethyl acetate. The extract was washed with saturated brine and dried over anhydrous magnesium sulfate. The solvent was evaporated under reduced pressure and the residue was crystallized from diisopropyl ether to give 4-{[3-{[(tert-butoxycarbonyl)amino]methyl}-2-isobutyl-4-(4-methylphenyl)quinolin-6-yl]oxy}butanoic acid (1.3 g, yield 76%) as crystals.

$^1$H-NMR (CDCl$_3$) δ: 1.11 (6H, d, J=6.6 Hz), 1.40 (9H, s), 2.05-2.13 (2H, m), 2.33-2.42 (1H, m), 2.52 (3H, s), 2.52-2.57 (2H, m), 3.46 (2H, d, J=7.0 Hz), 3.90 (2H, t, J=5.8 Hz), 4.36 (2H, d, J=5.3 Hz), 4.63 (1H, s), 6.65 (1H, d, J=2.5 Hz), 7.19 (2H, d, J=8.0 Hz), 7.43 (2H, d, J=8.0 Hz), 7.44-7.48 (1H, m), 8.92 (1H, d, J=7.9 Hz).

2) 4-{[3-{[(tert-butoxycarbonyl)amino]methyl}-2-isobutyl-4-(4-methylphenyl)quinolin-6-yl]oxy}butanoic acid was treated according to a method similar to the method shown in Example 13(5) to synthesize the title compound.

$^1$H-NMR (DMSO-d$_6$) δ: 1.02 (6H, d, J=6.6 Hz), 1.85-1.94 (2H, m), 2.26-2.41 (3H, m), 2.47 (3H, s), 3.16 (2H, d, J=5.5 Hz), 3.88 (2H, t, J=5.9 Hz), 3.97-4.01 (2H, m), 6.59 (1H, d, J=2.5 Hz), 7.35 (2H, d, J=7.9 Hz), 7.46 (2H, d, J=7.9 Hz), 7.63-7.66 (1H, m), 8.25-8.45 (4H, m).

Example 113

4-{[3-(aminomethyl)-2-isobutyl-4-(4-methylphenyl)-6-quinolinyl]oxy}butanamide

1) A mixture of 4-{[3-{[(tert-butoxycarbonyl)amino]methyl}-2-isobutyl-4-(4-methylphenyl)quinolin-6-yl]oxy}butanoic acid (0.8 g, 1.6 mmol), 1-ethyl-3-(3-dimethylaminopropyl)carbodiimide hydrochloride (0.34 g, 2.0 mmol), 1-hydroxy-1H-benzotriazole ammonium salt (0.24 g, 1.6 mmol) and N,N-dimethylformamide (10 ml) was stirred at room temperature for 15 hrs. Water was added to the reaction mixture, and the mixture was extracted with a mixed solvent of ethyl acetate-tetrahydrofuran (2:1). The extract was washed successively with saturated aqueous sodium hydrogen carbonate, 1N hydrochloric acid and saturated brine, dried over anhydrous magnesium sulfate and concentrated under reduced pressure. The residue was crystallized from isopropyl ether to give tert-butyl {[6-(4-amino-4-oxobutoxy)-2-isobutyl-4-(4-methylphenyl)quinolin-3-yl]methyl}carbamate (0.68 g, yield 84%) as crystals.

$^1$H-NMR (DMSO-d$_6$) δ: 0.96 (6H, d, J=6.6 Hz), 1.38 (9H, s), 1.81-1.90 (2H, m), 2.17 (2H, t, J=7.4 Hz), 2.30-2.39 (1H, m), 2.43 (3H, s), 2.73-2.78 (2H, m), 3.79 (2H, t, J=6.1 Hz), 4.01 (2H, d, J=4.3 Hz), 6.51 (1H, d, J=2.8 Hz), 6.74 (1H, s), 7.02 (1H, t, J=4.2 Hz), 7.27-7.30 (3H, m), 7.34-7.37 (3H, m), 7.89 (1H, d, J=9.0 Hz).

2) A solution of tert-butyl {[6-(4-amino-4-oxobutoxy)-2-isobutyl-4-(4-methylphenyl)quinolin-3-yl]methyl}carbamate (0.5 g, 0.99 mmol) in trifluoroacetic acid (10 ml) was stirred at 0° C. for 3 hrs. The reaction mixture was concentrated under reduced pressure and the residue was dissolved in ethyl acetate. The obtained-solution was washed twice with saturated aqueous sodium hydrogen carbonate, dried over anhydrous magnesium sulfate and concentrated under reduced pressure. The residue was crystallized from diethyl ether to give the title compound (0.25 g, yield 63%) as crystals.

$^1$H-NMR (DMSO-d$_6$) δ: 0.98 (6H, d, J=6.6 Hz), 1.81-1.93 (2H, m), 2.17 (2H, t, J=7.4 Hz), 2.32-2.41 (1H, m), 2.44 (3H, s), 2.96 (2H, d, J=7.0 Hz), 3.32 (2H, s), 3.56 (2H, s), 3.78 (2H, t, J=6.1 Hz), 6.48 (1H, d, J=2.6 Hz), 6.73 (1H, s), 7.24-7.26 (3H, m), 7.30-7.37 (3H, m), 7.87 (1H, d, J=9.0 Hz).

Example 114

Ethyl 5-{[3-(aminomethyl)-2-isobutyl-4-(4-methylphenyl)-6-quinolinyl]oxy}pentanoate Dihydrochloride 1) A mixture of tert-butyl {[6-hydroxy-2-isobutyl-4-(4-methylphenyl)quinolin-3-yl]methyl}carbamate (2.7 g, 6.3 mmol), ethyl 5-bromopentanoate (1.4 g, 7.0 mmol), potassium carbonate (0.97 g, 7.0 mmol) and N,N-dimethylformamide (30 ml) was stirred at 50° C. for 3 hrs. Water was added to the reaction mixture and the mixture was extracted with ethyl acetate. The extract was washed successively with 1N hydrochloric acid, saturated aqueous sodium hydrogen carbonate and saturated brine, dried over anhydrous magnesium sulfate, and concentrated under reduced pressure. The residue was purified by silica gel column chromatography to give ethyl 5-{[3-{[(tert-butoxycarbonyl)amino]methyl}-2-isobutyl-4-(4-methylphenyl)quinolin-6-yl]oxy}pentanoate (2.2 g, yield 67%) as crystals.

$^1$H-NMR (CDCl$_3$) δ: 1.02 (6H, d, J=6.6 Hz), 1.24 (3H, t, J=7.2 Hz), 1.41 (9H, s), 1.74-1.78 (4H, m), 2.29-2.38 (3H, m), 2.48 (3H, s), 2.93 (2H, d, J=7.2 Hz), 3.79-3.83 (2H, m), 4.11 (2H, q, J=7.2 Hz), 4.25-4.33 (3H, m), 6.55 (1H, d, J=2.8 Hz), 7.12 (2H, d, J=7.9 Hz), 7.28-7.34 (3H, m), 7.96 (1H, d, J=9.0 Hz).

2) Ethyl 5-{[3-{[(tert-butoxycarbonyl)amino]methyl}-2-isobutyl-4-(4-methylphenyl)quinolin-6-yl]oxy}pentanoate was treated according to a method similar to the method shown in Example 13(5) to synthesize the title compound.

$^1$H-NMR (DMSO-d$_6$) δ: 1.02 (6H, d, J=6.6 Hz), 1.15 (3H, t, J=7.1 Hz), 1.58-1.73 (4H, m), 2.25-2.35 (1H, m), 2.31 (2H, t, J=6.97 Hz), 2.47 (3H, s), 3.15-3.25 (2H, m), 3.88 (2H, t, J=4.9 Hz), 4.02 (2H, q, J=7.1 Hz), 3.99 (2H, s), 6.61 (1H, s), 7.35-7.36 (2H, m), 7.46-7.48 (2H, m), 7.68 (1H, s), 8.36-8.55 (4H, m).

Example 115

5-{[3-(aminomethyl)-2-isobutyl-4-(4-methylphenyl)-6-quinolinyl]oxy}pentanoic Acid Dihydrochloride 1) To a solution of ethyl 5-{[3-{[(tert-butoxycarbonyl)amino]methyl}-2-isobutyl-4-(4-methylphenyl)quinolin-6-yl]oxy}pentanoate (1.6 g, 2.9 mmol) in tetrahydrofuran (10 ml)-ethanol (10 ml) was added 2N aqueous sodium hydroxide solution (3 ml), and the mixture was stirred at room temperature for 5 hrs. The reaction mixture was acidified with 1N hydrochloric acid and the mixture was extracted with ethyl acetate. The extract was washed with saturated brine, and dried over anhydrous magnesium sulfate. The solvent was evaporated under-reduced pressure and the residue was crystallized from diisopropyl ether to give 5-{[3-{[(tert-butoxycarbonyl)amino]methyl}-2-isobutyl-4-(4-methylphenyl)quinolin-6-yl]oxy}pentanoic acid (1.3 g, yield 87%) as crystals.

$^1$H-NMR (CDCl$_3$) δ: 1.07 (6H, d, J=6.6 Hz), 1.41 (9H, s), 1.70-1.85 (4H, m), 2.30-2.43 (3H, m), 2.50 (3H, s), 3.18-3.30 (2H, m), 3.75-3.85 (2H, m), 4.32 (2H, d, J=4.7 Hz), 4.42 (1H, s), 6.60 (1H, d, J=1.5 Hz), 7.15 (2H, d, J=7.4 Hz), 7.37-7.43 (3H, m), 8.50-8.60 (1H, m).

2) 5-{[3-{[(tert-Butoxycarbonyl)amino]methyl}-2-isobutyl-4-(4-methylphenyl)quinolin-6-yl]oxy}pentanoic acid was treated according to a method similar to the method shown in Example 13(5) to synthesize the title compound.

$^1$H-NMR (DMSO-d$_6$) δ: 1.02 (6H, d, J=6.6 Hz), 1.55-1.71 (4H, m), 2.23 (2H, t, J=7.3 Hz), 2.28-2.37 (1H, m), 2.47 (3H, s), 3.15-3.25 (2H, m), 3.88 (2H, t, J=5.8 Hz), 3.95-4.04 (2H, m), 6.61 (1H, s), 7.37 (2H, d, J=7.9 Hz), 7.47 (2H, d, J=7.9 Hz), 7.68-7.70 (1H, m), 8.35-8.50 (4H, m).

Example 116

5-{[3-(aminomethyl)-2-isobutyl-4-(4-methylphenyl)-6-quinolinyl]oxy}pentanamide

1) A mixture of 5-{[3-{[(tert-butoxycarbonyl)amino]methyl}-2-isobutyl-4-(4-methylphenyl)quinolin-6-yl]oxy}pentanoic acid (0.8 g, 1.5 mmol), 1-ethyl-3-(3-dimethylaminopropyl)carbodiimide hydrochloride (0.38 g, 2.0 mmol), 1-hydroxy-1H-benzotriazole ammonium salt (0.24 g, 1.6 mmol) and N,N-dimethylformamide (10 ml) was stirred at room temperature for 15 hrs. Water was added to the reaction mixture and the mixture was extracted with ethyl acetate. The extract was washed successively with saturated aqueous sodium hydrogen carbonate, 1N hydrochloric acid and saturated brine, dried over anhydrous magnesium sulfate and concentrated under reduced pressure. The residue was crystallized from isopropyl ether to give tert-butyl {{6-[(5-amino-5-oxopentyl)oxy]-2-isobutyl-4-(4-methylphenyl)quinolin-3-yl}methyl}carbamate (0.6 g, yield 77%) as crystals.

$^1$H-NMR (CDCl$_3$) δ: 1.02 (6H, d, J=6.6 Hz), 1.41 (9H, s), 1.77-1.81 (4H, m), 2.25-2.38 (3H, m), 2.48 (3H, s), 2.89-2.96 (2H, m), 3.82 (2H, t, J=5.1 Hz), 4.26 (2H, d, J=4.1 Hz), 4.32 (1H, s), 5.29 (1H, s), 5.40 (1H, s), 6.56 (1H, d, J=2.6 Hz), 7.12 (2H, d, J=7.9 Hz), 7.28-7.34 (3H, m), 7.96 (1H, d, J=9.2 Hz).

2) tert-Butyl {{6-[(5-amino-5-oxopentyl)oxy]-2-isobutyl-4-(4-methylphenyl)quinolin-3-yl}methyl}carbamate (0.26 g, 0.53 mmol) was treated according to a method similar to the method shown in Example 113(2) to give the title compound (0.27 g, yield 84%) as crystals.

$^1$H-NMR (DMSO-d$_6$) δ: 0.98 (6H, d, J=6.6 Hz), 1.52-1.65 (4H, m), 2.04 (2H, t, J=7.2 Hz), 2.31-2.41 (1H, m), 2.43 (3H, s), 2.96 (2H, d, J=7.0 Hz), 3.32 (2H, s), 3.57 (2H, s), 3.79 (2H, t, J=5.8 Hz), 6.49 (1H, d, J=2.6 Hz) 6.69 (1H, s), 7.22 (1H, s), 7.25 (2H, d, J=7.9 Hz), 7.32 (1H, dd, J=9.0, 2.6 Hz), 7.36 (2H, d, J=7.9 Hz), 7.87 (1H, d, J=9.0 Hz).

Example 117 tert-butyl (2-{[3-(aminomethyl)-2-isobutyl-4-(4-methylphenyl)-6-quinolinyl]oxy}ethoxy)acetate p-toluenesulfonic Acid Salt 1) A mixture of 6-hydroxy-2-isobutyl-4-(4-methylphenyl)quinoline-3-carbonitrile (5.0 g, 15.8 mmol), 2-bromoethyl acetate (3.2 g, 19 mmol) and N,N-dimethylformamide (20 ml) was stirred at 50° C. for 15 hrs. Water was added to the reaction mixture and the mixture was extracted with ethyl acetate. The extract was washed successively with 1N hydrochloric acid, saturated aqueous sodium hydrogen carbonate and saturated brine, dried over anhydrous-magnesium sulfate, and concentrated under reduced pressure. The residue was crystallized from diethyl ether and filtered to give 2-{[3-cyano-2-isobutyl-4-(4-methylphenyl)quinolin-6-yl]oxy}ethyl acetate (5.0 g, yield 79%) as crystals.

$^1$H-NMR (CDCl$_3$) δ: 1.05 (6H, d, J=6.6 Hz), 2.08 (3H, s), 2.31-2.45 (1H, m), 2.50 (3H, s), 3.08 (2H, d, J=7.2 Hz) 4.08 (2H, t, J=4.5 Hz), 4.41 (2H, t, J=4.5 Hz), 6.93 (1H, d, J=2.8 Hz), 7.35 (2H, d, J=8.10 Hz), 7.40 (2H, d, J=8.10 Hz), 7.48 (1H, dd, J=9.2, 2.8 Hz), 8.04 (1H, d, J=9.2 Hz).

2) To a solution of 2-{[3-cyano-2-isobutyl-4-(4-methylphenyl)quinolin-6-yl]oxy}ethyl acetate (4.0 g, 9.9 mmol) in tetrahydrofuran (20 ml)-methanol (20 ml) was added 2N aqueous sodium hydroxide solution (20 ml). The obtained mixture was stirred at room temperature for 3 hrs. Water was added to the reaction mixture and the mixture was extracted with ethyl acetate. The extract was washed successively with saturated aqueous sodium hydrogen carbonate and saturated brine, dried over anhydrous magnesium sulfate, and concentrated under reduced pressure. The residue was crystallized from diisopropyl ether to give 6-(2-hydroxyethoxy)-2-isobutyl-4-(4-methylphenyl)quinoline-3-carbonitrile (3.2 g, yield 89%) as crystals.

$^1$H-NMR (CDCl$_3$) δ: 1.05 (6H, d, J=6.8 Hz), 1.96 (1H, t, J=5.8 Hz), 2.31-2.45 (1H, m), 2.49 (3H, s), 3.08 (2H, d, J=7.2 Hz), 3.93-4.02 (4H, m), 6.96 (1H, d, J=2.7 Hz), 7.34-7.41 (4H, m), 7.48 (1H, dd, J=9.2, 2.7 Hz), 8.04 (1H, d, J=9.2 Hz).

3) To a solution of 6-(2-hydroxyethoxy)-2-isobutyl-4-(4-methylphenyl)quinoline-3-carbonitrile (1.0 g, 2.8 mmol) in N,N-dimethylformamide (10 ml) was added sodium hydride (60% in oil, 0.14 g, 3.4 mmol), and the mixture was stirred at room temperature for 1 hr. tert-Butyl bromoacetate (1 ml, 6.8 mmol) was added to the reaction mixture and the mixture was stirred at room temperature for 17 hrs. Water was added to the reaction mixture and the mixture was extracted with ethyl acetate. The extract was washed successively with 1N hydrochloric acid, saturated aqueous sodium hydrogen carbonate and saturated brine, dried over anhydrous magnesium sulfate, and concentrated under reduced pressure. The residue was purified by silica gel column chromatography to give tert-butyl (2-{[3-cyano-2-isobutyl-4-(4-methylphenyl)quinolin-6-yl]oxy}ethoxy)acetate (0.9 g, yield 69%) as an oil.

$^1$H-NMR (CDCl$_3$) δ: 1.05 (6H, d, J=6.6 Hz), 1.47 (9H, s), 2.39 (1H, m), 2.49 (3H, s), 3.08 (2H, d, J=7.2 Hz), 3.90 (2H, dd, J=5.7, 3.8 Hz), 4.06 (2H, s), 4.10 (2H, m), 6.95 (1H, d, J=2.7 Hz), 7.34 (2H, d, J=8.1 Hz), 7.39 (2H, d, J=8.1 Hz), 7.49 (1H, dd, J=9.2, 2.7 Hz), 8.02 (1H, d, J=9.2 Hz).

4) To a mixture of tert-butyl (2-{[3-cyano-2-isobutyl-4-(4-methylphenyl)quinolin-6-yl]oxy}ethoxy)acetate (0.9 g, 1.9 mmol), 25% aqueous ammonia (5 ml) and methanol (50 ml) was added Raney-nickel (1 ml), and the mixture was stirred under a hydrogen atmosphere at 0.5 MPa, room temperature for 5 hrs. The reaction mixture was filtered, and the filtrate was concentrated under reduced pressure. The residue was purified by silica gel column chromatography to give tert-butyl (2-{[3-(aminomethyl)-2-isobutyl-4-(4-methylphenyl)-6-quinolinyl]oxy}ethoxy)acetate as an oil (0.6 g). The oil and p-toluenesulfonic acid monohydrate (0.23 g, 1.2 mmol) were dissolved in ethanol (50 ml) and concentrated under reduced pressure. The residue was crystallized from diethyl ether and recrystallized from methanol-diethyl ether to give the title compound (0.7 g, yield 58%) as crystals.

$^1$H-NMR (DMSO-d$_6$) δ: 1.01 (6H, d, J=6.8 Hz), 1.40 (9H, s), 2.28 (3H, s), 2.31-2.40 (1H, m), 2.46 (3H, s), 2.91 (2H, d, J=7.0 Hz), 3.74-3.76 (2H, m), 3.94-3.97 (4H, m), 4.00 (2H, s), 6.54 (1H, d, J=2.6 Hz), 7.10 (2H, d, J=7.9 Hz), 7.28 (2H, d, J=7.9 Hz), 7.42-7.48 (5H, m), 7.96 (1H, d, J=9.2 Hz), 7.99 (3H, s).

elemental analysis for C$_{36}$H$_{46}$N$_2$O$_7$S
Calculated: C, 66.44; H, 7.12; N, 4.30.
Found: C, 66.15; H, 7.11; N, 4.17.

Example 118

(2-{[3-(aminomethyl)-2-isobutyl-4-(4-methylphenyl)quinolin-6-yl]oxy}-ethoxy)acetic Acid p-toluenesulfonic Acid Salt A solution of tert-butyl (2-{[3-(aminomethyl)-2-isobutyl-4-(4-methylphenyl)-6-quinolinyl]oxy}ethoxy)acetate p-toluenesulfonic acid salt (0.2 g, 0.3 mmol) in trifluoroacetic acid (5 ml) was stirred at room temperature for 4 hrs. The reaction mixture was concentrated under reduced pressure and the residue was solidified from diethyl ether. The obtained solid was dissolved in methanol and concentrated under reduced pressure. The residue was again solidified from diethyl ether to give the title compound (0.15 g, yield 83%) as an amorphous form.

$^1$H-NMR (DMSO-d$_6$) δ: 1.01 (6H, d, J=6.6 Hz), 2.28 (3H, s), 2.32-2.39 (1H, m), 2.46 (3H, s), 2.94 (2H, d, J=7.0 Hz), 3.74-3.77 (2H, m), 3.93-3.99 (4H, m), 4.04 (2H, s), 6.56 (1H, d, J=2.5 Hz), 7.10 (2H, d, J=7.9 Hz), 7.29 (2H, d, J=7.9 Hz), 7.43-7.53 (5H, m), 7.99 (1H, d, J=9.2 Hz), 8.02 (3H, s).

Example 119

Ethyl 5-[3-(aminomethyl)-2-isobutyl-4-(4-methylphenyl)quinolin-6-yl]pentanoate

1) A mixture of 6-bromo-2-isobutyl-4-(4-methylphenyl)quinoline-3-carbonitrile (5.00 g, 13.2 mmol), acrolein (2.22 g, 39.6 mmol), benzyltriethylammonium chloride (3.00 g, 13.2 mmol), triethylamine (5.5 ml, 39.6 mmol), palladium acetate (150 mg, 0.66 mmol) and N,N-dimethylformamide (40 ml) was stirred under an argon atmosphere at 70° C. After 3 hrs., palladium acetate (150 mg, 0.66 mmol) and acrolein (2.22 g, 39.6 mmol) were added to the reaction mixture and the mixture was stirred at the same temperature for 17 hrs. The reaction mixture was diluted with ethyl acetate, washed 4 times with saturated brine, and dried over anhydrous magnesium sulfate. The solvent was evaporated under reduced pressure and the residue was purified by silica gel column chromatography to give 2-isobutyl-4-(4-methylphenyl)-6-[(1E)-3-oxoprop-1-en-1-yl]quinoline-3-carbonitrile (3.26 g, yield 70%) as white crystals.

$^1$H-NMR (CDCl$_3$) δ: 1.07 (1H, d, J=6.0 Hz), 2.36-2.47 (1H, m), 2.52 (3H, s), 3.14 (2H, d, J=9.0 Hz), 6.74 (1H, dd, J=9.0, 15.0 Hz), 7.37 (2H, d, J=9.0 Hz), 7.44 (2H, d, J=9.0 Hz), 7.52 (1H, d, J=15.0 Hz), 7.84 (1H, d, J=3.0 Hz), 8.01 (1H, d, J=9.0 Hz), 8.06 (1H, d, J=9.0 Hz), 9.71 (1H, d, J=9.0 Hz).

2) To a solution of ethyl diethylphosphonoacetate (1.90 g, 10.2 mmol) in tetrahydrofuran (50 ml) was added sodium hydride (60% in oil, 408 mg, 10.2 mmol) at 0° C. and the mixture was stirred for 10 min. To the reaction mixture was added 2-isobutyl-4-(4-methylphenyl)-6-[(1E)-3-oxoprop-1-en-1-yl]quinoline-3-carbonitrile (3.00 g, 8.47 mmol). The temperature of the mixture was raised to room temperature and the mixture was stirred for 10 min. The reaction mixture was diluted with a mixture of tetrahydrofuran and ethyl acetate, washed successively with 2N aqueous sodium hydroxide solution, 1N hydrochloric acid, saturated aqueous sodium hydrogen carbonate and saturated brine and dried over anhydrous magnesium sulfate. The solvent was evaporated under reduced pressure to give yellow crystals. The crystals were washed with diisopropyl ether to give ethyl (2E,4E)-5-[3-cyano-2-isobutyl-4-(4-methylphenyl)quinolin-6-yl]penta-2,4-dienoate (2.71 g, yield 75%) as yellow crystals. The solvent of the mother liquor was removed under reduced pressure and the residue was purified by silica gel column chromatography to give ethyl (2E,4E)-5-[3-cyano-2-isobutyl-4-(4-methylphenyl)quinolin-6-yl]penta-2,4-dienoate (320 mg, yield 9%) as yellow crystals.

$^1$H-NMR (CDCl$_3$) δ: 1.06 (6H, d, J=6.0 Hz), 1.31 (3H, t, J=6.0 Hz), 2.33-2.45 (1H, m), 2.51 (3H, s), 3.12 (2H, d, J=9.0 Hz), 4.23 (2H, q, J=6.0 Hz), 6.03 (1H, d, J=15.0 Hz), 6.90-6.92 (2H, m), 7.35-7.45 (5H, m), 7.63 (1H, d, J=3.0 Hz), 7.99 (1H, dd, J=3.0, 9.0 Hz), 8.10 (1H, d, J=9.0 Hz).

3) ethyl 5-[3-(aminomethyl)-2-isobutyl-4-(4-methylphenyl)quinolin-6-yl]pentanoate (Synthesized according to a method similar to the method shown in Example 25(2).)

$^1$H-NMR (CDCl$_3$) δ: 1.03 (6H, d, J=6.0 Hz), 1.22 (2H, t, J=6.0 Hz), 1.20-1.28 (2H, m), 1.55 (2H, bs), 1.59-1.62 (2H, m), 2.27 (2H, t, J=6.0 Hz), 2.33-2.39 (1H, m), 2.49 (3H, s), 2.60-2.66 (2H, m), 3.00 (2H, d, J=9.0 Hz), 3.77 (2H, bs), 4.06-4.16 (2H, m), 7.03 (1H, bs); 7.17 (2H, d, J=9.0 Hz), 7.34 (2H, d, J=9.0 Hz), 7.47 (1H, dd, J=3.0, 9.0 Hz), 7.97 (1H, d, J=9.0 Hz).

Example 120

5-[3-(aminomethyl)-2-isobutyl-4-(4-methylphenyl)quinolin-6-yl]pentanoic Acid Dihydrochloride 1) Ethyl 5-[3-{[(tert-butoxycarbonyl)amino]methyl}-2-isobutyl-4-(4-methylphenyl)quinolin-6-yl]pentanoate was synthesized by a method similar to the method shown in Example 27(1). Subsequently, 5-[3{[(tert-butoxycarbonyl)amino]methyl}-2-isobutyl-4-(4-methylphenyl)quinolin-6-yl]pentanoic acid was synthesized by a method similar to the method shown in Example 6(1).

$^1$H-NMR (CDCl$_3$) δ: 1.03 (6H, d, J=6.0 Hz), 1.41 (9H, s), 1.59-1.67 (4H, m), 2.27-2.37 (3H, m), 2.48 (3H, s), 2.61-2.69 (2H, m), 2.99-3.06 (2H, m), 4.30 (2H, bs), 7.08 (1H, d, J=3.0 Hz), 7.13 (2H, d, J=9.0 Hz), 7.34 (2H, d, J=6.0 Hz), 7.53 (1H, dd, J=3.0, 9.0 Hz), 8.10 (1H, bs).

2) 5-[3-(aminomethyl)-2-isobutyl-4-(4-methylphenyl)quinolin-6-yl]pentanoic acid dihydrochloride (Synthesized according to a method similar to the method shown in Example 44(3).)

$^1$H-NMR (CD$_3$OD) δ: 1.11-1.15 (6H, m), 1.50-1.69 (4H, m), 2.27 (2H, t, J=6.0 Hz), 2.31-2.36 (1H, m), 2.55 (3H, s), 2.80 (2H, t, J=6.0 Hz), 3.32-3.34 (2H, m), 4.33 (2H, bs), 7.39 (2H, d, J=9.0 Hz), 7.41 (1H, s), 7.58 (2H, d, J=6.0 Hz), 8.10 (1H, dd, J=3.0, 9.0 Hz), 8.28 (1H, d, J=9.0 Hz).

Example 121

5-[3-(aminomethyl)-2-isobutyl-4-(4-methylphenyl)quinolin-6-yl]pentanamide tert-Butyl [6-(5-amino-5-oxopentyl)-2-isobutyl-4-(4-methylphenyl)quinolin-3-yl]methylcarbamate was synthesized by a method similar to the method shown in Example 19(4). Subsequently, 5-[3-(aminomethyl)-2-isobutyl-4-(4-methylphenyl)quinolin-6-yl]pentanamide was synthesized by a method similar to the method shown in Example 32(2).

$^1$H-NMR (CDCl$_3$) δ: 1.03 (6H, d, J=6.0 Hz), 1.58-1.71 (6H, m), 2.14-2.21 (2H, m), 2.30-2.40 (1H, m), 2.49 (3H, s), 2.61-2.69 (2H, m), 3.01 (2H, d, J=9.0 Hz), 3.80 (2H, bs), 7.04 (1H, bs), 7.17 (2H, d, J=9.0 Hz), 7.35 (2H, d, J=9.0 Hz), 7.48 (1H, dd, J=3.0, 9.0 Hz), 7.99 (1H, d, J=9.0 Hz).

Example 122

Methyl (4E)-5-[3-(aminomethyl)-2-isobutyl-4-(4-methylphenyl)quinolin-6-yl]pent-4-enoate Dihydrochloride 1) A mixture of tert-butyl [6-(hydroxymethyl)-2-isobutyl-4-(4-methylphenyl)quinolin-3-yl]methylcarbamate (0.46 g, 1.1 mmol), manganese dioxide (chemically treated product, 1.4 g, 16 mmol) and tetrahydrofuran (20 ml) was stirred at room temperature for 12 hrs. The reaction mixture was filtered, and the filtrate was partitioned between ethyl acetate and 1N aqueous sodium hydroxide solution. The organic layer was washed with saturated brine, and dried over anhydrous magnesium sulfate. The solvent was evaporated under reduced pressure and the residue was purified by silica gel column chromatography to give tert-butyl [6-formyl-2-isobutyl-4-(4-methylphenyl)quinolin-3-yl]methylcarbamate (0.28 g, yield 62%) as a white powder.

$^1$H-NMR (CDCl$_3$) δ: 1.05 (6H, d, J=6.6 Hz), 1.42 (9H, s), 2.30-2.50 (1H, m), 2.50 (3H, s), 3.01 (2H, d, J=7.2 Hz), 4.30-4.40 (3H, m), 7.16 (2H, d, J=8.0 Hz), 7.38 (2H, d, J=8.0 Hz), 7.80-7.85 (1H, m), 8.10-8.20 (2H, m), 9.96 (1H, s).

2) To a solution (1.4 ml) of (3-carboxypropyl)(triphenyl)phosphonium bromide (259 mg, 0.601 mmol) in tetrahydrofuran (5 ml) was added 1.0 M solution (1.4 ml) of lithium bis(trimethylsilyl)amide in tetrahydrofuran and the mixture was stirred at room temperature for 15 min. To the reaction mixture was added tert-butyl [6-formyl-2-isobutyl-4-(4-ethylphenyl)quinolin-3-yl]methylcarbamate (200 mg, 0.463 mmol) at −78° C., the temperature of the mixture was raised to room temperature, and the mixture was stirred for 30 min. The reaction mixture was diluted with ethyl acetate, washed with saturated aqueous ammonium chloride solution, and dried over anhydrous magnesium sulfate. The solvent was evaporated under reduced pressure to give a mixture of (4E)-5-[3-([(tert-butoxycarbonyl)amino]methyl)-2-isobutyl-4-(4-methylphenyl)quinolin-6-yl]pent-4-enoic acid and (4Z)-5-[3-{[(tert-butoxycarbonyl)amino]methyl}-2-isobutyl-4-(4-methylphenyl)quinolin-6-yl]pent-4-enoic acid. Subsequently, this mixture, 1-ethyl-3-(3-dimethylaminopropyl)carbodiimide hydrochloride (178 mg, 0.926 mmol), 1-hydroxy-1H-benzotriazole (70.9 mg, 0.463 mmol) and methanol (0.5 ml) were dissolved in N,N-dimethylformamide (5 ml) and the mixture was stirred for 1 hr. The reaction mixture was diluted with ethyl acetate, washed with 1N hydrochloric acid, saturated aqueous sodium hydrogen carbonate and saturated brine, and dried over anhydrous magnesium sulfate. The solvent was evaporated under reduced pressure to give a mixture of methyl (4E)-5-[3-{[(tert-butoxycarbonyl)amino]methyl}-2-isobutyl-4-(4-methylphenyl)quinolin-6-yl]pent-4-enoate and methyl (4Z)-5-[3-{[(tert-butoxycarbonyl)amino]methyl}-2-isobutyl-4-(4-methylphenyl)quinolin-6-yl]pent-4-enoate.

3) This mixture was purified by silica gel column chromatography to give methyl (4E)-5-[3-{[(tert-butoxycarbonyl)amino]methyl}-2-isobutyl-4-(4-ethylphenyl)quinolin-6-yl]pent-4-enoate (70.0 mg, yield 29%) as a yellow oil.

$^1$H-NMR (CDCl$_3$) δ: 1.02 (6H, d, J=6.0 Hz), 1.41 (9H, s), 2.29-2.55 (8H, m), 2.95 (2H, d, J=9.0 Hz), 3.66 (3H, s), 4.27-4.36 (3H, m), 6.20 (1H, dt, J=6.0, 15.0 Hz), 6.42 (1H, d, J=15.0 Hz), 7.10 (1H, bs), 7.13 (2H, d, J=9.0 Hz), 7.34 (2H, d, J=9.0 Hz), 7.76 (1H, dd, J=3.0, 9.0 Hz), 7.98 (1H, d, J=9.0 Hz).

4) methyl (4E)-5-[3-(aminomethyl)-2-isobutyl-4-(4-methylphenyl)quinolin-6-yl]pent-4-enoate dihydrochloride (Synthesized according to a method similar to the method shown in Example 44(3).)

$^1$H-NMR (CD$_3$OD) δ: 1.15 (6H, d, J=9.0 Hz), 2.28-2.38 (1H, m), 2.49-2.59 (7H, m), 3.28-3.36 (2H, m), 3.64 (3H, s), 4.32 (2H, bs), 6.50-6.62 (2H, m), 7.36-7.49 (3H, m), 7.53-7.61 (2H, m), 8.27-8.40 (2H, m).

Example 123

Methyl (4Z)-5-[3-(aminomethyl)-2-isobutyl-4-(4-methylphenyl)quinolin-6-yl]pent-4-enoate Dihydrochloride 1) methyl (4Z)-5-[3-{[(tert-butoxycarbonyl)amino]methyl}-2-isobutyl-4-(4-methylphenyl)quinolin-6-yl]pent-4-enoate (Synthesized according to a method similar to the method shown in Example 122(3).)

$^1$H-NMR (CDCl$_3$) δ: 1.03 (6H, d, J=6.0 Hz), 1.42 (9H, s), 2.30-2.41 (3H, m), 2.47 (3H, s), 2.48-2.55 (2H, m), 2.97 (2H, d, J=9.0 Hz), 3.66 (3H, s), 4.25-4.41 (3H, m), 5.61 (1H, dt, J=6.0, 9.0 Hz), 6.48 (1H, d, J=9.0 Hz), 7.12-7.15 (3H, m), 7.32 (2H, d, J=6.0 Hz), 7.57 (1H, d, J=3.0, 9.0 Hz), 8.01 (1H, d, J=6.0 Hz).

2) methyl (4Z)-5-[3-(aminomethyl)-2-isobutyl-4-(4-methylphenyl)quinolin-6-yl]pent-4-enoate dihydrochloride (Synthesized according to a method similar to the method shown in Example 44(3).)

$^1$H-NMR (CD$_3$OD) δ: 1.07-1.18 (6H, m), 2.28-2.38 (1H, m), 2.39-2.57 (7H, m), 3.52-3.76 (5H, m), 4.37 (2H, bs), 5.79-5.91 (1H, m), 6.48-6.62 (1H, m), 7.37-7.50 (3H, m), 7.51-7.61 (2H, m), 8.06-8.13 (1H, m), 8.33-8.45 (1H, m).

Example 124

6-[3-(aminomethyl)-2-isobutyl-4-(4-methylphenyl)quinolin-6-yl]hexanoic Acid Dihydrochloride 1) To a solution of 3-{[(tert-butoxycarbonyl)amino]methyl}-2-isobutyl-4-(4-methylphenyl)quinolin-6-yl trifluoromethanesulfonate (3.03 g, 6.13 mmol), copper iodide (176 mg, 0.920 mmol) and hex-5-ynenitrile (2.86 g, 30.7 mmol) in tetrahydrofuran (30 ml)-triethylamine (10 ml) was added dichlorobistriphenylphosphinepalladium (431 mg, 0.613 mmol), and the mixture was stirred under an argon atmosphere at 80° C. for 10 min. The reaction mixture was diluted with ethyl acetate, washed with saturated aqueous ammonium chloride solution, and dried over anhydrous magnesium sulfate. The solvent was evaporated under reduced pressure to give black crystals. The crystals were recrystallized from ethyl acetate-n-hexane to give tert-butyl {[6-(5-cyanopent-1-yn-1-yl)-2-isobutyl-4-(4-methylphenyl)quinolin-3-yl]methyl}carbamate (2.56 g, yield 84%) as white crystals. Subsequently, tert-butyl {[6-(5-cyanopent-1-yn-1-yl)-2-isobutyl-4-(4-methylphenyl)quinolin-3-yl]methyl}carbamate (2.56 g, 5.17 mmol) and 10% palladium-carbon (550 mg) were suspended in a mixed solvent of ethanol (200 ml)-tetrahydrofuran (35 ml) and the mixture was stirred under a hydrogen atmosphere at room temperature for 3.5 hrs. The reaction mixture was filtered, and the filtrate was concentrated under reduced pressure to give tert-butyl {[6-(5-cyanopentyl)-2-isobutyl-4-(4-methylphenyl)quinolin-3-yl]methyl}carbamate (2.37 g, yield 92%) as white crystals.

$^1$H-NMR (CDCl$_3$) δ: 1.02 (6H, d, J=6.0 Hz), 1.41 (9H, s), 1.56-1.69 (6H, m), 2.29 (2H, t, J=6.0 Hz), 2.32-2.39 (1H, m), 2.49 (3H, s), 2.64 (2H, t, J=6.0 Hz), 2.95 (2H, d, J=6.0 Hz), 4.24-4.36 (3H, m), 7.05 (1H, d, J=3.0 Hz), 7.13 (2H, d, J=9.0 Hz), 7.34 (2H, d, J=6.0 Hz), 7.49 (1H, d, J=9.0 Hz), 7.99 (1H, d, J=9.0 Hz).

2) To a solution of tert-butyl {[6-(5-cyanopentyl)-2-isobutyl-4-(4-methylphenyl)quinolin-3-yl]methyl})carbamate (2.37 g, 4.74 mmol) in ethanol (40 ml) was added 2N aqueous sodium hydroxide solution (12 ml), and the mixture was heated under reflux for 6 hrs. The reaction mixture was acidified with 6N hydrochloric acid and the mixture was extracted 3 times with ethyl acetate. The combined organic layer was washed with saturated brine, and dried over anhydrous magnesium sulfate. The solvent was evaporated under reduced pressure and the obtained solid was washed with diisopropyl ether to give 6-[3-{[(tert-butoxycarbonyl)amino]methyl}-2-isobutyl-4-(4-methylphenyl)quinolin-6-yl]hexanoic acid (2.37 g, yield 70%) as white crystals. The solvent of the mother liquor was evaporated under reduced pressure and the residue was purified by silica gel column chromatography to give 6-[3-{[(tert-butoxycarbonyl)amino]methyl}-2-isobutyl-4-(4-methylphenyl)quinolin-6-yl]hexanoic acid (720 mg, yield 29%) as white crystals.

$^1$H-NMR (CDCl$_3$) δ: 1.13 (6H, d, J=6.0 Hz), 1.40 (9H, s), 1.45-1.98 (6H, m), 2.30 (2H, t, J=6.0 Hz), 2.34-2.43 (1H, m), 2.52 (3H, s), 2.69 (2H, d, J=6.0 Hz), 3.38-3.57 (2H, m), 4.30-4.48 (2H, m), 7.10-7.20 (3H, m), 7.43 (2H, J=6.0 Hz), 7.69-7.78 (1H, m), 8.85-8.99 (1H, m).

3) 6-[3-(aminomethyl)-2-isobutyl-4-(4-methylphenyl)quinolin-6-yl]hexanoic acid dihydrochloride (Synthesized according to a method similar to the method shown in Example 44(3).)

$^1$H-NMR (CD$_3$OD) δ: 1.14 (6H, d, J=6.0 Hz), 1.27-1.38 (2H, m), 1.51-1.70 (4H, m), 2.24 (2H, t, J=6.0 Hz), 2.27-2.35 (1H, m), 2.55 (3H, s), 2.79 (2H, t, J=6.0 Hz), 3.32-3.34 (2H, m), 4.33 (2H, bs), 7.36-7.43 (3H, m), 7.58 (2H, d, J=6.0 Hz), 8.10 (1H, dd, J=3.0, 9.0 Hz), 8.29 (1H, d, J=9.0 Hz).

Example 125

Methyl 6-[3-(aminomethyl)-2-isobutyl-4-(4-methylphenyl)quinolin-6-yl]hexanoate

To a solution of 6-[3-{[(tert-butoxycarbonyl)amino]methyl}-2-isobutyl-4-(4-methylphenyl)quinolin-6-yl]hexanoic acid (885 mg, 1.71 mmol) and potassium carbonate (469 mg, 3.39 mmol) in N,N-dimethylformamide (40 ml) was added methyl iodide (291 mg, 2.05 mmol), and the mixture was stirred at room temperature for 12 hrs. The reaction mixture was diluted with ethyl acetate, washed with 1N hydrochloric acid, saturated aqueous sodium hydrogen carbonate and saturated brine, and dried over anhydrous magnesium sulfate. The solvent was evaporated under reduced pressure and the residue was purified by silica gel column chromatography to give methyl 6-[3-{[(tert-butoxycarbonyl)amino]methyl}-2-isobutyl-4-(4-methylphenyl)quinolin-6-yl]hexanoate (870 mg, yield 96%) as white crystals. Subsequently, methyl 6-[3-(aminomethyl)-2-isobutyl-4-(4-methylphenyl)quinolin-6-yl]hexanoate was synthesized by a method similar to the method shown in Example 32(2).

$^1$H-NMR (CDCl$_3$) δ: 1.01 (6H, d, J=6.0 Hz), 1.27-1.36 (2H, m), 1.51-1.65 (2H, m), 2.26 (2H, t, J=6.0 Hz), 2.49 (3H, s), 2.63 (2H, t, J=6.0 Hz), 3.03 (2H, d, J=9.0 Hz), 3.64 (3H, s), 3.94 (2H, bs), 7.06 (1H, d, J=3.0 Hz), 7.18 (2H, d, J=6.0 Hz), 7.36 (2H, d, J=6.0 Hz), 7.52 (1H, dd, J=3.0, 9.0 Hz), 8.03 (1H, d, J=9.0 Hz).

Example 126

6-[3-(aminomethyl)-2-isobutyl-4-(4-methylphenyl) quinolin-6-yl]hexanamide (Synthesized according to a method similar to the method shown in Example 120(2).)
$^1$H-NMR (CDCl$_3$) δ: 1.02 (6H, d, J=6.0 Hz), 1.50-1.62 (2H, m), 2.09-2.18 (2H, m), 2.21-2.35 (1H, m), 2.49 (3H, s), 2.62 (2H, t, J=6.0 Hz), 3.03 (2H, d, J=6.0 Hz), 3.93 (2H, bs), 7.05 (1H, bs), 7.17 (2H, d, J=9.0 Hz), 7.36 (2H, d, J=9.0 Hz), 7.51 (1H, dd, J=3.0, 9.0 Hz), 8.04 (1H, d, J=9.0 Hz).

Example 127

4-[3-(aminomethyl)-2-isobutyl-4-(4-methylphenyl) quinolin-6-yl]butanoic Acid Dihydrochloride 1) To a solution of 2-isobutyl-4-(4-methylphenyl)-6-[(1E)-3-oxoprop-1-en-1-yl]quinoline-3-carbonitrile (4.04 g, 11.4 mmol) in methanol (30 ml)-tetrahydrofuran (30 ml) was added sodium borohydride (216 mg, 5.69 mmol) at 0° C. and the mixture was stirred at room temperature for 10 min. Saturated aqueous ammonium chloride solution was added to the reaction mixture and the mixture was extracted 3 times with ethyl acetate. The combined organic layer was washed with saturated brine and dried over anhydrous magnesium sulfate. The solvent was evaporated under reduced pressure and the residue was purified by silica gel column chromatography to give 6-[(1E)-3-hydroxyprop-1-en-1-yl]-2-isobutyl-4-(4-methylphenyl)quinoline-3-carbonitrile (3.08 g, yield 76%) as yellow crystals. Subsequently, tert-butyl {[6-(3-hydroxypropyl)-2-isobutyl-4-(4-methylphenyl)quinolin-3-yl] methyl}carbamate was synthesized by a method similar to the method shown in Example 39(1).
$^1$H-NMR (CDCl$_3$) δ: 1.02 (6H, d, J=6.0 Hz), 1.41 (9H, s), 1.79-1.89 (2H, m), 2.29-2.41 (1H, m), 2.48 (3H, s), 2.72 (2H, t, J=6.0 Hz), 2.95 (2H, d, J=6.0 Hz), 3.64 (2H, q, J=6.0 Hz), 4.24-4.34 (3H, m), 7.09 (1H, bs), 7.12 (2H, d, J=9.0 Hz), 7.33 (2H, d, J=9.0 Hz), 7.52 (1H, dd, J=3.0, 9.0 Hz), 7.99 (1H, d, J=9.0 Hz).

2) To a solution of tert-butyl {[6-(3-hydroxypropyl)-2-isobutyl-4-(4-methylphenyl)quinolin-3-yl]
methyl}carbamate (3.00 g, 6.48 mmol) and triethylamine (1.8 ml, 12.9 mmol) in tetrahydrofuran (50 ml) was added dropwise methanesulfonyl chloride (1.12 g, 9.73 mmol) at 0° C., and the mixture was stirred at the same temperature for 30 min. Saturated aqueous sodium hydrogen carbonate was added to the reaction mixture and the mixture was extracted twice with ethyl acetate. The combined organic layer was washed with saturated brine and dried over anhydrous magnesium sulfate. The solvent was evaporated under reduced pressure and the residue was dissolved in dimethyl sulfoxide (40 ml). Potassium cyanide (2.1 g, 32.4 mmol) was added and the mixture was stirred at 60° C. for 2.5 hrs. The reaction mixture was diluted with ethyl acetate, washed twice with saturated aqueous sodium hydrogen carbonate, water and saturated brine, and dried over anhydrous magnesium sulfate. The solvent was evaporated under reduced pressure, and the residue was purified by silica gel column chromatography to give tert-butyl {[6-(3-cyanopropyl)-2-isobutyl-4-(4-methylphenyl)quinolin-3-yl]methyl}carbamate (2.73 g, yield 89%) as yellow crystals.
$^1$H-NMR (CDCl$_3$) δ: 1.03 (6H, d, J=9.0 Hz), 1.42 (9H, s), 1.89-1.98 (2H, m), 2.28 (2H, t, J=6.0 Hz), 2.32-2.43 (1H, m), 2.49 (3H, m), 2.49 (3H, s), 2.79 (2H, t, J=6.0 Hz), 2.96 (2H, d, J=6.0 Hz), 4.26-4.36 (3H, m), 7.09 (1H, d, J=3.0 Hz), 7.12 (2H, d, J=9.0 Hz), 7.34 (2H, d, J=6.0 Hz), 7.48 (1H, dd, J=3.0, 9.0 Hz), 8.02 (1H, d, 9.0 Hz).

3) To a solution of tert-butyl {[6-(3-cyanopropyl)-2-isobutyl-4-(4-methylphenyl)quinolin-3-yl]methyl}carbamate (3.10 g, 6.57 mmol) in ethanol (60 ml) was added 2N aqueous sodium hydroxide solution (16.5 ml), and the mixture was heated under reflux for 13 hrs. The reaction mixture was acidified with 6N hydrochloric acid and extracted 3 times with ethyl acetate. The combined organic layer was washed with saturated brine, and dried over anhydrous magnesium sulfate. The solvent was evaporated under reduced pressure to give a yellow solid. This solid was washed with diisopropyl ether to give 4-[3-{[(tert-butoxycarbonyl)amino]methyl}-2-isobutyl-4-(4-methylphenyl)quinolin-6-yl]butanoic acid (2.68 g, yield 83%) as yellow crystals. Subsequently, 4-[3-(aminomethyl)-2-isobutyl-4-(4-methylphenyl)quinolin-6-yl]butanoic acid dihydrochloride was synthesized by a method similar to the method shown in Example 44(3).
$^1$H-NMR (CD$_3$OD) δ: 1.14 (6H, d, J=6.0 Hz), 1.83-1.93 (2H, m), 2.28 (2H, t, J=6.0 Hz), 2.30-2.36 (1H, m), 2.54 (3H, s), 2.82 (2H, t, J=6.0 Hz), 4.33 (2H, bs), 7.35-7.44 (3H, m), 7.58 (2H, d, J=9.0 Hz), 8.11 (1H, d, J=9.0 Hz), 8.25-8.33 (1H, m).

Example 128

Methyl 4-[3-(aminomethyl)-2-isobutyl-4-(4-methylphenyl)quinolin-6-yl]butanoate Dihydrochloride Methyl 4-[3-{[(tert-butoxycarbonyl)amino]methyl}-2-isobutyl-4-(4-methylphenyl)quinolin-6-yl]butanoate was synthesized by a method similar to the method shown in Example 125. Subsequently, methyl 4-[3-(aminomethyl)-2-isobutyl-4-(4-methylphenyl)quinolin-6-yl]butanoate dihydrochloride was synthesized by a method similar to the method shown in Example 44(3).
$^1$H-NMR (CD$_3$OD) δ: 1.11-1.16 (6H, m), 1.83-1.94 (2H, m), 2.27-2.34 (3H, m), 2.54 (3H, s), 2.74-2.83 (2H, m), 3.60 (3H, s), 4.26-4.33 (2H, m), 7.31-7.42 (3H, m), 7.52-7.61 (2H, m), 7.94-8.00 (1H, m), 8.18 (1H, d, J=9.0 Hz).

Example 129

4-[3-(aminomethyl)-2-isobutyl-4-(4-methylphenyl) quinolin-6-yl]butanamide (Synthesized according to a method similar to the method shown in Example 120(2).)
$^1$H-NMR (CDCl$_3$) δ: 1.03 (6H, d, J=6.0 Hz), 1.85-1.98 (2H, m), 2.15 (2H, t, J=6.0 Hz), 2.29-2.41 (1H, m), 2.49 (3H, s), 2.67 (2H, t, J=6.0 Hz), 3.00 (2H, d, J=6.0 Hz), 3.82 (2H, bs), 5.29 (2H, bs), 7.05 (1H, s), 7.16 (2H, d, J=6.0 Hz), 7.35 (2H, d, J=9.0 Hz), 7.48 (1H, dd, J=3.0, 9.0 Hz), 8.00 (1H, d, J=9.0 Hz).

Example 130

Ethyl ({[3-(aminomethyl)-2-isobutyl-4-(4-methylphenyl)quinolin-6-yl]methyl}thio)acetate Dihydrochloride 1) To a mixture of tert-butyl [6-(hydroxymethyl)-2-isobutyl-4-(4-methylphenyl)quinolin-3-yl]methylcarbamate (1.1 g, 2.5 mmol), triethylamine (0.53 ml, 3.8 mmol) and tetrahydrofuran (50 ml) was added methanesulfonyl chloride (0.3 ml, 3.8 mmol) under ice-cooling, and the mixture was stirred for 30 min. A mixture of ethyl thioglycollate (0.42 ml, 3.8 mmol), sodium hydride (60% in oil, 0.15 g, 3.8 mmol) and N,N-dimethylformamide (3 ml) were added to the reaction mixture and the mixture was stirred at room temperature for 15 min. The reaction mixture was partitioned between ethyl acetate and water and the aqueous layer was extracted with ethyl acetate. The organic layer and the extract were combined, washed with saturated brine, and dried over anhydrous magnesium sulfate. The solvent was evaporated under reduced pressure and the residue was purified by silica gel column chromatography to give ethyl ({[3-{[(tert-butoxycarbonyl)amino]methyl}-2-isobutyl-4-(4-methylphenyl)quinolin-6-yl]methyl}thio)acetate (1.1 g, yield 83%) as a white powder.

$^1$H-NMR (CDCl$_3$) δ: 1.03 (6H, d, J=6.6 Hz), 1.19 (3H, t, J=7.2 Hz), 1.42 (9H, s), 2.25-2.40 (1H, m), 2.48 (3H, s), 2.96 (2H, d, J=7.7 Hz), 2.98 (2H, s), 3.83 (2H, s), 4.08 (2H, q, J=7.2 Hz), 4.25-4.40 (3H, m), 7.12 (2H, d, J=7.9 Hz), 7.18 (1H, d, J=1.9 Hz), 7.33 (2H, d, J=7.9 Hz), 7.68 (1H, dd, J=1.9, 8.7 Hz), 8.03 (1H, d, J=8.7 Hz).

2) ethyl ({[3-(aminomethyl)-2-isobutyl-4-(4-methylphenyl)quinolin-6-yl]methyl}thio)acetate dihydrochloride (Synthesized according to a method similar to the method shown in Example 44(3).)

$^1$H-NMR (DMSO-d$_6$) δ: 1.03 (6H, d, J=6.6 Hz), 1.08 (3H, t, J=7.2 Hz), 2.25-2.40 (1H, m), 2.47 (3H, s), 3.10 (2H, s), 3.22 (2H, d, J=6.6 Hz), 3.90 (2H, s), 3.96 (2H, q, J=7.2 Hz), 4.00 (2H, d, J=3.4 Hz), 7.25-7.30 (1H, m), 7.36 (2H, d, J=8.0 Hz), 7.46 (2H, d, J=8.0 Hz), 7.94 (1H, d, J=8.5 Hz), 8.30-8.40 (1H, m), 8.46 (3H, bs).

Example 131

({[3-(aminomethyl)-2-isobutyl-4-(4-methylphenyl)quinolin-6-yl]methyl}thio)acetic Acid Dihydrochloride 1) ({[3-{[(tert-butoxycarbonyl)amino]methyl}-2-isobutyl-4-(4-methylphenyl)quinolin-6-yl]methyl}thio)acetic acid (Synthesized according to a method similar to the method shown in Example 6(1).)

$^1$H-NMR (CDCl$_3$) δ: 1.08 (6H, d, J=6.6 Hz), 1.41 (9H, s), 2.20-2.45 (1H, m), 2.51 (3H, s), 3.07 (2H, s), 3.34 (2H, d, J=7.2 Hz), 3.86 (2H, s), 4.36 (2H, d, J=5.1 Hz), 4.93 (1H, bs), 7.10-7.30 (3H, m), 7.41 (2H, d, J=7.9 Hz), 7.90 (1H, d, J=7.5 Hz), 8.55-8.70 (1H, m).

2) ({[3-(aminomethyl)-2-isobutyl-4-(4-methylphenyl)quinolin-6-yl]methyl}thio)acetic acid dihydrochloride (Synthesized according to a method similar to the method shown in Example 44(3).)

$^1$H-NMR (DMSO-d$_6$) δ: 1.04 (6H, d, J=6.2 Hz), 2.15-2.45 (1H, m), 2.48 (3H, s), 3.06 (2H, s), 3.26 (2H, d, J=6.4 Hz), 3.90 (2H, s), 4.01 (2H, d, J=5.1 Hz), 7.25-7.30 (1H, m), 7.37 (2H, d, J=7.9 Hz), 7.47 (2H, d, J=7.9 Hz), 7.97 (1H, d, J=8.7 Hz), 8.39 (1H, d, J=8.7 Hz), 8.50 (3H, bs).

Example 132

2-({[3-(aminomethyl)-2-isobutyl-4-(4-methylphenyl)quinolin-6-yl]methyl}thio)acetamide Dihydrochloride 1) tert-butyl [6-{[(2-amino-2-oxoethyl)thio]methyl}-2-isobutyl-4-(4-methylphenyl)quinolin-3-yl]methylcarbamate (Synthesized according to a method similar to the method shown in Example 19(4).)

$^1$H-NMR (CDCl$_3$) δ: 1.03 (6H, d, J=6.6 Hz), 1.41 (9H, s), 2.25-2.45 (1H, m), 2.48 (3H, s), 2.96 (2H, d, J=7.2 Hz), 3.04 (2H, s), 3.77 (2H, s), 4.25-4.35 (3H, m), 5.28 (1H, bs), 6.38 (1H, bs), 7.05-7.20 (3H, m), 7.35 (2H, d, J=7.8 Hz), 7.63 (1H, dd, J=1.9, 7.5 Hz), 8.04 (1H, d, J=8.7 Hz).

2) 2-({[3-(aminomethyl)-2-isobutyl-4-(4-methylphenyl)quinolin-6-yl]methyl}thio)acetamide dihydrochloride (Synthesized according to a method similar to the method shown in Example 44(3).)

$^1$H-NMR (DMSO-d$_6$) δ: 1.03 (6H, d, J=6.4 Hz), 2.25-2.40 (1H, m), 2.47 (3H, s), 2.93 (2H, s), 3.23 (2H, d, J=5.6 Hz), 3.90 (2H, s), 4.00 (2H, d, J=4.5 Hz), 6.99 (1H, bs), 7.25-7.35 (1H, m), 7.37 (2H, d, J=7.6 Hz), 7.40 (1H, bs), 7.46 (2H, d, J=7.6 Hz), 7.97 (1H, d, J=7.5 Hz), 8.25-8.40 (1H, m), 8.46 (3H, bs).

Example 133

3-[3-(aminomethyl)-2-isobutyl-4-(4-methylphenyl)quinolin-6-yl]propanoic Acid Dihydrochloride The title compound was synthesized from 3-[3-{[(tert-butoxycarbonyl)amino]methyl}-2-isobutyl-4-(4-methylphenyl)quinolin-6-yl]propanoic acid by a method similar to the method shown in Example 13(6).

$^1$H-NMR (DMSO-d$_6$) δ: 1.02 (6H, d, J=6.6 Hz), 2.25-2.36 (1H, m), 2.48-2.54 (5H, m), 2.91 (2H, t, J=7.2 Hz), 3.25 (2H, d, J=6.3 Hz), 4.00 (2H, d, J=6.9 Hz), 7.22 (1H, s), 7.36 (2H, d, J=8.0 Hz), 7.47 (2H, d, J=8.0 Hz), 7.93 (1H, d, J=8.4 Hz), 8.34-8.53 (4H, m).

Example 134

[({(1E)-[3-(aminomethyl)-2-isobutyl-4-(4-methylphenyl)quinolin-6-yl]methylene}amino)oxy]acetic Acid Dihydrochloride 1) [({(1E)-[3-{[(tert-butoxycarbonyl)amino]methyl}-2-isobutyl-4-(4-methylphenyl)quinolin-6-yl]methylene}amino)oxy]acetic acid A solution of tert-butyl [6-formyl-2-isobutyl-4-(4-methylphenyl)quinolin-3-yl]methylcarbamate (300 mg, 0.694 mmol), (aminooxy)acetic acid hemihydrochloride (75.8 mg, 0.694 mmol) and triethylamine (70.3 mg, 0.694 mmol) in 90% ethanol (7.5 ml) was heated under reflux for 1.5 hrs. The solvent was evaporated under reduced pressure and the residue was purified by silica gel column chromatography to give [({(1E)-[3-{[(tert-butoxycarbonyl)amino]methyl}-2-isobutyl-4-(4-methylphenyl)quinolin-6-yl]methylene}amino)oxy]acetic acid (183 mg, yield 52%) as white crystals.

$^1$H-NMR (CDCl$_3$) δ: 1.02 (6H, d, J=6.0 Hz), 1.40 (9H, s), 2.22-2.37 (1H, m), 2.47 (3H, s), 3.05 (2H, d, J=6.0 Hz), 4.30 (2H, bs), 4.69 (2H, s), 7.11 (2H, d, J=9.0 Hz), 7.24 (1H, s), 7.33 (2H, d, J=6.0 Hz), 8.05-8.21 (2H, m).

2) [({(1E)-[3-(aminomethyl)-2-isobutyl-4-(4-methylphenyl)quinolin-6-yl]methylene}amino)oxy]acetic acid dihydrochloride (Synthesized according to a method similar to the method shown in Example 44(3).)

$^1$H-NMR (CD$_3$OD) δ: 1.12 (6H, d, J=6.0 Hz), 2.28-2.39 (1H, m), 2.53 (3H, s), 3.18 (2H, d, J=6.0 Hz), 4.28 (2H, bs), 4.72 (2H, s), 7.35 (2H, d, J=9.0 Hz), 7.55 (2H, d, J=6.0 Hz), 7.62-7.64 (1H, m), 8.19-8.39 (3H, m).

Experimental Example 1

1) Preparation of Dipeptidyl Peptidase IV Crude Enzyme Solution

The enzyme activity of dipeptidyl peptidase IV present in human colonic adenocarcinoma-derived cell line Caco-2 cell membrane has been already reported by Yong S. Chung et al. (Cancer Research, vol. 45, pp. 2976-2982, 1985).

A dipeptidyl peptidase IV crude enzyme solution was prepared from cultured Caco-2 (ATCC HTB-37) cells. The Caco-2 cells were cultured in D-MEM medium (manufactured by Nissui Pharmaceutical Co., Ltd.) containing 10% FBS (fetal bovine serum (manufactured by GIBCO)). The cell extract was prepared by soaking the cells collected by removing the medium in 20 mM phosphate buffer (pH 7.5) containing 0.5% Triton X-100, extracting for 30 min in an ice bath and separating the supernatant obtained by centrifugation at 1500 g for 30 min. The cell extract (22 ml) was applied to a column of Sephadex G-200 (600 ml, manufactured by Pharmacia Corporation) equilibrated with 20 mM Tris-hydrochloride buffer (pH 7.5) and eluted with the same buffer. The elution was fractionated by 10 ml, examined for enzyme activity and 190 ml-280 ml fractions (90 ml) were collected. The same buffer (260 ml) was added for dilution to give a crude enzyme solution (14 mU/ml, 350 ml). One unit of the dipeptidyl peptidase IV enzyme activity was defined as an enzyme amount that produces 1 μmol of p-nitroaniline from glycylprolyl-p-nitroanilide in 1 min.

2) Determination of Caco-2-Derived Dipeptidyl Peptidase IV Inhibitory Activity

The reaction was carried out according to the method of Nagatsu et al. (Analytical Biochemistry, vol. 74, pp. 466-467, 1976) using a 96 well flat-bottomed plate at 37° C.

An N,N-dimethylformamide solution (5 μl) containing the test compound was added to a mixture of water (25 μl), 1M Tris-hydrochloride buffer (10 μl, pH 7.5) and 1 mM aqueous glycylprolyl-p-nitroanilide (Gly-Pro-p-NA; manufactured by Backem AG) solution (50 μl) to prepare a mixed solution. The Caco-2-derived dipeptidyl peptidase IV crude enzyme solution (10 μl) obtained in the aforementioned 1) was added to the above-mentioned mixed solution and the enzyme reaction was started at 37° C. The absorbance after 0 hr. and 3 hrs. was measured using a microplate reader (Multiskan Bichromatic; manufactured by Labsystems) at a wavelength of 405 nm and an increase ($\Delta ODs$) was determined. At the same time, an increase ($\Delta ODc$) in absorbance of the reaction mixture without the test compound, and an increase ($\Delta ODb$) in absorbance of the reaction mixture without the test compound and the enzyme were determined and percent inhibition of dipeptidyl peptidase IV enzyme activity was calculated from the following formula:

$$\{1-[(\Delta ODs-\Delta ODb)/(\Delta ODc-\Delta ODb)]\}\times 100$$

The dipeptidyl peptidase IV inhibitory activity of the test compound group is expressed in $IC_{50}$ value (μM) and shown in Table 1.

TABLE 1

| Test compound (Example No.) | $IC_{50}$ value (μM) |
|---|---|
| 1 | 0.71 |

As shown above, the compound of the present invention has a superior dipeptidyl peptidase IV inhibitory activity, and is useful as a prophylactic or therapeutic agent of diabetes and the like.

Experimental Example 2

Determination of Dipeptidyl Peptidase IV Inhibitory Activity in Rat Plasma

The reaction was carried out according to the method of Raymond et al. (Diabetes, vol. 47, pp. 1253-1258, 1998) using a 96 well flat-bottomed plate at 30° C. An N,N-dimethylformamide solution (1 μl) containing the test compound was added to a mixture of water (69 μl), 1 M Tris-hydrochloride buffer (10 μl, pH 7.5) and 1 mM aqueous Gly-Pro-p-NA solution (100 μl) to prepare a mixed solution. Plasma (20 μl) prepared from blood of SD rat by a conventional method was added to the above-mentioned mixed solution and the enzyme reaction was started at 30° C. The absorbance after 0 hr. and 1 hr. was measured using a microplate reader at a wavelength of 405 nm and an increase ($\Delta ODs$) was determined. At the same time, an increase ($\Delta ODc$) in absorbance of the reaction mixture without the test compound, and an increase ($\Delta ODb$) in absorbance of the reaction mixture without the test compound and the enzyme were determined and percent inhibition of dipeptidyl peptidase IV enzyme activity was calculated from the following formula:

$$\{1-[(\Delta ODs-\Delta ODb)/(\Delta ODc-\Delta ODb)]\}\times 100$$

The dipeptidyl peptidase IV inhibitory activity of the test compound group is expressed in $IC_{50}$ value (μM) and shown in Table 2.

TABLE 2

| Test compound (Example No.) | $IC_{50}$ value (μM) |
|---|---|
| 1 | 1.6 |

As shown above, the compound of the present invention has a superior dipeptidyl peptidase IV inhibitory activity, and is useful as a prophylactic or therapeutic agent of diabetes and the like.

Formulation Example 1

Production of Capsule

| 1) compound of Example 1 | 30 mg |
|---|---|
| 2) fine cellulose powder | 10 mg |
| 3) lactose | 19 mg |
| 4) magnesium stearate | 1 mg |
| total | 60 mg |

1), 2), 3) and 4) are mixed and filled in gelatin capsules.

Formulation Example 2

Production of Tablet

| | |
|---|---|
| 1) compound of Example 1 | 30 g |
| 2) lactose | 50 g |
| 3) corn starch | 15 g |
| 4) carboxymethylcellulose calcium | 44 g |
| 5) magnesium stearate | 1 g |
| total of 1000 tablets | 140 g |

The entire amounts of 1), 2) and 3), and 30 g of 4) are kneaded with water, dried in vacuo and granulated. The granules are mixed with 14 g of 4) and 1 g of 5) and the mixture is compressed with a tableting machine, whereby 1000 tablets containing 30 mg of compound of Example 1 per tablet are obtained.

INDUSTRIAL APPLICABILITY

The compound of the present invention and the pharmaceutical agent of the present invention show a superior peptidase-inhibitory activity and are useful as a prophylactic or therapeutic agent of diabetes and the like.

This application is based on patent application Nos. 231950/2002 and 51575/2003 filed in Japan, the content of which is hereby incorporated by reference.

The invention claimed is:

1. A compound represented by the formula

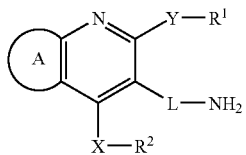

(I)

wherein
  ring A is an optionally substituted 5- to 10-membered aromatic ring;
  one of $R^1$ and $R^2$ is an optionally substituted phenyl group and the other is an optionally substituted $C_{1-10}$ alkyl group;
  both X and Y are bonds: and
  L is a $C_{1-10}$ alkylene group,
or a salt thereof.

2. The compound of claim 1, wherein the 5- to 10-membered aromatic ring for ring A is a benzene ring.

3. The compound of claim 1, wherein the ring A is a 5- to 10-membered aromatic ring optionally having 1 to 3 substituents selected from (1) a halogen atom;
(2) a nitro group;
(3) a cyano group;
(4) an alkylenedioxy group having 1 to 3 carbon atoms;
(5) an alkyl group having 1 to 10 carbon atoms or an alkenyl group having 2 to 10 carbon atoms, each optionally having 1 to 3 substituents selected from a halogen atom, a hydroxy group, a carboxyl group, an alkoxycarbonyl group having 2 to 8 carbon atoms, a carbamoyl group, a cyano group, an amino group, an alkylcarbonylamino group having 2 to 8 carbon atoms, an alkoxycarbonylamino group having 2 to 8 carbon atoms and an alkylsulfonylamino group having 1 to 8 carbon atoms;
(6) an optionally substituted hydroxy group;
(7) an acyl group;
(8) an optionally substituted amino group;
(9) an optionally substituted cycloalkyl group having 3 to 10 carbon atoms;
(10) an aryl group having 6 to 14 carbon atoms;
(11) an optionally substituted thiol group;
(12) an optionally substituted heterocyclic group; and
(13) an amidino group.

4. The compound of claim 1, wherein $R^1$ is an alkyl group having 1 to 10 carbon atoms which is optionally substituted by a cycloalkyl group having 3 to 10 carbon atoms.

5. The compound of claim 1, wherein $R^2$ is an alkyl group having 1 to 10 carbon atoms or a phenyl group, each optionally having 1 to 3 substituents selected from halogen atom, hydroxy group, nitro group, amino group, optionally halogenated alkyl group having 1 to 6 carbon atoms, alkoxy group having 1 to 6 carbon atoms, aromatic heterocyclic group and cycloalkyl group having 3 to 10 carbon atoms.

6. The compound of claim 1, which is (2E)-3-[3-(aminomethyl)-2-isobutyl-4-(4-methylphenyl)quinolin-6-yl]acrylamide;

5-{[3-(aminomethyl)-2-isobutyl-4-(4-methylphenyl) quinolin-6-yl]oxy}pentanoic acid;

4-[3-(aminomethyl)-2-isobutyl-4-(4-methylphenyl) quinolin-6-yl]piperazin-2-one; or 1-[3-(aminomethyl)-2-isobutyl-4-(4-methylphenyl) quinolin-6-yl]piperazine-2,5-dione;
or a salt thereof.

7. A pharmaceutical composition comprising a compound of claim 1 and a pharmacologically acceptable carrier.

8. A method for the treatment of diabetes in a mammal, which comprises administering a compound of claim 1 to the mammal.

9. A method for the treatment of diabetic complications in a mammal, which comprises administering a compound of claim 1 to the mammal.

10. A method for the treatment of impaired glucose tolerance in a mammal, which comprises administering a compound of claim 1 to the mammal.

11. A method for the treatment of obesity in a mammal, which comprises administering a compound of claim 1 to the mammal.

* * * * *